United States Patent
Yu et al.

(10) Patent No.: US 11,542,272 B2
(45) Date of Patent: Jan. 3, 2023

(54) FIVE-MEMBERED HETEROARYL-FUSED IMIDAZOLE COMPOUND AND APPLICATION THEREOF

(71) Applicant: Hangzhou Sciwind Biosciences Co., Ltd, Zhejiang (CN)

(72) Inventors: Tao Yu, Shanghai (CN); Lu Gan, Shanghai (CN); Chengde Wu, Shanghai (CN); Shuhui Chen, Shanghai (CN)

(73) Assignee: Hangzhou Sciwind Biosciences Co., Ltd, Zhejiang (CN)

( * ) Notice: Subject to any disclaimer, the term of this patent is extended or adjusted under 35 U.S.C. 154(b) by 0 days.

(21) Appl. No.: 17/574,817

(22) Filed: Jan. 13, 2022

(65) Prior Publication Data

US 2022/0135588 A1    May 5, 2022

Related U.S. Application Data

(63) Continuation of application No. PCT/CN2021/098424, filed on Jun. 4, 2021.

(30) Foreign Application Priority Data

Jun. 4, 2020 (CN) .......................... 202010499820.5
Jul. 14, 2020 (CN) .......................... 202010676014.0
Aug. 19, 2020 (CN) .......................... 202010838768.1

(51) Int. Cl.
*C07D 495/04* (2006.01)
*A61P 3/10* (2006.01)
*C07D 487/04* (2006.01)
*C07D 491/048* (2006.01)
*C07D 498/04* (2006.01)
*C07D 513/04* (2006.01)

(52) U.S. Cl.
CPC ............. *C07D 495/04* (2013.01); *A61P 3/10* (2018.01); *C07D 487/04* (2013.01); *C07D 491/048* (2013.01); *C07D 498/04* (2013.01); *C07D 513/04* (2013.01)

(58) Field of Classification Search
CPC ....... A61P 3/10; C07D 495/04; C07D 513/04; C07D 498/04; C07D 491/048
USPC .......................................................... 514/269
See application file for complete search history.

(56) References Cited

FOREIGN PATENT DOCUMENTS

| CN | 110325530 A | 10/2019 |
|---|---|---|
| WO | WO-2019239371 A1 | 12/2019 |
| WO | WO-2020103815 A1 | 5/2020 |

OTHER PUBLICATIONS

Aug. 24, 2021 International Search Report issued in International Patent Application No. PCT/CN2021/098424.

*Primary Examiner* — Kahsay Habte
(74) *Attorney, Agent, or Firm* — Harness, Dickey & Pierce, P.L.C.

(57) ABSTRACT

A novel five-membered heteroaromatic imidazole compound and use thereof is disclosed herein. Specifically, disclosed is a compound as shown in formula (III) or a pharmaceutically acceptable salt thereof. Also disclosed is a method for treating a disease related to GLP-1 receptor such as type II diabetes.

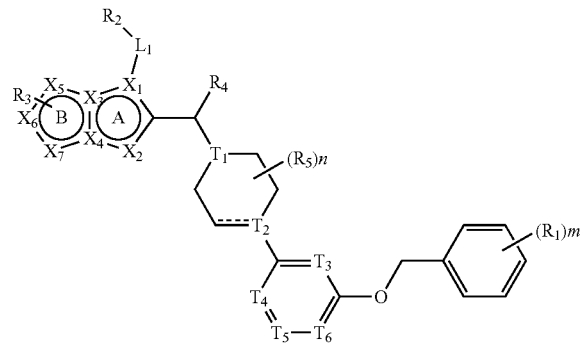

19 Claims, No Drawings

FIVE-MEMBERED HETEROARYL-FUSED IMIDAZOLE COMPOUND AND APPLICATION THEREOF

CROSS-REFERENCE TO RELATED APPLICATIONS

The present application is a continuation application of International Application No. PCT/CN2021/098424, filed on Jun. 4, 2021, which claims the priorities of the Chinese Application No. CN202010499820.5, filed on Jun. 4, 2020, the Chinese Application No. CN202010676014.0, filed on Jul. 14, 2020 and the Chinese Application No. CN202010838768.1, filed on Aug. 19, 2020. The entire disclosures of the above applications are incorporated herein by reference.

FIELD OF THE INVENTION

The present disclosure relates to a novel five-membered heteroaromatic imidazole compound and a use thereof in preparing a medicament for treating related diseases. Specifically relates to a compound represented by formula (III) and a pharmaceutically acceptable salt thereof.

BACKGROUND OF THE INVENTION

Diabetes is a common type of metabolic disease characterized by hyperglycemia. Several major types of diabetes are caused by complex interactions between genetic and environmental factors. The factors leading to hyperglycemia include the decrease of insulin secretion, the decrease of glucose utilization and the increase of glucose output, and the dominance of these factors varies according to the etiology of diabetes. Metabolic abnormalities related to diabetes lead to secondary pathophysiological changes in multiple systems throughout the body. Long-term abnormal blood glucose levels can lead to serious complications, including cardiovascular disease, chronic renal failure, retinal injury, nerve injury, microvascular injury and obesity and the like. Diabetes is classified based on different pathological processes leading to hyperglycemia, and can be divided into two main types: type 1 diabetes and type 2 diabetes. In the development of the disease, type 1 and type 2 diabetes are preceded by a phase of abnormal glucose homeostasis. Type 1 diabetes is the result of complete or almost complete insulin deficiency. Type 2 diabetes is a group of heterogeneous diseases, manifested by varying degrees of insulin resistance, decreased insulin secretion, and increased glucose production. In the early stages of diabetes treatment, diet control and exercise therapy are the preferred control options of blood glucose. When control of blood glucose is difficult to achieve with these methods, treatment with insulin or oral hypoglycemic drugs is required. Currently, drugs used in the treatment of diabetes include insulin, insulin secretagogue, metformin, insulin sensitizers, α-glucosidase inhibitor, dipeptidyl peptidase-IV inhibitor (liptins), sodium-glucose cotransport protein (SGLT2) inhibitor, and glucagon-like peptide-1 (GLP-1) receptor agonist and the like. These drugs have good therapeutic effects, but there are still safety issues in long-term treatment, for example, biguanides can easily cause lactic acidosis; sulfonylureas can cause symptoms of hypoglycemia; insulin sensitizers can cause edema, heart failure, and weight gain; α-glucosidase inhibitors can cause abdominal pain, bloating, diarrhea and other symptoms; sodium-glucose cotransporter protein (SGLT2) inhibitors increase the risk of urinary and reproductive system infections and the like. Therefore, there is an urgent need to develop a safer and more effective novel hypoglycemic drug to meet the needs of diabetes treatment.

Glucagon-like peptide-1 receptor (GLP-1R) is one of the most important therapeutic targets for type 2 diabetes. GLP-1R belongs to the subfamily of G protein-coupled receptor B cluster and is widely expressed in the stomach, small intestine, heart, kidney, lung, brain and other tissues in the body. In islet cells, GLP-1R mainly promotes the release of insulin, increases the regeneration of islet B cells, inhibits the apoptosis of B cells, and reduces the release of glucagon. In tissues such as the gastrointestinal tract, GLP-1R can inhibit gastrointestinal peristalsis and gastric juice secretion by combining with its agonists, delaying gastric emptying, and increasing satiety. In nerve tissue, small molecule GLP-1R agonists can penetrate into the brain to activate the subset of neurons expressing GLP-1R, protect nerve cells from apoptosis and enhance learning and memory abilities. Moreover, GLP-1R can also control food intake to lose weight. GLP-1 receptor agonists or endogenous GLP-1 activity enhancers have been approved for the treatment of type 2 diabetes. Such drugs do not cause hypoglycemia because the secretion of insulin stimulated by secretin is glucose-dependent. Exenatide is a synthetic peptide, such peptide was originally found in the saliva of a poisonous lizard and is an analog of GLP-1. Compared with natural GLP-1, exenatide has a different amino acid sequence, which makes exenatide resistant to the enzyme [dipeptidase IV (DPP-IV)] that degrades GLP-1. Therefore, exenatide has prolonged GLP-1-like activity and can bind to GLP-1 receptors in islets, gastrointestinal tract and brain. Liraglutide, another GLP-1 receptor agonist, is almost identical to natural GLP-1 except that it replaces one of the amino acids and adds a fatty acyl, the fatty acyl can promote its binding with albumin and plasma proteins and prolong its half-life. GLP-1 receptor agonists increase glucose-stimulated insulin secretion, inhibit glucagon, and delay gastric emptying. These drugs do not increase body weight, in fact, most patients will lose weight and lose appetite to some extent.

DPP-IV inhibitors inhibit the degradation of natural GLP-1, thereby enhancing the effect of secretin. DPP-IV, fully expressed on the cell surface of endothelial cells and some lymphocytes, can degrade a variety of polypeptides (not just GLP-1). DPP-IV inhibitors promote insulin secretion without lowering blood glucose, without gaining weight, and are more advantageous in reducing blood glucose after meals. Patients using GLP-1 receptor agonists had higher levels of GLP-1 action in their bodies than those using DPP-IV inhibitors.

Developing small molecule GLP-1 receptor agonists with oral activity can effectively avoid long-term self-injection and has good compliance. Small molecule GLP-1 receptor agonists control blood glucose through multiple pathways of glucose metabolism and excretion, it is expected that safer and more effective novel hypoglycemic drugs can be developed to meet the needs of diabetes treatment.

BRIEF SUMMARY OF THE INVENTION

The present disclosure provides a compound represented by formula (III) or a pharmaceutically acceptable salt thereof, (III)

[Chemical structure diagram showing formula III with R2, L1, R3, X5, X1, X, R4, X6, B, A, X7, X4, X2, T1, (R5)n, T2, T3, T4, T5, T6, O, (R1)m]

wherein,

⹀ is selected from a single bond and a double bond;
$T_1$ is selected from N, C and $CR_6$;
$T_2$ is selected from N, C and CH;
$T_3$, $T_4$, $T_5$ and $T_6$ are each independently selected from N and $CR_7$;
$X_1$, $X_2$, $X_3$ and $X_4$ are each independently selected from C, CH and N;
$X_5$, $X_6$ and $X_7$ are each independently selected from $CR_8$, N, O and S;
$L_1$ is selected from a single bond and —$C_{1-3}$ alkyl-;
$R_1$ is each independently selected from F, Cl, Br, I, OH, $NH_2$ and CN;
m is selected from 0, 1, 2, 3, 4 and 5;
$R_2$ is selected from

[Chemical structures showing ring systems with Y, Y1, Y2, o, p substituents]

and the

[Chemical structures showing ring systems with Y, Y1, Y2, o, p substituents]

are optionally substituted by 1, 2 or 3 $R_a$;
$Y_1$ and $Y_2$ are each independently selected from CH, $CH_2$, N, NH and O;
o and p are each independently selected from 0, 1, 2 and 3;
$R_3$ is selected from —C(═O)—NH—$R_b$, —C(═O)—$R_b$, —C(═O)—NH—S(═O)$_2$—$R_b$, —S(═O)$_2$—NH—$R_b$, —S(═O)$_2$—$R_b$, —P(═O)($R_b$)$_2$, $C_{1-3}$ alkyl, tetrazolyl, isoxazolyl,

[Chemical structures of HN-O-N heterocycle and cyclobutenedione]

and the $C_{1-3}$ alkyl, tetrazolyl, isoxazolyl,

[Chemical structures of HN-O-N heterocycle and cyclobutenedione]

and are optionally substituted by 1, 2 or 3 $R_b$;
$R_5$ is each independently selected from F, Cl, Br, I and $C_{1-3}$ alkyl;
n is selected from 0, 1 and 2;
or, two adjacent $R_5$ together form $C_{3-5}$ cycloalkyl;
$R_4$ is selected from H, F, Cl, Br, I and $CH_3$;
$R_6$ is selected from H, F, Cl, Br, I and $CH_3$;
or, $R_4$ and $R_6$ combining with the bonds to which they are attached form a double bond or $C_{3-5}$ cycloalkyl;
$R_7$ is each independently selected from H, F, Cl and CN;
$R_8$ is each independently selected from H, F, Cl and $CH_3$;
$R_a$ is selected from F, Cl, Br and I;
$R_b$ is selected from OH, CN, $C_{1-3}$ alkyl, $C_{1-3}$ alkoxy, $C_{1-3}$ alkylamino and oxazolyl, and the $C_{1-3}$ alkyl, $C_{1-3}$ alkoxy and oxazolyl are optionally substituted by 1, 2 or 3 R;
R is selected from F, Cl and Br.

In some embodiments of the present disclosure, the $X_1$, $X_2$, $X_3$ and $X_4$ constitute ring A, $X_3$, $X_4$, $X_5$, $X_6$ and $X_7$ constitute ring B, and the other variables are as defined in the present disclosure.

In some embodiments of the present disclosure, the $R_2$ is selected from

[Chemical structures of cyclobutane, azetidine (NH), oxetane (O), cyclopentane, and spiro ring systems]

, the

[Chemical structures of cyclobutane, azetidine (NH), oxetane (O), cyclopentane]

,

[Chemical structures of spiro ring systems with O]

and are optionally substituted by 1, 2 or 3 $R_a$, the other variables are as defined in the present disclosure.

In some embodiments of the present disclosure, the $R_2$ is selected from

[Chemical structures of cyclobutane, azetidine (NH), oxetane (O), spirocyclopropane-cyclobutane, spiro oxetane systems]

and the other variables are as defined in the present disclosure.

In some embodiments of the present disclosure, the $L_1$ is selected from a single bond and —$CH_2$—, the other variables are as defined in the present disclosure.

In some embodiments of the present disclosure, the m is selected from 0, 1 and 2, the other variables are as defined in the present disclosure.

In some embodiments of the present disclosure, the $R_b$ is selected from OH, CN, $CH_3$, $CF_3$ and $OCH_3$, the other variables are as defined in the present disclosure.

In some embodiments of the present disclosure, the $R_3$ is selected from —COOH, —C(=O)—NH—CN, —C(=O)—NH—OH, —C(=O)—NH—$OCH_3$, —C(=O)—$CF_3$, —S(=O)$_2$—NH—$CH_3$ and —S(=O)$_2$— OH, the other variables are as defined in the present disclosure.

In some embodiments of the present disclosure, the structural moiety

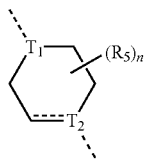

is selected from

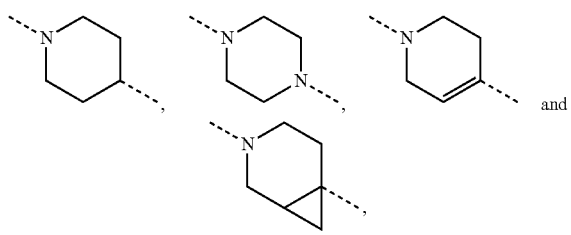

the other variables are as defined in the present disclosure.

In some embodiments of the present disclosure, the structural moiety

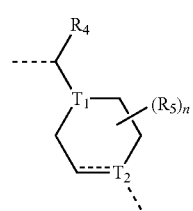

is selected from

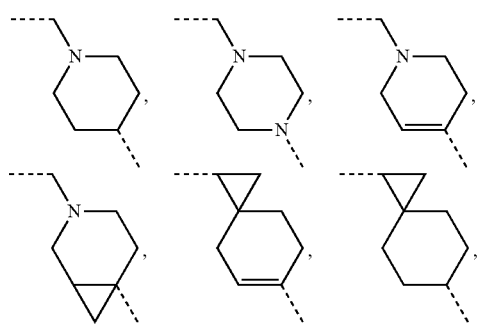

-continued

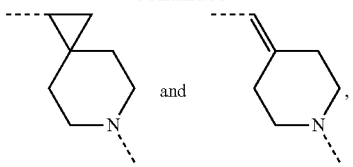

the other variables are as defined in the present disclosure.

In some embodiments of the present disclosure, the structural moiety

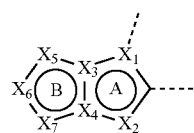

is selected from

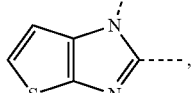 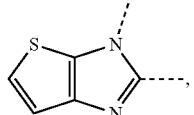

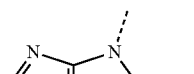 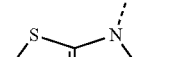

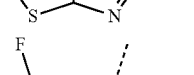 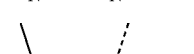

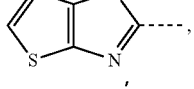 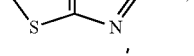

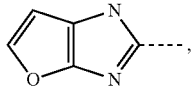 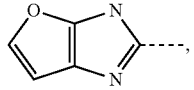

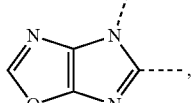 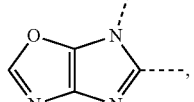

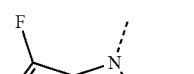 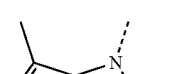

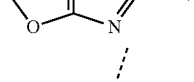 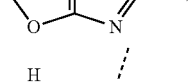

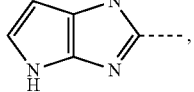 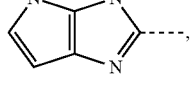

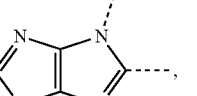 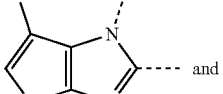 and

-continued

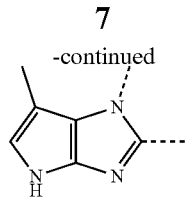

the other variables are as defined in the present disclosure.

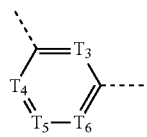

In some embodiments of the present disclosure, the structural moiety is selected from

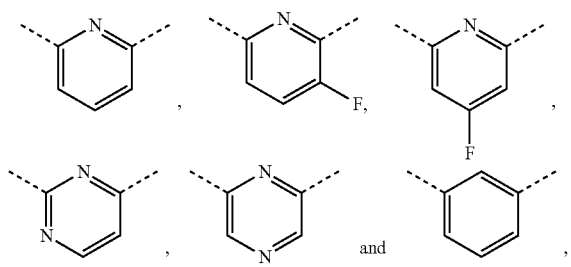

the other variables are as defined in the present disclosure.

The present disclosure provides a compound represented by formula (III) or a pharmaceutically acceptable salt thereof,

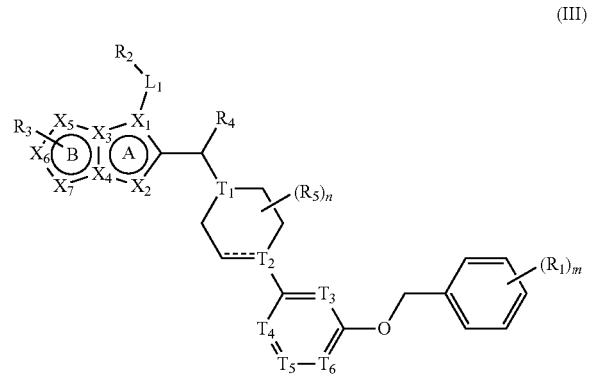

wherein,

╌╌ is selected from a single bond and a double bond, when $T_2$ is selected from N, ╌╌ is selected from the single bond;

$T_1$ is selected from N, C and $CR_6$;

$T_2$ is selected from N, C and CH;

$T_3$, $T_4$, $T_5$ and $T_6$ are each independently selected from N and $CR_7$;

$X_1$, $X_2$, $X_3$ and $X_4$ are each independently selected from C, CH and N;

$X_5$, $X_6$ and $X_7$ are each independently selected from $CR_8$, N, O and S;

$L_1$ is selected from a single bond and —$C_{1-3}$ alkyl-;

$R_1$ is each independently selected from F, Cl, Br, I, OH, $NH_2$ and CN;

m is selected from 0, 1, 2, 3, 4 and 5;

$R_2$ is selected from

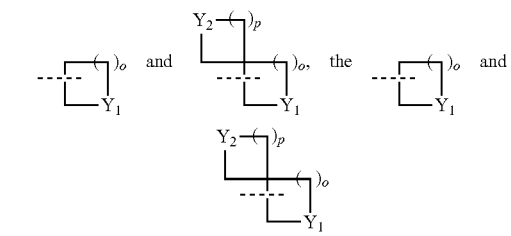

are optionally substituted by 1, 2 or 3 $R_a$;

$Y_1$ and $Y_2$ are each independently selected from CH, $CH_2$, N, NH and O;

o and p are each independently selected from 0, 1, 2 and 3;

$R_3$ is selected from —C(=O)—NH—$R_b$, —C(=O)—$R_b$, —C(=O)—NH—S(=O)$_2$—$R_b$, —S(=O)$_2$—NH—$R_b$, —S(=O)$_2$—$R_b$, —P(=O)($R_b$)$_2$, $C_{1-3}$ alkyl, tetrazolyl, isoxazolyl,

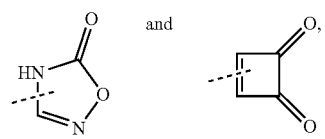

the $C_{1-3}$ alkyl, tetrazolyl, isoxazolyl,

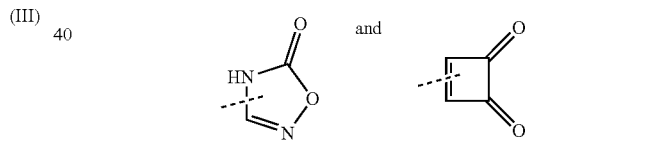

are optionally substituted by 1, 2 or 3 $R_b$;

$R_5$ is each independently selected from F, Cl, Br, I and $C_{1-3}$ alkyl;

n is selected from 0, 1 and 2;

or, two adjacent $R_5$ together form $C_{3-5}$ cycloalkyl;

$R_4$ is selected from H, F, Cl, Br, I and $CH_3$;

$R_6$ is selected from H, F, Cl, Br, I and $CH_3$;

or, $R_4$ and $R_6$ combining with the bonds to which they are attached form $C_{3-5}$ cycloalkyl;

$R_7$ is each independently selected from H, F, Cl and CN;

$R_8$ is each independently selected from H, F, Cl and $CH_3$;

$R_a$ is selected from F, Cl, Br and I;

$R_b$ is selected from OH, CN, $C_{1-3}$ alkyl, $C_{1-3}$ alkoxy, $C_{1-3}$ alkylamino and oxazolyl, and the $C_{1-3}$ alkyl, $C_{1-3}$ alkoxy and oxazolyl are optionally substituted by 1, 2 or 3 R;

R is selected from F, Cl and Br.

The present disclosure provides a compound represented by formula (I) or a pharmaceutically acceptable salt thereof,

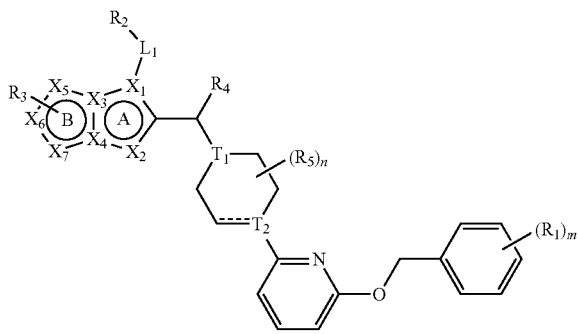

(I)

wherein,

═ is selected from a single bond and a double bond, when T$_2$ is selected from N, ═ is selected from the single bond;

T$_1$ is selected from N and CR$_6$;

T$_2$ is selected from N and CH;

X$_1$, X$_2$, X$_3$ and X$_4$ are each independently selected from C, CH and N;

X$_5$, X$_6$ and X$_7$ are each independently selected from CH, N, O and S;

L$_1$ is selected from a single bond and —C$_{1-3}$ alkyl-;

R$_1$ is selected from F, Cl, Br, I, OH, NH$_2$ and CN;

m is selected from 0, 1, 2, 3, 4 and 5;

R$_2$ is selected from

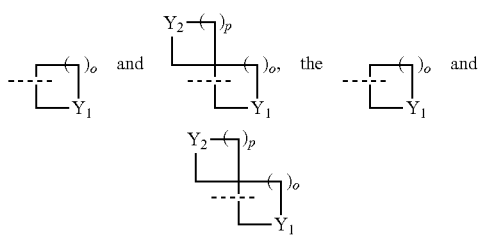

are optionally substituted by 1, 2 or 3 R$_a$;

Y$_1$ and Y$_2$ are each independently selected from CH, CH$_2$, N, NH and O;

o and p are each independently selected from 0, 1, 2 and 3;

R$_3$ is selected from —C(═O)—NH—R$_b$, —C(═O)—R$_b$, —S(═O)$_2$—NH—R$_b$ and —S(═O)$_2$—R$_b$;

R$_5$ is selected from F, Cl, Br, I and C$_{1-3}$ alkyl;

n is selected from 0, 1 and 2;

or, two adjacent R$_5$ together form C$_{3-5}$ cycloalkyl;

R$_4$ is selected from H, F, Cl, Br, I and CH$_3$;

R$_6$ is selected from H, F, Cl, Br, I and CH$_3$;

or, R$_4$ and R$_6$ combining with the bonds to which they are attached form C$_{3-5}$ cycloalkyl;

R$_a$ is selected from F, Cl, Br and I;

R$_b$ is selected from OH, CN, C$_{1-3}$ alkyl and C$_{1-3}$ alkoxy, and the C$_{1-3}$ alkyl and C$_{1-3}$ alkoxy are optionally substituted by 1, 2 or 3 R;

R is selected from F, Cl and Br.

In some embodiments of the present disclosure, the R$_2$ is selected from

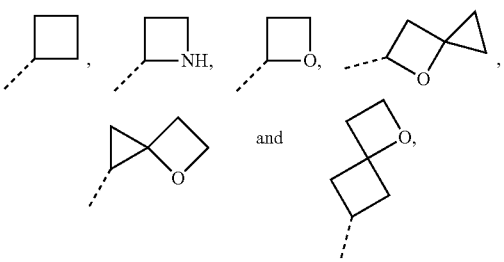

are optionally substituted by 1, 2 or 3 R$_a$, the other variables are as defined in the present disclosure.

In some embodiments of the present disclosure, the R$_2$ is selected from the other variables are as defined in the present disclosure.

In some embodiments of the present disclosure, the L$_1$ is selected from a single bond and —CH$_2$—, the other variables are as defined in the present disclosure.

In some embodiments of the present disclosure, the m is selected from 0, 1 and 2, the other variables are as defined in the present disclosure.

In some embodiments of the present disclosure, the R$_b$ is selected from OH, CN, CH$_3$, CF$_3$ and OCH$_3$, the other variables are as defined in the present disclosure.

In some embodiments of the present disclosure, the R$_3$ is selected from —COOH, —C(═O)—NH—CN, —C(═O)—NH—OH, —C(═O)—NH—OCH$_3$, —C(═O)—CF$_3$, —S(═O)$_2$—NH—CH$_3$ and —S(═O)$_2$—OH, the other variables are as defined in the present disclosure.

In some embodiments of the present disclosure, the R$_3$ is selected from —C(═O)—NH—CN, —C(═O)—NH—OH, —C(═O)—NH—OCH$_3$, —C(═O)—CF$_3$, —S(═O)$_2$—NH—CH$_3$ and —S(═O)$_2$—OH, the other variables are as defined in the present disclosure.

In some embodiments of the present disclosure, the structural moiety is

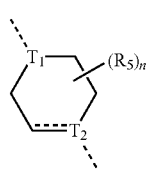

selected from

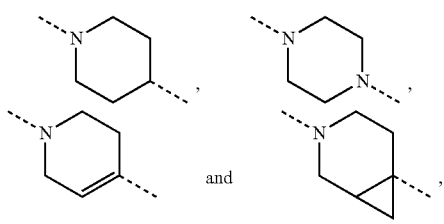

the other variables are as defined in the present disclosure.

In some embodiments of the present disclosure, the structural moiety

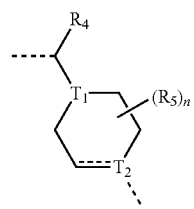

is selected from

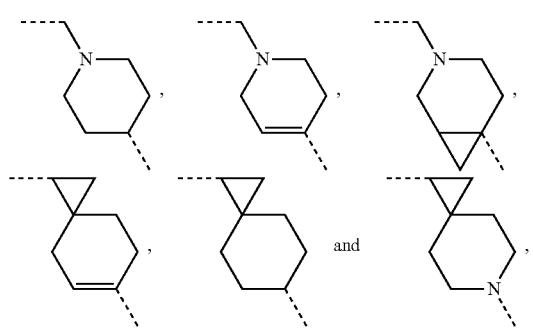

the other variables are as defined in the present disclosure.

In some embodiments of the present disclosure, the structural moiety

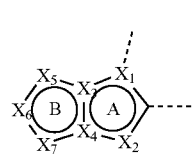

is selected from

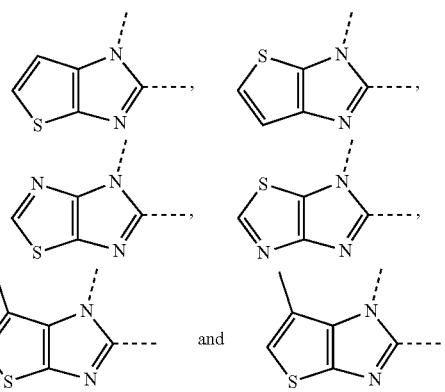

the other variables are as defined in the present disclosure.

In some embodiments of the present disclosure, the structural moiety

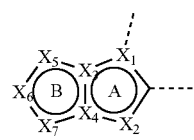

is selected from

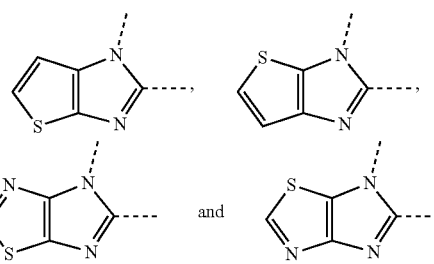

the other variables are as defined in the present disclosure.

In some embodiments of the present disclosure, the structural moiety

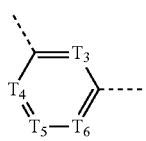

is selected from

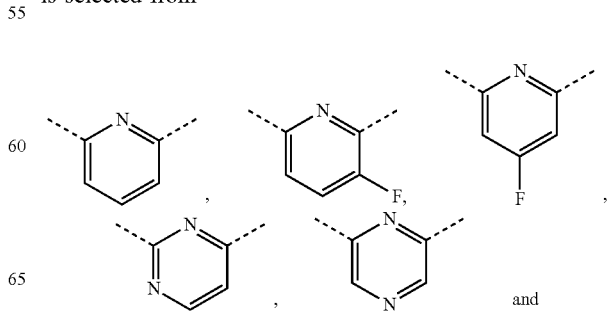

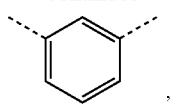

the other variables are as defined in the present disclosure.

There are also some embodiments of the present disclosure obtained by an arbitrary combination of the above variables.

In some embodiments of the present disclosure, the compound or the pharmaceutically acceptable salt thereof is selected from:

(I-2)

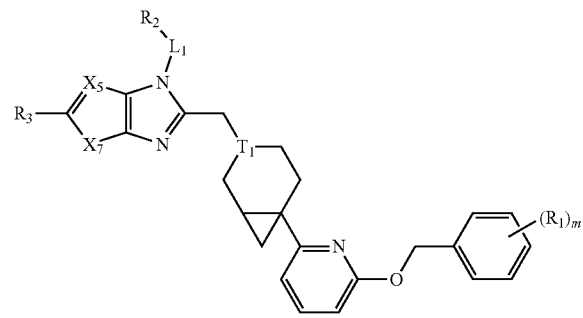

(I-3)

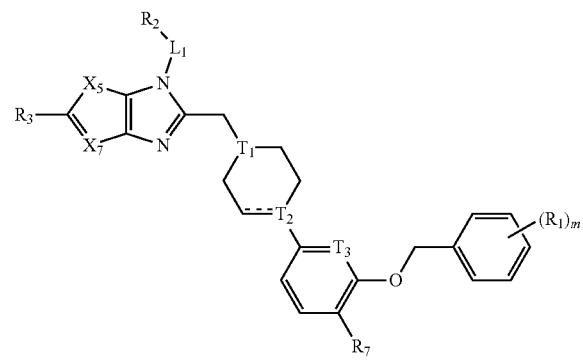

(P-1)

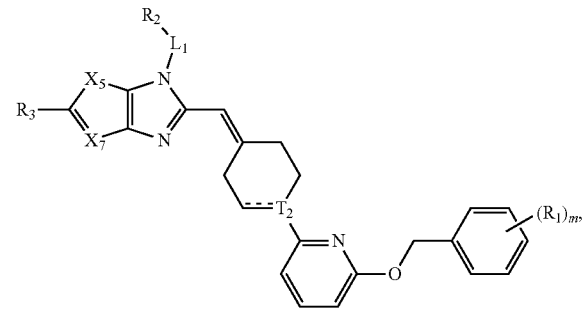

(P-2)

wherein,

⫽ is selected from a single bond and a double bond, when T₂ is selected from N, ⚌ is selected from the single bond;

R₁, R₂, R₃, L₁, T₁, T₂, m, X₅ and X₇ are as defined in the present disclosure.

In some embodiments of the present disclosure, the compound or the pharmaceutically acceptable salt thereof is selected from:

(I-1)

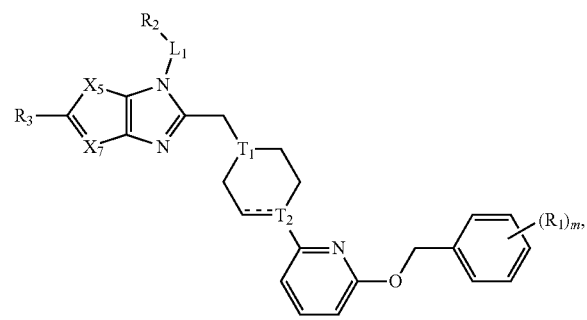

wherein,

⫽ is selected from a single bond and a double bond, when T₂ is selected from N, ⚌ is selected from the single bond;

R₁, R₂, R₃, L₁, T₁, T₂, m, X₅ and X₇ are as defined in the present disclosure.

In some embodiments of the present disclosure, the compound or the pharmaceutically acceptable salt thereof is selected from:

(III-1a)

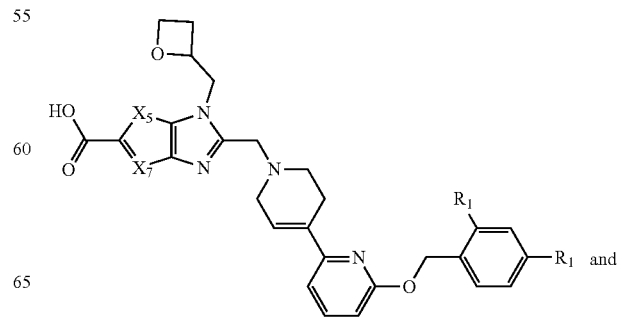

and

-continued
(III-1b)
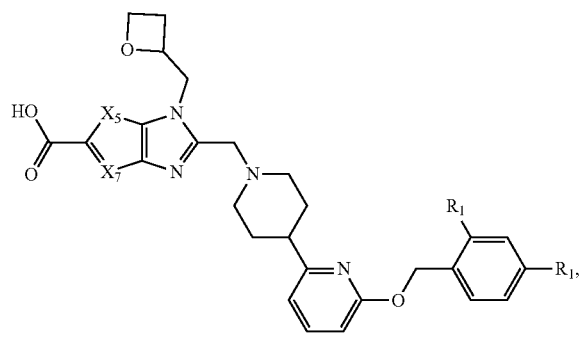
wherein, $R_1$, $X_5$ and $X_7$ are as defined in the present disclosure.
The present disclosure also provides a compound represented by the following formula or a pharmaceutically acceptable salt thereof,
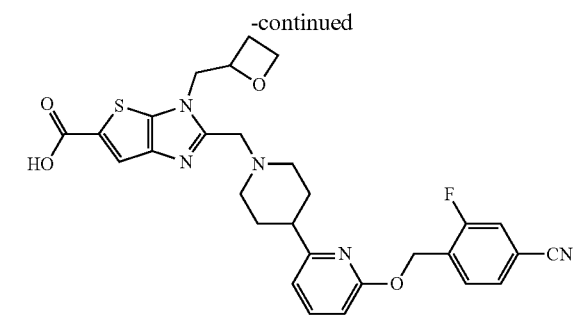
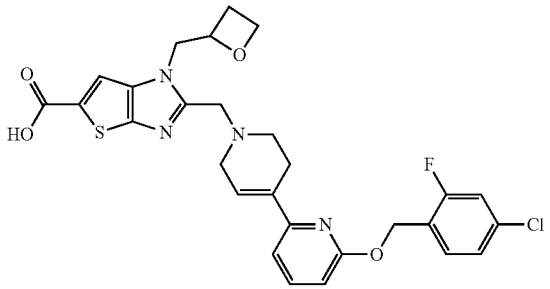
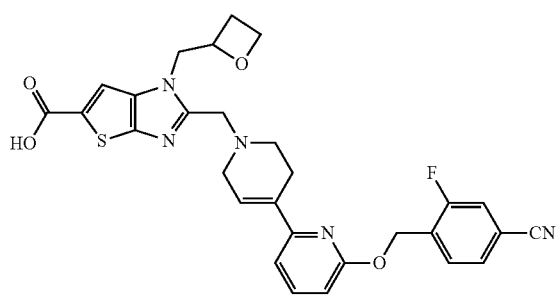
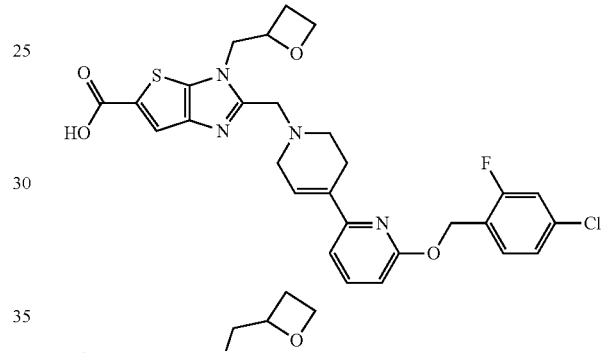
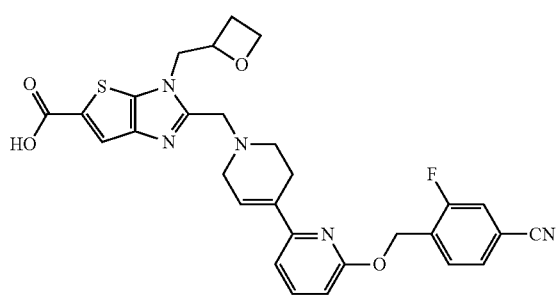
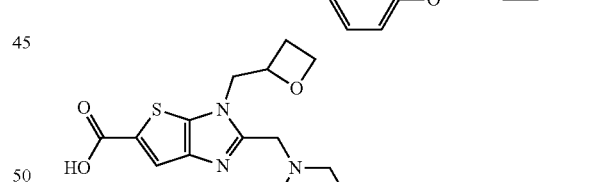
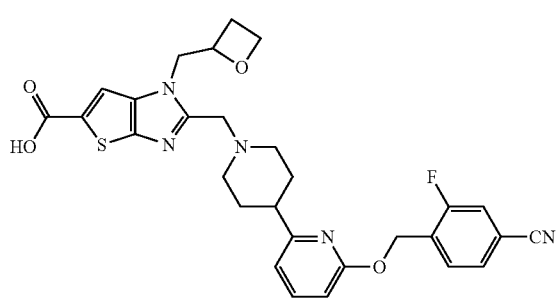
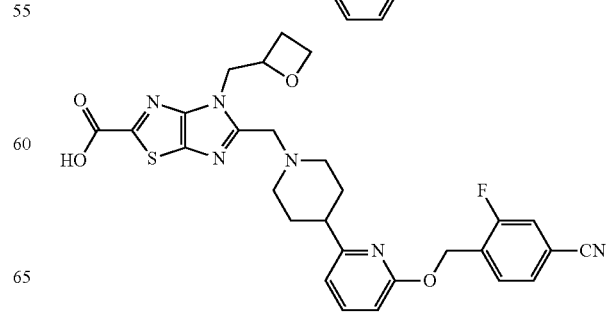

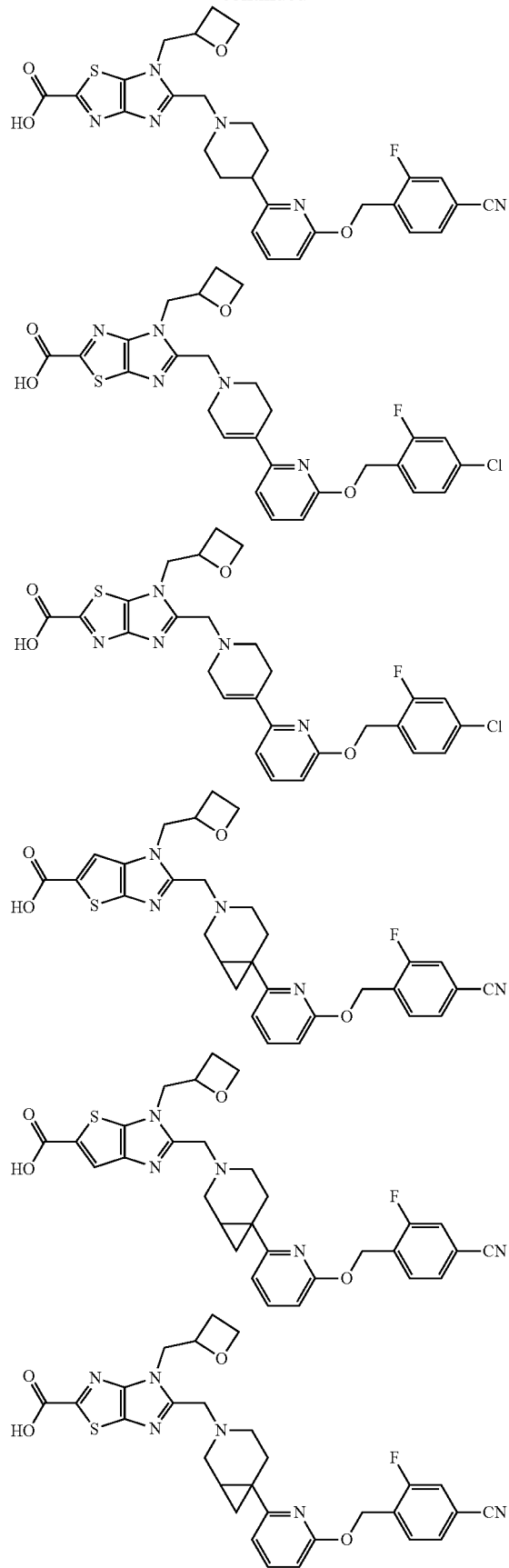
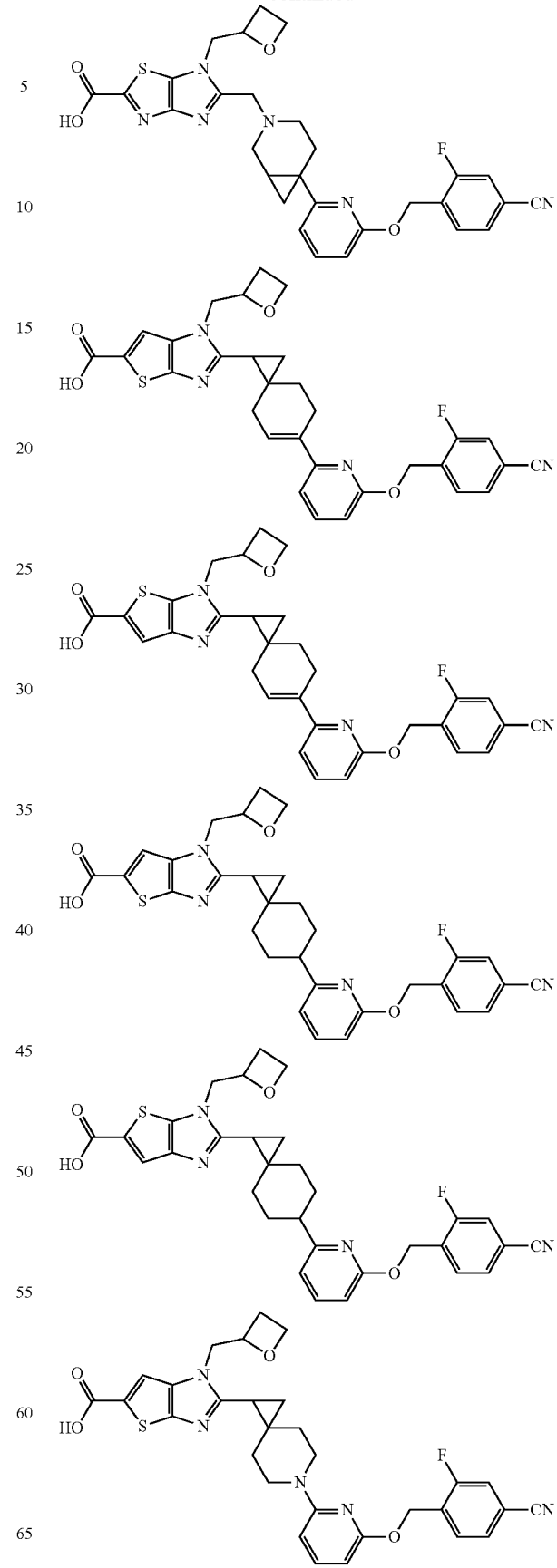

-continued
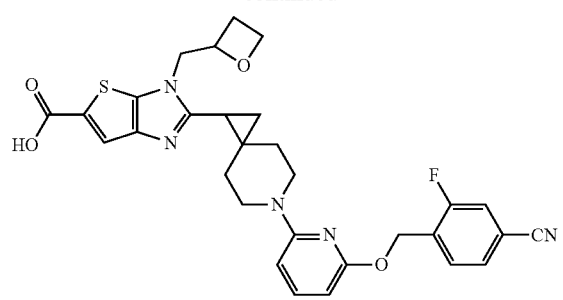
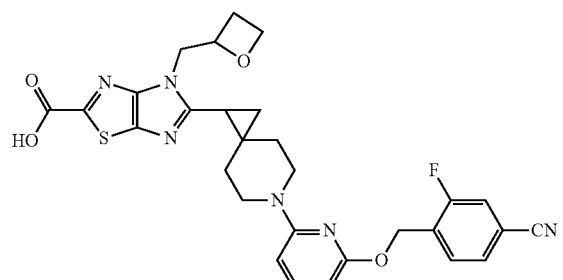
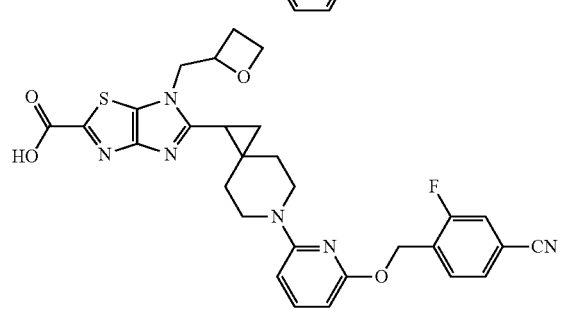
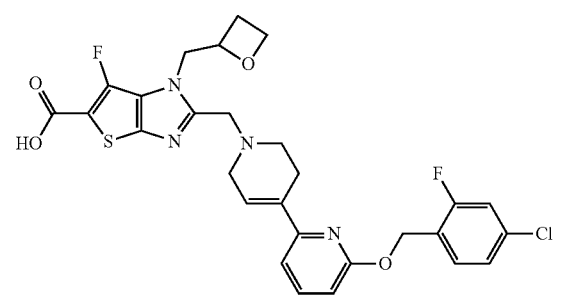
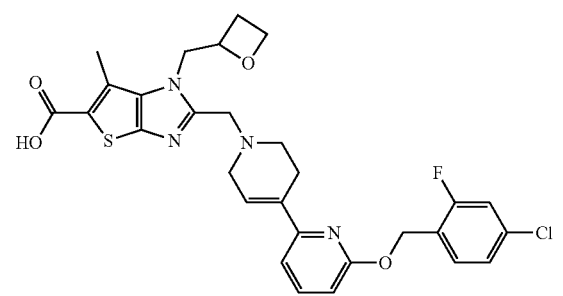
-continued
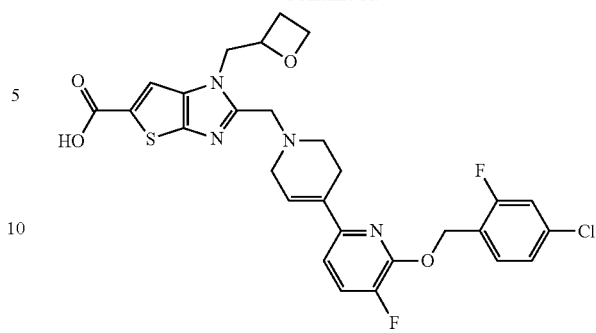
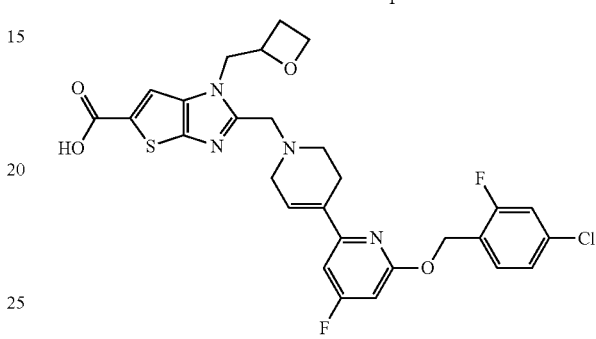
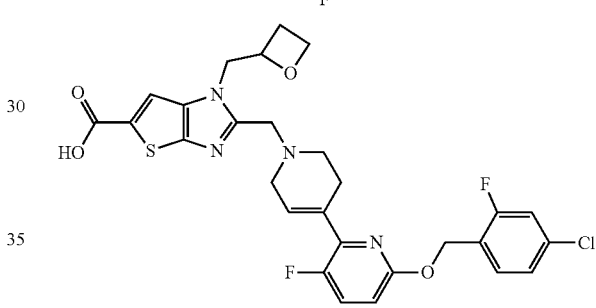
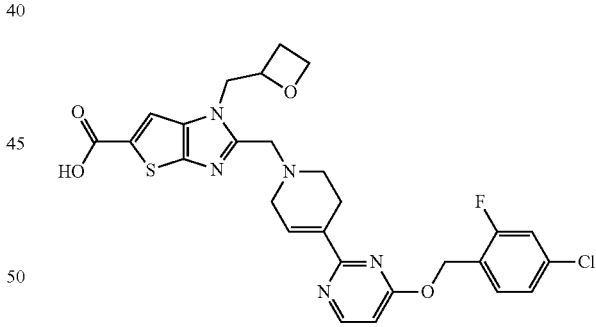
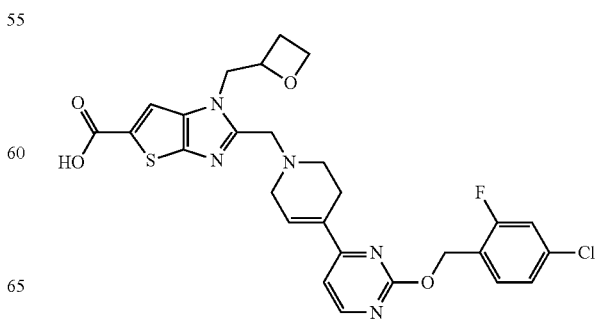

-continued
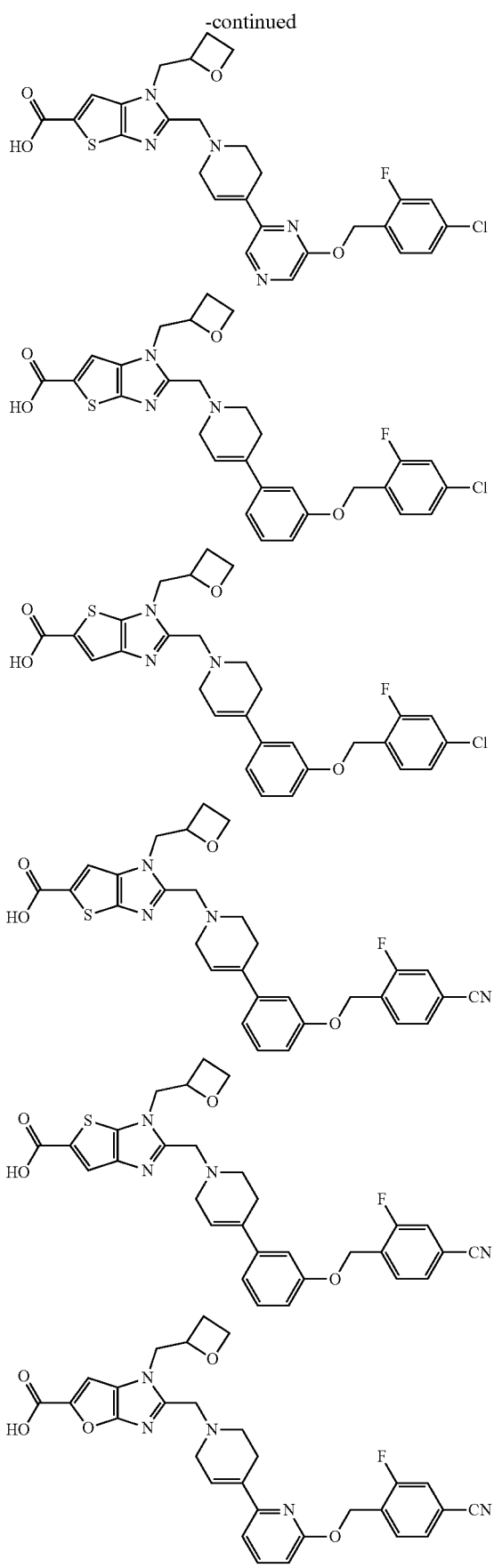
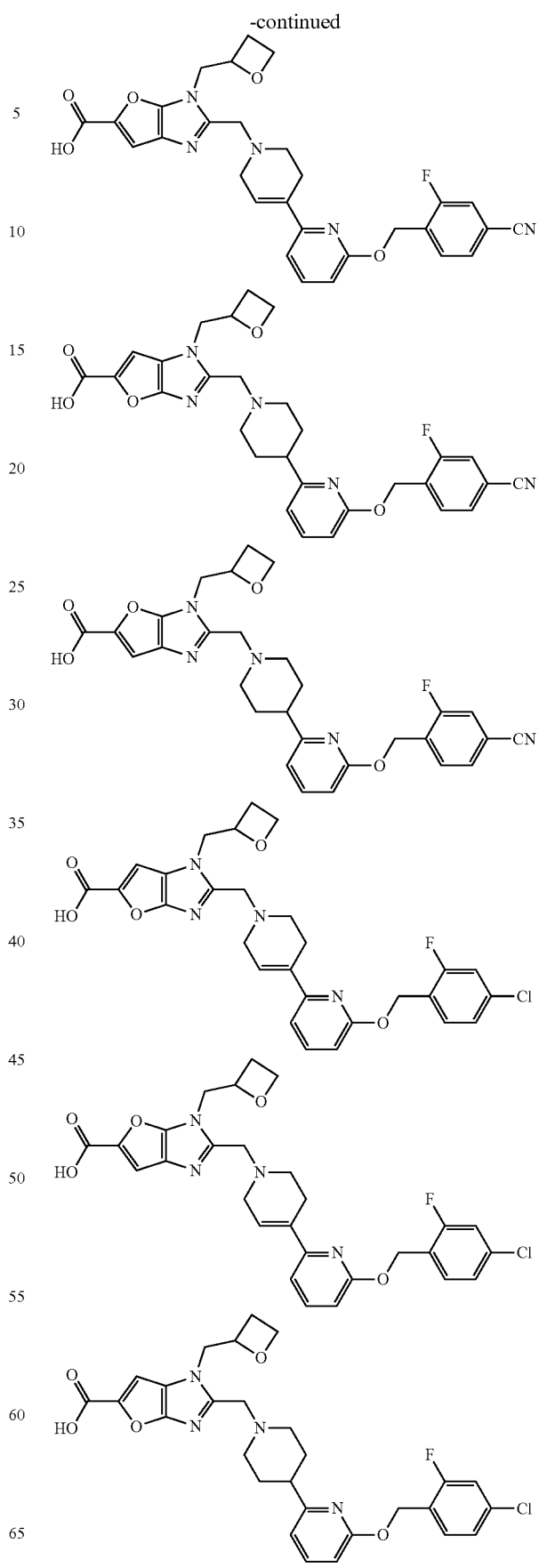

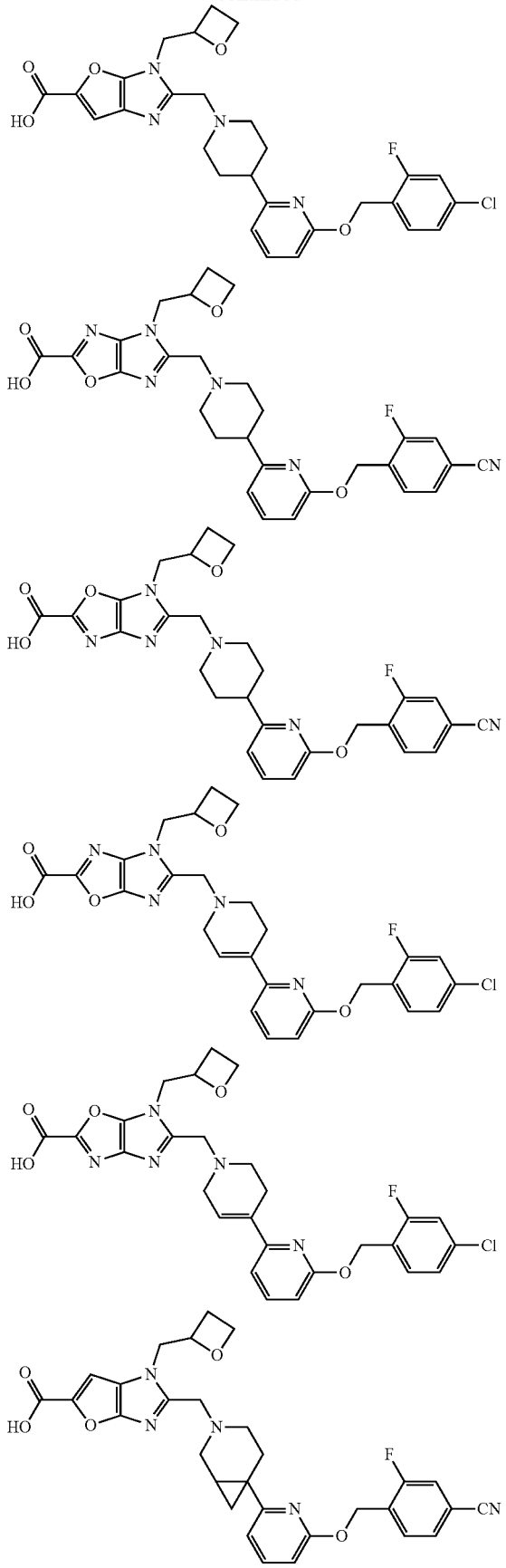
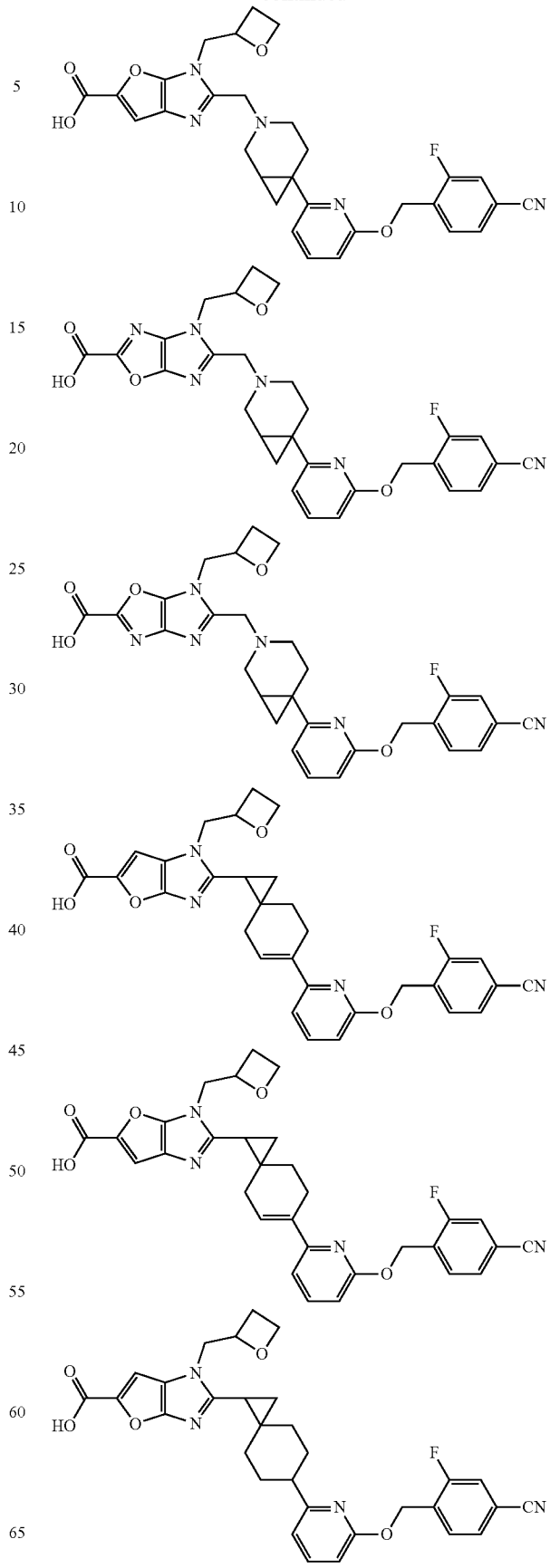

-continued
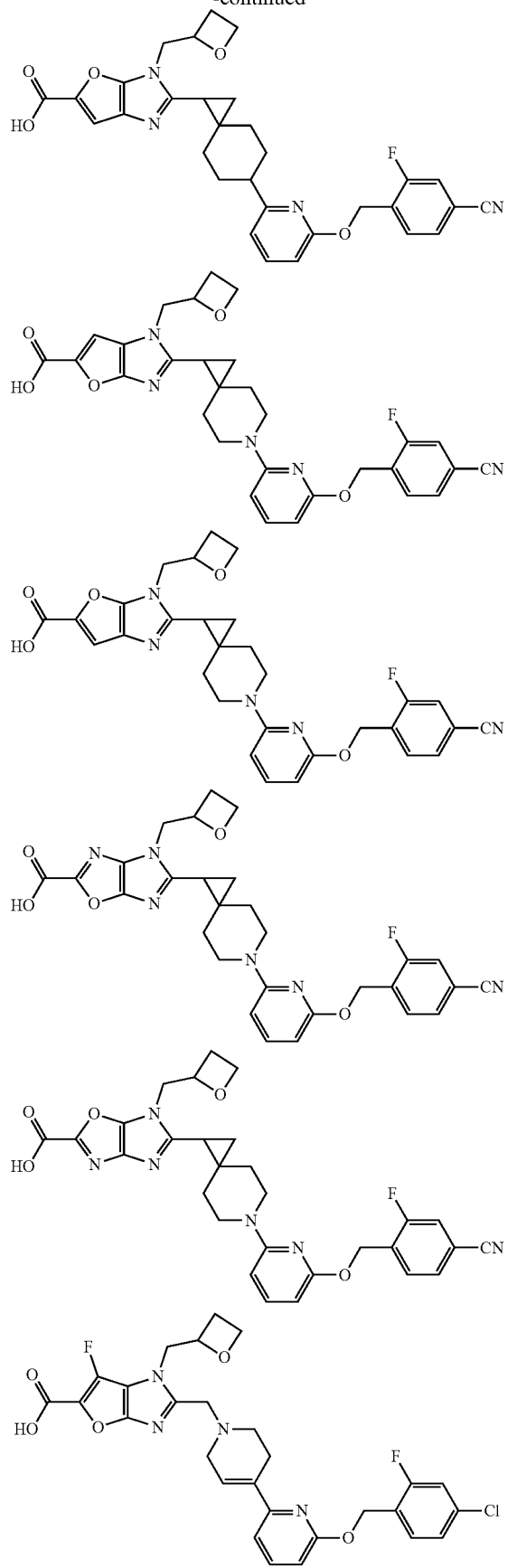
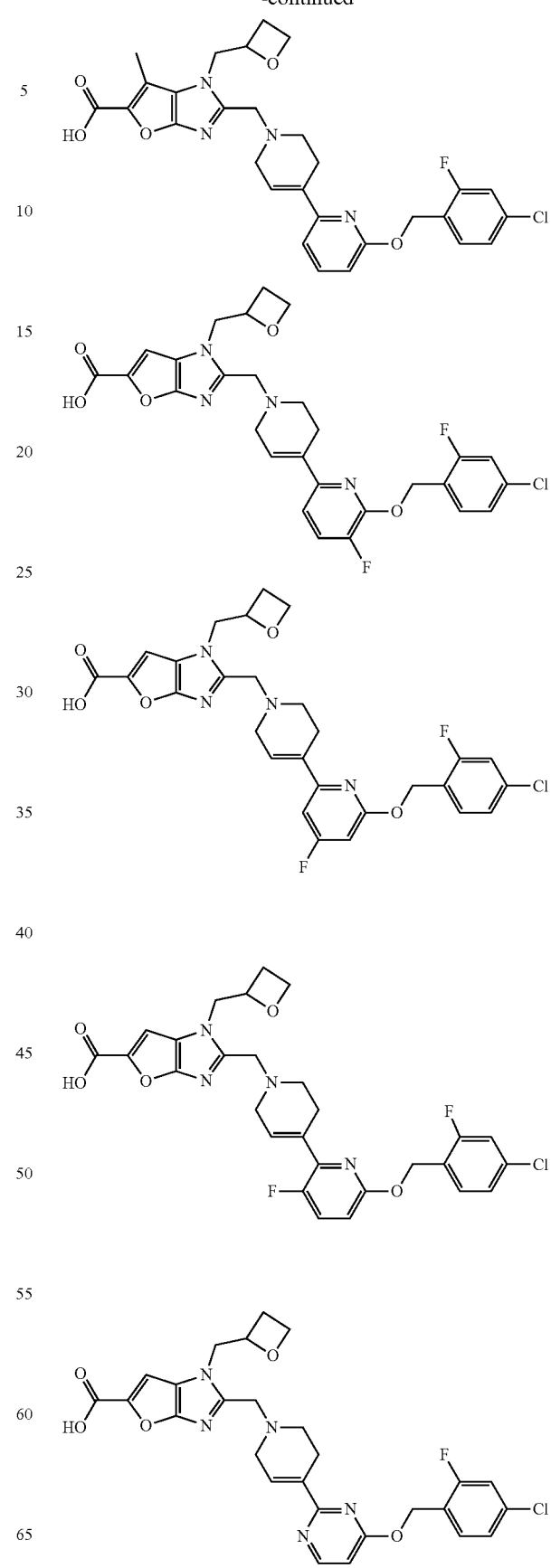

-continued
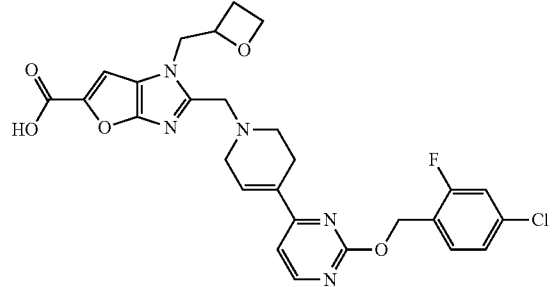
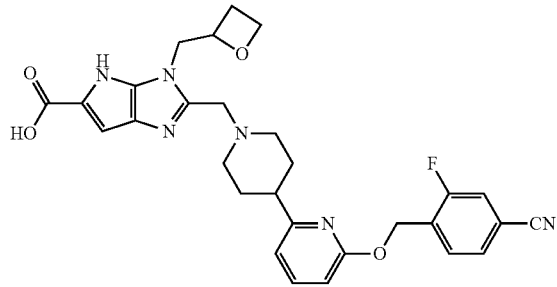
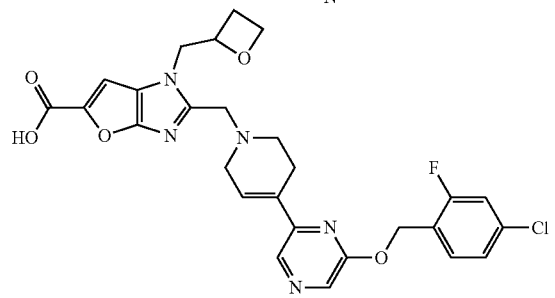
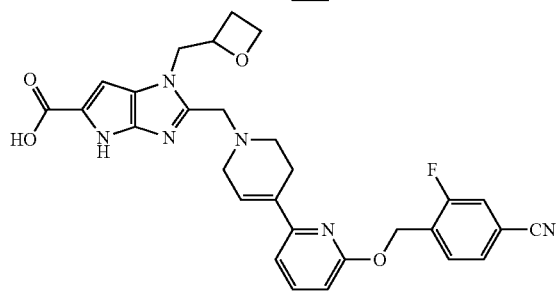
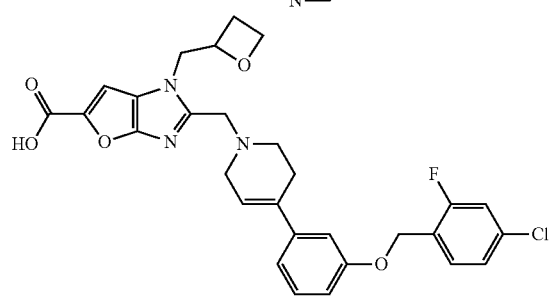
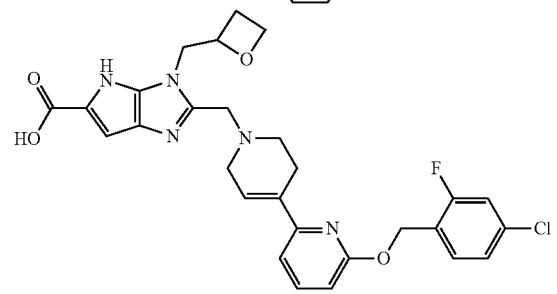
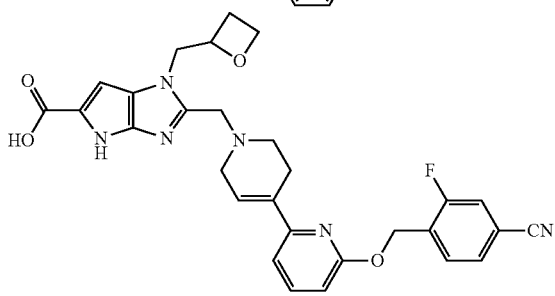
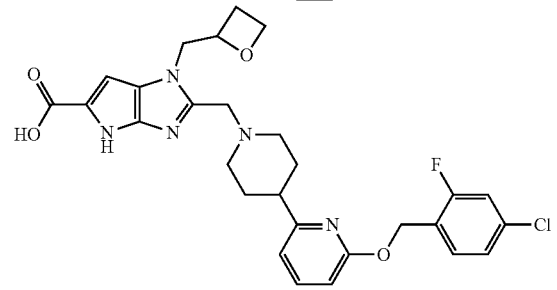
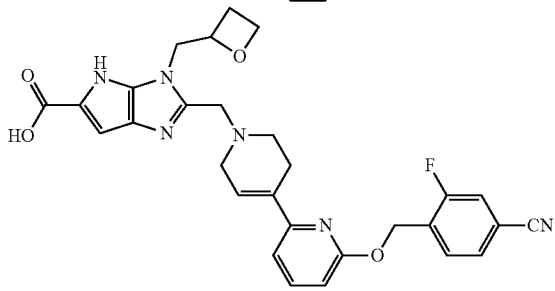
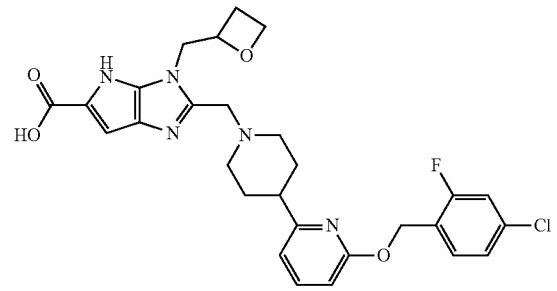
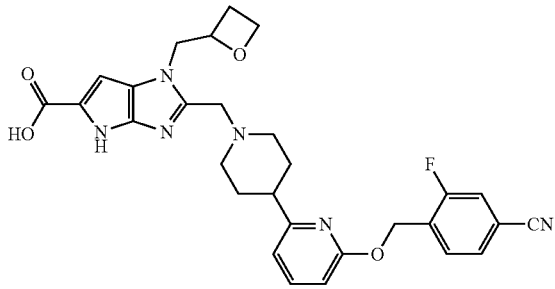
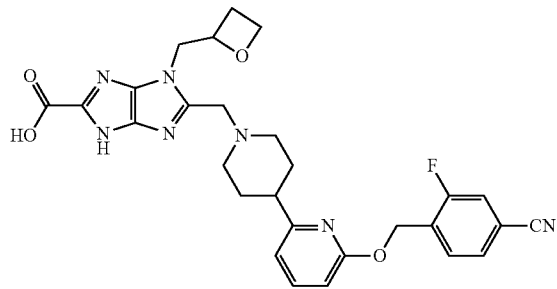

-continued
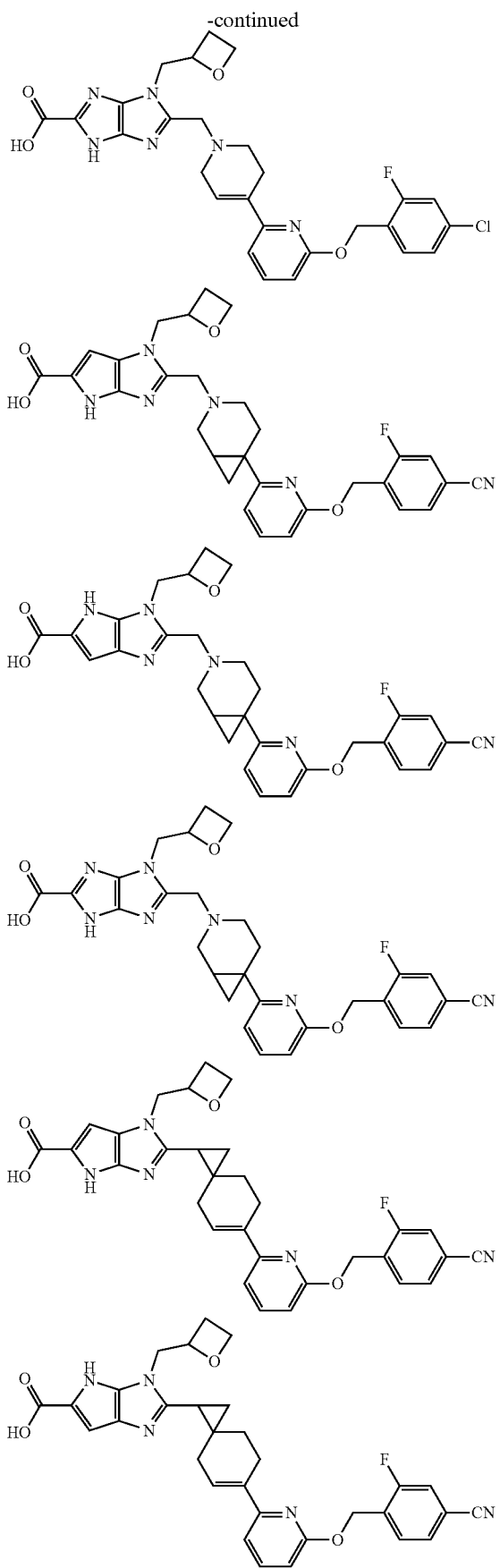
-continued
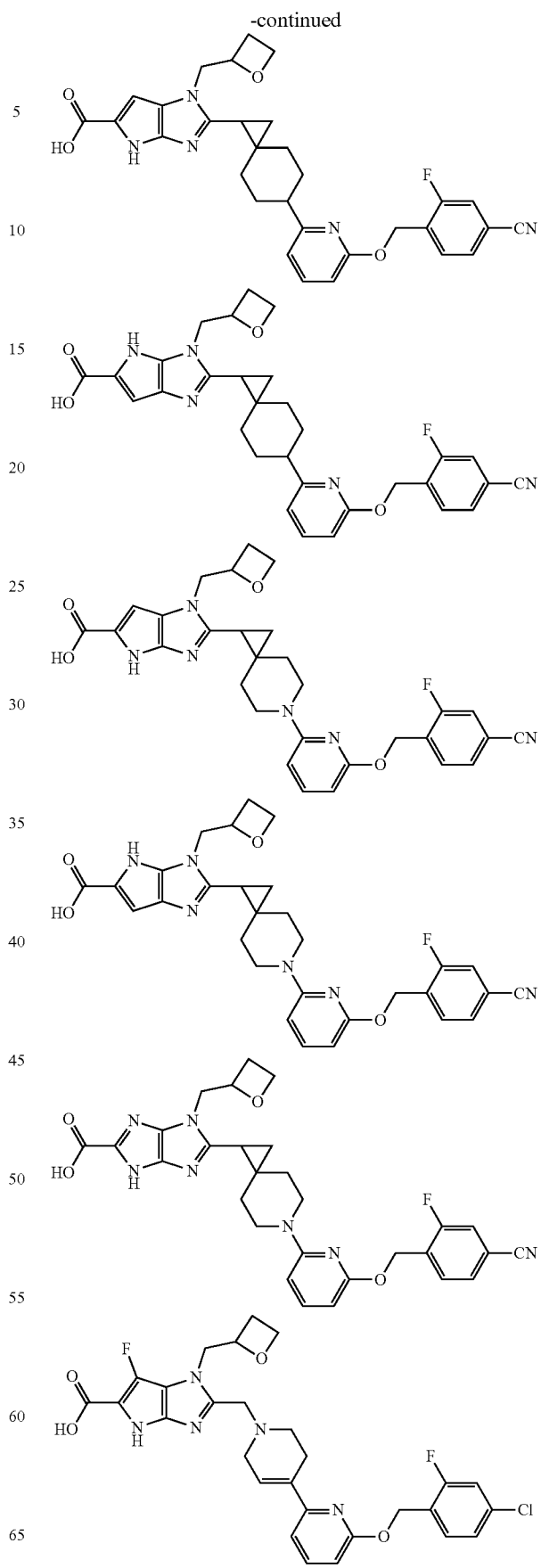

31
-continued
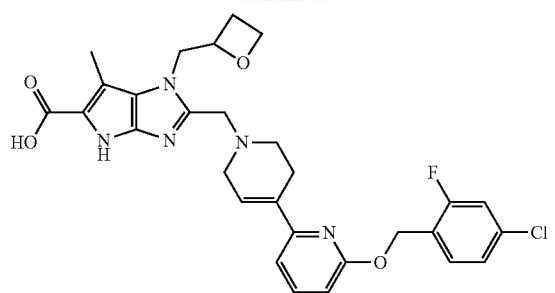
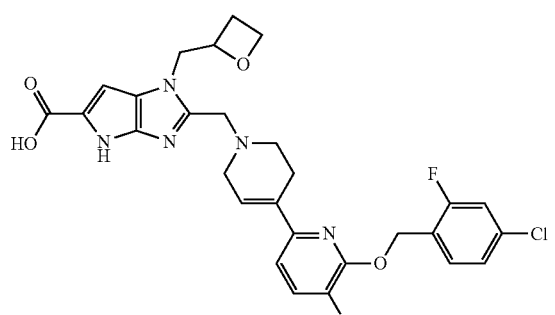
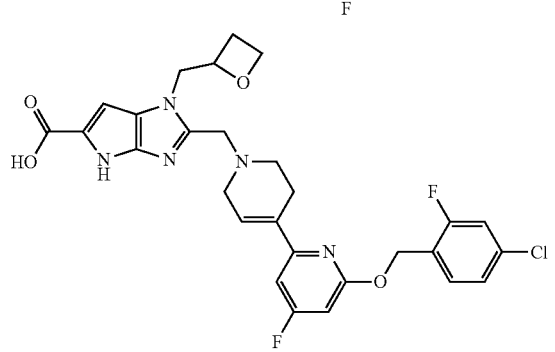
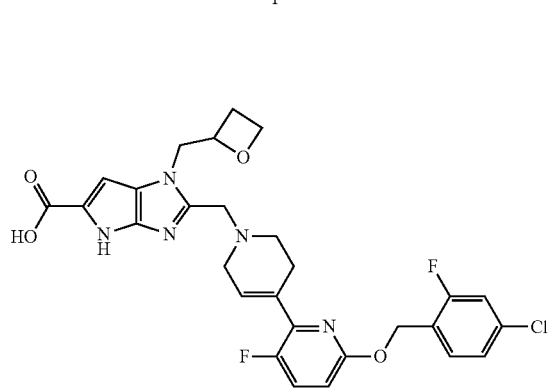
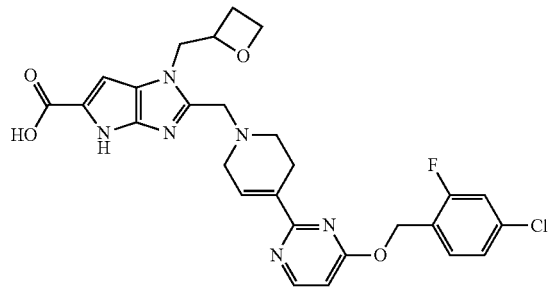
32
-continued
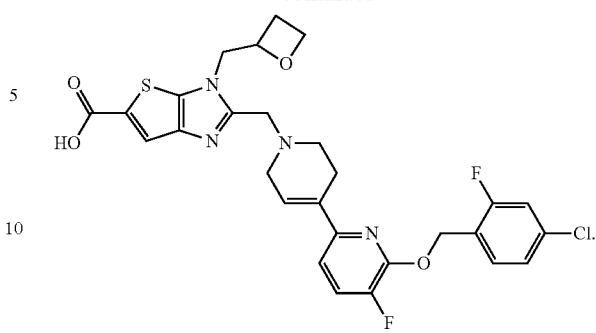
In some embodiments of the present disclosure, the compound or the pharmaceutically acceptable salt thereof is selected from:
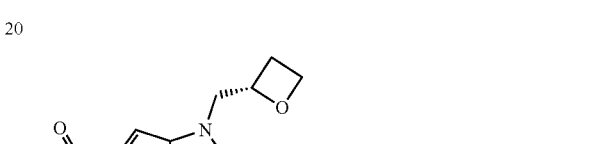
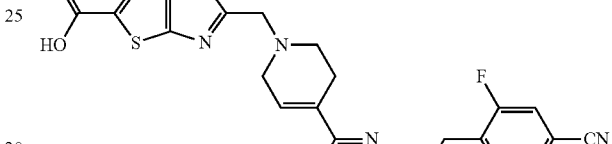
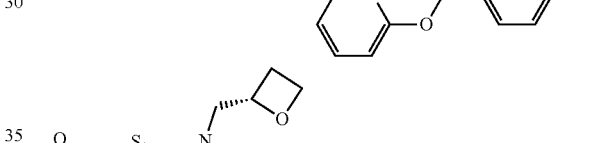
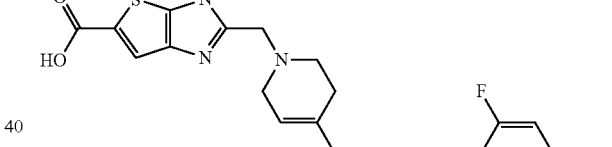
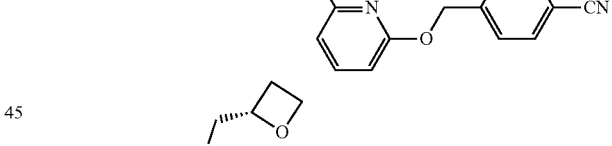

33
-continued
34
-continued
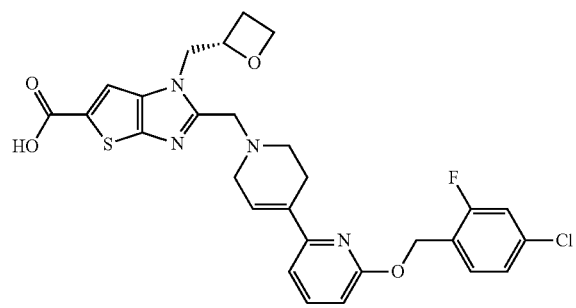
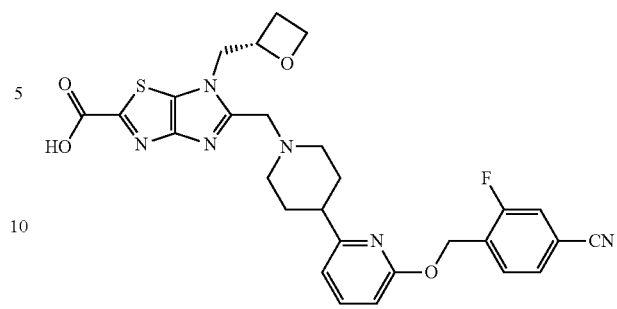
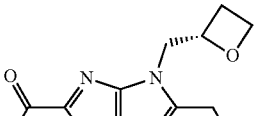

35
-continued
36
-continued
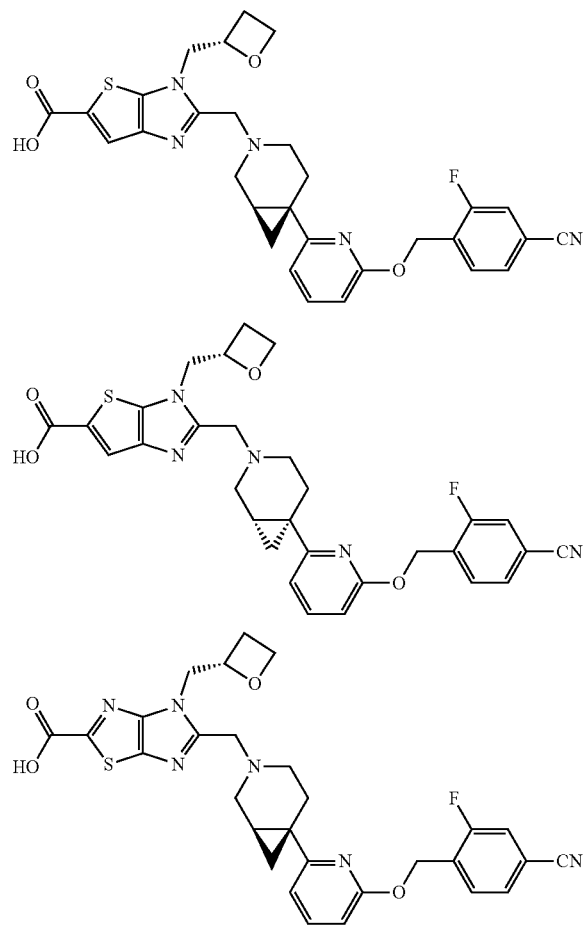
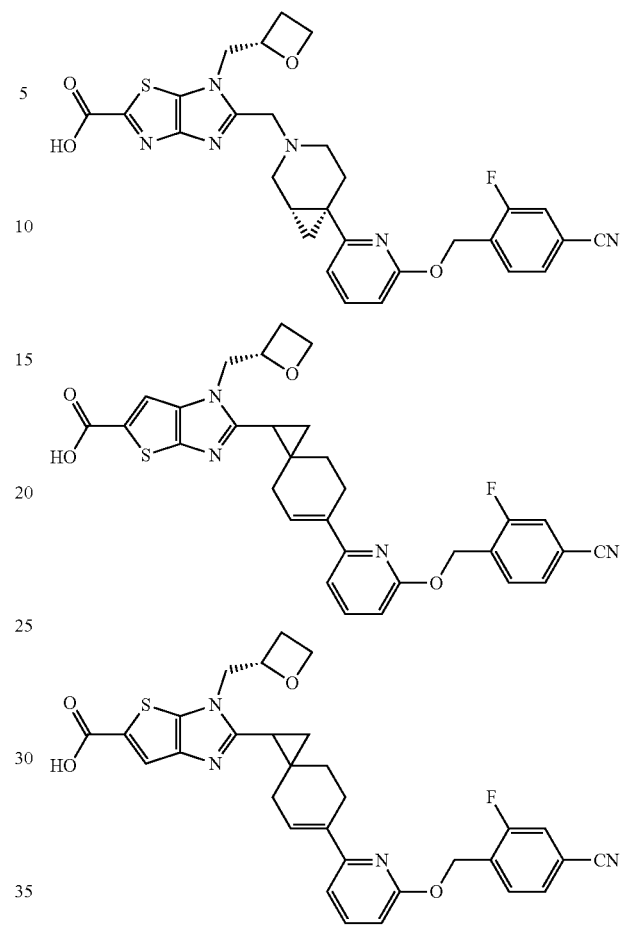
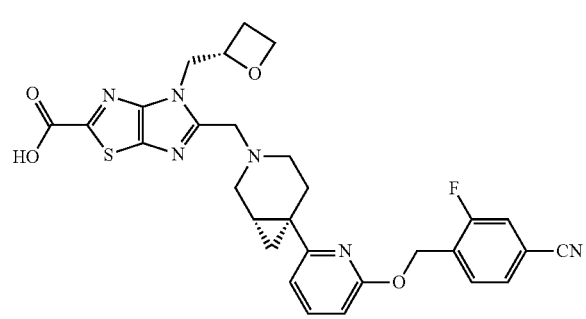
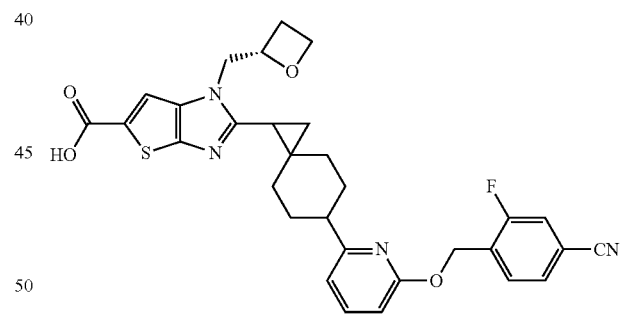
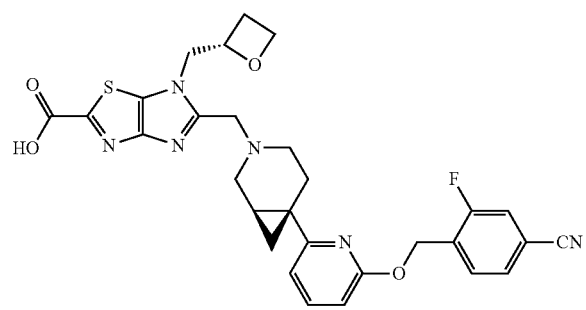
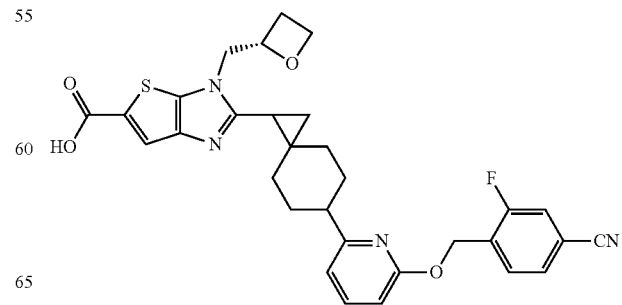

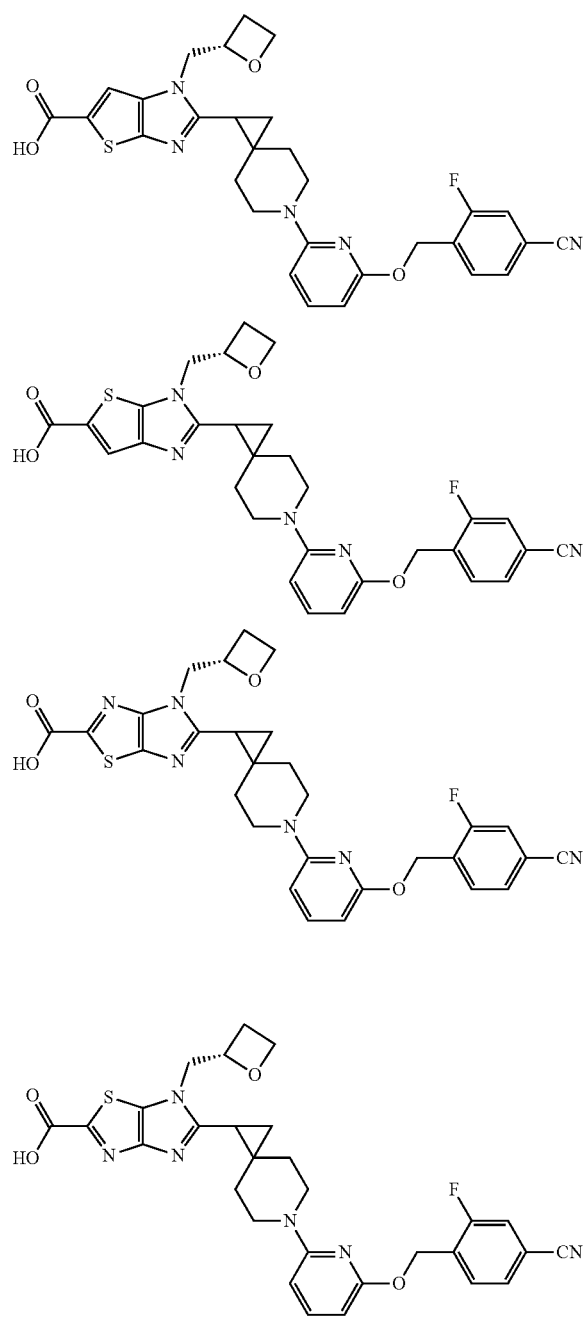
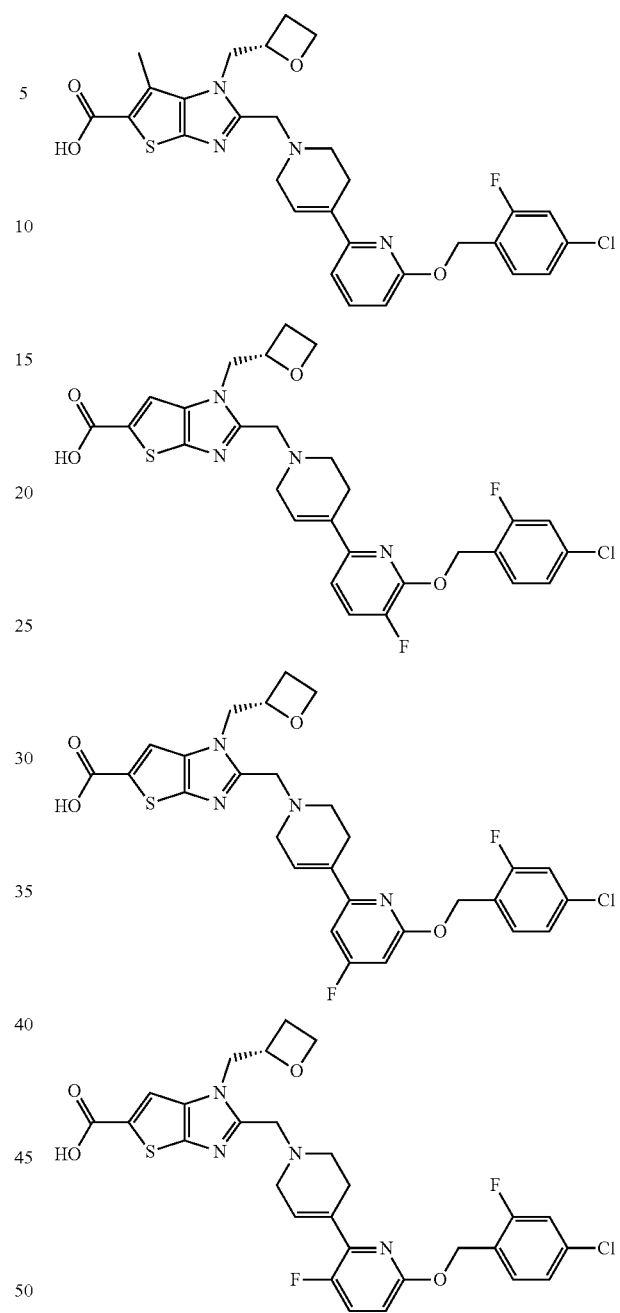
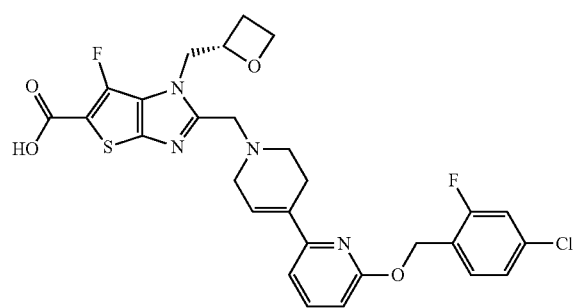
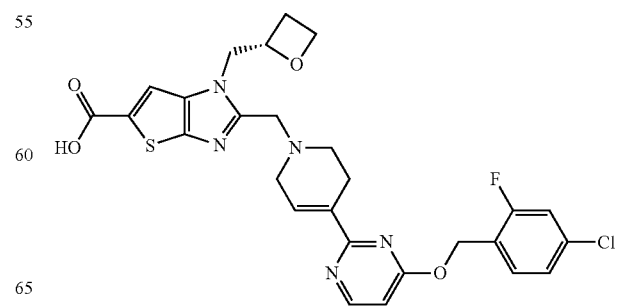

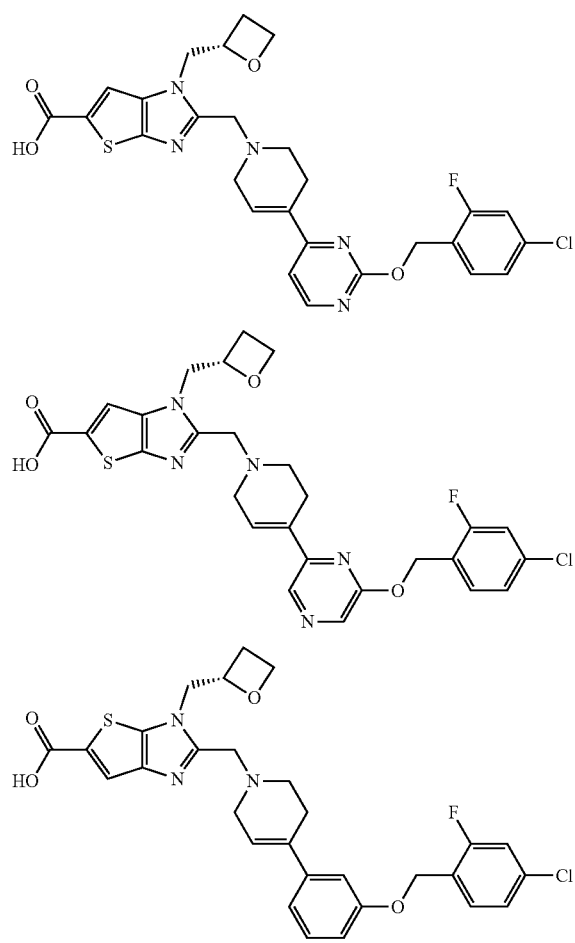
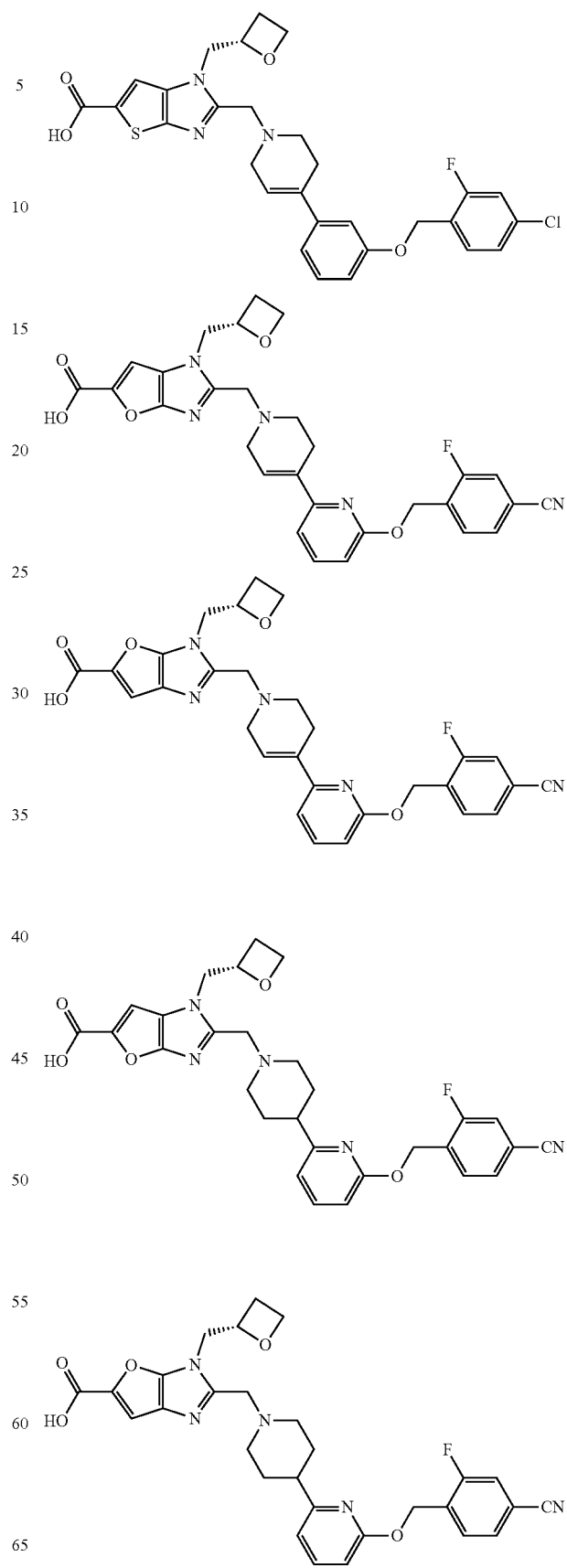

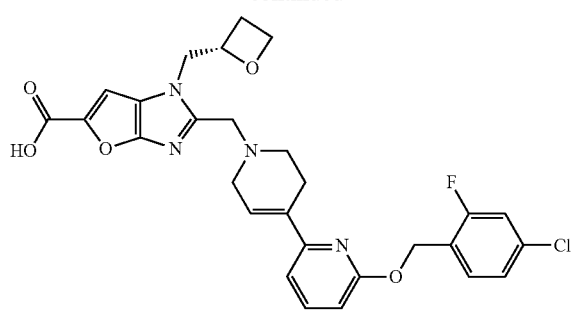
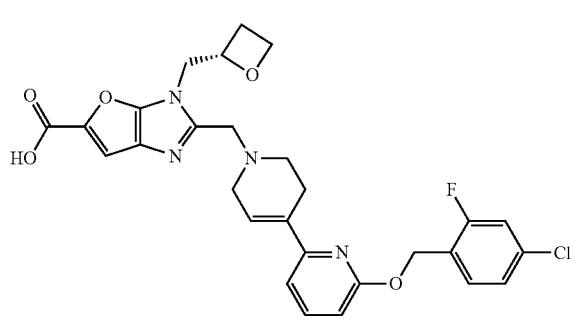
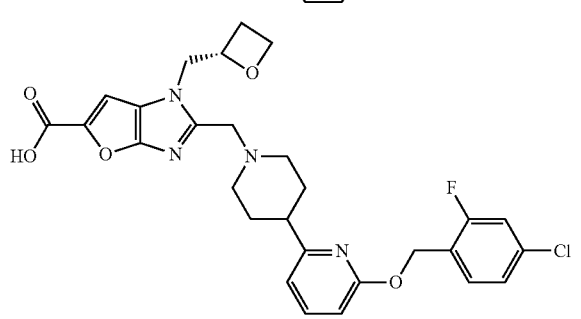
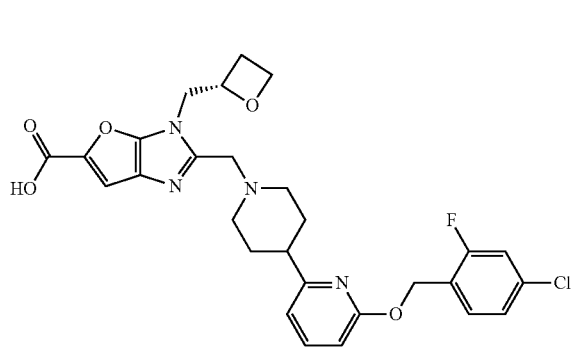
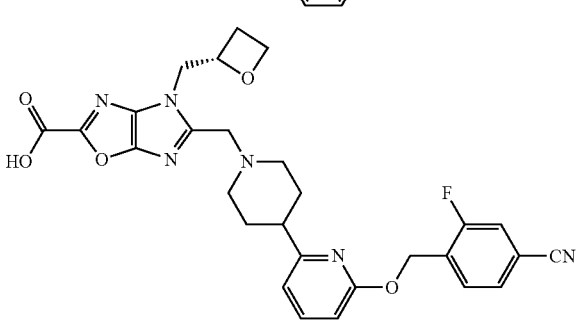
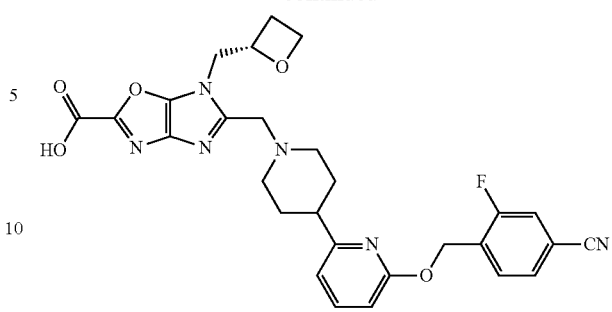

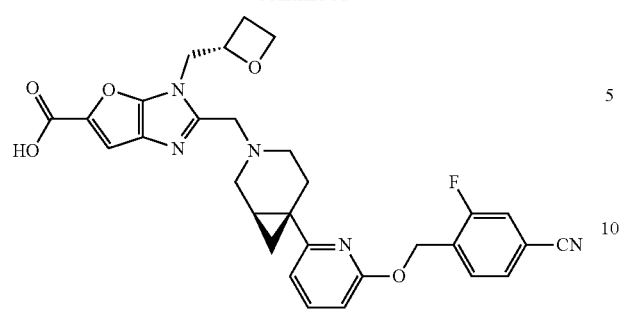
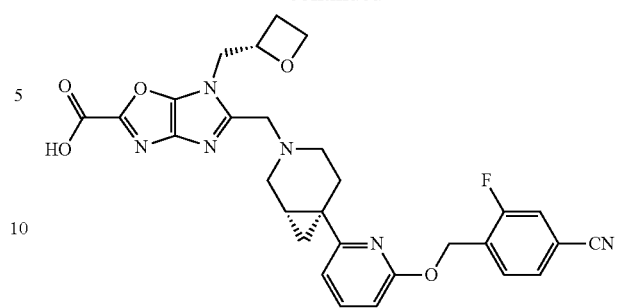
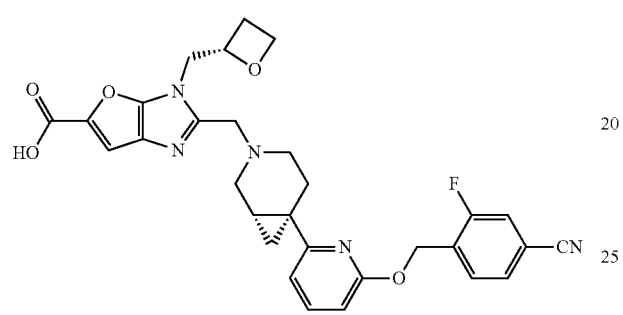
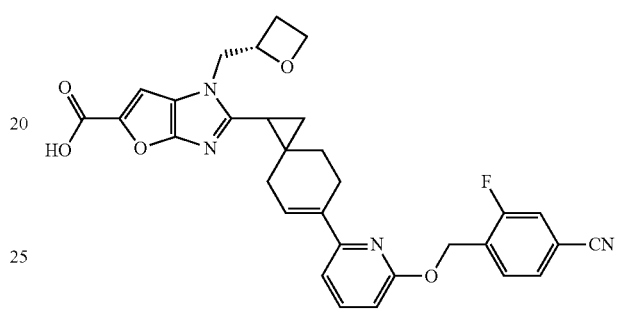
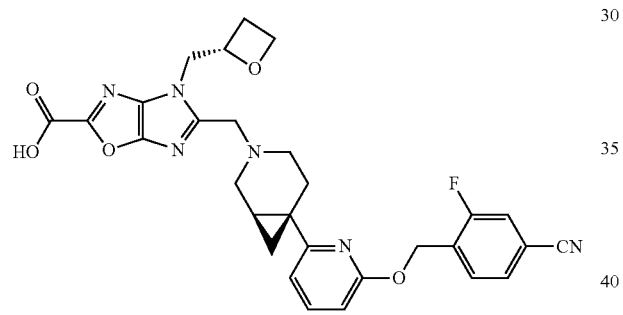
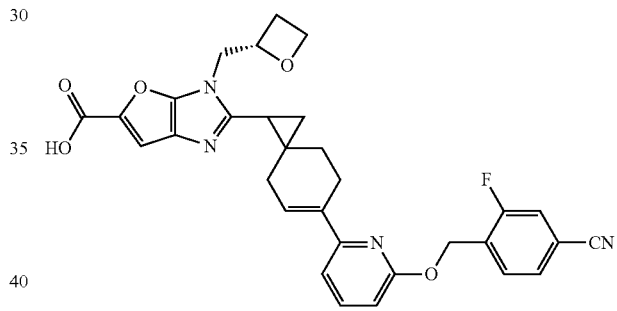
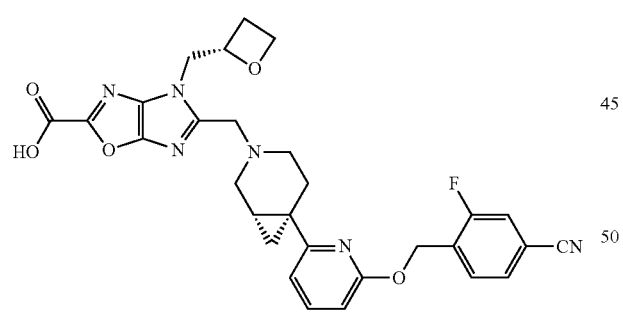
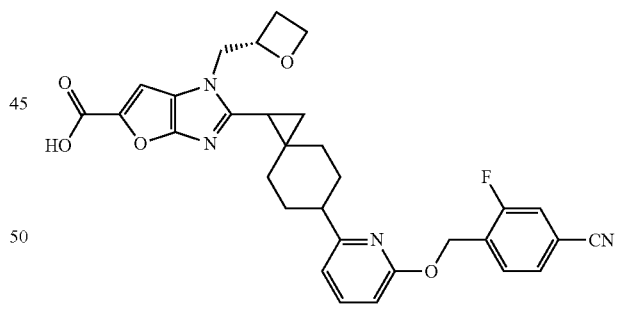
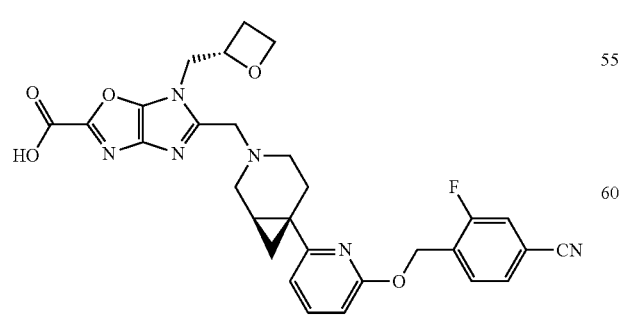
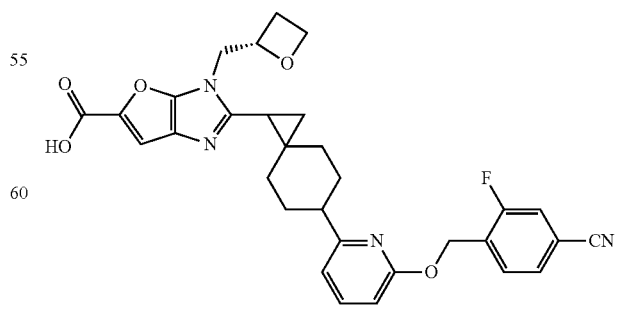

45
-continued
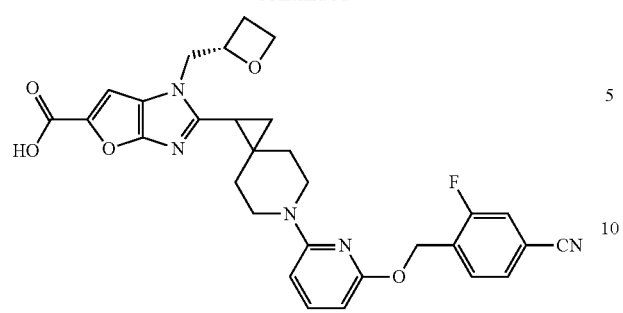
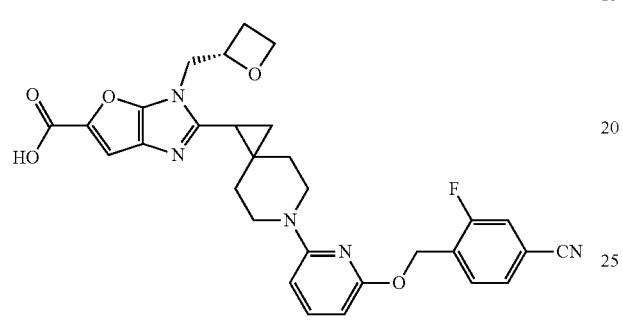
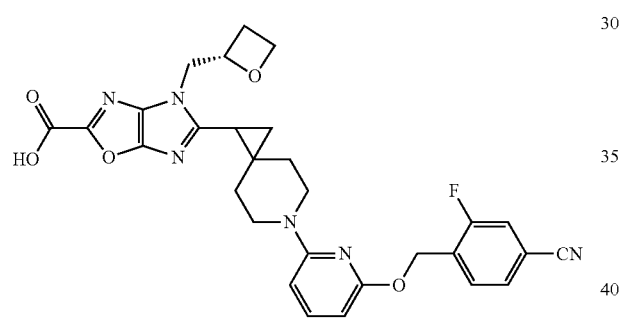
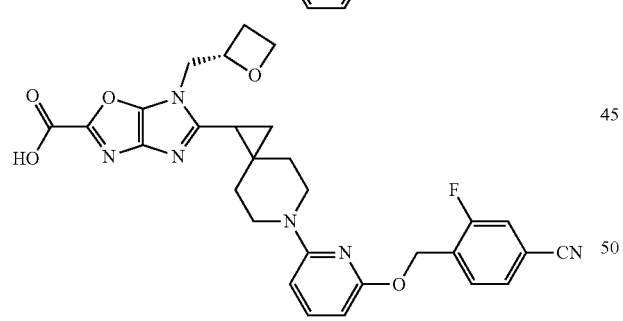
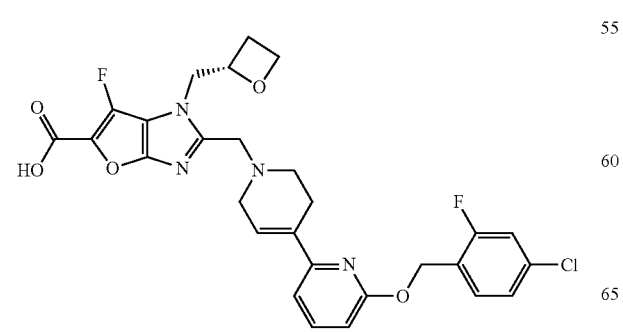
46
-continued
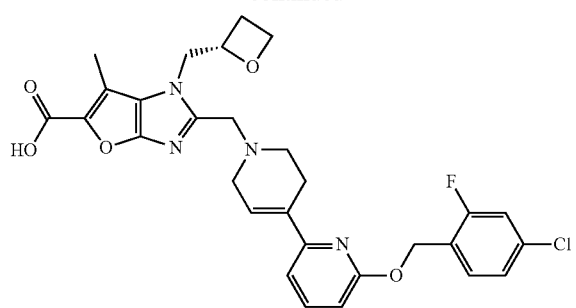
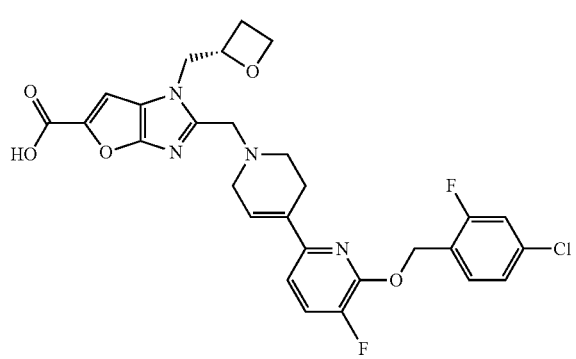
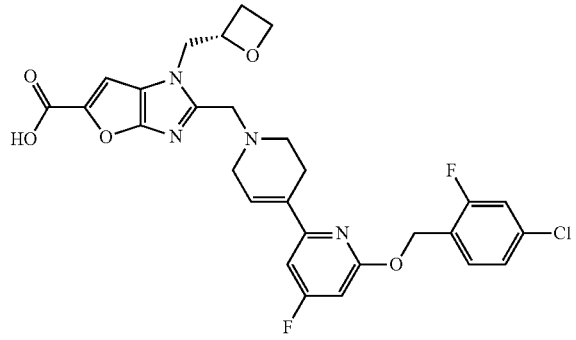
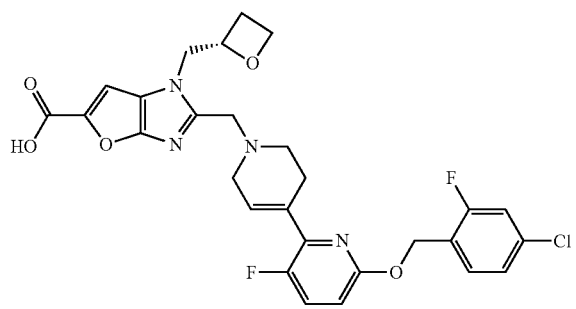
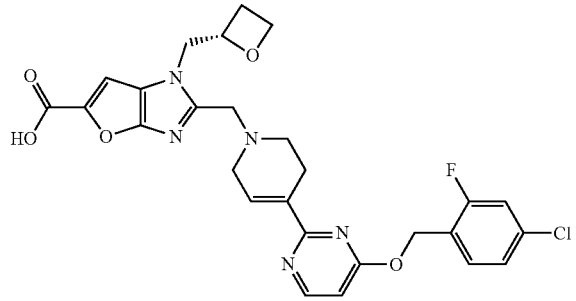

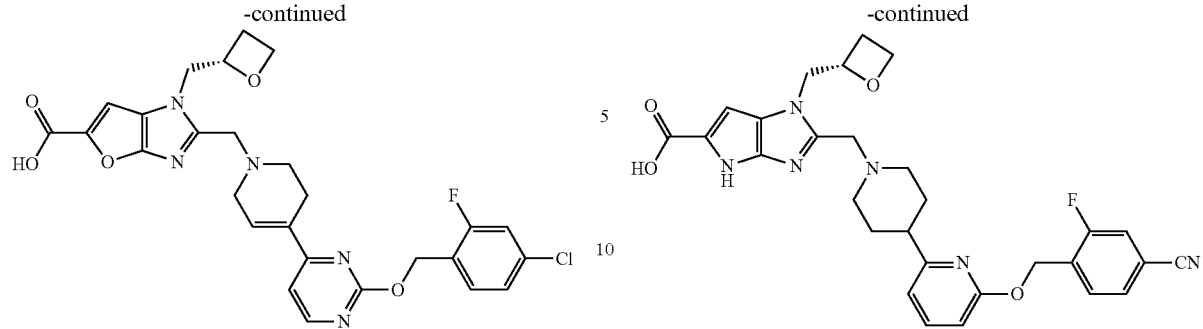
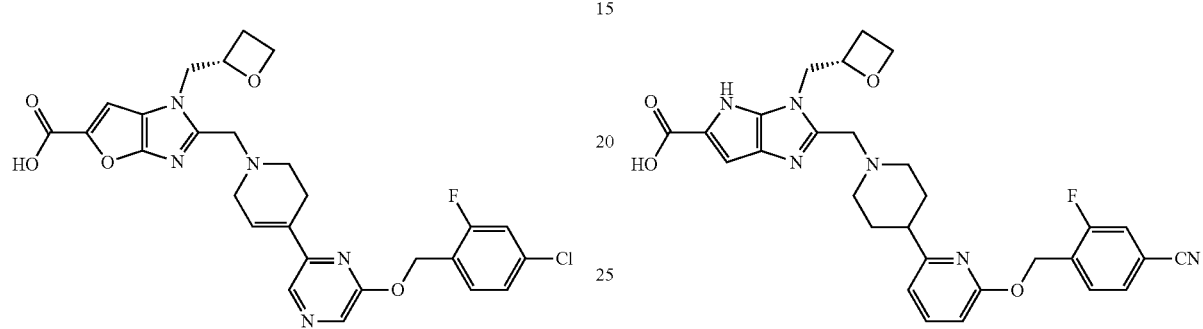
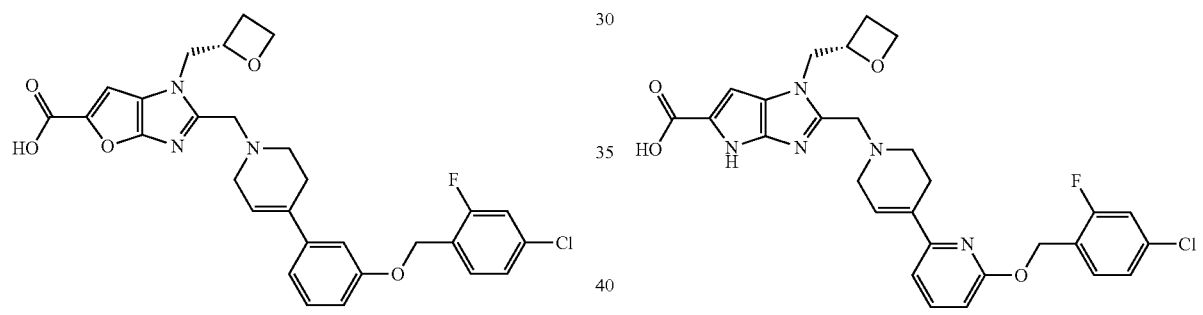
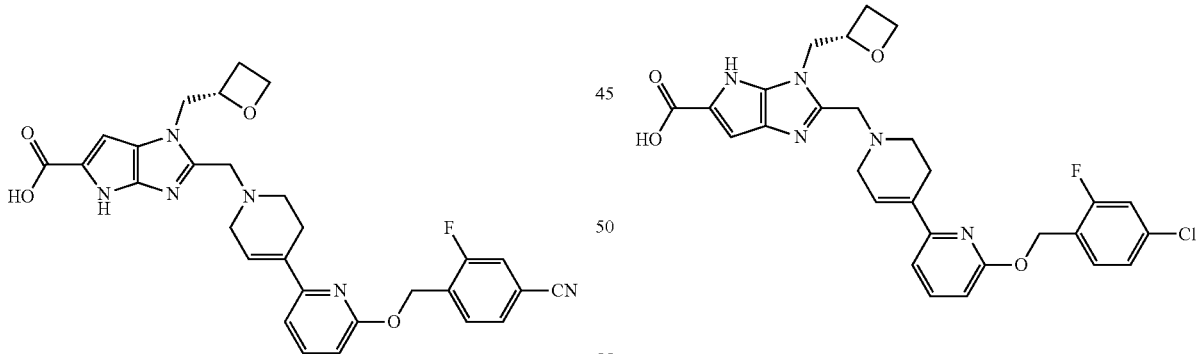
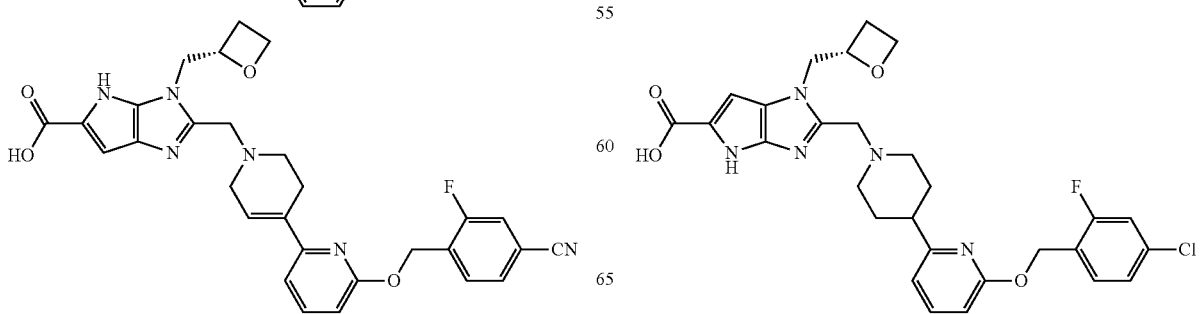

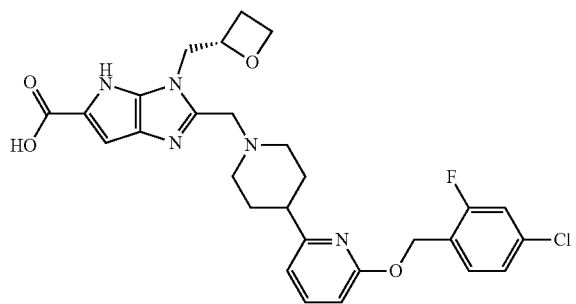
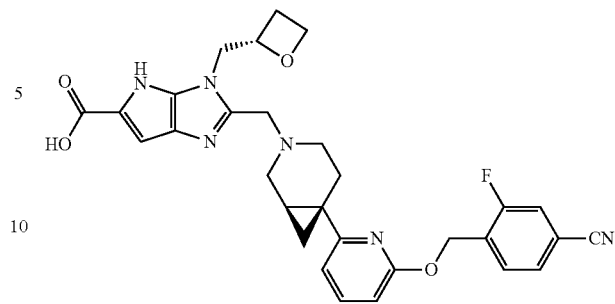
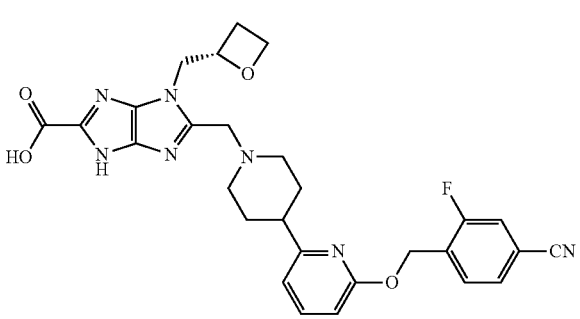
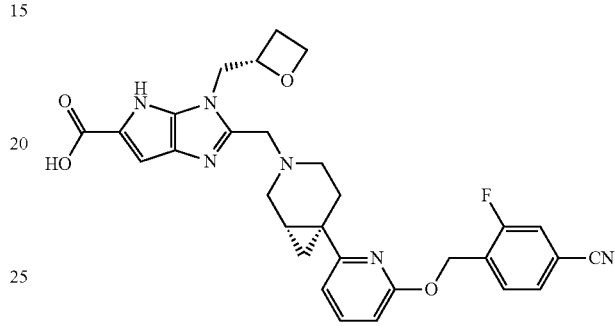
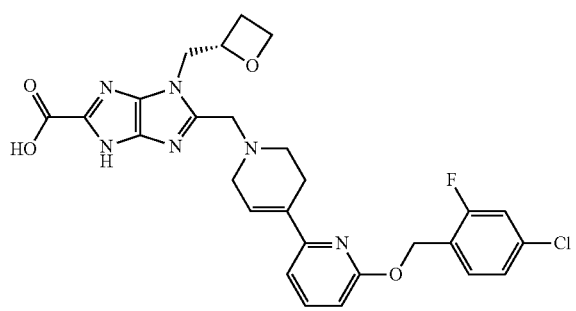
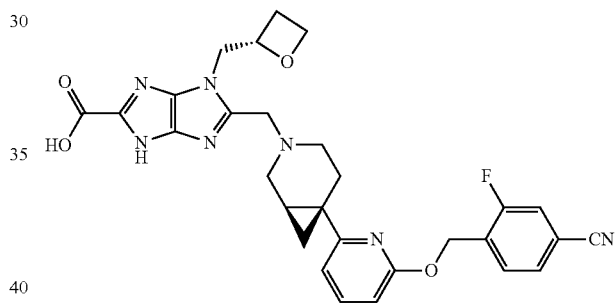
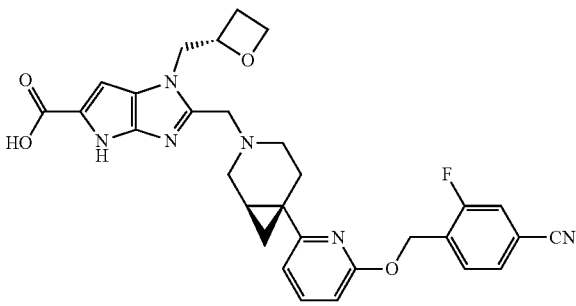
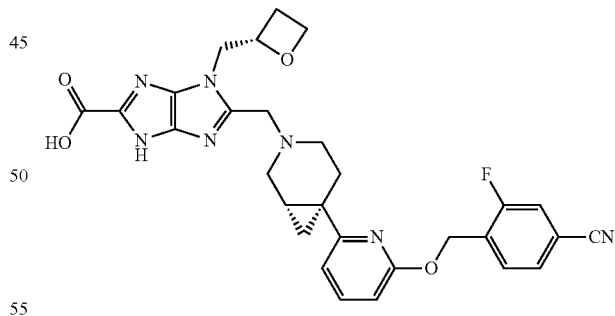
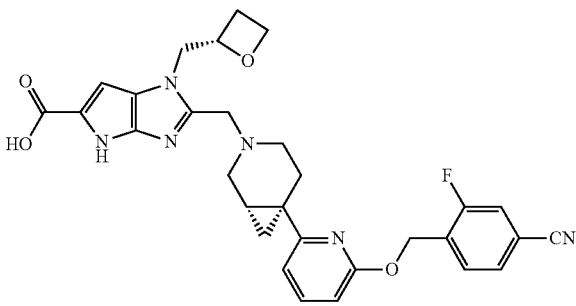
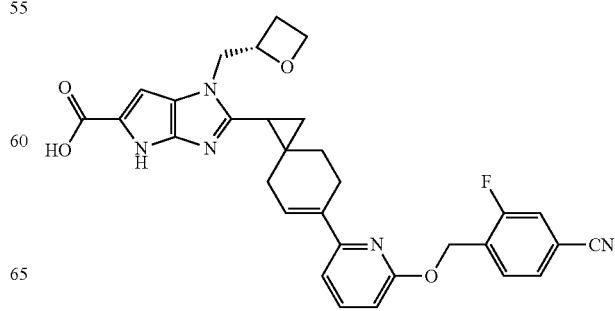

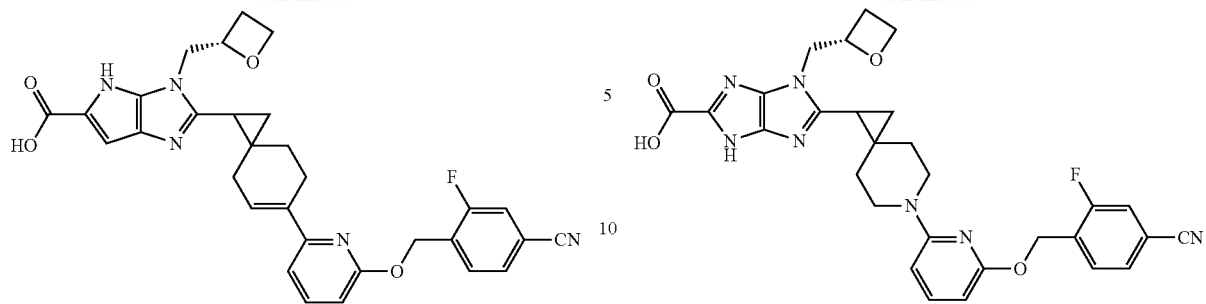
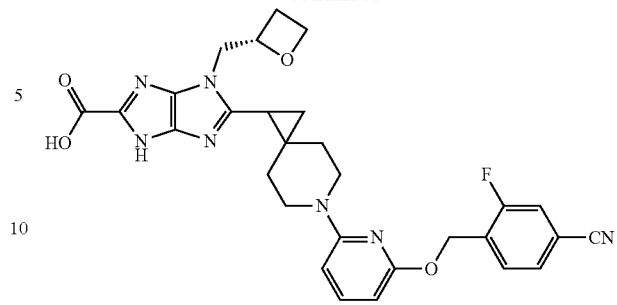
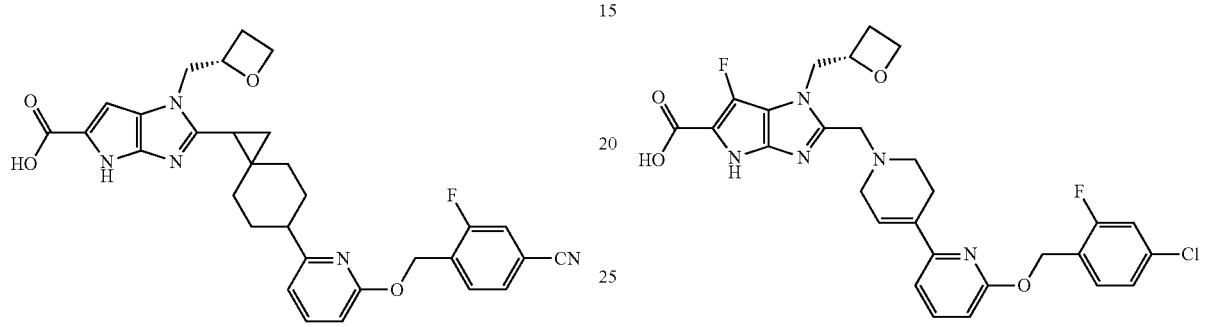
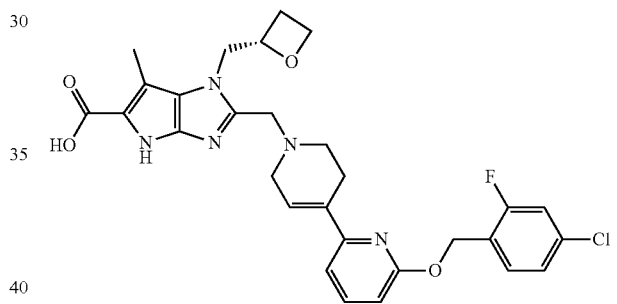
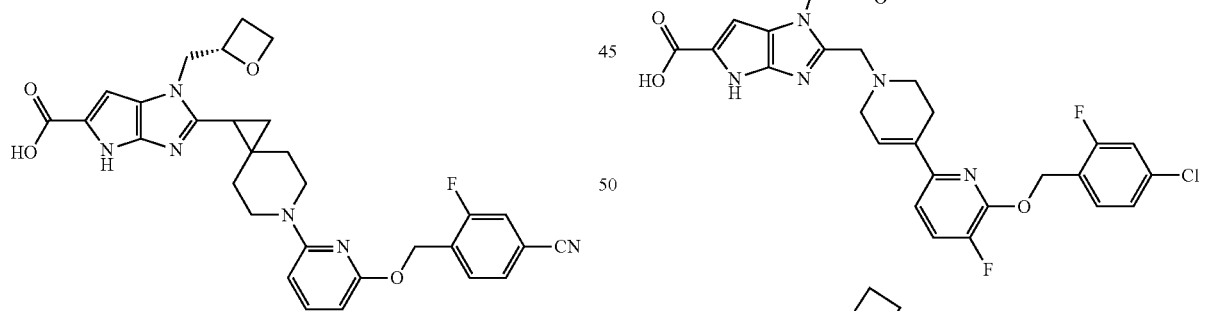
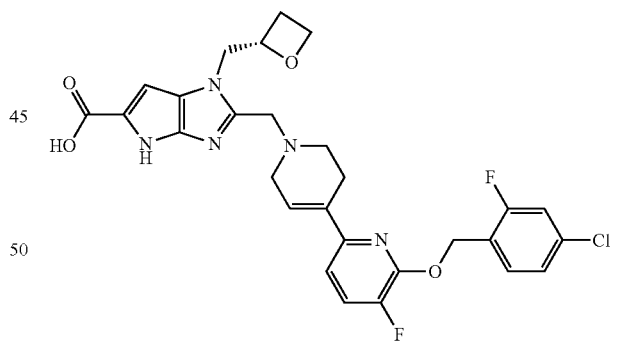
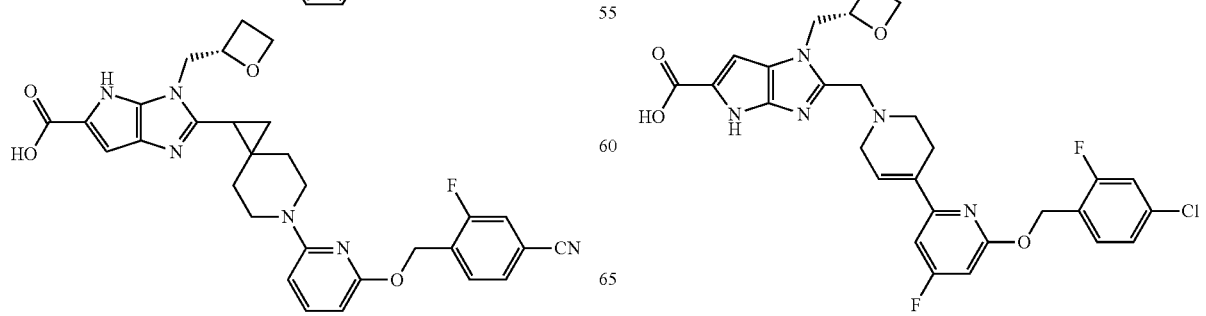
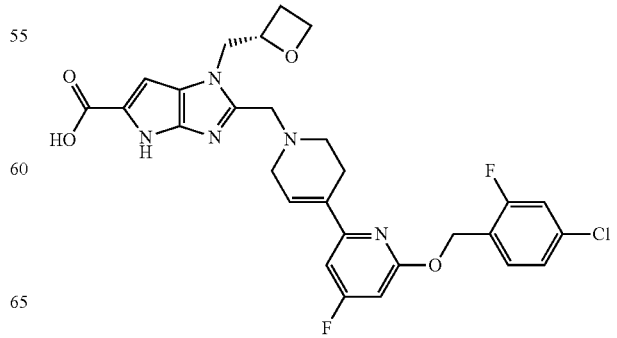

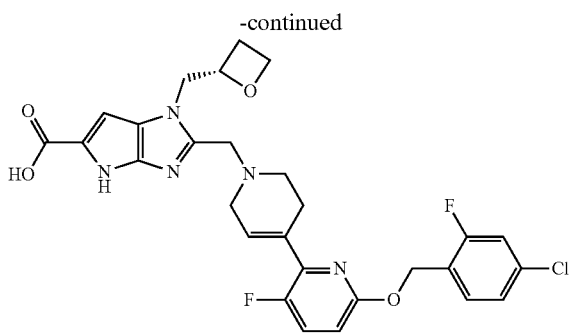

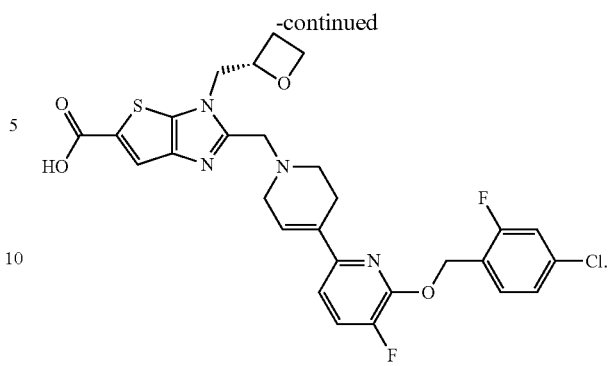

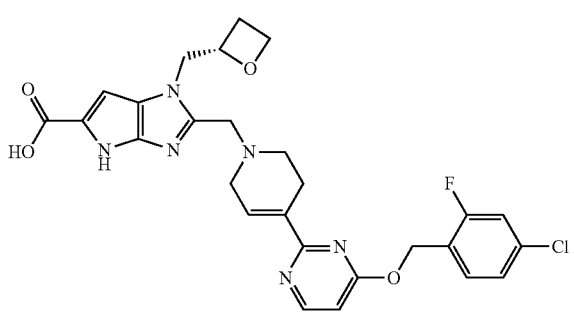

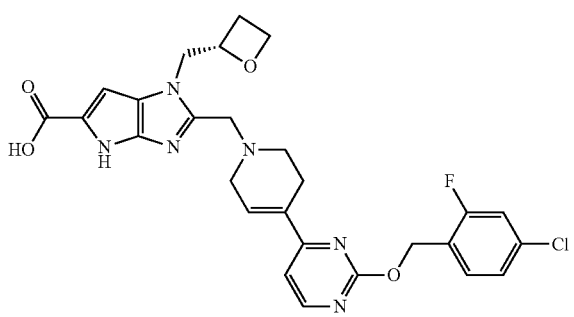

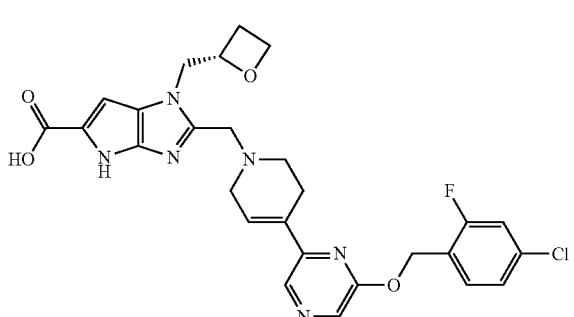

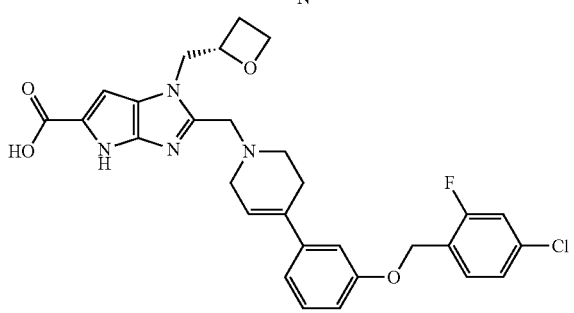

In some embodiments of the present disclosure, a use of the compound or the pharmaceutically acceptable salt thereof in the preparation of a medicament for the treatment of diseases related to small molecule GLP-1 receptor agonists.

In some embodiments of the present disclosure, in the use, wherein, the medicament for the treatment of diseases related to small molecule GLP-1 receptor agonists is a medicament for the treatment of type II diabetes.

Technical Effect

The compound of the present disclosure exhibits a superior agonistic ability to GLP-1 receptor; the compound of the present disclosure exhibits a higher oral exposure, a larger distribution volume and better oral bioavailability, exhibits the advantages of good pharmacokinetic properties of oral drugs; the compound of the present disclosure has a weak inhibitory effect on the hERG potassium channel current, lower risk of cardiotoxicity, and higher safety; the compound of the present disclosure has better permeability.

DETAILED DESCRIPTION OF THE INVENTION

Definition and Description

Unless otherwise specified, the following terms and phrases when used herein have the following meanings. A specific term or phrase should not be considered indefinite or unclear in the absence of a particular definition, but should be understood in the ordinary sense. When a trading name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

Unless otherwise specified, the term "isomer" is intended to include geometric isomers, cis-trans isomers, stereoisomers, enantiomers, optical isomers, diastereomers and tautomers.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and or "(±)" refers to racemic.

Unless otherwise specified, the absolute configuration of a stereogenic center is represented by a wedged solid bond ( ) and a wedged dashed bond ( ) and the relative configuration of a stereogenic center is represented by a straight solid bond ( ) and a straight dashed bond ( ) a wave line ( ) is used to represent a wedged solid bond ( ) or a wedged dashed bond ( ), or the wave line ( ) is used to represent a straight solid bond ( ) or a straight dashed bond ( ).

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to obtain the pure enantiomer. In addition, the enantiomer and the diastereoisomer are generally isolated through chromatography which uses a chiral stationary phase and optionally combines with a chemical derivative method (such as carbamate generated from amine).

The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs and the like. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone.

The term "optionally substituted" means an atom can be substituted with a substituent or not, unless otherwise specified, the type and number of the substituent may be arbitrary as long as is chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When the number of substituent is 0, it means that the substituent does not exist, for example, -A-(R)$_0$ means that its structure is actually A.

When a substituent is vacant, it means that the substituent does not exist, for example, when X is vacant in A-X, the structure of A-X is actually A.

When one of the variables is selected from a single bond, it means that the two groups linked by the single bond are connected directly. For example, when L in A-L-Z represents a single bond, the structure of A-L-Z is actually A-Z.

When the bond of a substituent can be cross-connected to two or more atoms on a ring, the substituent can be bonded to any atom on the ring, for example, the structural moiety

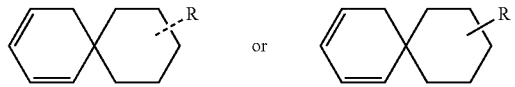

means that the substitution can take place with the substituent R at any position on cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

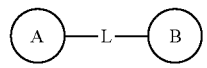

is -M-W—, then -M-W— can link ring A and ring B to form

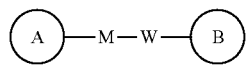

in the direction same as left-to-right reading order, and form

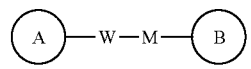

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of the chemical bond linking thereto so as to meet the corresponding valence. The chemical bond between the site and other groups can be represented by a straight solid bond (╱), a straight dashed bond (╱) or a wavy line (∿). For example, the straight solid bond in —OCH$_3$ means that it is linked to other groups through the oxygen atom in the group; the straight dashed bonds in

means that it is linked to other groups through the two ends of nitrogen atom in the group; the wave lines in

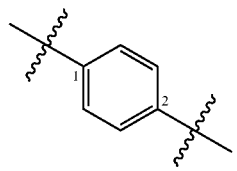 [SMILES: *c1ccc(*)cc1]

means that the phenyl group is linked to other groups through carbon atoms at position 1 and position 2;

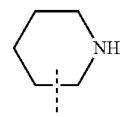

means that it can be linked to other groups through any linkable sites on the piperidinyl by one chemical bond, including at least four types of linkage, including

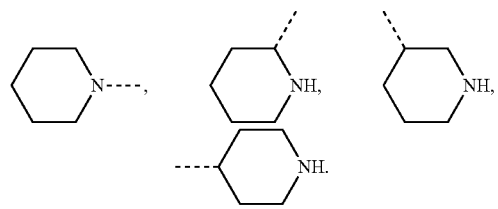

Even though the H atom is drawn on the —N—,

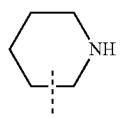

still includes the linkage of

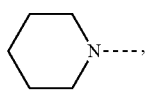

merely when one chemical bond was connected, the H of this site will be reduced by one to the corresponding monovalent piperidinyl.

Unless otherwise specified, the number of atoms in a ring is usually defined as the number of ring members, for example, "5-7 membered ring" refers to a "ring" in which 5-7 atoms are arranged around.

Unless otherwise specified, the term "$C_{1-3}$ alkyl" refers to a linear or branched saturated hydrocarbon group composing of 1 to 3 carbon atoms. The $C_{1-3}$ alkyl includes $C_{1-2}$ and $C_{2-3}$ alkyl and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl) and the like.

Unless otherwise specified, the term "$C_{1-3}$ alkoxy" refers to an alkyl composing of 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy and the like. Examples of $C_{1-3}$ alkoxy include, but are not limited to, methoxy, ethoxy, propoxy (including n-propoxy and isopropoxy) and the like.

Unless otherwise specified, the term "$C_{1-3}$ alkylamino" refers to an alkyl composing of 1 to 3 carbon atoms that are connected to the rest of the molecule through an amino. The $C_{1-3}$ alkylamino includes $C_{1-2}$, $C_3$ and $C_2$ alkylamino and the like. Examples of $C_{1-3}$ alkylamino include, but are not limited to, —NHCH$_3$, —N(CH$_3$)$_2$, —NHCH$_2$CH$_3$, —N(CH$_3$)CH$_2$CH$_3$, —NHCH$_2$CH$_2$CH$_3$, —NHCH$_2$(CH$_3$)$_2$, and the like.

Unless otherwise specified, "$C_{3-5}$ cycloalkyl" refers to a saturated cyclic hydrocarbon group composing of 3 to 5 carbon atoms, which is a monocyclic ring system, and the $C_{3-5}$ cycloalkyl includes $C_{3-4}$ and $C_{4-5}$ cycloalkyl and the like; it can be monovalent, divalent or multivalent. Examples of $C_{3-5}$ cycloalkyl include, but are not limited to, cyclopropyl, cyclobutyl, cyclopentyl and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The solvent used in the present disclosure is commercially available.

The following abbreviations are used in the present disclosure: aq refers to water; eq refers to equivalence or equivalent; DCM refers to dichloromethane; PE refers to petroleum ether; DMF refers to N,N-dimethylformamide; DMSO refers to dimethyl sulfoxide; EtOAc refers to ethyl acetate; EtOH refers to ethanol; MeOH refers to methanol; Cbz refers to benzyloxycarbonyl, which is an amine protecting group; BOC refers to tert-butoxycarbonyl which is an amine protecting group; HOAc refers to acetic acid; r.t. refers to room temperature; O/N refers to overnight; THF refers to tetrahydrofuran; Boc$_2$O refers to di-tert-butyl dicarbonate; TFA refers to trifluoroacetic acid; DIPEA refers to diisopropylethylamine; TEA refers to triethylamine; iPrOH refers to 2-propanol; mp refers to melting point; LDA refers to lithium diisopropylamide; Pd(PPh$_3$)$_4$ refers to tetrakis (triphenylphosphine)palladium; AcOH refers to acetic acid; LiHMDS refers to lithium bistrimethylsilylamide; Pd(dppf) Cl$_2$ refers to [1,1'-bis(diphenylphosphino)ferrocene]dichloropalladium; Pd(dppf)Cl$_2$.CH$_2$Cl$_2$ refers to 1,1'-bis(diphenylphosphino)ferrocene-palladium(II)dichloride dichloromethane complex; LiAlH$_4$ refers to lithium aluminum hydride; Pd(OH)$_2$ refers to palladium hydroxide; TBDPSCl refers to tert-butyldiphenylchlorosilane; TLC refers to thin layer chromatography silica gel plate.

The compounds of the present disclosure are named according to the conventional naming principles in the art or by ChemDraw® software, and the commercially available compounds use the supplier catalog names.

EXAMPLES

The following embodiments further illustrate the present disclosure, but the present disclosure is not limited thereto. The present disclosure has been described in detail herein, and its specific embodiments have also been disclosed, for one skilled in the art, it is obvious to make various modifications and improvements to the embodiments of the present disclosure without departing from the spirit and scope of the present disclosure.

Reference Embodiment 1: Fragment B-1

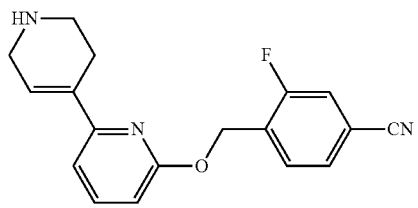

Synthetic Route:

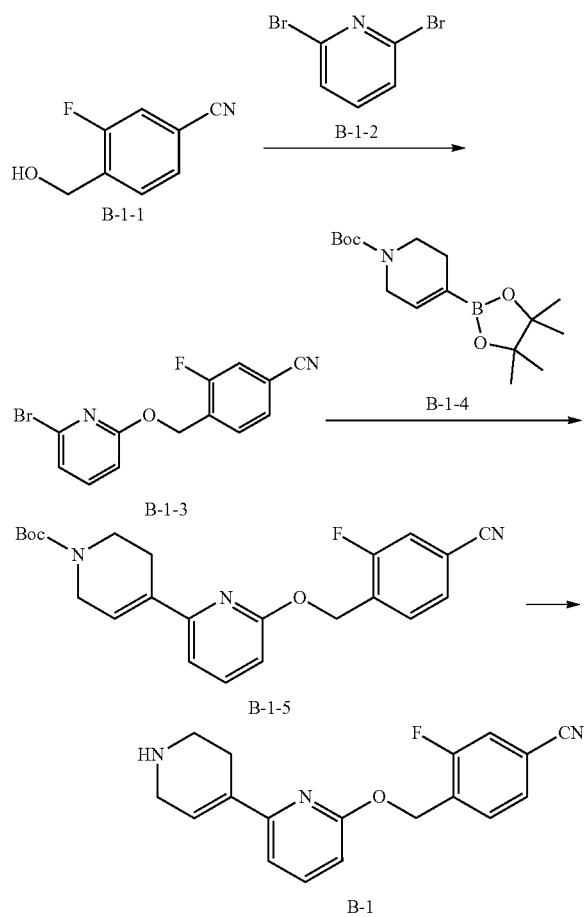

Step 1: Synthesis of Compound B-1-3

B-1-1 (670 mg, 4.43 mmol, 1.05 eq) was placed in a 50 mL egg-shaped flask, the system was pumped and replaced with protective gas for three times, and THF (20 mL) was added to dissolve B-1-1, then the mixture was stirred in an ice water bath, NaH (204 mg, 5.10 mmol, 60% content, 1.21 eq) was added to the system, a large number of bubbles were generated, when the addition was completed, the system was slowly raised to room temperature (15° C.) and stirred for 1 hour, B-1-2 (1 g, 4.22 mmol, 1 eq) was added, then the reaction was carried out at 60° C. for 16 hours. 2 mL of water was added to the system, the mixture was stirred for 5 minutes under open conditions, then transferred to a separatory funnel, ethyl acetate (150 mL) and saturated sodium chloride aqueous solution (70 mL) were added to extract, the phases were separated, and the organic phase was collected, dried over anhydrous sodium sulfate, filtered and evaporated to dryness by rotary evaporation to obtain a crude product. The crude product was purified by column chromatography (PE:EA=1:0-1:1) to obtain B-1-3. LCMS: m/z 306.7[M+H]$^+$; $^1$H NMR (400 MHz, CDCl$_3$) δ ppm 7.68 (t, J=7.53 Hz, 1H), 7.46-7.53 (m, 2H), 7.41 (dd, J=9.29, 1.25 Hz, 1H), 7.14 (d, J=7.53 Hz, 1H), 6.79 (d, J=8.03 Hz, 1H), 5.50 (s, 2H).

Step 2: Synthesis of Compound B-1-5

B-1-3 (935 mg, 3.04 mmol, 1 eq), B-1-4 (1.04 g, 3.35 mmol, 1.1 eq), Pd(PPh$_3$)$_4$ (352 mg, 304.61 μmol, 0.1 eq) and sodium carbonate (1.29 g, 12.18 mmol, 4 eq) were placed in a 50 mL egg-shaped flask, the system was pumped and replaced with protective gas for three times, ethylene glycol dimethyl ether (14 mL) and H$_2$O (7 mL) were added, the mixture was then stirred in an oil bath at 85° C. and the reaction was carried out for 16 hours. The system was cooled to room temperature, then transferred to a separatory funnel, ethyl acetate (150 mL) and water (70 mL) were added to extract, the phases were separated, and the organic phase was collected, dried over anhydrous sodium sulfate, filtered and evaporated to dryness by rotary evaporation to obtain a crude product. The crude product was purified by column chromatography (PE:EA=1:0-1:1) to obtain B-1-5. LCMS: m/z 432.1[M+Na]$^+$; $^1$H NMR (400 MHz, CDCl$_3$) δ ppm 7.62 (dt, J=15.56, 7.78 Hz, 2H), 7.46 (dd, J=8.03, 1.25 Hz, 1H), 7.39 (dd, J=9.41, 1.38 Hz, 1H), 6.99 (d, J=7.53 Hz, 1H), 6.72 (d, J=8.03 Hz, 1H), 6.67 (br s, 1H), 5.55 (s, 2H), 4.13 (br d, J=2.26 Hz, 2H), 3.64 (br t, J=5.52 Hz, 2H), 2.57 (br s, 2H), 1.50 (s, 9H).

Step 3: Synthesis of Compound B-1

B-1-5 (1 g, 2.44 mmol, 1 eq) was dissolved in DCM (20 mL), and TFA (1.16 g, 10.13 mmol, 0.75 mL, 4.15 eq) was added thereto, the mixture was stirred for 18 hours at room temperature (15° C.). TFA and DCM were evaporated to dryness by rotary evaporation under reduced pressure to obtain a crude product, the crude product was purified by column chromatography (DCM:MeOH=1:0-10:1) to obtain B-1. LCMS: m/z=310.0 [M+H]$^+$; $^1$H NMR (400 MHz, CDCl$_3$) δ ppm 7.58-7.66 (m, 2H), 7.46 (d, J=8.03 Hz, 1H), 7.39 (dd, J=9.41, 1.38 Hz, 1H), 7.02 (d, J=7.53 Hz, 1H), 6.79 (d, J=8.03 Hz, 1H), 6.61 (br s, 1H), 5.53 (s, 2H), 3.89 (br s, 2H), 3.43 (br s, 2H), 2.86 (br s, 2H).

Reference Embodiment 2: Fragment B-2

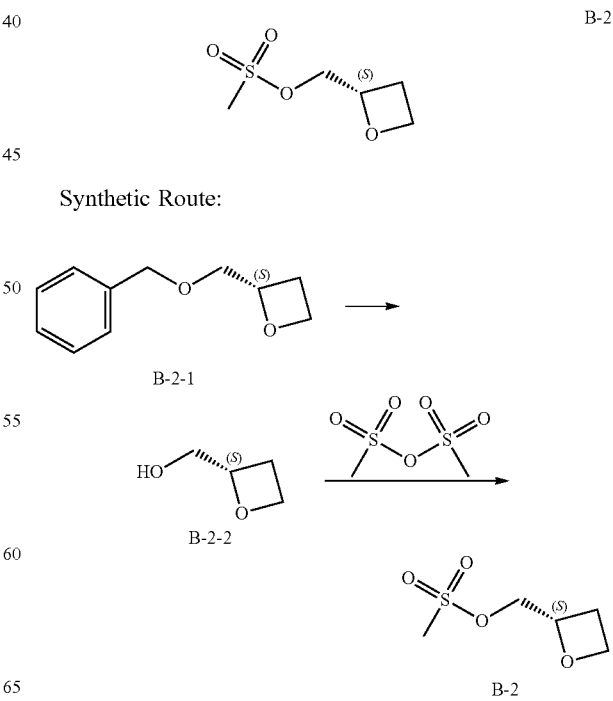

Synthetic Route:

Step 1: Synthesis of Compound B-2-2

Compound B-2-1 (12 g, 67.33 mmol, 1 eq) was dissolved in THF (120 mL), the system was replaced with argon, then Pd(OH)$_2$ (6.00 g, 4.27 mmol, 10% content, 6.35 e-2 eq) was added thereto, and hydrogen gas was introduced until the pressure was 50 psi, the mixture was stirred at 45° C. for 24 hours. The reaction mixture was filtered with celite and rinsed with anhydrous THF. The THF solution of B-2-2 was obtained, and the next step was directly carried out without post-treatment. $^1$H NMR (400 MHz, CDCl$_3$) δ ppm 7.10-7.16 (m, 2H), 7.03-7.07 (m, 2H), 4.75-4.83 (m, 1H), 4.52-4.61 (m, 1H), 4.39-4.46 (m, 1H).

Step 2: Synthesis of Compound B-2

Compound B-2-2 (2 g, 22.70 mmol, 1 eq) and TEA (13.78 g, 136.20 mmol, 18.96 mL, 6 eq) were added to a reaction flask, and the system was replaced with nitrogen, and methanesulfonic anhydride (11.86 g, 68.10 mmol, 2.64 mL, 3 eq) was added in batches at 0° C., and then the reaction was carried out at 25° C. for 24 hours. The reaction mixture was quenched with water (125 mL), the organic phase was separated, the aqueous phase was extracted with ethyl acetate (50 mL), and the organic phases were combined, washed with saturated brine (100 mL), dried over anhydrous sodium sulfate, filtered, and the filtrate was concentrated at 45° C. under reduced pressure with a water pump to obtain a crude product. Then the crude product was separated and purified by column chromatography (PE:EA=1:0-1:1, gradient elution) to obtain B-2. $^1$H NMR (400 MHz, CDCl$_3$) δ ppm 4.99-5.05 (m, 1H), 4.64-4.71 (m, 1H), 4.57 (dt, J=9.10, 6.08 Hz, 1H), 4.36 (d, J=3.88 Hz, 2H), 3.10 (s, 3H), 2.70-2.81 (m, 1H), 2.58-2.68 (m, 1H).

Reference Embodiment 3: Fragment B-3

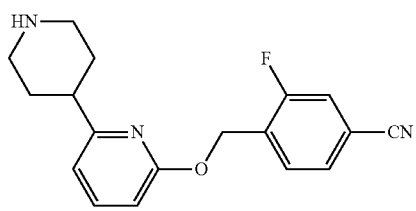

B-3

Synthetic Route:

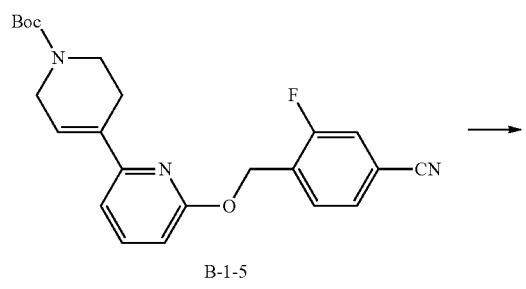

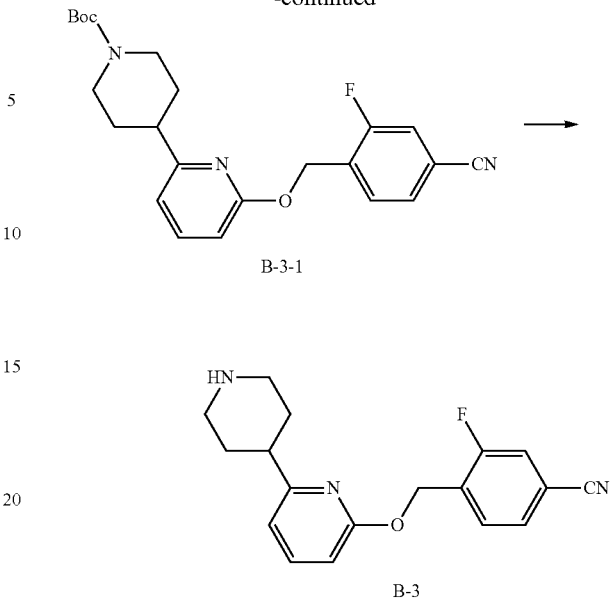

Step 1: Synthesis of Compound B-3-1

Palladium carbon (300 mg, 10% content), toluene (12 mL), and a mixture of B-1-5 (1 g, 2.44 mmol, 1 eq) and toluene (12 mL) were added successively to a reaction flask, then the system was replaced with hydrogen, and the mixture was stirred at 25° C. and the reaction was carried out for 0.5 hours. The reaction mixture was filtered with celite, and the filtrate was concentrated under reduced pressure to obtain a crude product. The crude product was separated and purified by column chromatography (petroleum ether:ethyl acetate=1:0 to 6:1) to obtain B-3-1. $^1$H NMR (CDCl$_3$, 400 MHz) δ (ppm) 7.62 (t, J=7.5 Hz, 1H), 7.54 (dd, J=8.1, 7.4 Hz, 1H), 7.44 (dd, J=7.9, 1.1 Hz, 1H), 7.38 (dd, J=9.3, 1.4 Hz, 1H), 6.75 (d, J=7.3 Hz, 1H), 6.66 (d, J=8.1 Hz, 1H), 5.47-5.54 (m, 2H), 4.20 (br s, 2H), 2.82 (br t, J=12.4 Hz, 2H), 2.71 (tt, J=11.8, 3.7 Hz, 1H), 1.83 (br d, J=12.5 Hz, 2H), 1.62-1.73 (m, 2H), 1.49 (s, 9H).

Step 2: Synthesis of Compound B-3

B-3-1 (700 mg, 1.70 mmol, 1 eq) and DCM (12 mL) were successively added to a reaction flask, then the temperature was lowered to 0° C., then trifluoroacetic acid (4 mL) was slowly added dropwise, and then the temperature was raised to 25° C. and the mixture was stirred for 0.5 hours. The reaction mixture was directly concentrated to dryness, then washed with saturated sodium carbonate (70 mL), and extracted with ethyl acetate (50 mL) for 3 times, the organic phases were combined, then dried over anhydrous sodium sulfate, filtered, and the filtrate was concentrated under reduced pressure to obtain a crude product of B-3. The crude product was directly used in the next step without purification. LCMS: m/z=312.1 [M+H]$^+$; $^1$H NMR (CD$_3$OD, 400 MHz) δ (ppm) 7.69 (t, J=7.4 Hz, 1H), 7.53-7.64 (m, 3H), 6.84 (d, J=7.4 Hz, 1H), 6.69 (d, J=8.3 Hz, 1H), 5.53 (s, 2H), 3.15 (br d, J=12.4 Hz, 2H), 2.69-2.80 (m, 3H), 1.81-1.89 (m, 2H), 1.67-1.80 (m, 2H).

Reference Embodiment 4: Fragment B-4

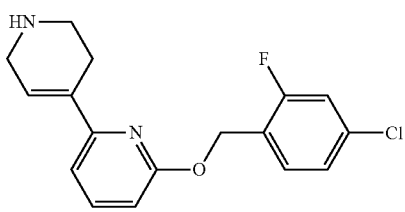

Synthetic Route:

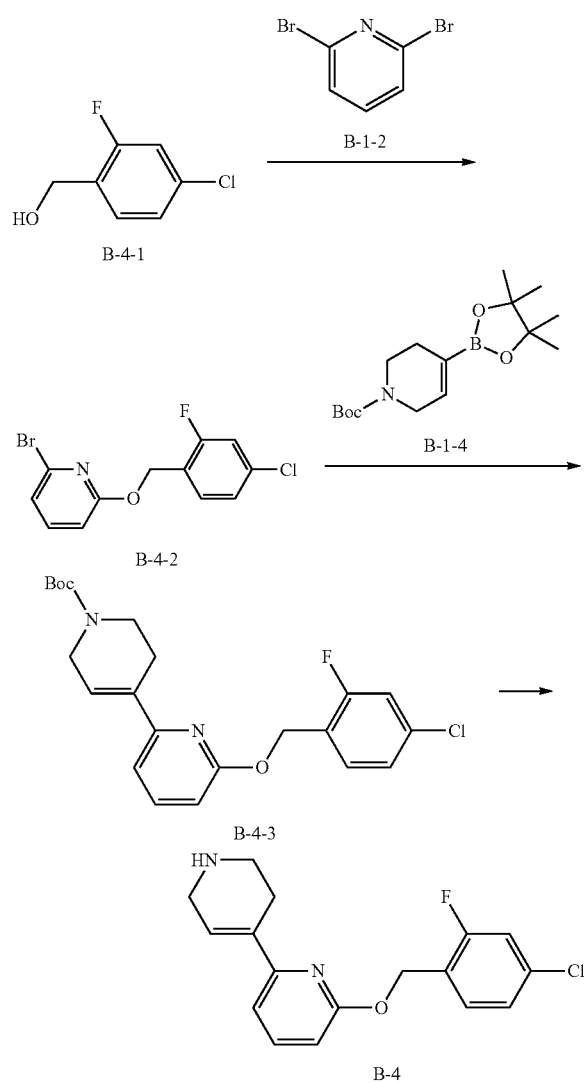

Step 1: Synthesis of Compound B-4-2

B-4-1 (1.00 g, 6.23 mmol, 1 eq) was added to a reaction flask containing THF (40 mL), NaH (375 mg, 9.38 mmol, 60% content, 1.51 eq) was added at 0° C. under the protection of nitrogen, the temperature was raised to 22° C. and the mixture was stirred for 1 hour, and B-1-2 (1.5 g, 6.33 mmol, 1.02 eq) was added, the mixture was stirred at 60° C. for 16 hours. The reaction mixture was quenched with 20 mL of water, and extracted with DCM (20 mL*3), the organic phase was collected, dried over anhydrous sodium sulfate, and concentrated to obtain a crude product. The crude product was separated and purified by column chromatography (petroleum ether:ethyl acetate=1:0) to obtain B-4-2. LCMS: m/z=317.8 [M+H]$^+$.

Step 2: Synthesis of Compound B-4-3

B-4-2 (1.50 g, 4.74 mmol, 1 eq), B-1-4 (1.50 g, 4.85 mmol, 1.02 eq), sodium carbonate (1.50 g, 14.15 mmol, 2.99 eq), dioxane (30 mL) and water (6 mL) were added to a reaction flask, Pd(dppf)Cl$_2$ (0.17 g, 232.33 μmol, 0.05 eq) was added under nitrogen atmosphere, and the reaction system was stirred at 100° C. for 3 hours. The reaction mixture was concentrated to obtain a crude product, water (50 mL) was added, then the mixture was extracted with ethyl acetate for 3 times (50 mL each time), the organic phases were combined, then washed with saturated sodium chloride aqueous solution (50 mL), dried over anhydrous sodium sulfate, filtered, and the filtrate was concentrated to obtain a crude product. The crude product was separated and purified by column chromatography (petroleum ether:ethyl acetate=1:0-20:1) to obtain B-4-3. LCMS: m/z=419.2 [M+H]$^+$.

Step 3: Synthesis of Compound B-4

B-4-3 (1.80 g, 4.30 mmol, 1 eq) and anhydrous DCM (30 mL) were added to a reaction flask, and trifluoroacetic acid (7.70 g, 67.53 mmol, 5.0 mL, 15.72 eq) was added, the reaction system was stirred at room temperature (20° C.) for 12 hours. Sodium carbonate solution (30 mL) was added to the reaction mixture, the pH value of the reaction mixture was adjusted with sodium carbonate solid to about 9-10, then extracted with ethyl acetate for three times (30 mL each time), the organic phases were combined, the organic phases were washed with saturated sodium chloride aqueous solution (30 mL), dried over anhydrous sodium sulfate, filtered, and the filtrate was concentrated to obtain a crude product. The crude product was separated and purified by column chromatography (DCM:MeOH=1:0-10:1) to obtain B-4. LCMS: m/z=319.1 [M+H]$^+$.

Reference Embodiment 5: Fragment B-5

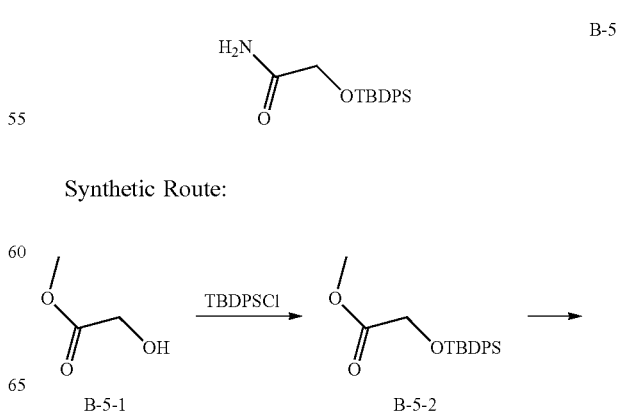

Synthetic Route:

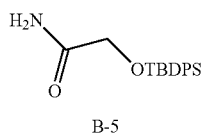

B-5

Step 1: Synthesis of Compound B-5-2

B-5-1 (10.00 g, 111.02 mmol, 8.55 mL, 1 eq), TBDPSCl (36.62 g, 133.22 mmol, 1.2 eq), imidazole (8.92 g, 131.00 mmol, 1.18 eq) and anhydrous DMF (150.00 mL) were added to a reaction flask and stirred at 20° C. for 3 hours. The reaction mixture was concentrated, dissolved with ethyl acetate (200 mL), washed twice with water (200 mL) successively, then washed with saturated sodium chloride aqueous solution (30 mL), the organic phase was collected and dried over anhydrous sodium sulfate, filtered, the filtrate was concentrated to obtain a crude product, the crude product was separated and purified by column chromatography (PE:EA=1:0-10:1) to obtain B-5-2. $^1$H NMR (400 MHz, CDCl$_3$) δ ppm 7.69 (dd, J=7.88, 1.38 Hz, 4H), 7.37-7.45 (m, 6H), 4.26 (s, 2H), 3.69 (s, 3H), 1.10 (s, 9H).

Step 2: Synthesis of Compound B-5

B-5-2 (35.00 g, 106.55 mmol, 1 eq) and 10 mL of ammonia-methanol solution (7 M) were added to a reaction flask and stirred at 50° C. for 16 hours. The reaction mixture was concentrated to obtain a crude product, the crude product was separated and purified by column chromatography (PE:EA=1:0-1:1) to obtain B-5. $^1$H NMR (400 MHz, DMSO-d$_6$) δ ppm 7.64 (dd, J=7.91, 1.63 Hz, 4H), 7.42-7.52 (m, 6H), 7.40 (br s, 1H), 7.11 (br s, 1H), 3.94 (s, 2H), 1.02 (s, 9H).

Reference Embodiment 6: Fragment B-6

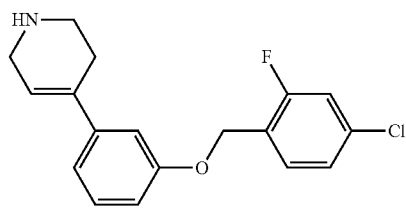 [SMILES: Fc1cc(Cl)ccc1COc1cccc(C2=CCNCC2)c1]

Synthetic Route:

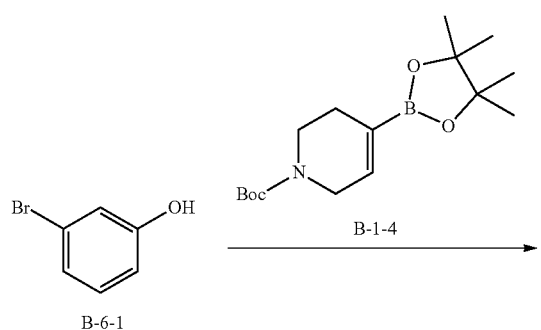

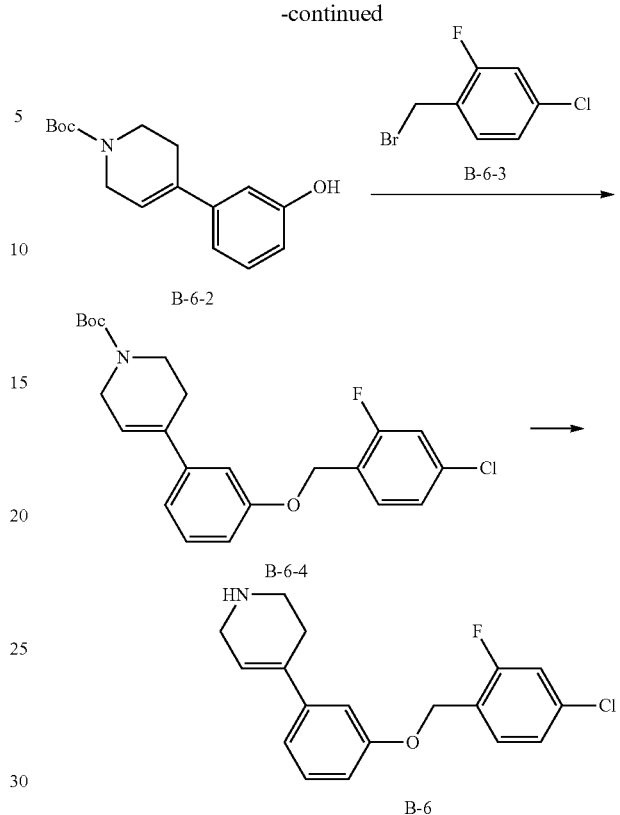

Step 1: Synthesis of Compound B-6-2

B-6-1 (4 g, 23.12 mmol, 1 eq) and B-1-4 (7.20 g, 23.29 mmol, 1.01 eq) were added to a reaction flask containing dioxane (50 mL); and Pd(dppf)Cl$_2$ (1.69 g, 2.31 mmol, 0.1 eq) and cesium carbonate (15.07 g, 46.24 mmol, 2 eq) were added thereto under nitrogen atmosphere, the mixture was stirred at 90° C. for 12 hours. The reaction mixture was filtered with celite, concentrated under reduced pressure, 20 mL of water was added, the mixture was extracted with DCM (20 mL) for 3 times, the combined organic phases were dried over anhydrous sodium sulfate, then concentrated to obtain a crude product, the crude product was separated and purified by column chromatography (PE:EA=1:0-17:3) to obtain B-6-2. $^1$H NMR (400 MHz, CDCl$_3$) δ ppm 7.20 (t, J=7.91 Hz, 1H), 6.84-6.98 (m, 2H), 6.78 (dd, J=7.91, 1.88 Hz, 1H), 6.36 (br s, 1H), 6.02 (br s, 1H), 4.08 (br s, 2H), 3.57-3.69 (m, 2H), 2.50 (br s, 2H), 1.51 (s, 9H).

Step 2: Synthesis of Compound B-6-4

B-6-2 (1.1 g, 4.00 mmol, 1 eq) and B-6-3 (900 mg, 4.03 mmol, 1.01 eq) were added to a reaction flask containing THF (10 mL), and potassium carbonate (1.38 g, 9.99 mmol, 2.5 eq) was added thereto, the mixture was stirred at 50° C. for 12 hours. 20 mL of water was added to the reaction mixture, then the phases were separated, the aqueous phase was extracted with ethyl acetate (20 mL) for 3 times, the combined organic phases were dried over anhydrous sodium sulfate, then concentrated to obtain a crude product, the crude product was separated and purified by column chromatography (PE:EA=1:0-25:2) to obtain B-6-4. $^1$H NMR (400 MHz, CDCl$_3$) δ ppm 7.46 (t, J=8.03 Hz, 1H), 7.27 (s, 1H), 7.11-7.21 (m, 2H), 6.95-7.04 (m, 2H), 6.87 (dd, J=8.03, 2.26 Hz, 1H), 6.05 (br s, 1H), 5.11 (s, 2H), 4.04-4.12 (m, 2H), 3.64 (t, J=5.65 Hz, 2H), 2.51 (br s, 2H), 1.50 (s, 9H).

Step 3: Synthesis of Compound B-6

B-6-4 (800 mg, 1.91 mmol, 1 eq) was added to a reaction flask containing DCM (8 mL), and trifluoroacetic acid (1.85 g, 16.21 mmol, 1.2 mL, 8.47 eq) was added, the mixture was stirred at 25° C. for 12 hours. The reaction mixture was concentrated, 15 mL of saturated sodium bicarbonate solution was added, and the mixture was extracted with DCM (15 mL) for three times, the organic phase was collected and dried over anhydrous sodium sulfate and concentrated to obtain B-6 without purification. LCMS: m/z=317.9 [M+H]⁺.

Reference Embodiment 7: Fragment B-7

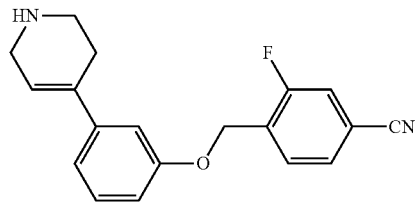 [SMILES: N#Cc1ccc(COc2cccc(C3=CCNCC3)c2)c(F)c1]

Synthetic Route:

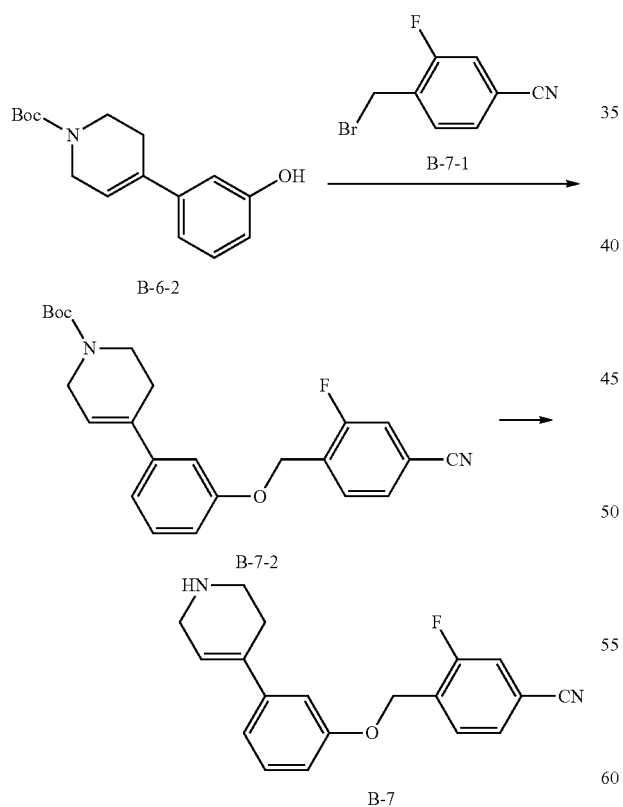

Step 1: Synthesis of Compound B-7-2

B-6-2 (4.3 g, 15.62 mmol, 1 eq) and B-7-1 (3.44 g, 16.07 mmol, 1.03 eq) were added to a reaction flask containing THF (50 mL), and potassium carbonate (4.34 g, 31.42 mmol, 2.01 eq) was added thereto, the mixture was stirred at 80° C. for 12 hours. Water (80 mL) was added to the reverse reaction solution, the mixture was extracted with ethyl acetate (80 mL) for 3 times, the organic phases were combined, washed with saturated brine solution (100 mL), dried over anhydrous sodium sulfate, and the filtrate was concentrated to obtain a crude product, the crude product was separated and purified by column chromatography (PE:EA=1:0-100:9) to obtain B-7-2. ¹H NMR (400 MHz, CDCl₃) δ ppm 7.70 (t, J=7.53 Hz, 1H), 7.50 (dd, J=7.91, 1.13 Hz, 1H), 7.40 (dd, J=9.29, 1.25 Hz, 1H), 7.27 (s, 1H), 7.03 (d, J=8.03 Hz, 1H), 6.97-7.00 (m, 1H), 6.86 (dd, J=8.16, 2.38 Hz, 1H), 6.04 (br s, 1H), 5.19 (s, 2H), 4.07 (br d, J=2.26 Hz, 2H), 3.63 (t, J=5.65 Hz, 2H), 2.51 (br s, 2H), 1.45-1.53 (m, 9H).

Step 2: Synthesis of Compound B-7

B-7-2 (800 mg, 1.96 mmol, 1 eq) was added to a reaction flask containing DCM (5 mL), trifluoroacetic acid (2.16 g, 18.91 mmol, 1.4 mL, 9.65 eq) was added, the mixture was stirred at 28° C. for 2 hours, then concentrated, DCM (20 mL) was added thereto, then the mixture was washed twice with saturated sodium bicarbonate aqueous solution (20 mL) for 2 times, and washed with water (20 mL), dried over anhydrous sodium sulfate, and the filtrate was concentrated to obtain B-6 without purification. LCMS: m/z=308.9 [M+H]⁺.

Reference Embodiment 8: Fragment B-8

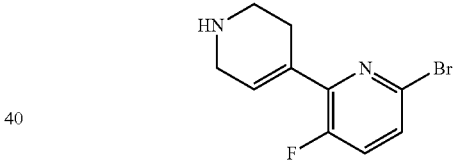

Synthetic Route:

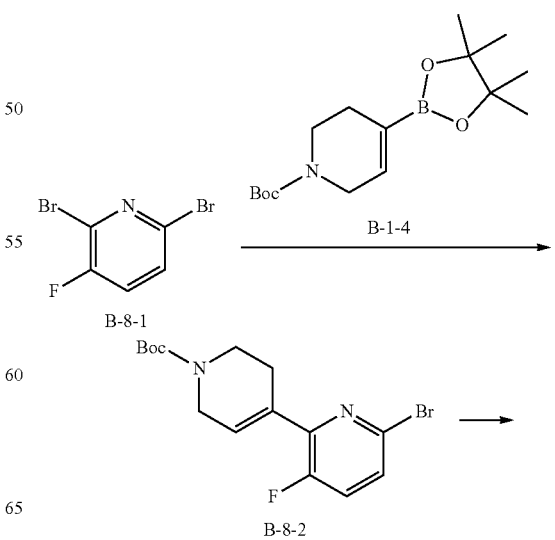

-continued

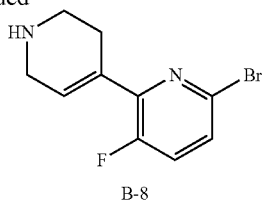
B-8

Step 1: Synthesis of Compound B-8-2

B-8-1 (3.7 g, 14.52 mmol, 1 eq), B-1-4 (4.49 g, 14.52 mmol, 1 eq), sodium carbonate (6.14 g, 57.95 mmol, 3.99 eq), dioxane (40 mL) and water (8 mL) were added to a reaction flask, Pd(dppf)Cl$_2$·CH$_2$Cl$_2$ (100 mg, 122.45 μmol, 8.44 e-3 eq) was added under nitrogen atmosphere, and the mixture was stirred at 100° C. for 4 hours. The reaction mixture was concentrated, water (50 mL) was added thereto, and the mixture was extracted with ethyl acetate (50 mL) for 3 times, the organic phases were combined, washed with saturated brine (50 mL), dried over anhydrous sodium sulfate, and the filtrate was concentrated to obtain a crude product, the crude product was separated and purified by column chromatography (PE:EA=1:0-10:1) to obtain B-8-2. $^1$H NMR (400 MHz, CDCl$_3$) δ ppm 7.37-7.43 (m, 1H), 7.30-7.34 (m, 1H), 6.63 (br s, 1H), 4.15 (br s, 2H), 3.66 (br d, J=4.02 Hz, 2H), 2.61 (br s, 2H), 1.49-1.52 (m, 9H).

Step 2: Synthesis of Compound B-8

B-8-2 (0.95 g, 2.66 mmol, 1 eq) and DCM (10 mL) were added to a reaction flask, trifluoroacetic acid (2.93 g, 25.66 mmol, 1.90 mL, 9.65 eq) was added dropwise, the mixture was stirred at 25° C. for 2 hours, water (50 mL) was added to the reaction mixture, the pH value was adjusted to about 9 with sodium carbonate, then the mixture was extracted with DCM (50 mL) for 3 times, the organic phases were combined, washed with saturated brine (50 mL), dried over anhydrous sodium sulfate, the filtrate was concentrated to obtain a crude product, the crude product was separated and purified by column chromatography (DCM:MeOH=1:0-10:1) to obtain B-8. LCMS: m/z=258.7 [M+H]$^+$.

Embodiment 1

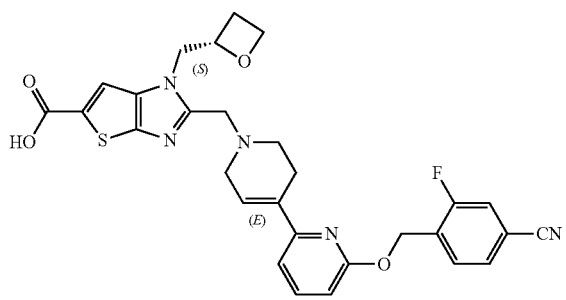

Synthetic Route:

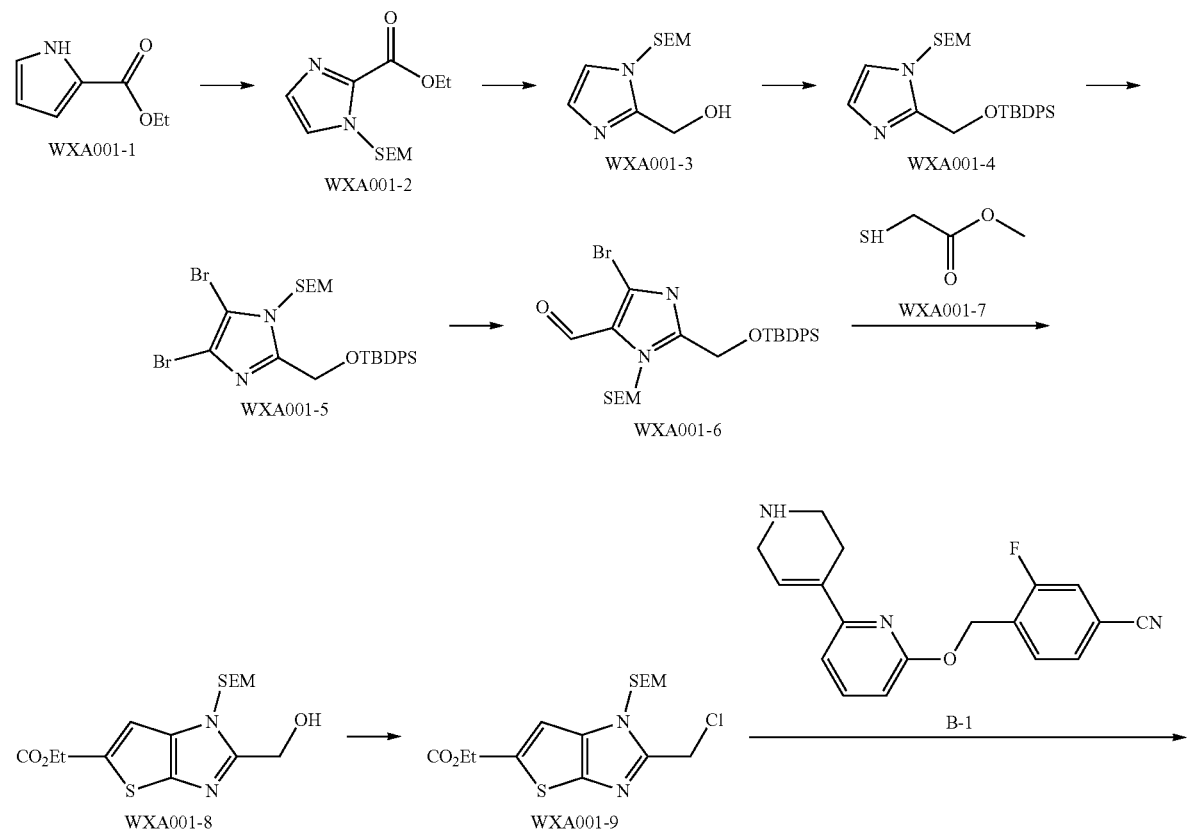

-continued
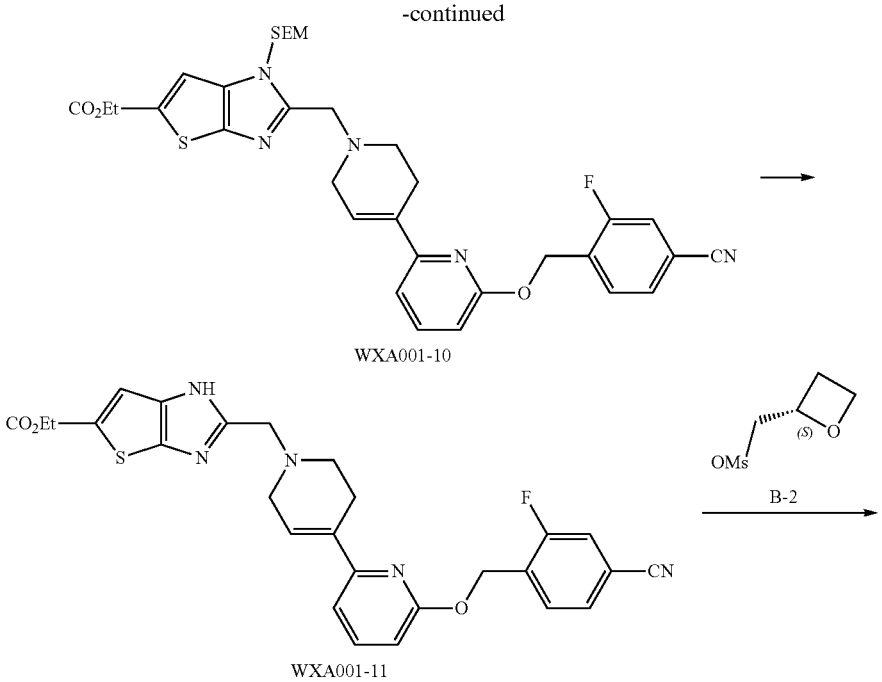
WXA001-10
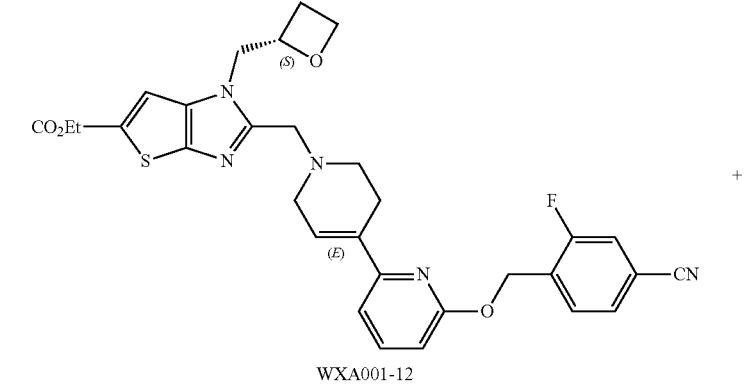
WXA001-11
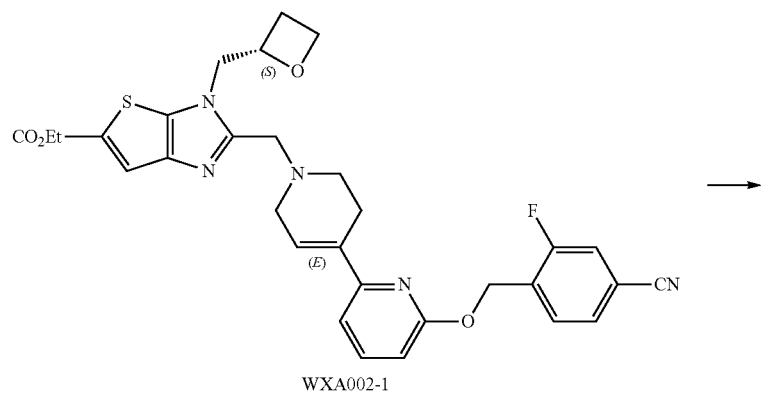
WXA001-12
+
WXA002-1

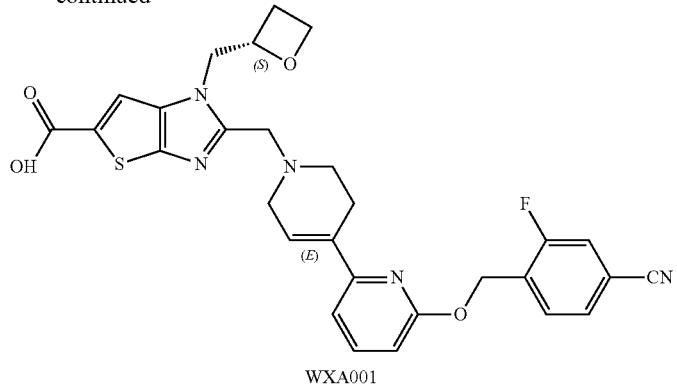

WXA001

Step 1: Synthesis of Compound WXA001-2

Compound WXA001-1 (23 g, 164.12 mmol, 1 eq) and DMF (115 mL) were added to a reaction flask, the system was replaced with nitrogen, cooled to 0° C., then NaH (9.85 g, 246.18 mmol, 60% content, 1.5 eq) was added, the system was replaced with nitrogen again, and 2-(trimethylsilyl) ethoxymethyl chloride (41.04 g, 246.18 mmol, 43.57 mL, 1.5 eq) was added dropwise, when the dropwise addition was completed, the temperature was raised to 25° C. and the reaction was carried out for 12 hours. The reaction mixture was quenched with ice water (500 mL), extracted with ethyl acetate (200 mL*3), the organic phases were combined, washed with saturated brine (200 mL*2), dried over anhydrous sodium sulfate, filtered, and the filtrate was concentrated at 45° C. under reduced pressure with a water pump to obtain a crude product. Then the crude product was separated and purified by column chromatography (PE:EA=1:0-1:1, gradient elution) to obtain WXA001-2. $^1$H NMR (400 MHz, CDCl$_3$) δ ppm 7.24 (d, J=0.63 Hz, 1H), 7.17 (s, 1H), 5.76 (s, 2H), 4.39 (q, J=7.13 Hz, 2H), 3.49-3.56 (m, 2H), 1.40 (t, J=7.13 Hz, 3H), 0.86-0.93 (m, 2H), −0.07--0.04 (m, 9H).

Step 2: Synthesis of Compound WXA001-3

THF (1000 mL) was added to a reaction flask, LiAlH$_4$ (6.04 g, 159.21 mmol, 1.5 eq) was added in batches, the system was replaced with nitrogen, the temperature was lowered to 0° C. and the mixture was stirred for 15 min, then compound WXA001-2 (28.7 g, 106.14 mmol, 1 eq) was added at 0° C., and the mixture was heated to 25° C. and the reaction was carried out for 0.5 hours. The reaction mixture was cooled to 0° C., then 6 mL of water, 6 mL of 15% sodium hydroxide and 18 mL of water were added successively, the reaction mixture was stirred at 25° C. for 15 minutes, then anhydrous magnesium sulfate was added and the mixture was stirred for 15 minutes, and then filtered. The filtrate was collected and washed with saturated brine (500 mL), dried over anhydrous sodium sulfate, filtered, and the filtrate was concentrated at 45° C. under reduced pressure with a water pump to obtain compound WXA001-3. $^1$H NMR (400 MHz, CDCl$_3$) δ ppm 6.98 (d, J=1.13 Hz, 1H), 6.93 (d, J=1.13 Hz, 1H), 5.37 (s, 2H), 4.72 (s, 2H), 3.52 (dd, J=8.76, 7.75 Hz, 2H), 0.89-0.95 (m, 2H), −0.02--0.01 (m, 9H).

Step 3: Synthesis of Compound WXA001-4

Compound WXA001-3 (18.81 g, 82.37 mmol, 1 eq), tert-butyl diphenyl chlorosilane (27.17 g, 98.84 mmol, 25.39 mL, 1.2 eq), imidazole (14.02 g, 205.92 mmol, 2.5 eq) and DMF (188 mL) were added to a reaction flask, then the system was replaced with nitrogen, the reaction was carried out at 25° C. for 16 hours. The reaction mixture was quenched with water (1000 mL), extracted with ethyl acetate (200 mL*3), the organic phases were combined, washed with saturated brine (200 mL*3), dried over anhydrous sodium sulfate, filtered, and the filtrate was concentrated at 45° C. under reduced pressure with a water pump to obtain a crude product. Then the crude product was separated and purified by column chromatography (PE:EA=1:0-1:1, gradient elution) to obtain WXA001-4. $^1$H NMR (400 MHz, CDCl$_3$) δ ppm 7.66-7.72 (m, 4H), 7.37-7.46 (m, 6H), 6.96-7.02 (m, 2H), 5.41 (s, 2H), 4.84 (s, 2H), 3.41-3.48 (m, 2H), 1.06 (s, 9H), 0.85-0.91 (m, 2H), −0.03 (s, 9H).

Step 4: Synthesis of Compound WXA001-5

Compound WXA001-4 (22 g, 47.13 mmol, 1 eq) and THF (440 mL) were added to a reaction flask, then the system was replaced with nitrogen, N-bromosuccinimide (25.17 g, 141.40 mmol, 44.18 μL, 3 eq) was added in batches at 0° C., and then the temperature was raised to 25° C. the reaction was carried out for 12 hours. The reaction mixture was quenched with water (440 mL), extracted with ethyl acetate (2200 mL*2), the organic phases were combined, washed with saturated brine (2200 mL*1), dried over anhydrous sodium sulfate, filtered, and the filtrate was concentrated at 30° C. under reduced pressure with a water pump to obtain a crude product. Then the crude product was separated and purified by column chromatography (PE:EA=1:1-2:1, gradient elution) to obtain WXA001-5. $^1$H NMR (400 MHz, CDCl$_3$) δ ppm 7.64-7.67 (m, 4H), 7.37-7.48 (m, 6H), 5.44 (s, 2H), 4.80 (s, 2H), 3.45-3.51 (m, 2H), 1.07 (s, 9H), 0.85-0.90 (m, 2H), −0.02 (s, 9H).

Step 5: Synthesis of Compound WXA001-6

Compound WXA001-5 (6 g, 9.61 mmol, 1 eq) and THF (60 mL) were added to a reaction flask, then the system was replaced with nitrogen, the temperature was reduced to −40° C., then i-PrMgCl—LiCl (1.3 M, 8.13 mL, 1.1 eq) was added dropwise, the mixture was stirred for 1.5 hours, then DMF (61.62 g, 843.09 mmol, 64.86 mL, 87.76 eq) was added dropwise, the reaction mixture was stirred at 25° C. for 30 minutes. The reaction mixture was quenched with water (120 mL), extracted with ethyl acetate (50 mL*2), the organic phases were combined, washed with saturated brine (100 mL), dried over anhydrous sodium sulfate, filtered, and the filtrate was concentrated at 45° C. under reduced pressure with a water pump to obtain a crude product. Then the crude product was separated and purified by column chromatography (PE:EA=1:0-10:1, gradient elution) to obtain WXA001-6. $^1$H NMR (400 MHz, CDCl$_3$) δ ppm 9.76 (s, 1H), 7.64-7.68 (m, 5H), 7.38-7.42 (m, 5H), 5.85 (s, 2H), 4.86 (s, 2H), 3.49-3.54 (m, 2H), 1.07 (s, 9H), 0.84-0.88 (m, 2H), −0.03 (s, 9H).

Step 6: Synthesis of Compound WXA001-8

Compound WXA001-6 (1.23 g, 2.14 mmol, 1 eq) was dissolved in EtOH (61.5 mL), sodium ethoxide (2.19 g, 6.43 mmol, 20% content, 3 eq), WXA001-7 (273.10 mg, 2.57 mmol, 233.42 μL, 1.2 eq) were added, the mixture was stirred at 20° C. for 2 hours, then heated to 80° C. and stirred for 12 hours. The reaction mixture was quenched with water (50 mL), extracted with ethyl acetate (25 mL) for 2 times, the organic phases were combined, washed with saturated brine (50 mL), filtered, and the filtrate was concentrated at 45° C. under reduced pressure with a water pump and evaporated to dryness by rotary evaporation to obtain a crude product. Then the crude product was separated and purified by column chromatography (PE:EA=1:0-10:1, gradient elution) to obtain compound WXA001-8. $^1$H NMR (400 MHz, CDCl$_3$) δ ppm 7.72 (s, 1H), 5.54 (s, 2H), 4.91 (s, 2H), 4.39 (q, J=7.13 Hz, 2H), 3.55-3.61 (m, 2H), 2.30-2.64 (m, 1H), 1.40 (t, J=7.13 Hz, 3H), 0.91-0.96 (m, 2H), −0.02 (s, 9H).

Step 7: Synthesis of Compound WXA001-9

Compound WXA001-8 (120 mg, 336.59 μmol, 1 eq), triethylamine (102.18 mg, 1.01 mmol, 140.55 μL, 3 eq) and DCM (2 mL) were added to a reaction flask, the system was replaced with nitrogen, then methyl sulfonyl chloride (57.84 mg, 504.89 μmol, 39.08 μL, 1.5 eq) was added in batches at 0° C., and then the mixture was heated to 25° C. and the reaction was carried out for 12 hours. The reaction mixture was concentrated under reduced pressure to obtain a crude product. The crude product was separated and purified by thin layer chromatography on silica gel plate (DCM:MeOH=20:1) to obtain compound WXA001-9. $^1$H NMR (400 MHz, CDCl$_3$) δ ppm 7.72 (s, 1H), 5.57 (s, 2H), 4.85 (s, 2H), 4.39 (q, J=7.13 Hz, 2H), 3.56-3.61 (m, 2H), 1.40 (t, J=7.13 Hz, 3H), 0.92-0.97 (m, 2H), −0.02 (s, 9H).

Step 8: Synthesis of Compound WXA001-10

Compound WXA001-9 (76 mg, 202.69 μmol, 1 eq), compound B-1 (62.70 mg, 202.69 μmol, 1 eq), potassium carbonate (42.02 mg, 304.03 μmol, 1.5 eq) and acetonitrile (1.5 mL) were added to a reaction flask and stirred at 60° C. for 12 hours. The reaction mixture was concentrated under reduced pressure to obtain a crude product. The crude product was separated and purified by thin layer chromatography on silica gel plate (DCM:MeOH=20:1) to obtain compound WXA001-10. $^1$H NMR (400 MHz, CDCl$_3$) δ ppm 7.73 (s, 1H), 7.60 (dt, J=17.98, 7.71 Hz, 2H), 7.45 (d, J=7.88 Hz, 1H), 7.38 (d, J=9.38 Hz, 1H), 6.96 (d, J=7.38 Hz, 1H), 6.66-6.72 (m, 2H), 5.65 (s, 2H), 5.53 (s, 2H), 4.38 (q, J=7.13 Hz, 2H), 3.94 (s, 2H), 3.51-3.57 (m, 2H), 3.28 (br d, J=2.50 Hz, 2H), 2.81 (t, J=5.44 Hz, 2H), 2.58 (br s, 2H), 1.40 (t, J=7.13 Hz, 3H), 0.88-0.94 (m, 2H), −0.06 (s, 9H).

Step 9: Synthesis of Compound WXA001-11

Compound WXA001-10 (145 mg, 223.82 μmol, 1 eq) and DCM (1.5 mL) were added to a reaction flask, trifluoroacetic acid (1.03 g, 8.99 mmol, 665.76 μL, 40.17 eq) was added dropwise to the flask, when the addition was completed, the reaction was carried out at 40° C. for 12 hours. The reaction mixture was concentrated under reduced pressure to obtain a crude product. The crude product was separated and purified by thin layer chromatography on silica gel plate (DCM:MeOH=20:1) to obtain compound WXA001-11. $^1$H NMR (400 MHz, CDCl$_3$) δ ppm 7.68 (br s, 1H), 7.62 (dt, J=10.38, 7.67 Hz, 2H), 7.46 (d, J=7.91 Hz, 1H), 7.38 (d, J=9.29 Hz, 1H), 7.00 (d, J=7.40 Hz, 1H), 6.73 (d, J=8.16 Hz, 1H), 6.69 (br s, 1H), 5.54 (s, 2H), 4.38 (q, J=7.07 Hz, 2H), 3.97 (s, 2H), 3.35 (br s, 2H), 2.84-2.90 (m, 2H), 2.66 (br s, 2H), 1.40 (t, J=7.15 Hz, 3H).

Step 10: Synthesis of Compound WXA001-12

Compound WXA001-11 (55 mg, 106.27 μmol, 1 eq), compound B-2 (52.98 mg, 318.81 μmol, 3 eq), cesium carbonate (103.87 mg, 318.81 μmol, 3 eq) and acetonitrile (0.5 mL) were added to a pre-dried reaction flask and the reaction was carried out at 60° C. for 16 hours. The reaction mixture was concentrated under reduced pressure to obtain a crude product. The crude product was separated and purified by thin layer chromatography on silica gel plate (DCM:MeOH=20:1) to obtain compound WXA001-12 and WXA002-1. Thin layer chromatography (DCM:MeOH=20:1) $R_f$=0.64 corresponded to WXA001-12, $R_f$=0.57 corresponded to WXA002-1. The nuclear magnetism of WXA001-12: $^1$H NMR (400 MHz, CDCl$_3$) δ ppm 7.73 (s, 1H), 7.60 (dt, J=16.05, 7.81 Hz, 2H), 7.45 (d, J=8.93 Hz, 1H), 7.38 (dd, J=9.29, 1.22 Hz, 1H), 6.97 (d, J=7.58 Hz, 1H), 6.66-6.72 (m, 2H), 5.53 (s, 2H), 5.14-5.19 (m, 1H), 4.59-4.65 (m, 1H), 4.54 (br s, 2H), 4.36-4.39 (m, 2H), 4.00-4.10 (m, 1H), 3.95 (br s, 2H), 3.26 (br s, 2H), 2.79 (br s, 2H), 2.66-2.72 (m, 1H), 2.55-2.61 (m, 2H), 2.38-2.47 (m, 1H), 1.38-1.42 (m, 3H). The nuclear magnetism of WXA002-1: $^1$H NMR (400 MHz, CDCl$_3$) δ ppm 7.86 (s, 1H), 7.56-7.64 (m, 2H), 7.42-7.47 (m, 1H), 7.36-7.40 (m, 1H), 6.97 (br d, J=7.82 Hz, 1H), 6.65-6.72 (m, 2H), 5.53 (s, 2H), 5.19-5.27 (m, 1H), 4.61-4.68 (m, 1H), 4.47-4.54 (m, 1H), 4.41-4.45 (m, 1H), 4.34-4.40 (m, 2H), 4.13 (d, J=7.21 Hz, 1H), 3.93 (br s, 2H), 3.26 (br s, 2H), 2.73-2.83 (m, 2H), 2.66-2.72 (m, 1H), 2.56 (br s, 2H), 2.42-2.49 (m, 1H), 1.37-1.41 (m, 3H).

Step 11: Synthesis of Compound WXA001

Compound WXA001-12 (52 mg, 88.49 μmol, 1 eq) was added to a reaction flask containing 1,5,7-triazabicyclo [4.4.0]dec-5-ene (25.62 mg, 184.05 μmol, 2.08 eq), acetonitrile (1 mL) and water (0.2 mL), and the mixture was stirred at 25° C. for 12 hours. When reaction was completed, without post-treatment, the reaction mixture was separated and purified by high performance liquid chromatography (chromatographic column: Waters Xbridge BEH C18 100*30 mm*10 μm; mobile phase: [Water (10 mM ammonium bicarbonate)-acetonitrile]; B (acetonitrile) %: 20%-50%, 8 min) to obtain WXA001. LCMS: m/z=560.1 [M+1]$^+$; $^1$H NMR (400 MHz, CD$_3$OD) δ ppm 7.75 (s, 1H), 7.66 (q, J=8.05 Hz, 2H), 7.52-7.59 (m, 2H), 7.08 (d, J=7.38 Hz, 1H), 6.74 (d, J=8.13 Hz, 1H), 6.68 (br s, 1H), 5.53 (s, 2H), 5.19 (br dd, J=7.38, 2.75 Hz, 1H), 4.66-4.71 (m, 1H), 4.60-4.64 (m, 1H), 4.54-4.59 (m, 1H), 4.41 (dt, J=9.13, 6.00 Hz, 1H), 4.05-4.15 (m, 2H), 3.41 (br s, 2H), 2.93-3.00 (m, 2H), 2.69-2.76 (m, 1H), 2.64 (br s, 2H), 2.42-2.50 (m, 1H). Two-dimensional NMR NOE identified that $C_8$—H was related to $C_{10}$—H, and the product structure was correct.

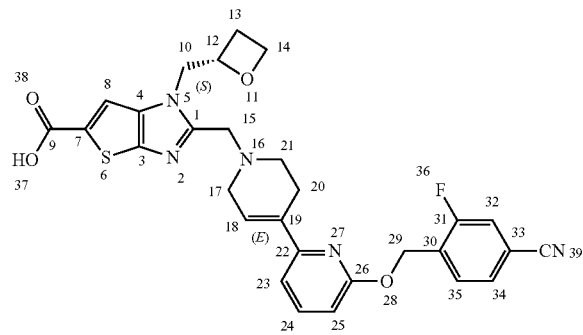

Embodiment 2

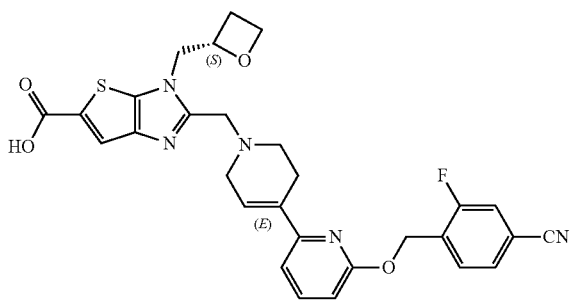

Synthetic Route:

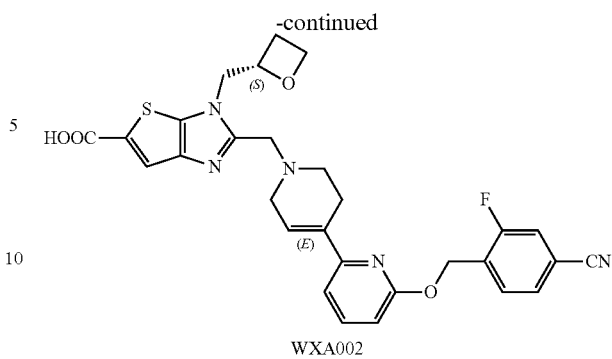

Step 1: Synthesis of Compound WXA002

Compound WXA002-1 (21.00 mg, 35.73 μmol, 1 eq) was added to a reaction flask containing 1,5,7-triazabicyclo[4.4.0]dec-5-ene (10.35 mg, 74.33 μmol, 2.08 eq), acetonitrile (0.5 mL) and water (0.1 mL); and the mixture was stirred at 25° C. for 12 hours. When the reaction was completed, without post-treatment, the reaction mixture was separated and purified by high performance liquid chromatography (chromatographic column: Waters Xbridge BEH C18 100*30 mm*10 μm; mobile phase: [Water (10 mM ammonium bicarbonate)-acetonitrile]; B (acetonitrile) %: 20%-50%, 8 min) to obtain WXA002. LCMS: m/z=560.1 [M+1]$^+$; $^1$H NMR (400 MHz, CD$_3$OD) δ ppm 7.72 (s, 1H), 7.62-7.67 (m, 2H), 7.52-7.58 (m, 2H), 7.07 (d, J=7.50 Hz, 1H), 6.73 (d, J=8.13 Hz, 1H), 6.67 (br s, 1H), 5.53 (s, 2H), 5.25 (br dd, J=7.13, 2.38 Hz, 1H), 4.58-4.70 (m, 3H), 4.43-4.51 (m, 2H), 4.02 (d, J=3.50 Hz, 2H), 3.33-3.34 (m, 2H), 2.89 (br t, J=5.13 Hz, 2H), 2.70-2.76 (m, 1H), 2.61 (br s, 2H), 2.46-2.53 (m, 1H).

Embodiment 3

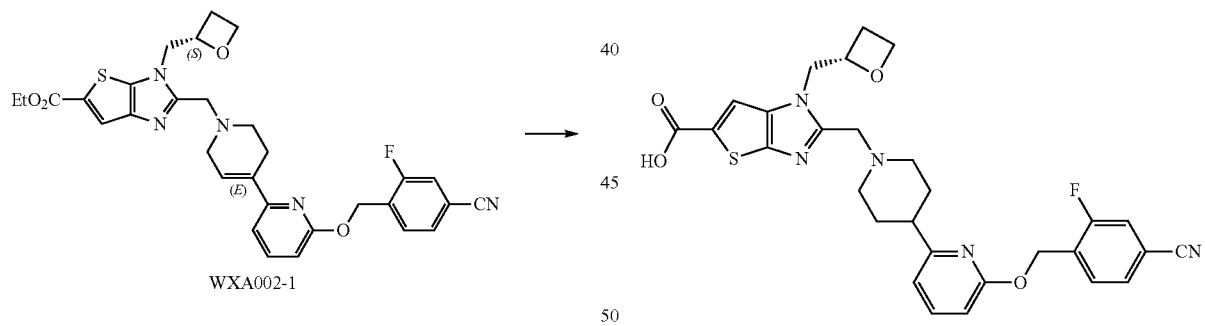

Synthetic Route:

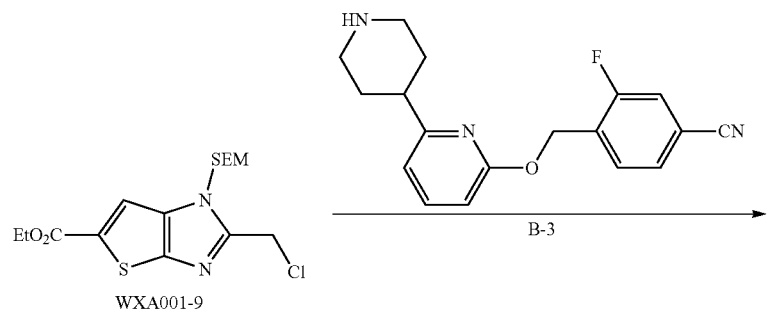

-continued
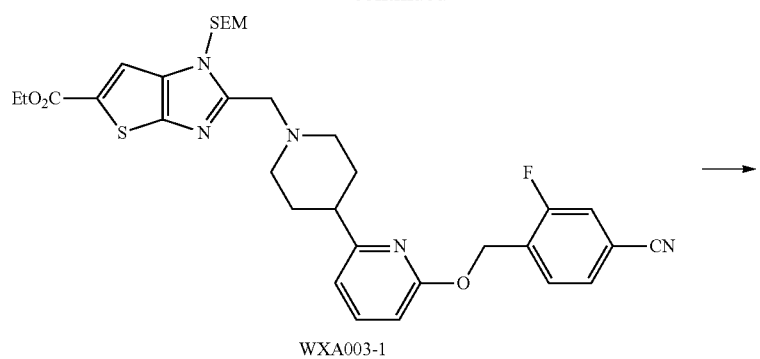
WXA003-1
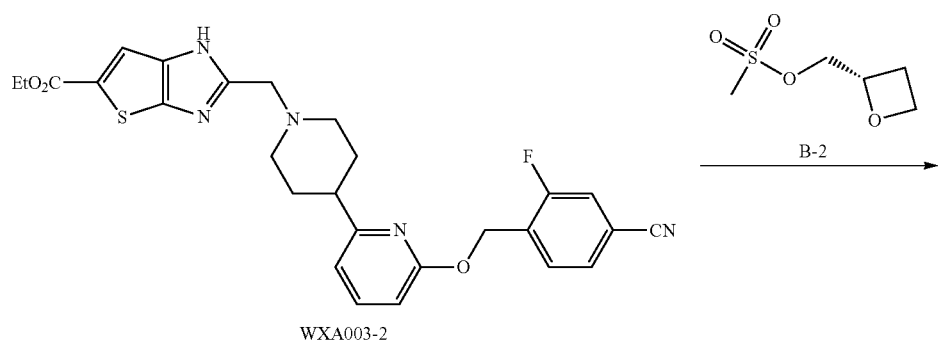
WXA003-2
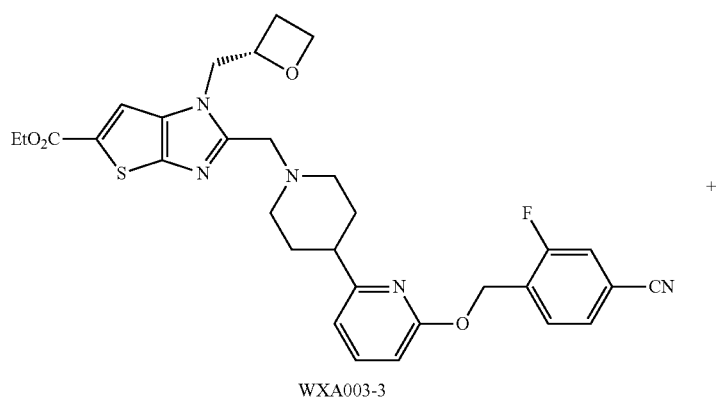
WXA003-3
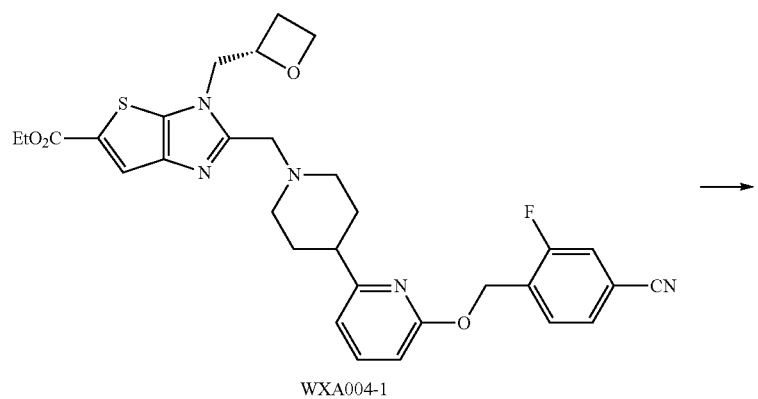
WXA004-1

-continued

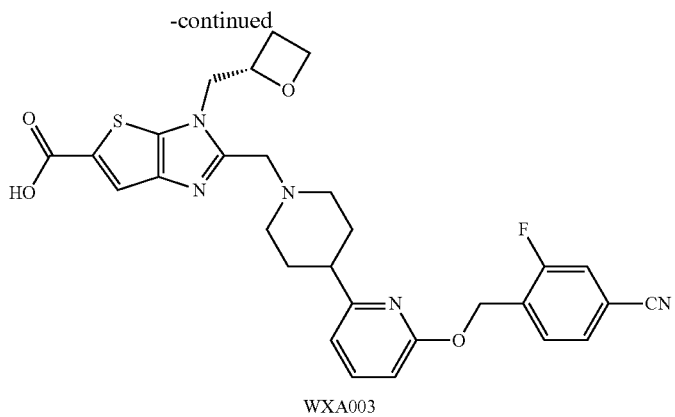

WXA003

Step 1: Synthesis of Compound WXA003-1

WXA001-9 (150 mg, 400.05 μmol, 1 eq), acetonitrile (8 mL), B-3 (143.24 mg, 460.05 μmol, 1.15 eq) and potassium carbonate (82.93 mg, 600.07 μmol, 1.5 eq) were successively added to a reaction flask, and the mixture was stirred at 60° C. and the reaction was carried out for 12 hours. The reaction mixture was washed with saturated ammonium chloride solution (100 mL), and extracted with ethyl acetate (60 mL) for 3 times, the organic phases were combined, then dried over anhydrous sodium sulfate, filtered, and the filtrate was concentrated under reduced pressure to obtain a crude product. The crude product was separated and purified by column chromatography (petroleum ether:ethyl acetate=1:0 to 2:1) to obtain WXA003-1. LCMS: m/z=650.1 [M+H]$^+$; $^1$H NMR (CDCl$_3$, 400 MHz) δ (ppm) 7.73 (s, 1H), 7.62 (t, J=7.5 Hz, 1H), 7.52 (t, J=7.8 Hz, 1H), 7.44 (d, J=8.6 Hz, 1H), 7.38 (d, J=9.3 Hz, 1H), 6.75 (d, J=7.3 Hz, 1H), 6.64 (d, J=8.1 Hz, 1H), 5.69 (s, 2H), 5.50 (s, 2H), 4.38 (q, J=7.1 Hz, 2H), 3.83 (s, 2H), 3.54-3.62 (m, 2H), 2.98 (br d, J=11.4 Hz, 2H), 2.55-2.66 (m, 1H), 2.21-2.32 (m, 2H), 1.84-1.91 (m, 2H), 1.71-1.82 (m, 2H), 1.39 (t, J=7.1 Hz, 3H), 0.93 (t, J=8.1 Hz, 2H), −0.08-0.01 (m, 9H).

Step 2: Synthesis of Compound WXA003-2

WXA003-1 (200 mg, 307.76 μmol, 1 eq) and DCM (3 mL) were added to a reaction flask successively, trifluoroacetic acid (1 mL) was added dropwise, the mixture was stirred at 40° C. for 5 hours. The reaction mixture was slowly added dropwise to saturated sodium carbonate solution (50 mL), then extracted with ethyl acetate (50 mL) for 2 times, the organic phases were combined, then dried over anhydrous sodium sulfate, filtered, and the filtrate was concentrated under reduced pressure to obtain a crude product of WXA003-2. The crude product was directly used in the next step without purification. LCMS: m/z=520.0 [M+H]$^+$; $^1$H NMR (CDCl$_3$, 400 MHz) δ (ppm) 7.70 (s, 1H), 7.64 (t, J=7.5 Hz, 1H), 7.55 (t, J=7.8 Hz, 1H), 7.43-7.47 (m, 1H), 7.38 (dd, J=9.4, 1.3 Hz, 1H), 6.77 (d, J=7.3 Hz, 1H), 6.67 (d, J=8.3 Hz, 1H), 5.51 (s, 2H), 4.33-4.40 (m, 2H), 3.88 (s, 2H), 3.06 (br d, J=11.4 Hz, 2H), 2.62-2.70 (m, 1H), 2.34-2.43 (m, 2H), 1.86-1.96 (m, 4H), 1.39 (t, J=7.1 Hz, 3H).

Step 3: Synthesis of Compound WXA003-3

WXA003-2 (150 mg, 288.69 μmol, 1 eq), B-2 (143.94 mg, 866.07 μmol, 3 eq), acetonitrile (6 mL) and cessium carbonate (282.18 mg, 866.07 μmol, 3 eq) were successively added to a reaction flask, the mixture was stirred at 60° C. and the reaction was carried out for 12 hours. The reaction mixture was washed with saturated ammonium chloride solution (60 mL), and extracted with ethyl acetate (50 mL) for 3 times, the organic phases were combined, then dried over anhydrous sodium sulfate, filtered, and the filtrate was concentrated under reduced pressure to obtain a crude product. The crude product was separated and purified by preparative TLC (DCM:MeOH=20:1) to obtain WXA003-3 and WXA004-1. The retention time of WXA003-3 was 3.628 min and the retention time of WXA004-1 was 3.541 min for HPLC detection (method: 10-80HPLC-AB-6.0 min). LCMS of WXA003-3: m/z=590.1 [M+H]$^+$. LCMS of WXA004-1: m/z=590.1 [M+H]$^+$.

Step 4: Synthesis of Compound WXA003

WXA003-3 (100 mg, 169.58 μmol, 1 eq), acetonitrile (5 mL), 1,5,7-triazabicyclo[4.4.0]dec-5-ene (118.03 mg, 847.92 μmol, 5 eq) and water (1 mL) were successively added to a reaction flask, and the mixture was stirred at 25° C. for 5 hours. The reaction mixture was washed with ammonium chloride solution (30 mL), extracted with ethyl acetate (20 mL) for 4 times, the organic phases were combined, washed with saturated brine (40 mL), dried over anhydrous sodium sulfate, filtered, and the filtrate was concentrated to obtain a crude product. The crude product was separated and purified by preparative high performance liquid chromatography (chromatographic column: Waters Xbridge BEH C18 100*30 mm*10 μm; mobile phase: [Water (10 mM ammonium bicarbonate)-acetonitrile]; B (acetonitrile) %: 15%-45%, 8 min) to obtain WXA003. LCMS: m/z=562.1 [M+H]$^+$; $^1$H NMR (400 MHz, CDCl$_3$) δ 7.55 (t, J=7.53 Hz, 1H), 7.45 (t, J=7.78 Hz, 1H), 7.35 (d, J=7.91 Hz, 1H), 7.22-7.32 (m, 2H), 6.69 (d, J=7.28 Hz, 1H), 6.57 (d, J=8.16 Hz, 1H), 5.40 (s, 2H), 5.02 (br s, 1H), 4.60 (br dd, J=5.52, 15.43 Hz, 1H), 4.41-4.53 (m, 2H), 4.30 (br d, J=8.53 Hz, 1H), 4.08-4.18 (m, 1H), 3.95-4.06 (m, 1H), 3.36-3.60 (m, 2H), 2.41-2.76 (m, 4H), 2.32 (br d, J=8.28 Hz, 1H), 1.83-2.07 (m, 4H). Two-dimensional NMR NOE identified that C$_8$—H was related to C$_{10}$—H, and the product structure was correct.

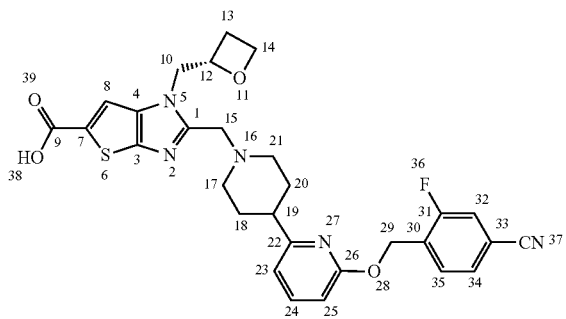 [SMILES: N#Cc1ccc(COc2cccc(C3CCN(Cc4nc5sc(C(=O)O)cc5n4C[C@@H]4CCO4)CC3)n2)c(F)c1]

Embodiment 4

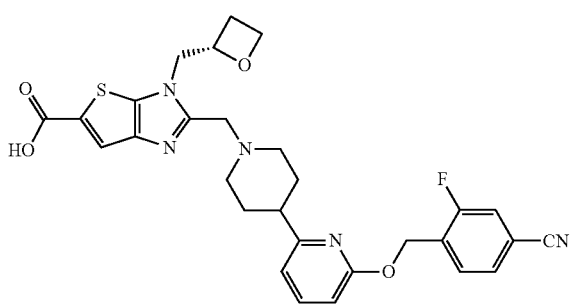 [SMILES: N#Cc1ccc(COc2cccc(C3CCN(Cc4nc5cc(C(=O)O)sc5n4C[C@@H]4CCO4)CC3)n2)c(F)c1]

Synthetic Route:

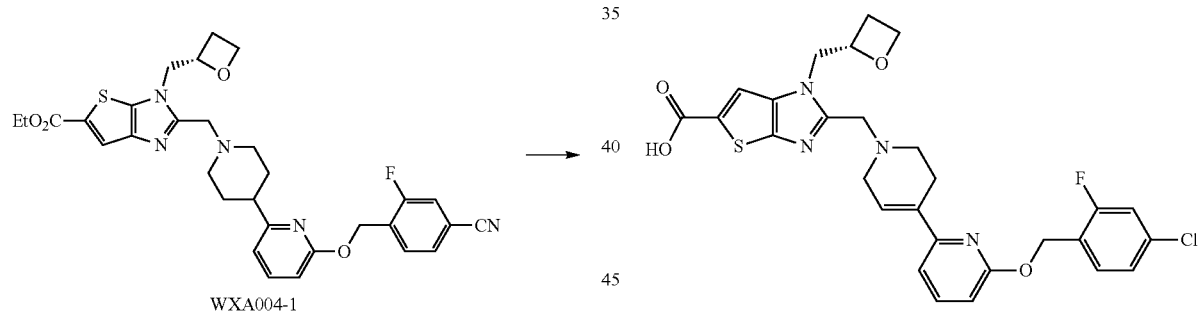

Step 1: Synthesis of Compound WXA004

WXA004-1 (100 mg, 169.58 μmol, 1 eq), acetonitrile (5 mL), 1,5,7-triazabicyclo[4.4.0]dec-5-ene (118.03 mg, 847.92 μmol, 5 eq) and water (1 mL) were successively added to a reaction flask. The reaction system was stirred at 25° C. for 5 hours. The reaction mixture was washed with ammonium chloride solution (30 mL), extracted with ethyl acetate (20 mL) for 4 times, the organic phases were combined, washed with saturated brine (40 mL), dried over anhydrous sodium sulfate, filtered, and the filtrate was concentrated to obtain a crude product. The crude product was separated and purified by preparative high performance liquid chromatography (chromatographic column: Phenomenex Gemini-NX C18 75*30 mm*3 μm; mobile phase: [Water (10 mM ammonium bicarbonate)-acetonitrile]; B (acetonitrile) %: 30%-60%, 6 min), then separated by supercritical fluid chromatography (column: DAICEL CHIRALPAK IG (250 mm*30 mm, 10 μm); mobile phase A: ethanol (0.1% ammonia water), B: carbon dioxide, 50%-50%, 9.3 min) to obtain WXA004. LCMS: m/z=562.1 [M+H]$^+$; $^1$H NMR (400 MHz, CDCl$_3$) δ 7.55 (t, J=7.53 Hz, 1H), 7.45 (t, J=7.78 Hz, 1H), 7.35 (d, J=7.91 Hz, 1H), 7.22-7.32 (m, 2H), 6.69 (d, J=7.28 Hz, 1H), 6.57 (d, J=8.16 Hz, 1H), 5.40 (s, 2H), 5.02 (br s, 1H), 4.60 (br dd, J=5.52, 15.43 Hz, 1H), 4.41-4.53 (m, 2H), 4.30 (br d, J=8.53 Hz, 1H), 4.08-4.18 (m, 1H), 3.95-4.06 (m, 1H), 3.36-3.60 (m, 2H), 2.41-2.76 (m, 4H), 2.32 (br d, J=8.28 Hz, 1H), 1.83-2.07 (m, 4H).

Embodiment 5

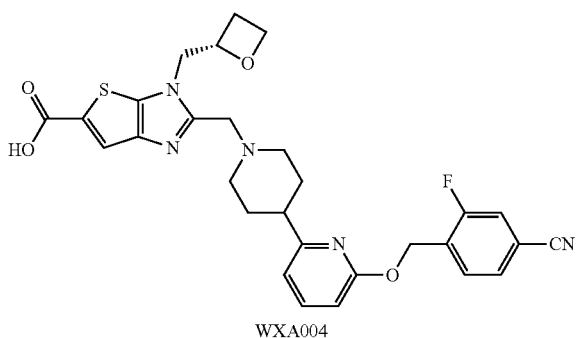

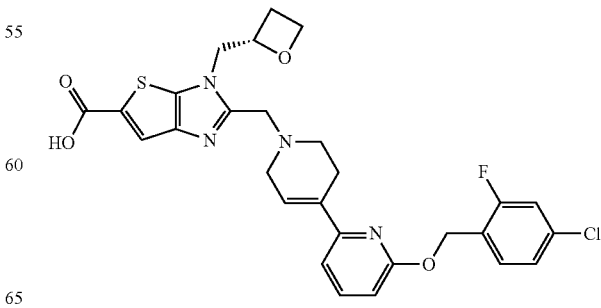

Synthetic Route:
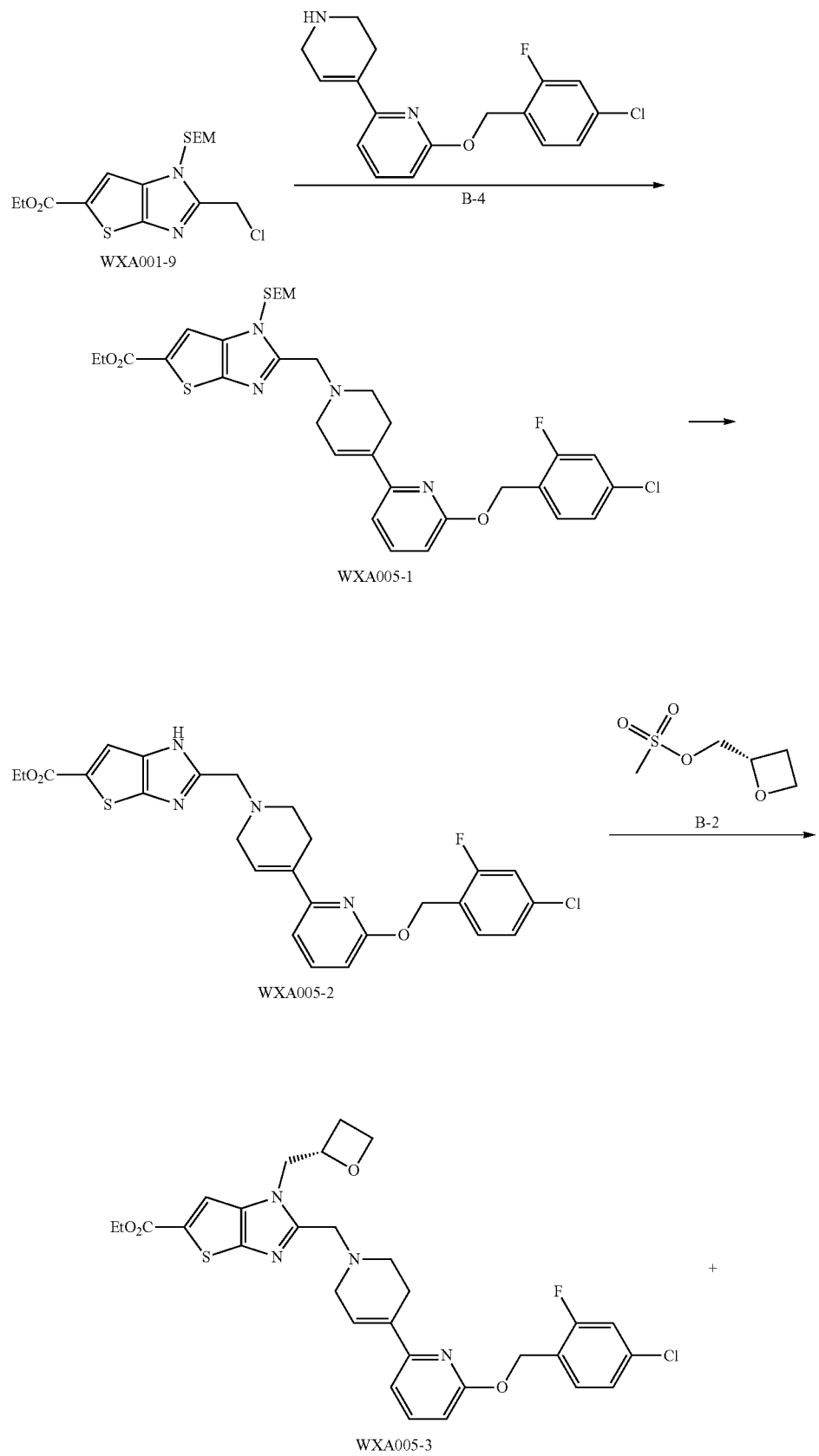

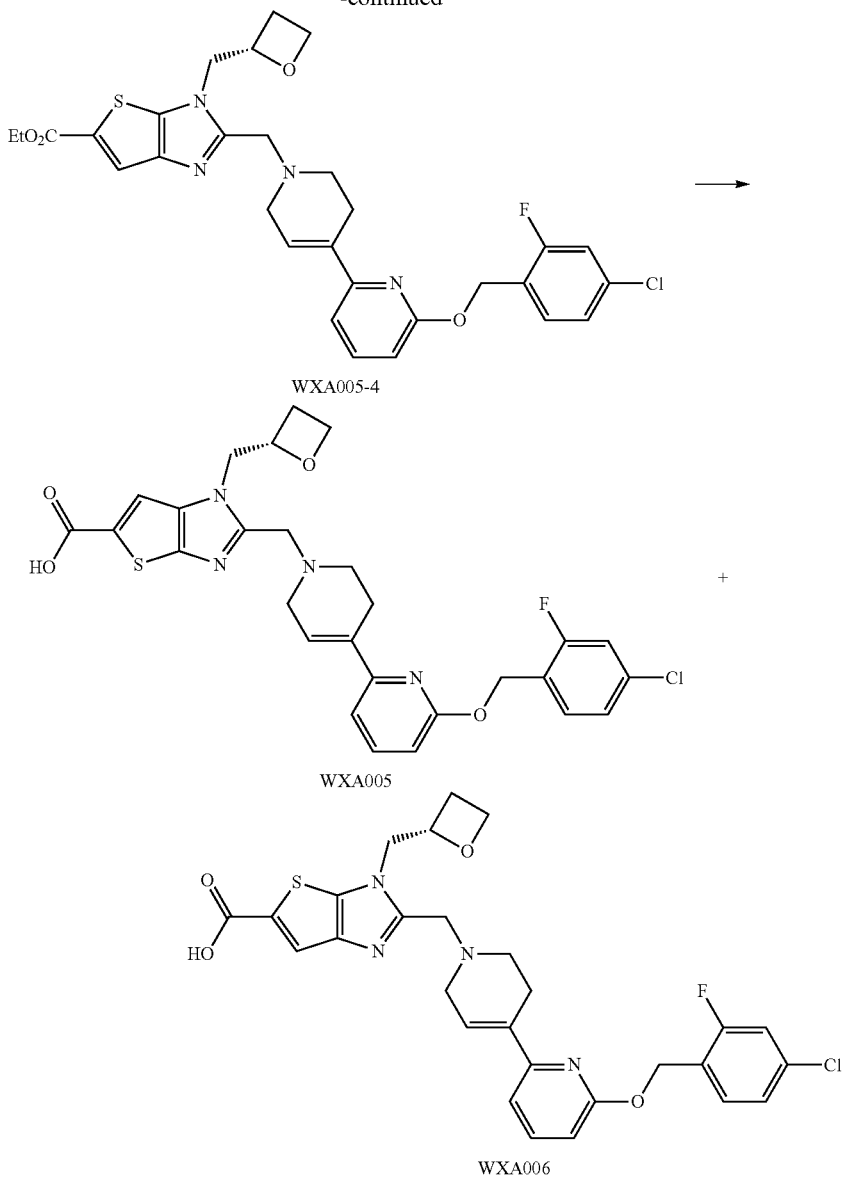

Step 1: Synthesis of Compound WXA005-1

WXA001-9 (0.16 g, 426.72 μmol, 1 eq), B-4 (0.30 g, 941.11 μmol, 2.21 eq), potassium carbonate (0.10 g, 723.56 μmol, 1.70 eq) and acetonitrile (10 mL) were successively added to a reaction flask, and the reaction system was stirred at 60° C. for 10 hours. The reaction mixture was concentrated to obtain a crude product, water (10 mL) was added, then the mixture was extracted with ethyl acetate for 3 times (10 mL each time), the organic phases were combined, then washed with saturated sodium chloride aqueous solution (10 mL), dried over anhydrous sodium sulfate, filtered, and the filtrate was concentrated to obtain a crude product. The crude product was separated and purified by column chromatography (petroleum ether:ethyl acetate=1:0-5:1) to obtain WXA005-1. LCMS: m/z=657.3 [M+H]$^+$; $^1$H NMR (400 MHz, CDCl$_3$) δ ppm 7.74 (s, 1H), 7.55 (t, J=7.91 Hz, 1H), 7.43 (t, J=8.03 Hz, 1H), 7.08-7.17 (m, 2H), 6.94 (d, J=7.28 Hz, 1H), 6.72 (br s, 1H), 6.66 (d, J=8.28 Hz, 1H), 5.66 (s, 2H), 5.43 (s, 2H), 4.38 (q, J=7.03 Hz, 2H), 3.95 (s, 2H), 3.52-3.57 (m, 2H), 3.29 (br s, 2H), 2.79-2.85 (m, 2H), 2.61 (br s, 2H), 1.40 (t, J=7.03 Hz, 3H), 0.89-0.94 (m, 2H), −0.10−−0.03 (m, 9H).

Step 2: Synthesis of Compound WXA005-2

WXA005-1 (0.30 g, 456.43 μmol, 1 eq), anhydrous DCM (5.0 mL), and trifluoroacetic acid (1.54 g, 13.51 mmol, 1.0 ml, 29.59 eq) were successively added to a reaction flask, and the reaction system was stirred at 40° C. for 5 hours. Sodium carbonate solution (10 mL) was added to the reaction mixture, the pH value of the reaction mixture was adjusted with sodium carbonate solid to about 9-10, then the mixture was extracted with ethyl acetate for three times (10 mL each time), the organic phases were combined, and the organic phases were washed with saturated sodium chloride aqueous solution (10 mL), dried over anhydrous sodium sulfate, filtered, and the filtrate was concentrated to obtain a crude product. The crude product was separated and purified by column chromatography (petroleum ether:ethyl acetate=10: 1-1:1) to obtain WXA005-2. LCMS: m/z=527.2 [M+H]$^+$; $^1$H NMR (400 MHz, CDCl$_3$) δ ppm 10.08 (br s, 1H), 7.68 (br s, 1H), 7.57 (t, J=7.78 Hz, 1H), 7.43 (t, J=8.16 Hz, 1H), 7.09-7.17 (m, 2H), 6.96 (d, J=7.53 Hz, 1H), 6.73 (br s, 1H), 6.69 (d, J=8.28 Hz, 1H), 5.44 (s, 2H), 4.37 (q, J=7.11 Hz, 2H), 3.96 (s, 2H), 3.35 (br d, J=3.01 Hz, 2H), 2.83-2.91 (m, 2H), 2.68 (br s, 2H), 1.39 (t, J=7.15 Hz, 3H).

Step 3: Synthesis of Compound WXA005-3

WXA005-2 (0.20 g, 379.50 μmol, 1 eq), B-2 (0.35 g, 2.11 mmol, 5.55 eq), potassium carbonate (0.40 g, 1.23 mmol, 3.23 eq) and acetonitrile (5 mL) were successively added to a reaction flask, and the reaction system was stirred at 80° C. for 10 hours. The reaction mixture was concentrated to obtain a crude product, water (10 mL) was added, then the mixture was extracted with ethyl acetate for 3 times (10 mL each time), the organic phases were combined, then washed with saturated sodium chloride aqueous solution (10 mL), dried over anhydrous sodium sulfate, filtered, and the filtrate was concentrated to obtain a crude product. The crude product was separated and purified by column chromatography (petroleum ether:ethyl acetate=1:0-1:1) to obtain a mixture of WXA005-3 and WXA005-4. LCMS (retention time: 3.508): M/Z=597.1 [M+H]$^+$; LCMS (retention time: 3.566): m/z=597.3 [M+H]$^+$.

Step 4: Synthesis of Compound WXA005 and WXA006

A mixture of WXA005-3 and WXA005-4 (90 mg, 150.73 μmol, 1 eq), water (0.4 mL), acetonitrile (2 mL) and 1,5,7-triazabicyclo[4.4.0]dec-5-ene (50 mg, 359.20 μmol, 2.38 eq) were successively added to a reaction flask, and the reaction system was stirred at 20° C. for 10 hours. The reaction mixture was concentrated to obtain a crude product. The crude product was separated and purified by preparative TLC (DCM:MeOH=10:1) to obtain a mixture of WXA005 and WXA006. The mixture was separated by supercritical fluid chromatography (chromatographic column DAICEL CHIRALPAK IG (250 mm*30 mm, 10 μm); mobile phase: [0.1% NH$_3$H$_2$O MeOH]; CO$_2$: 55%-55%, min) to obtain WXA005 (retention time: 6.815 min) and WXA006 (retention time: 10.4 min).

WXA005: Detection method (chromatographic column: Chiralpak IG-3 50 ¡Å 4.6 mm I.D., 3 μm, mobile phase: A: CO$_2$ B: Methanol (0.05% diethylamine), constant-gradient elution: Methanol (0.05% diethylamine) 40%, flow rate: 4 mL/min, column temperature: 35° C., back pressure: 1500 psi). LCMS: m/z=569.2 [M+H]$^+$; $^1$H NMR (400 MHz, DMSO-d$_6$) δ ppm 7.68 (t, J=7.91 Hz, 1H), 7.55 (t, J=8.16 Hz, 1H), 7.40-7.50 (m, 2H), 7.30 (dd, J=8.28, 1.76 Hz, 1H), 7.08 (d, J=7.53 Hz, 1H), 6.68-6.77 (m, 2H), 5.39 (s, 2H), 4.97-5.08 (m, 1H), 4.52-4.60 (m, 1H), 4.40-4.50 (m, 2H), 4.28-4.38 (m, 1H), 3.74-3.92 (m, 2H), 3.18 (br s, 2H), 2.68 (br d, J=5.52 Hz, 2H), 2.58-2.66 (m, 1H), 2.32-2.38 (m, 1H); $^1$H NMR (400 MHz, CD$_3$OD) δ ppm 7.64 (s, 1H), 7.62 (t, J=7.91 Hz, 1H), 7.48 (t, J=8.03 Hz, 1H), 7.16-7.24 (m, 2H), 7.05 (d, J=7.53 Hz, 1H), 6.71 (br s, 1H), 6.68 (d, J=8.03 Hz, 1H), 5.42 (s, 2H), 5.19 (br d, J=4.27 Hz, 2H), 4.36-4.45 (m, 1H), 3.93-4.05 (m, 2H), 2.82-2.90 (m, 2H), 2.68-2.76 (m, 1H), 2.63 (br s, 2H), 2.48 (br d, J=8.78 Hz, 1H).

WXA006: detection method (chromatographic column: Chiralpak IG-3 50 ¡Å 4.6 mm I.D., 3 mobile phase: A: CO$_2$ B: Methanol (0.05% diethylamine), constant-gradient elution: Methanol (0.05% diethylamine) 40%, flow rate: 4 mL/min, column temperature: 35° C., back pressure: 1500 psi); LCMS: m/z=569.2 [M+H]$^+$; $^1$H NMR (400 MHz, DMSO-d$_6$) δ ppm 7.67 (t, J=7.91 Hz, 1H), 7.54 (t, J=8.16 Hz, 1H), 7.45 (dd, J=9.91, 1.88 Hz, 1H), 7.26-7.33 (m, 2H), 7.07 (d, J=7.28 Hz, 1H), 6.68-6.75 (m, 2H), 5.39 (s, 2H), 5.08 (br s, 1H), 4.43-4.55 (m, 2H), 4.28-4.40 (m, 2H), 3.74-3.86 (m, 2H), 3.17 (br s, 2H), 2.58-2.71 (m, 3H), 2.32-2.39 (m, 1H); $^1$H NMR (400 MHz, CD$_3$OD) δ ppm 7.58-7.64 (m, 2H), 7.48 (t, J=8.03 Hz, 1H), 7.15-7.25 (m, 2H), 7.04 (d, J=7.53 Hz, 1H), 6.70 (br s, 1H), 6.67 (d, J=8.03 Hz, 1H), 5.42 (s, 2H), 5.25 (br d, J=4.27 Hz, 1H), 4.38-4.50 (m, 2H), 3.85-4.00 (m, 2H), 3.23 (br s, 2H), 2.76-2.85 (m, 2H), 2.67-2.75 (m, 1H), 2.60 (br s, 2H), 2.44-2.54 (m, 1H).

WXA005 was identified by two-dimensional NMR NOE that C$_8$—H was related to C$_{10}$—H, and the product structure was correct.

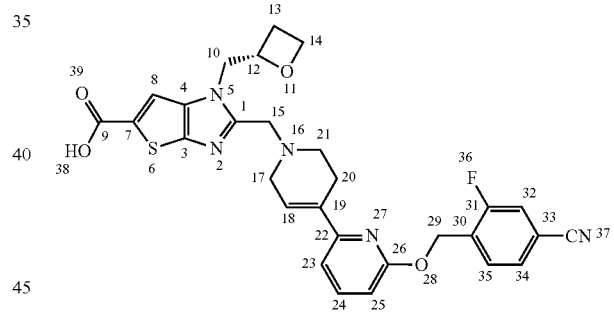

Embodiment 6

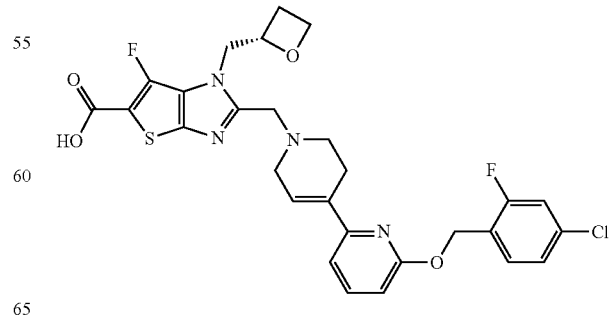

Synthetic Route:
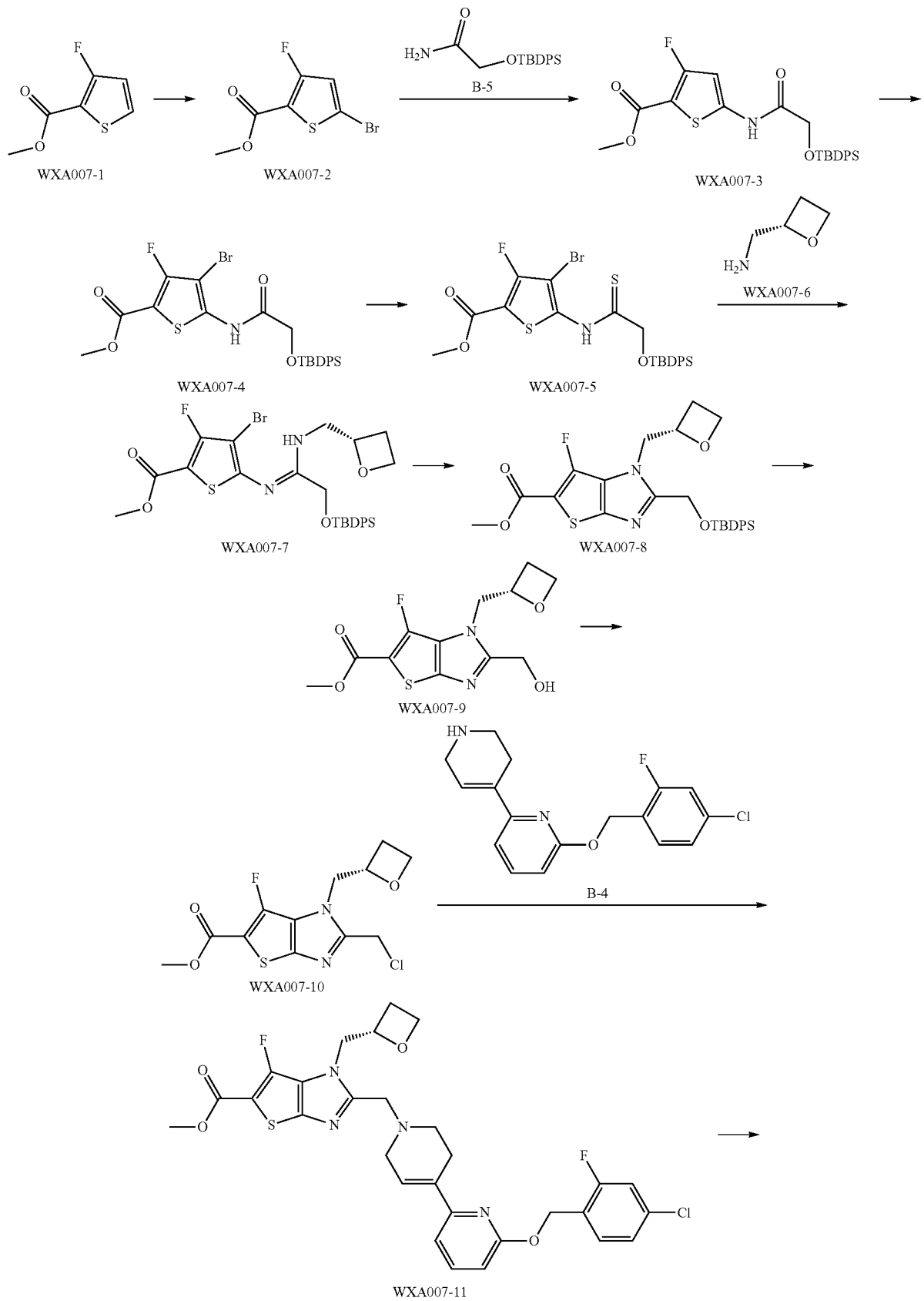

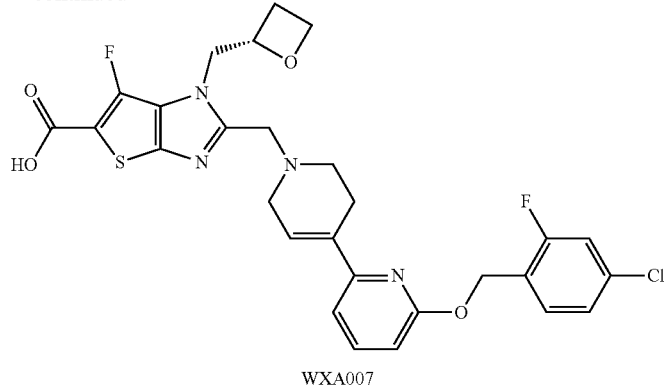

WXA007

Step 1: Synthesis of Compound WXA007-2

WXA007-1 (2.00 g, 12.49 mmol, 1 eq) and anhydrous THF (100 mL) were added to a reaction flask, a THF solution of 2,2,6,6-tetramethylpiperidinylmagnesium chloride lithium chloride complex (1 M, 24.00 mL, 1.92 eq) was added at −40° C., then the mixture was stirred at −40° C. for 0.5 hours, carbon tetrabromide (4.14 g, 12.49 mmol, 1 eq) was added, the mixture was stirred at −40° C. for 0.5 hours, and stirred at 20° C. for 11 hours. The reaction mixture was quenched with hydrochloric acid (0.5 M, 10 mL), extracted with ethyl acetate (50 mL) for 3 times, the organic phases were combined, washed with saturated sodium chloride aqueous solution (50 mL), dried over anhydrous sodium sulfate, then filtered and concentrated to obtain a crude product, the crude product was separated and purified by column chromatography (PE:EA=1:0-20:1) to obtain WXA007-2. $^1$H NMR (400 MHz, CDCl$_3$) δ ppm 6.89 (s, 1H), 3.88 (s, 3H).

Step 2: Synthesis of Compound WXA007-3

WXA007-2 (1.70 g, 7.11 mmol, 1 eq), B-5 (2.23 g, 7.11 mmol, 1.0 eq), potassium carbonate (1.97 g, 14.22 mmol, 2 eq), anhydrous toluene (50 mL) were added to a reaction flask, tris(dibenzylideneacetone)dipalladium (0.65 g, 709.82 µmol, 9.98 e-2 eq) and 9,9-dimethyl-4,5-bis(diphenylphosphino)xanthene (0.82 g, 1.42 mmol, 1.99 e-1 eq) were added under nitrogen atmosphere, and the mixture was stirred at 100° C. for 12 hours. The reaction mixture was filtered, water (50 mL) was added to the filtrate, and the mixture was extracted with ethyl acetate (50 mL) for 3 times, the organic phases were combined, washed with saturated sodium chloride aqueous solution (50 mL), dried over anhydrous sodium sulfate, then filtered and concentrated to obtain a crude product, the crude product was separated and purified by column chromatography (PE:EA=1:0-4:1) to obtain WXA007-3. $^1$H NMR (400 MHz, CDCl$_3$) δ ppm 9.28 (br s, 1H), 7.57-7.68 (m, 5H), 7.41-7.47 (m, 5H), 6.42 (s, 1H), 4.31 (s, 2H), 3.87 (s, 3H), 1.16 (s, 9H).

Step 3: Synthesis of Compound WXA007-4

WXA007-3 (2.60 g, 2.84 mmol, 51.53% purity, 1 eq), N-bromosuccinimide (1.00 g, 5.62 mmol, 1.98 eq) and anhydrous THF (50 mL) were added to a reaction flask and stirred at 20° C. for 12 hours. Saturated sodium bicarbonate solution (50 mL) was added to the reaction mixture, the mixture was then extracted with ethyl acetate (50 mL) for 3 times, the organic phases were combined, washed with saturated sodium chloride aqueous solution (50 mL), dried over anhydrous sodium sulfate, then filtered and concentrated to obtain a crude product, the crude product was separated and purified by column chromatography (PE:EA=1:0-10:1) to obtain WXA007-4. $^1$H NMR (400 MHz, CDCl$_3$) δ ppm 9.65 (br s, 1H), 7.66 (br d, J=6.78 Hz, 4H), 7.42-7.50 (m, 6H), 4.31 (s, 2H), 3.89 (s, 3H), 1.19 (s, 9H).

Step 4: Synthesis of Compound WXA007-5

WXA007-4 (1.80 g, 3.27 mmol, 1 eq), Lawesson reagent (1.35 g, 3.34 mmol, 1.02 eq) and anhydrous dioxane (30 mL) were added to a reaction flask and stirred at 110° C. for 6 hours. The reaction mixture was concentrated to obtain a crude product, the crude product was purified by column chromatography (PE:EA=1:0-10:1) to obtain WXA007-5. $^1$H NMR (400 MHz, CDCl$_3$) δ ppm 11.18 (br s, 1H), 7.66 (dd, J=7.91, 1.38 Hz, 4H), 7.40-7.51 (m, 6H), 4.60 (s, 2H), 3.91 (s, 3H), 1.20 (s, 9H).

Step 5: Synthesis of Compound WXA007-7

WXA007-5 (1.50 g, 2.65 mmol, 1 eq), WXA007-6 (0.60 g, 6.89 mmol, 2.60 eq), silver acetate (0.90 g, 5.39 mmol, 276.07 µL, 2.04 eq) and anhydrous DMF (20 mL) were added to a reaction flask and stirred at 20° C. for 16 hours. The reaction mixture was filtered, water (50 mL) was added to the filtrate, and the mixture was extracted with ethyl acetate (50 mL) for 3 times, the organic phases were combined, washed with saturated sodium chloride aqueous solution (50 mL) for 3 times, dried over anhydrous sodium sulfate, then filtered and concentrated to obtain a crude product, the crude product was separated and purified by column chromatography (PE:EA=1:0-5:1) to obtain WXA007-7. LCMS: m/z=620.9 [M+H]$^+$; $^1$H NMR (400 MHz, CDCl$_3$) δ ppm 7.63 (br t, J=5.65 Hz, 4H), 7.39-7.52 (m, 6H), 6.95 (br s, 1H), 5.05-5.17 (m, 1H), 4.68-4.78 (m, 1H), 4.53 (dt, J=9.22, 5.93 Hz, 1H), 4.31-4.45 (m, 2H), 3.77-3.88 (m, 4H), 3.56-3.66 (m, 1H), 2.67-2.78 (m, 1H), 2.55-2.66 (m, 1H), 1.10 (s, 9H).

Step 6: Synthesis of Compound WXA007-8

WXA007-7 (0.80 g, 1.29 mmol, 1 eq), N,N-dimethylethylenediamine (0.16 g, 1.82 mmol, 195.36 µL, 1.41 eq) and acetonitrile (10 mL) were added to a reaction flask, cuprous iodide (0.16 g, 840.12 µmol, 6.51 e-1 eq) was added under nitrogen atmosphere, and the mixture was stirred at 80° C.

for 10 hours. The reaction mixture was filtered, water (20 mL) was added thereto, and the mixture was extracted with ethyl acetate (20 mL) for 3 times, the organic phases were combined, washed with saturated sodium chloride aqueous solution (20 mL) for 3 times, dried over anhydrous sodium sulfate, then filtered and concentrated to obtain a crude product, the crude product was separated and purified by preparative TLC (PE:EA=3:1) to obtain WXA007-8. LCMS: m/z=539.0 [M+H]$^+$; $^1$H NMR (400 MHz, CDCl$_3$) δ ppm 7.63-7.72 (m, 4H), 7.37-7.45 (m, 6H), 5.06 (br dd, J=7.03, 3.76 Hz, 1H), 4.98 (br s, 2H), 4.48-4.71 (m, 2H), 4.36-4.45 (m, 1H), 4.30 (dt, J=9.03, 6.15 Hz, 1H), 3.90 (s, 3H), 2.66-2.76 (m, 1H), 2.29-2.40 (m, 1H), 1.06-1.13 (m, 9H).

Step 7: Synthesis of Compound WXA007-9

WXA007-8 (0.40 g, 742.52 μmol, 1 eq) and anhydrous THF (5 mL) were added to a reaction flask, a THF solution of tetrabutylammonium fluoride (1 M, 1.00 mL, 1.35 eq) was added, and the mixture was stirred at 20° C. for 1 hour. 20 mL of water was added to the reaction mixture, the mixture was then extracted with ethyl acetate (20 mL) for three times, the organic phases were combined, washed with saturated sodium chloride aqueous solution (20 mL) for three times, dried over anhydrous sodium sulfate, filtered and concentrated to obtain a crude product. The crude product was separated and purified by column chromatography (PE:EA=1:0-0:1) to obtain WXA007-9. LCMS: m/z=300.8 [M+H]$^+$; $^1$H NMR (400 MHz, CDCl$_3$) δ ppm 5.19 (qd, J=6.90, 2.89 Hz, 1H), 4.80-4.90 (m, 2H), 4.67-4.74 (m, 1H), 4.40-4.56 (m, 3H), 3.91 (s, 3H), 2.78-2.89 (m, 1H), 2.48-2.58 (m, 1H).

Step 8: Synthesis of Compound WXA007-10

WXA007-9 (30 mg, 99.90 μmol, 1 eq) and anhydrous DCM (2 mL) were added to a reaction flask, methanesulfonyl chloride (30 mg, 261.89 μmol, 20.27 μL, 2.62 eq) and triethylamine (30 mg, 296.47 μmol, 41.27 μL, 2.97 eq) were successively added at 0° C., and the mixture was stirred at 20° C. for 1 hour. The reaction mixture was quenched with saturated sodium bicarbonate solution (0.5 mL) and concentrated to obtain WXA007-10. LCMS: m/z=318.8 [M+H]$^+$.

Step 9: Synthesis of Compound WXA007-11

WXA007-10 (50 mg, 156.86 μmol, 1 eq), B-4 (50 mg, 156.85 μmol, 1 eq), potassium carbonate (70 mg, 506.49 μmol, 3.23 eq) and acetonitrile (2 mL) were added to a reaction flask and stirred at 60° C. for 12 hours. Water (10 mL) was added to the reaction mixture, and the mixture was extracted with ethyl acetate (10 mL) for 3 times, the organic phases were combined, washed with saturated sodium chloride aqueous solution (10 mL) for 3 times, dried over anhydrous sodium sulfate, then filtered and concentrated to obtain a crude product, the crude product was separated and purified by preparative TLC (PE:EA=2:1) to obtain WXA007-11. LCMS: m/z=601.1 [M+H]$^+$; $^1$H NMR (400 MHz, CDCl$_3$) δ ppm 7.56 (t, J=7.78 Hz, 1H), 7.43 (t, J=8.16 Hz, 1H), 7.09-7.16 (m, 2H), 6.96 (d, J=7.53 Hz, 1H), 6.73 (br s, 1H), 6.68 (d, J=8.53 Hz, 1H), 5.44 (s, 2H), 5.14 (br d, J=4.77 Hz, 1H), 4.58-4.73 (m, 3H), 4.42 (dt, J=9.03, 6.27 Hz, 1H), 3.90 (s, 5H), 3.30 (br s, 2H), 2.39-2.89 (m, 6H).

Step 10: Synthesis of Compound WXA007

WXA007-11 (60 mg, 99.82 μmol, 1 eq), MeOH (1 mL), THF (1 mL), water (0.50 mL) were added to a reaction flask, lithium hydroxide monohydrate (50 mg, 1.19 mmol, 11.94 eq) was added, and the mixture was stirred at 20° C. for 12 hours. Hydrochloric acid (1 M) was added dropwise to the reaction mixture, the pH value was adjusted to about 7, the mixture was concentrated to obtain a crude product, and the crude product was separated and purified by preparative TLC (DCM:MeOH=10:1) to obtain WXA007. LCMS: m/z=586.9 [M+H]$^+$; $^1$H NMR (400 MHz, DMSO-d$_6$) δ ppm 7.68 (br t, J=7.91 Hz, 1H), 7.55 (br t, J=8.03 Hz, 1H), 7.47 (br d, J=10.29 Hz, 1H), 7.30 (br d, J=8.28 Hz, 1H), 7.08 (br d, J=7.28 Hz, 1H), 6.67-6.79 (m, 2H), 5.40 (s, 2H), 5.02 (br s, 1H), 4.43-4.61 (m, 3H), 4.32-4.40 (m, 1H), 3.78-3.94 (m, 2H), 3.21-3.24 (m, 2H), 2.70 (br s, 4H), 2.30-2.44 (m, 2H).

Embodiment 7

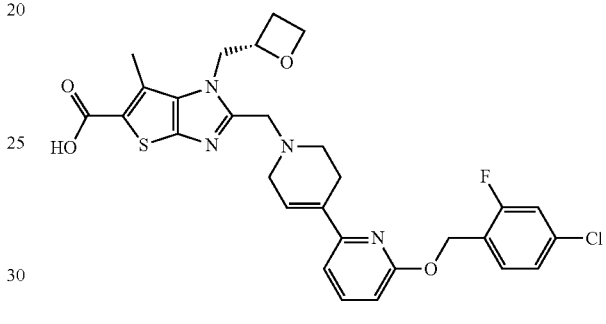

Synthetic Route:

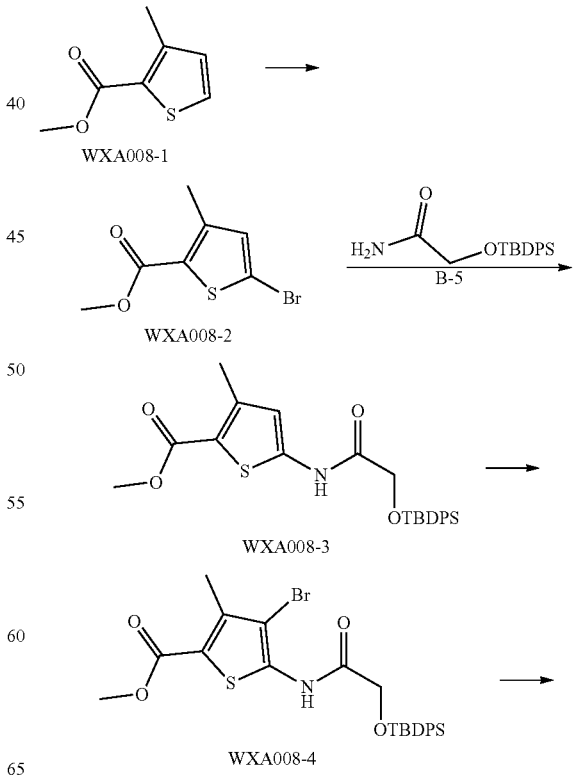

-continued

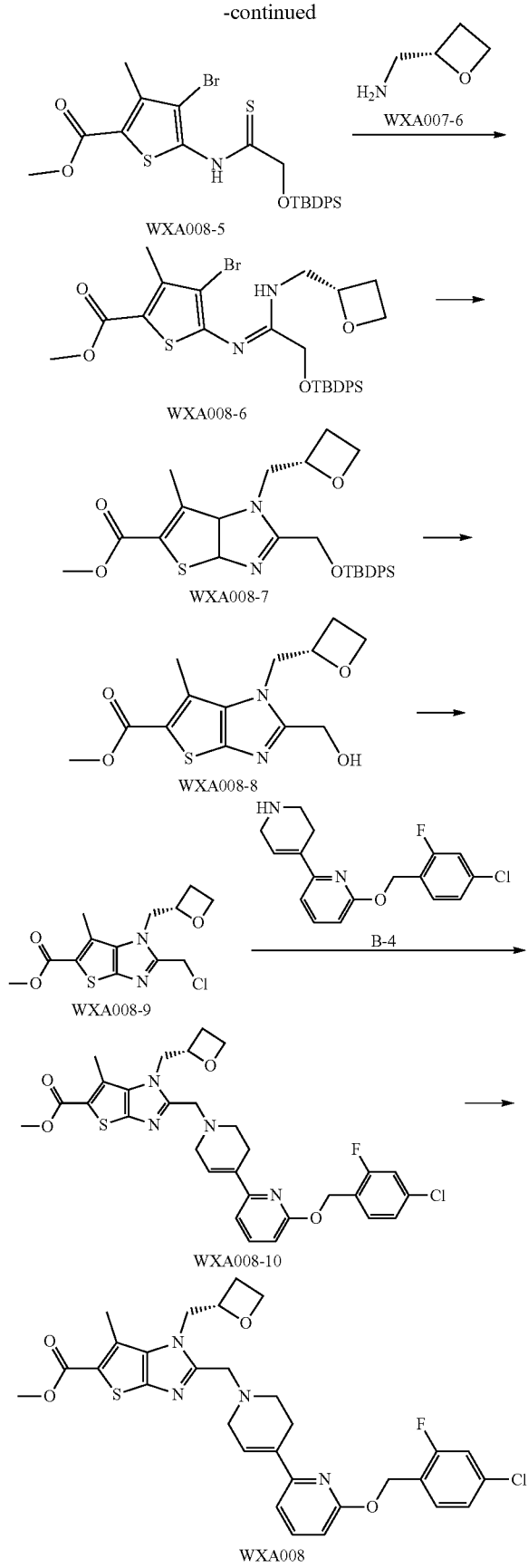

Step 1: Synthesis of Compound WXA008-2

WXA008-1 (6 g, 38.41 mmol, 1 eq) and anhydrous THF (75 mL) were added to a reaction flask, a THF solution of diisopropylamino lithium (2 M, 21.60 mL, 1.12 eq) was added at −30° C. under nitrogen atmosphere, the mixture was stirred at −30° C. for 0.5 hours, carbon tetrabromide (13.38 g, 40.35 mmol, 1.05 eq) was added, and the mixture was stirred at −30° C. for 0.5 hours, then stirred at 20° C. for 5 hours. The reaction mixture was evaporated to dryness by rotary evaporation, water (5 mL) was added, and the mixture was extracted with ethyl acetate (5 mL) for 3 times, the organic phases were combined and washed with saturated sodium chloride aqueous solution (5 mL), dried over anhydrous sodium sulfate, filtered and evaporated to dryness by rotary evaporation to obtain a crude product, the crude product was purified by column chromatography (PE:EA=1:0-20:1) to obtain WXA008-2. $^1$H NMR (400 MHz, CDCl$_3$) δ ppm 6.90 (s, 1H), 3.85 (s, 3H), 2.52 (s, 3H).

Step 2: Synthesis of Compound WXA008-3

WXA008-2 (1.6 g, 6.81 mmol, 1 eq), B-5 (2.13 g, 6.81 mmol, 1 eq), 9,9-dimethyl-4,5-bis(diphenylphosphino)xanthene (787.58 mg, 1.36 mmol, 0.2 eq), potassium carbonate (1.88 g, 13.61 mmol, 2 eq) and toluene (16 mL) were added to a reaction flask, tris(dibenzylideneacetone)dipalladium (623.21 mg, 680.57 μmol, 0.1 eq) was added under nitrogen atmosphere, and the mixture was stirred at 100° C. for 12 hours. The reaction mixture was filtered (with celite), the filter cake was washed with ethyl acetate (10 mL), the organic phase was washed with water (10 mL), the organic phase was collected, dried over anhydrous sodium sulfate, filtered and concentrated to obtain a crude product. MeOH (10 mL) was added to the crude product, the mixture was stirred at 20° C. for 16 hours, filtered, and the filter cake was collected to obtain WXA008-3. $^1$H NMR (400 MHz, CDCl$_3$) δ ppm 9.25 (s, 1H), 7.60-7.66 (m, 4H), 7.39-7.53 (m, 6H), 6.53 (s, 1H), 4.30 (s, 2H), 3.84 (s, 3H), 2.53 (s, 3H), 1.16 (s, 9H).

Step 3: Synthesis of Compound WXA008-4

WXA008-3 (1.3 g, 2.78 mmol, 1 eq), N-bromosuccinimide (519.50 mg, 2.92 mmol, 1.05 eq) and THF (13 mL) were added to a reaction flask and stirred at 20° C. for 5 hours. The reaction mixture was evaporated to dryness by rotary evaporation, water (15 mL) was added, and the mixture was extracted with ethyl acetate (15 mL) for 3 times, the organic phases were combined and washed with saturated sodium chloride aqueous solution (15 mL), dried over anhydrous sodium sulfate, filtered and concentrated to obtain a crude product, the crude product was separated and purified by column chromatography (PE:EA=5:1) to obtain WXA008-4. $^1$H NMR (400 MHz, CDCl$_3$) δ ppm 9.70 (s, 1H), 7.64-7.71 (m, 4H), 7.39-7.49 (m, 6H), 4.31 (s, 2H), 3.86 (s, 3H), 2.59 (s, 3H), 1.19 (s, 9H).

Step 4: Synthesis of Compound WXA008-5

WXA008-4 (1.1 g, 2.01 mmol, 1 eq) and dioxane (11 mL) were added to a reaction flask, Lawesson reagent (814.05 mg, 2.01 mmol, 1 eq) was added, and the mixture was stirred at 110° C. for 2 hours. The reaction mixture was evaporated to dryness by rotary evaporation to obtain a crude product, the crude product was separated and purified by column chromatography (PE:EA=1:0-5:1) to obtain WXA008-5. $^1$H NMR (400 MHz, CDCl₃) δ ppm 11.27 (br s, 1H), 7.67 (br d, J=6.53 Hz, 4H), 7.38-7.52 (m, 6H), 4.62 (s, 2H), 3.89 (s, 3H), 2.62 (s, 3H), 1.20 (s, 9H).

Step 5: Synthesis of Compound WXA008-6

WXA008-5 (1.3 g, 2.31 mmol, 1 eq), DMF (14 mL) were added to a reaction flask, silver acetate (771.34 mg, 4.62 mmol, 236.61 µL, 2 eq), WXA007-6 (390.00 mg, 4.48 mmol, 1.94 eq) were added, and the mixture was stirred at 20° C. for 12 hours. Water (50 mL) was added to the reaction mixture, and the mixture was extracted with ethyl acetate (50 mL) for 5 times, the organic phases were combined and washed with saturated sodium chloride aqueous solution (50 mL) for 2 times, dried over anhydrous sodium sulfate, filtered and concentrated to obtain a crude product, the crude product was separated and purified by column chromatography (PE:EA=1:0-5:1) to obtain WXA008-6. ¹H NMR (400 MHz, CDCl₃) δ ppm 7.62 (br d, J=5.52 Hz, 4H), 7.38-7.48 (m, 6H), 5.12 (br s, 1H), 4.73 (br d, J=6.78 Hz, 1H), 4.49-4.59 (m, 1H), 4.31-4.47 (m, 2H), 3.88 (br d, J=13.80 Hz, 1H), 3.78 (s, 3H), 3.67 (br s, 1H), 2.57-2.82 (m, 2H), 2.42 (s, 3H), 1.10 (s, 9H).

Step 6: Synthesis of Compound WXA008-7

WXA008-6 (200 mg, 324.86 µmol, 1 eq), DMF (4 mL) were added to a reaction flask, cuprous iodide (6.19 mg, 32.49 µmol, 0.1 eq), N,N-dimethylethylenediamine (5.73 mg, 64.97 µmol, 6.99 µL, 0.2 eq) and potassium carbonate (89.79 mg, 649.72 µmol, 2 eq) were added successively and the mixture was stirred under nitrogen atmosphere at 80° C. for 12 hours. Water (10 mL) was added to the reaction mixture, and the mixture was extracted with ethyl acetate (10 mL) for 4 times, the organic phases were combined, washed with saturated sodium chloride aqueous solution (10 mL), dried over anhydrous sodium sulfate, then filtered and concentrated to obtain a crude product, the crude product was separated and purified by preparative TLC (PE:EA=3:1) to obtain WXA008-7. LCMS: m/z=535.0 [M+H]⁺.

Step 7: Synthesis of Compound WXA008-8

WXA008-7 (90 mg, 168.31 µmol, 1 eq) and THF (1 mL) were added to a reaction flask, a THF solution of tetrabutylammonium fluoride (1 M, 201.97 µL, 1.2 eq) was added and the mixture was stirred at 20° C. for 2 hours. Water (10 mL) was added to the reaction mixture, and the mixture was extracted with ethyl acetate (10 mL) for 3 times, the organic phases were combined, washed with saturated sodium chloride aqueous solution (10 mL), dried over anhydrous sodium sulfate, then filtered and concentrated to obtain a crude product, the crude product was separated and purified by preparative TLC (DCM:MeOH=20:1) to obtain WXA008-8. ¹H NMR (400 MHz, CDCl₃) δ ppm 5.15-5.26 (m, 1H), 4.82-4.94 (m, 2H), 4.66-4.76 (m, 1H), 4.57-4.65 (m, 1H), 4.48-4.56 (m, 1H), 4.43 (dt, J=9.29, 6.02 Hz, 1H), 3.88 (s, 3H), 2.75-2.87 (m, 1H), 2.73 (s, 3H), 2.45-2.58 (m, 1H).

Step 8: Synthesis of Compound WXA008-9

WXA008-8 (24 mg, 80.99 µmol, 1 eq), DCM (1 mL) were added to a reaction flask, triethylamine (24.59 mg, 242.96 µmol, 33.82 µL, 3 eq) was added, p-toluenesulfonyl chloride (30.88 mg, 161.98 µmol, 2 eq) was added at 0° C., and the mixture was stirred at 20° C. for 2 hours. Water (10 mL) was added to the reaction mixture, and the mixture was extracted with DCM (10 mL) for 3 times, the organic phases were combined, washed with saturated sodium chloride aqueous solution (10 mL), dried over anhydrous sodium sulfate, then filtered and concentrated to obtain a crude product, the crude product was separated and purified by preparative TLC (PE:EA=3:1) to obtain WXA008-9. LCMS: m/z=314.8 [M+H]⁺.

Step 9: Synthesis of Compound WXA008-10

WXA008-9 (10 mg, 31.77 µmol, 1 eq), B-4 (10.23 mg, 32.09 µmol, 1.01 eq), potassium carbonate (9.00 mg, 65.12 µmol, 2.05 eq) and acetonitrile (1 mL) were added to a reaction flask and the mixture was stirred at 60° C. for 12 hours. The reaction mixture was evaporated to dryness by rotary evaporation, water (10 mL) was added thereto, and the mixture was extracted with ethyl acetate (10 mL) for 3 times, the organic phases were combined, washed with saturated sodium chloride aqueous solution (10 mL), dried over anhydrous sodium sulfate, then filtered and concentrated to obtain a crude product, the crude product was separated and purified by preparative TLC (DCM:MeOH=20:1) to obtain WXA008-10. LCMS: m/z=596.9 [M+H]⁺.

Step 10: Synthesis of Compound WXA008

WXA008-10 (10 mg, 16.75 µmol, 1 eq), lithium hydroxide monohydrate (3.51 mg, 83.74 µmol, 5 eq), THF (0.5 mL), MeOH (0.5 mL) and water (0.5 mL) were added to a reaction flask and stirred at 20° C. for 12 hours. The reaction mixture was separated and purified by preparative high performance liquid chromatography (chromatographic column: Phenomenex Gemini-NX 80*40 mm*3 µm; mobile phase: [Water (0.05% ammonia water)-acetonitrile]; B (acetonitrile) %: 16%-70%, 8 min) to obtain WXA008. LCMS: m/z=583.1 [M+H]⁺; ¹H NMR (400 MHz, DMSO-d₆) δ ppm 7.69 (t, J=7.78 Hz, 1H), 7.56 (t, J=8.16 Hz, 1H), 7.47 (dd, J=10.04, 2.01 Hz, 1H), 7.30 (dd, J=8.41, 1.63 Hz, 1H), 7.09 (d, J=7.53 Hz, 1H), 6.70-6.76 (m, 2H), 5.40 (s, 2H), 5.05 (br d, J=7.03 Hz, 1H), 4.71-4.82 (m, 1H), 4.60 (br d, J=13.05 Hz, 1H), 4.43-4.54 (m, 1H), 4.31-4.41 (m, 1H), 3.95 (d, J=13.55 Hz, 1H), 3.79 (d, J=13.30 Hz, 1H), 3.10-3.26 (m, 2H), 2.65-2.74 (m, 6H), 2.37-2.48 (m, 2H), 2.33 (s, 1H).

Embodiment 8

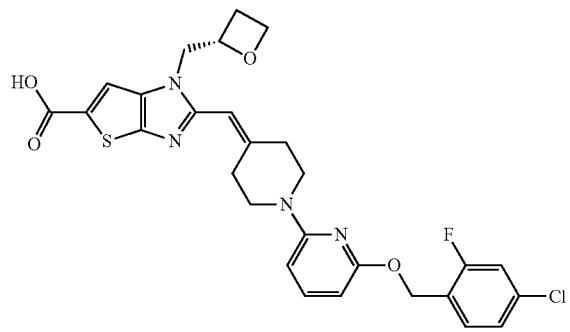

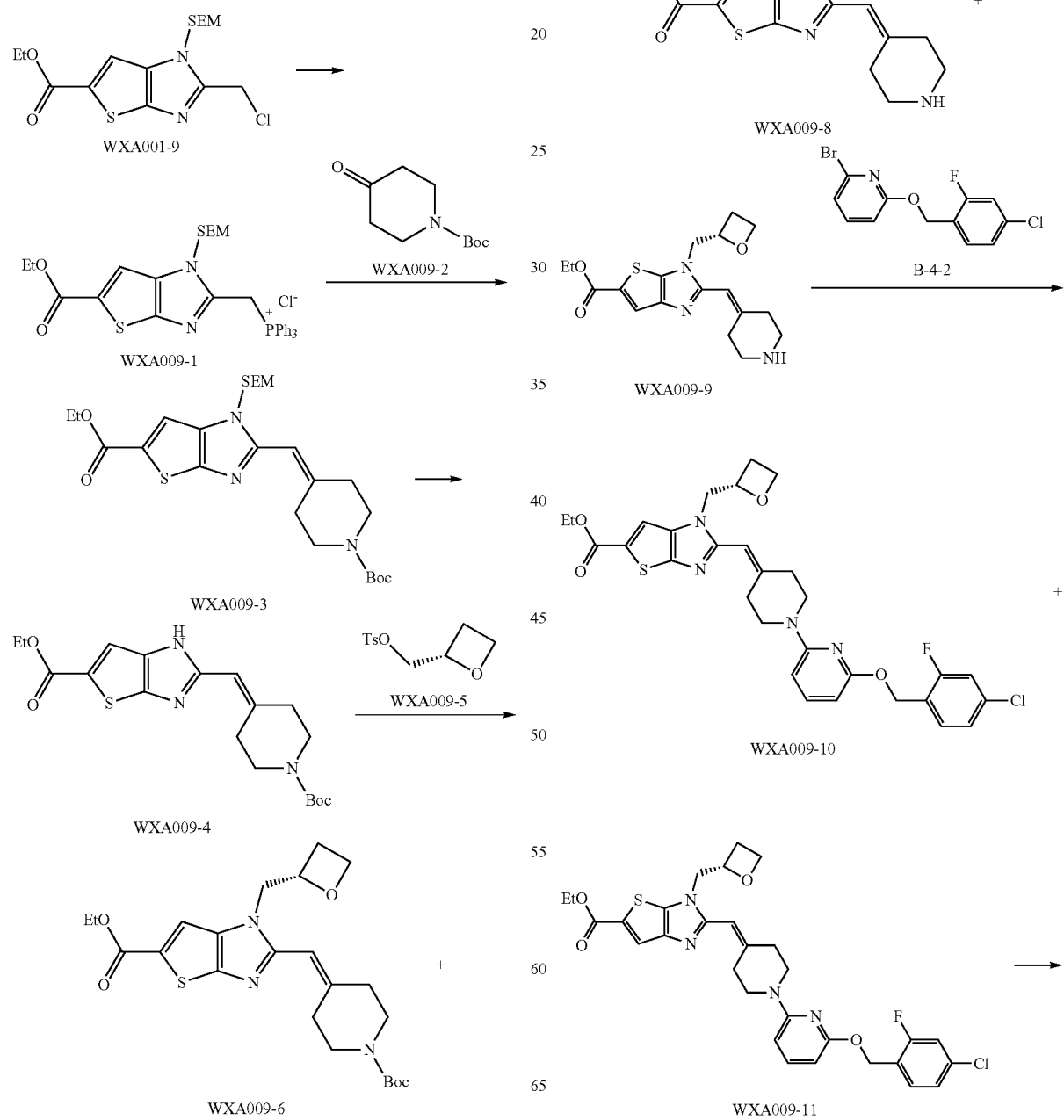

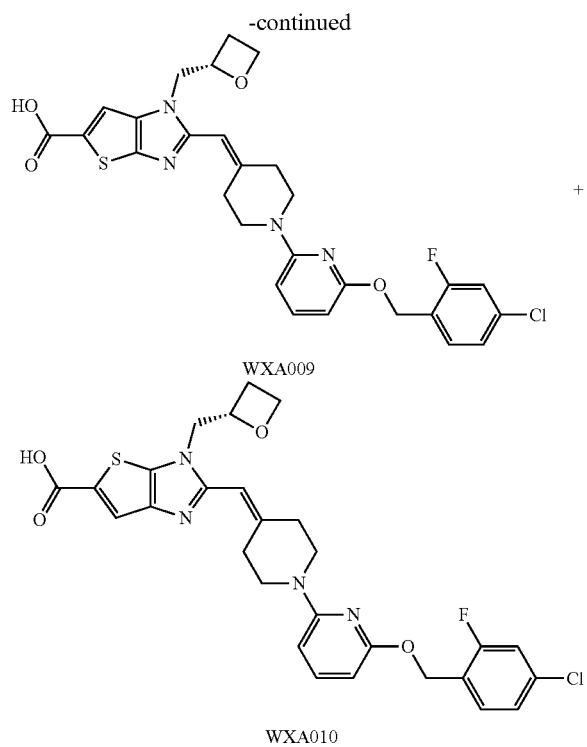

WXA009

WXA010

Step 1: Synthesis of Compound WXA009-1

WXA001-9 (200 mg, 533.39 μmol, 1 eq), triphenylphosphine (140.00 mg, 533.77 μmol, 1.00 eq) and acetonitrile (2 mL) were added to a reaction flask and stirred at 80° C. for 3 hours. An acetonitrile solution of WXA009-1 was obtained and directly used in the next step without post-treatment. LCMS: m/z=601.1 [M−Cl]$^+$.

Step 2: Synthesis of Compound WXA009-3

WXA009-2 (110 mg, 552.08 μmol, 1.04 eq), acetonitrile (2 mL) and cesium carbonate (260.68 mg, 800.09 μmol, 1.50 eq) were added to an acetonitrile solution containing WXA009-1 (339.9 mg, 533.39 μmol, 1 eq) and the reaction was carried out at 80° C. for 16 hours. 10 mL of water was added to the reaction mixture, the mixture was then extracted with ethyl acetate (10 mL) for 3 times, the organic phases were combined, dried over anhydrous sodium sulfate, filtered and concentrated to obtain a crude product of WXA009-3, the crude product was separated by preparative TLC (PE:EA=2:1) to obtain WXA009-3. LCMS: m/z=522.1 [M+H]$^+$.

Step 3: Synthesis of Compound WXA009-4

WXA009-3 (124 mg, 237.66 μmol, 1 eq) and a THF solution of tetrabutylammonium fluoride (1 M, 6 mL, 25.25 eq) were added to a reaction flask, the reaction was carried out at 25° C. for 16 hours, the reaction mixture was concentrated, 20 mL of water was added, the mixture was then extracted twice with DCM (10 mL), the organic phases were combined and dried over anhydrous sodium sulfate, then filtered and concentrated to obtain a crude product of WXA009-4. LCMS: m/z=391.9 [M+H]$^+$.

Step 4: Synthesis of Compound WXA009-6 and WXA009-7

WXA009-4 (134 mg, 342.29 μmol, 1 eq), WXA009-5 (114.8 mg, 421.62 μmol, 89% purity, 1.23 eq), cesium carbonate (300 mg, 920.76 μmol, 2.69 eq) and acetonitrile (2 mL) were added to a reaction flask and the reaction was carried out at 80° C. for 12 hours under nitrogen atmosphere. The reaction mixture was filtered with celite, the filter cake was rinsed with 10 mL of ethyl acetate, the organic phase was collected and washed with 10 mL of saturated brine, the aqueous phase was extracted twice with 10 mL of ethyl acetate, the combined organic phases were dried over anhydrous sodium sulfate, filtered and concentrated to obtain a crude product, the crude product was separated and purified by preparative TLC (PE:EA=1:1) to obtain a mixture of WXA009-6 and WXA009-7. LCMS (retention time: 0.908 min): m/z=462.1 [M+H]$^+$; LCMS (retention time: 0.983 min): m/z=462.1 [M+H]$^+$.

Step 5: Synthesis of Compound WXA009-8 and WXA009-9

A mixture of WXA009-6 and WXA009-7 (66 mg, 142.98 μmol, 1 eq), DCM (2 mL) and trifluoroacetic acid (308.00 mg, 2.70 mmol, 200 μL, 19 eq) were added to a reaction flask and the reaction was carried out at 25° C. for 16 hours. Saturated sodium bicarbonate aqueous solution was added to the reaction mixture, the pH value was adjusted to 7, then the mixture was extracted twice with DCM (10 mL), the organic phases were combined and dried over anhydrous sodium sulfate, and then filtered and concentrated to obtain a crude mixture of WXA009-8 and WXA009-9. LCMS: m/z=362.0 [M+H]$^+$.

Step 6: Synthesis of Compound WXA009-10 and WXA009-11

A mixture of WXA009-8 and WXA009-9 (18 mg, 49.80 μmol, 1 eq), B-4-2 (18.00 mg, 56.86 μmol, 1.14 eq), tris(dibenzylideneacetone)dipalladium (1.14 mg, 1.24 μmol, 0.025 eq), cesium carbonate (16.23 mg, 49.80 μmol, 1 eq), 2-dicyclohexylphosphino-2',6'-diisopropoxybiphenyl (1.16 mg, 2.49 μmol, 0.05 eq), toluene (1 mL) were added to a reaction flask, and the reaction was carried out for 12 hours at 100° C. under nitrogen atmosphere. The reaction mixture was concentrated to obtain a crude product, the crude product was separated and purified by preparative TLC (PE:EA=1:1) to obtain a mixture of WXA009-10 and WXA009-11. LCMS (retention time: 1.045 min): m/z=597.1 [M+H]$^+$; LCMS (retention time: 1.132 min): m/z=597.2 [M+H]$^+$.

Step 7: Synthesis of Compound WXA009 and WXA010

A mixture of WXA009-10 and WXA009-11 (48 mg, 80.38 μmol, 1 eq), lithium hydroxide monohydrate (12 mg, 285.96 μmol, 3.56 eq), THF (1 mL), MeOH (1 mL) and water (0.5 mL) were added to a reaction flask and stirred at 25° C. for 24 hours. The reaction mixture was concentrated, 10 mL of DCM was added thereto, the pH value was adjusted to 7 with 1 M hydrochloric acid aqueous solution, the organic phase was concentrated to obtain a crude product, and the crude product was separated and purified by preparative TLC (DCM:MeOH=10:1) to obtain a mixture of WXA009 and WXA010. LCMS (retention time: 0.939 min):

m/z=569.1 [M+H]+; LCMS (retention time: 1.017 min): m/z=569.1 [M+H]+. The mixture was separated by supercritical fluid chromatography (chromatographic column CHIRALPAK® IG (Particle Size: 10 μm; Dimensions: 30 mm Ø*250 mmL); mobile phase: supercritical $CO_2$, B: EtOH (0.1% $NH_3H_2O$), A:B=40:60, 80 mL/min (volume ratio, isocratic elution) to obtain WXA009 (retention time: 4.39 min) and WXA010 (retention time: 6.06 min).

WXA009: LCMS: m/z=569.1 [M+H]+; $^1$H NMR (400 MHz, DMSO-$d_6$) δ ppm 7.41-7.59 (m, 4H), 7.30 (br d, J=8.28 Hz, 1H), 6.34-6.50 (m, 2H), 6.07 (d, J=7.78 Hz, 1H), 5.34 (s, 2H), 4.98 (br s, 1H), 4.35-4.53 (m, 3H), 4.24-4.33 (m, 1H), 3.55-3.70 (m, 4H), 3.05 (br s, 2H), 2.60-2.73 (m, 1H), 2.28-2.43 (m, 3H).

WXA010: LCMS: m/z=569.1 [M+H]+; $^1$H NMR (400 MHz, DMSO-$d_6$) δ ppm 7.36-7.57 (m, 4H), 7.30 (br d, J=8.28 Hz, 1H), 6.34-6.48 (m, 2H), 6.07 (d, J=7.78 Hz, 1H), 5.34 (s, 2H), 5.05 (br s, 1H), 4.41-4.52 (m, 2H), 4.32 (br d, J=11.54 Hz, 2H), 3.62 (br d, J=17.32 Hz, 4H), 3.02 (br s, 2H), 2.63-2.75 (m, 1H), 2.30-2.43 (m, 3H).

WXA009 was identified by two-dimensional NMR NOE that $C_{35}$—H was related to $C_{30}$—H, and the product structure was correct.

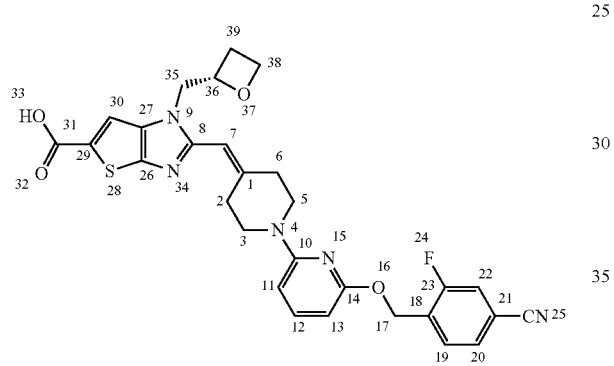

Embodiment 9

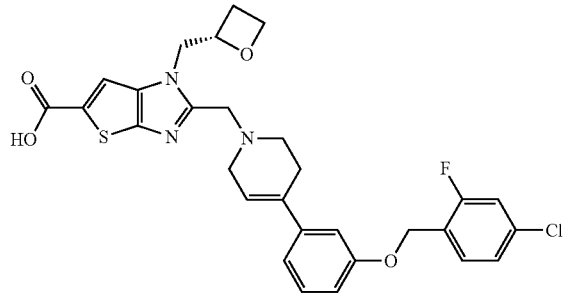 [SMILES: Cc1c(C(=O)O)sc2nc(CN3CC=C(c4cccc(OCc5ccc(Cl)cc5F)n4)CC3)n(C[C@@H]3CCO3)c12]

Synthetic Route:

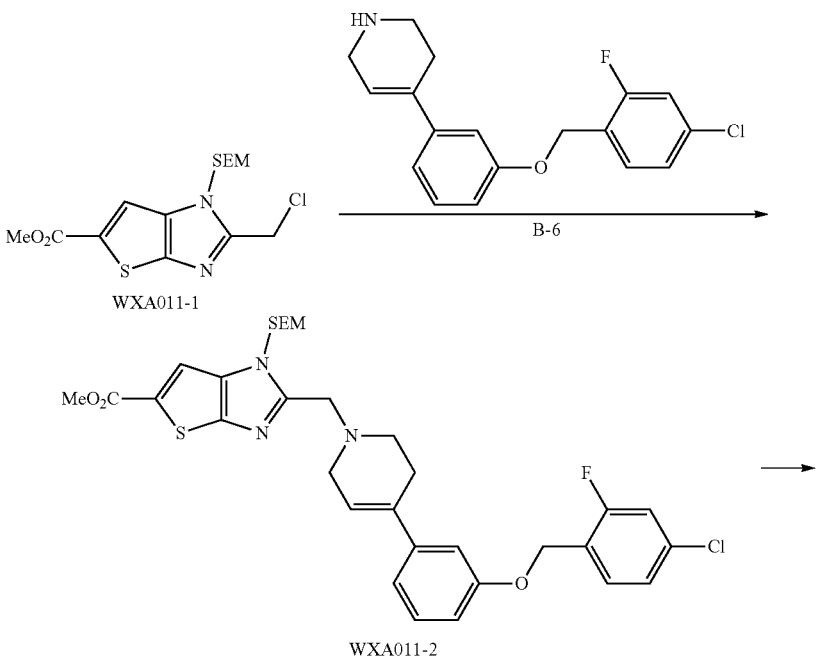

-continued
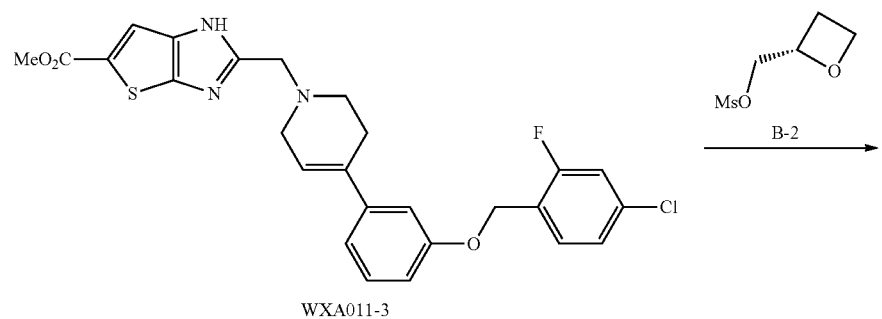
WXA011-3
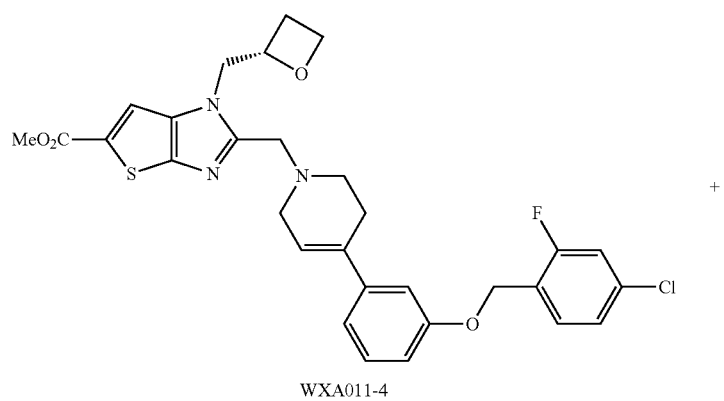
WXA011-4
+
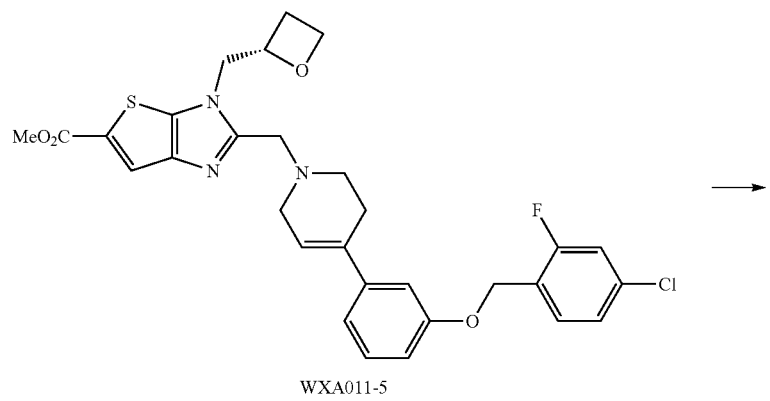
WXA011-5
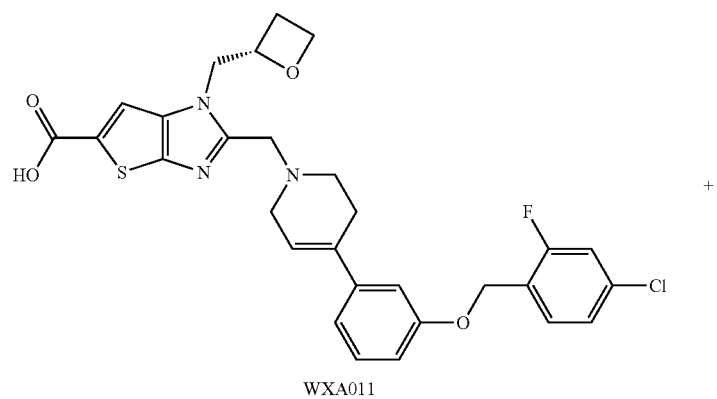
WXA011
+

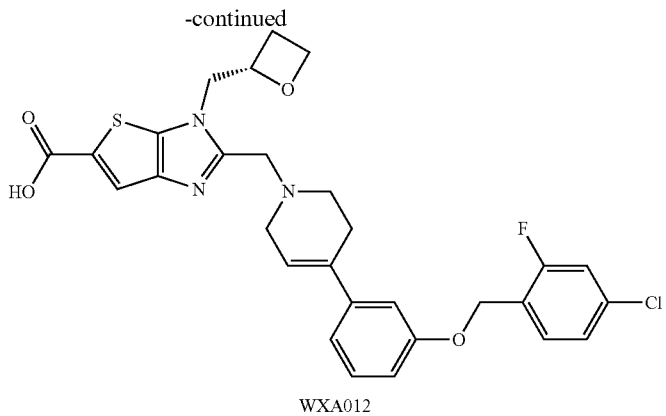

WXA012

Step 1: Synthesis of Compound WXA011-2

WXA011-1 (360 mg, 997.42 μmol, 1 eq) and B-6 (417 mg, 1.19 mmol, 91% purity, 1.2 eq) were added to a reaction flask containing 5 mL of acetonitrile, potassium carbonate (290 mg, 2.10 mmol, 2.10 eq) was added, the mixture was stirred at 80° C. for 12 hours, the reaction mixture was concentrated, 20 mL of water was added, then the mixture was extracted twice with ethyl acetate (20 mL), the organic phases were combined, dried over anhydrous sodium sulfate, the filtrate was concentrated to obtain a crude product, and the crude product was separated and purified by column chromatography (PE:EA=1:0-5:1) to obtain WXA011-2. LCMS: m/z=642.1 [M+H]$^+$.

Step 2: Synthesis of Compound WXA011-3

WXA011-2 (600 mg, 901.70 μmol, 96.52% purity, 1 eq) was added to a reaction flask containing 10 mL of DCM, trifluoroacetic acid (3.08 g, 27.01 mmol, 2 mL, 29.96 eq) was added, then the mixture was stirred at 28° C. for 12 hours, the reaction mixture was concentrated, dissolved with ethyl acetate (20 mL), the pH value was adjusted to 7-8 with saturated sodium bicarbonate aqueous solution, the mixture was extracted twice with ethyl acetate (20 mL), the organic phases were combined and washed with saturated brine (20 mL), dried over anhydrous sodium sulfate, the filtrate was concentrated to obtain a crude product, the crude product was separated and purified by column chromatography (PE:EA=1:0-1:1) to obtain WXA011-3. LCMS: m/z=512.1 [M+H]$^+$.

Step 3: Synthesis of Compound WXA011-4 and WXA011-5

WXA011-3 (200 mg, 367.31 μmol, 94.03% purity, 1 eq) was added to a reaction flask containing 5 mL of acetonitrile, B-2 (200 mg, 1.20 mmol, 3.28 eq) and cesium carbonate (350 mg, 1.07 mmol, 2.92 eq) were added, the mixture was stirred at 80° C. for 20 hours, the reaction mixture was concentrated, water (20 mL) was added, and then the mixture was extracted with ethyl acetate (20 mL) for three times, the organic phases were combined, dried over anhydrous sodium sulfate, the filtrate was concentrated to obtain a crude product, the crude product was separated and purified by column chromatography (PE:EA=1:0-1:1) to obtain a mixture of WXA011-4 and WXA011-5. LCMS (retention time: 2.467 min): m/z=582.1 [M+H]$^+$; LCMS (retention time: 2.501 min): m/z=582.1 [M+H]$^+$.

Step 4: Synthesis of Compound WXA011 and WXA012

A mixture of WXA011-4 and WXA011-5 (150 mg, 235.20 μmol, 91.27 purity, 1 eq) was added to a reaction flask containing water (1 mL) and THF (5 mL), lithium hydroxide monohydrate (210 mg, 5.00 mmol, 21.28 eq) was added, then the mixture was stirred at 50° C. for 16 hours and concentrated, then dissolved with 10 mL of water, the pH value was adjusted to about 6 with citric acid aqueous solution (1 M), the mixture was extracted with DCM (15 mL) for 3 times, the organic phases were combined and washed with saturated brine (10 mL), dried over anhydrous sodium sulfate, the filtrate was concentrated to obtain a crude product, the crude product was separated and purified by column chromatography (DCM:MeOH=1:0-16:1) to obtain a mixture of WXA011 and WXA012. Separation was carried out by supercritical fluid chromatography (chromatographic column: CHIRALPAK® AD (Particle Size: 10 μm; Dimensions: 30 mm Ø*250 mmL); mobile phase: Supercritical $CO_2$, B: EtOH (0.1% $NH_3H_2O$), A:B=70:50, 70 mL/min (volume ratio, isocratic elution) to obtain WXA011 (retention time: 6.6 min) and WXA012 (retention time: 11.6 min).

WXA011: LCMS: m/z=568.1 [M+H]$^+$; $^1$H NMR (400 MHz, CDCl$_3$) δ ppm 7.58 (br s, 1H), 7.45 (t, J=8.03 Hz, 1H), 7.22-7.27 (m, 1H), 7.10-7.18 (m, 2H), 6.98-7.05 (m, 2H), 6.86 (dd, J=8.28, 2.01 Hz, 1H), 6.07 (br s, 1H), 5.12 (br s, 1H), 5.09 (s, 2H), 4.50-4.64 (m, 3H), 4.33-4.40 (m, 1H), 4.08 (br s, 2H), 3.44 (br s, 2H), 3.02 (br s, 2H), 2.69 (br d, J=9.79 Hz, 1H), 2.63 (br s, 2H), 2.33-2.44 (m, 1H).

WXA012: LCMS: m/z=568.1 [M+H]$^+$; $^1$H NMR (400 MHz, CDCl$_3$) δ ppm 7.88 (s, 1H), 7.45 (t, J=8.03 Hz, 1H), 7.21-7.27 (m, 1H), 7.10-7.18 (m, 2H), 6.97-7.04 (m, 2H), 6.85 (dd, J=8.16, 2.13 Hz, 1H), 6.06 (br s, 1H), 5.22 (br s, 1H), 5.09 (s, 2H), 4.46-4.67 (m, 3H), 4.39-4.45 (m, 1H), 4.03 (s, 2H), 3.33 (br s, 2H), 2.87-2.95 (m, 2H), 2.65-2.69 (m, 1H), 2.57 (br s, 2H), 2.42-2.50 (m, 1H).

Embodiment 10

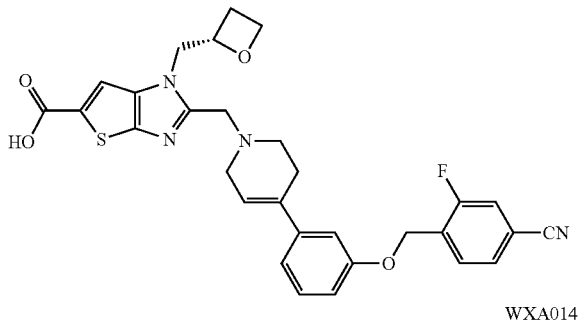

WXA013

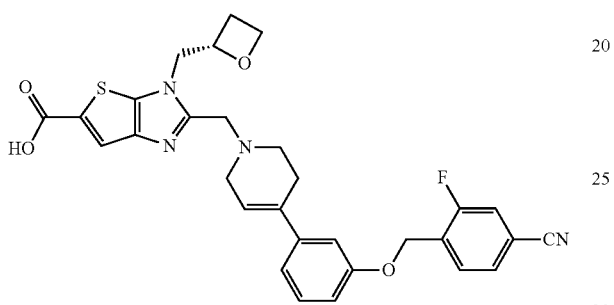

WXA014

The embodiment 10 was synthesized with reference to steps 1-4 of embodiment 9, by replacing fragment B-6 with B-7.

A mixture of WXA013 and WXA014 was separated by supercritical fluid chromatography (chromatographic column: CHIRALCEL ® IG (Particle Size: 10 μm; Dimensions: 30 mm Ø*250 mmL)); mobile phase: Supercritical $CO_2$, B: EtOH (0.1% $NH_3H_2O$), A:B=40:60, 80 mL/min (volume ratio, isocratic elution) to obtain WXA013 (retention time: 7.08 min) and WXA014 (retention time: 8.87 min).

WXA013: LCMS: m/z=559.1 [M+H]$^+$; $^1$H NMR (400 MHz, CDCl$_3$) δ ppm 7.70 (t, J=7.53 Hz, 1H), 7.60 (s, 1H), 7.47-7.53 (m, 1H), 7.40 (dd, J=9.29, 1.51 Hz, 1H), 7.24-7.27 (m, 1H), 7.04 (d, J=8.03 Hz, 1H), 7.00 (s, 1H), 6.86 (dd, J=8.16, 2.13 Hz, 1H), 6.08 (br s, 1H), 5.19 (s, 2H), 5.14 (br s, 1H), 4.49-4.66 (m, 3H), 4.37 (dt, J=9.29, 5.90 Hz, 1H), 4.07 (s, 2H), 3.42 (br s, 2H), 2.95-3.04 (m, 2H), 2.66-2.73 (m, 1H), 2.62 (br s, 2H), 2.34-2.46 (m, 1H).

WXA014: LCMS: m/z=559.2 [M+H]$^+$; $^1$H NMR (400 MHz, CDCl$_3$) δ ppm 7.77 (s, 1H), 7.68 (br t, J=7.28 Hz, 1H), 7.49 (br d, J=8.03 Hz, 1H), 7.38 (br d, J=9.29 Hz, 1H), 7.27 (s, 1H), 6.98-7.11 (m, 2H), 6.81-6.94 (m, 1H), 6.07 (br s, 1H), 5.19 (br s, 1H), 5.18 (s, 2H), 4.51-4.78 (m, 3H), 4.38-4.47 (m, 1H), 4.29 (br s, 2H), 3.64 (br s, 2H), 3.21 (br s, 2H), 2.73 (br s, 2H), 2.69 (br s, 1H), 2.41-2.51 (m, 1H).

WXA013 was identified by two-dimensional NMR NOE that $C_{10}$—H was related to $C_8$—H, and the product structure was correct.

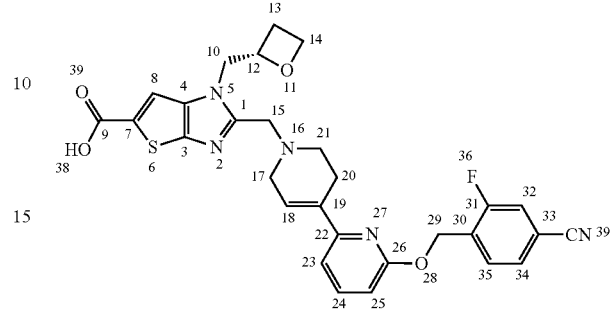

Embodiment 11

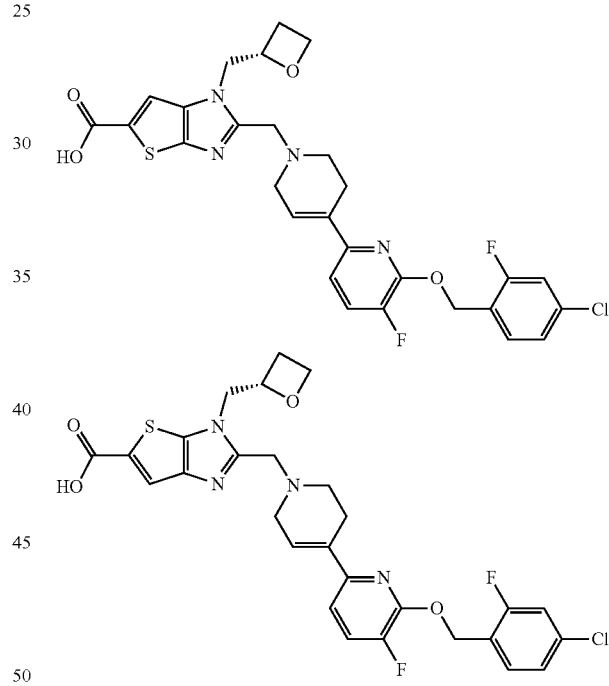

Synthetic Route:

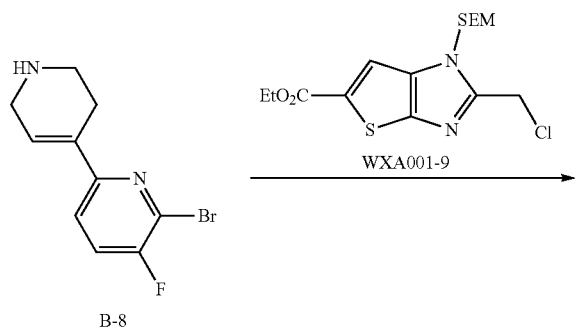

B-8

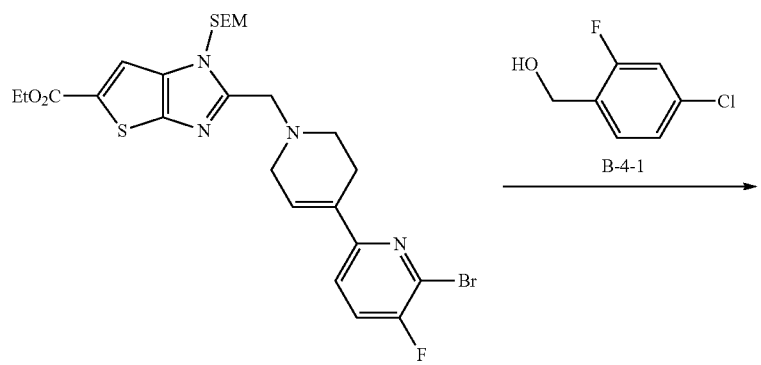
WXA015-1
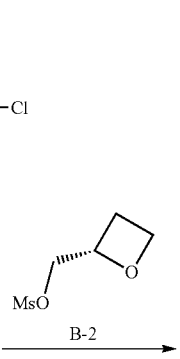
WXA015-2
WXA015-3
WXA015-4

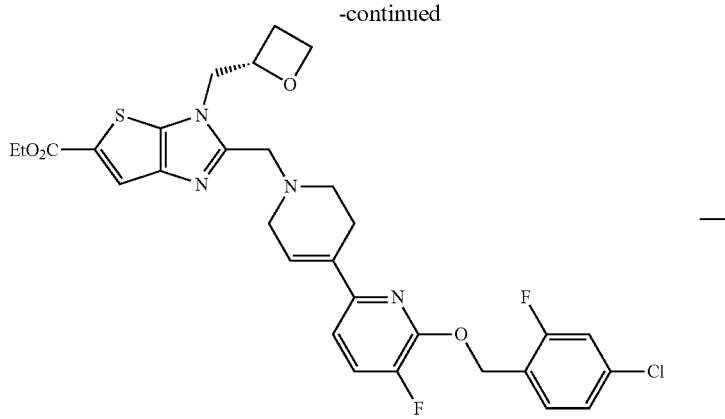

WXA015-5

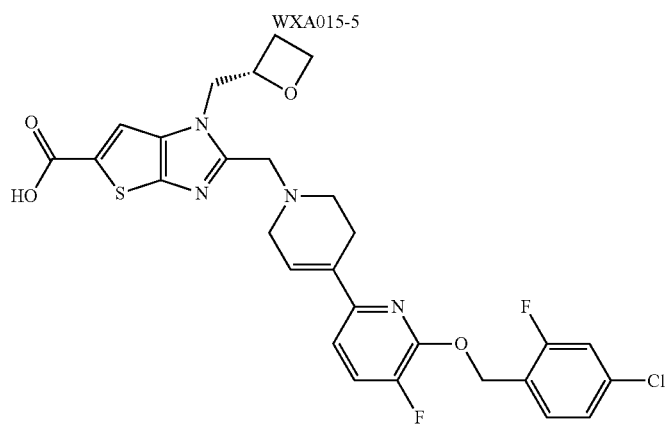

WXA015

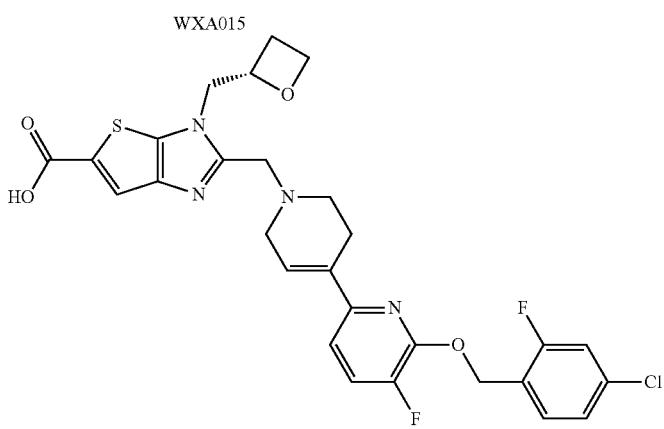

WXA016

Step 1: Synthesis of Compound WXA015-1

B-8 (0.39 g, 1.52 mmol, 1 eq), WXA001-9 (0.58 g, 1.55 mmol, 1.02 eq), potassium carbonate (0.39 g, 2.82 mmol, 1.86 eq) and 4 mL of acetonitrile were added to a reaction flask and stirred at 60° C. for 12 hours. The reaction mixture was concentrated, water (20 mL) was added thereto, and the mixture was extracted with ethyl acetate (20 mL) for 3 times, the organic phases were combined, washed with saturated brine (20 mL), dried over anhydrous sodium sulfate, and the filtrate was concentrated to obtain a crude product, the crude product was separated and purified by column chromatography (PE:EA=1:0-3:1) to obtain WXA015-1. LCMS: m/z=597.0 [M+H]$^+$.

Step 2: Synthesis of Compound WXA015-2

WXA015-1 (0.72 g, 1.21 mmol, 1 eq), B-4-1 (216.00 mg, 1.35 mmol, 1.11 eq), cesium carbonate (720.00 mg, 2.21 mmol, 1.83 eq), 2-dicyclohexylphosphino-2',6'-diisopropoxybiphenyl (72.00 mg, 154.30 μmol, 1.28 e-1 eq) and dioxane (8 mL) were added to a reaction flask, palladium acetate (72.00 mg, 320.70 μmol, 2.65 e-1 eq) was added under nitrogen atmosphere, the mixture was then stirred at 100° C. for 2.5 hours, the reaction mixture was concentrated, water (50 mL) was added, then the mixture was extracted with ethyl acetate (50 mL) for 3 times, the organic phases were combined and washed with saturated brine (50 mL), dried over anhydrous sodium sulfate, filtered and the filtrate was concentrated to obtain a crude product, the crude product was separated and purified by column chromatography (PE:EA=1:0-5:1) to obtain WXA015-2. LCMS: m/z=675.1 [M+H]+.

Step 3: Synthesis of Compound WXA015-3

WXA015-2 (0.15 g, 222.14 μmol, 1 eq) and THF (3 mL) were added to a reaction flask, tetrabutylammonium fluoride (1 M, 2.11 mL, 9.5 eq) was added, the mixture was stirred at 60° C. for 12 hours and concentrated, water (10 mL) was added thereto, then the mixture was extracted with ethyl acetate (10 mL) for 3 times, the organic phases were combined, washed with saturated brine (10 mL), dried over anhydrous sodium sulfate, and the filtrate was concentrated to obtain a crude product, the crude product was separated and purified by preparative TLC (DCM:MeOH=20:1) to obtain WXA015-3. LCMS: m/z=545.0 [M+H]+.

Step 4: Synthesis of Compound WXA015-4 and WXA015-5

WXA015-3 (0.1 g, 183.49 μmol, 1 eq), B-2 (92 mg, 553.57 μmol, 3.02 eq), cesium carbonate (0.18 g, 552.45 μmol, 3.01 eq) and acetonitrile (2 mL) were added to a reaction flask, the mixture was stirred at 80° C. for 12 hours, the reaction mixture was concentrated, water (10 mL) was added thereto, and then the mixture was extracted with ethyl acetate (10 mL) for three times, the organic phases were combined and washed with saturated brine (10 mL), dried over anhydrous sodium sulfate, the filtrate was concentrated to obtain a crude product, the crude product was separated and purified by preparative TLC (DCM:MeOH=20:1) to obtain a mixture of WXA015-4 and WXA015-5. LCMS: m/z=615.0 [M+H]+.

Step 5: Synthesis of Compound WXA015 and WXA016

A mixture of WXA015-4 and WXA015-5 (80 mg, 130.06 μmol, 1 eq), lithium hydroxide monohydrate (80 mg, 1.91 mmol, 14.66 eq), THF (0.5 mL), MeOH (0.5 mL) and water (0.5 mL) were added to a reaction flask, the mixture was stirred at 25° C. for 1.5 hours, then separated and purified by a preparative high performance liquid chromatography (chromatographic column: Welch Xtimate C18 100*25 mm*3 μm; mobile phase: [Water (0.05% $NH_3H_2O$)-acetonitrile]; B (acetonitrile) %: 15%-45%, 8 min) to obtain a mixture of WXA015 and WXA016. The mixture was separated by supercritical fluid chromatography (chromatographic column: DAICEL CHIRALPAK AD (250 mm*30 mm, 10 μm); mobile phase: Supercritical $CO_2$, B: EtOH (0.1% $NH_3H_2O$), A:B=55:45, 80 mL/min (volume ratio, isocratic elution) to obtain WXA015 (retention time: 5.05 min) and WXA016 (retention time: 7.2 min).

WXA015: LCMS: m/z=587.2 [M+H]+; $^1$H NMR (400 MHz, $CD_3OD$) δ ppm 7.62 (s, 1H), 7.51 (t, J=8.16 Hz, 1H), 7.41 (dd, J=10.16, 8.16 Hz, 1H), 7.18-7.25 (m, 2H), 7.04 (dd, J=8.16, 2.64 Hz, 1H), 6.63 (br s, 1H), 5.50 (s, 2H), 5.13-5.22 (m, 1H), 4.51-4.69 (m, 3H), 4.41 (dt, J=9.22, 5.93 Hz, 1H), 3.87-3.99 (m, 2H), 3.22 (br s, 2H), 2.75-2.84 (m, 2H), 2.66-2.74 (m, 1H), 2.58 (br s, 2H), 2.41-2.51 (m, 1H).

WXA016: LCMS: m/z=587.2 [M+H]+; $^1$H NMR (400 MHz, $CD_3OD$) δ ppm 7.61 (s, 1H), 7.53 (t, J=8.16 Hz, 1H), 7.43 (dd, J=10.29, 8.28 Hz, 1H), 7.20-7.28 (m, 2H), 7.05 (dd, J=8.16, 2.64 Hz, 1H), 6.65 (br s, 1H), 5.52 (s, 2H), 5.26 (br d, J=5.02 Hz, 1H), 4.57-4.73 (m, 2H), 4.39-4.55 (m, 2H), 3.85-4.04 (m, 2H), 3.24 (br s, 2H), 2.77-2.83 (m, 2H), 2.72 (br d, J=6.27 Hz, 1H), 2.59 (br s, 2H), 2.53 (br d, J=8.78 Hz, 1H).

WXA015 was identified by two-dimensional NMR NOE that $C_{12}$—H was related to $C_8$—H, and the product structure was correct.

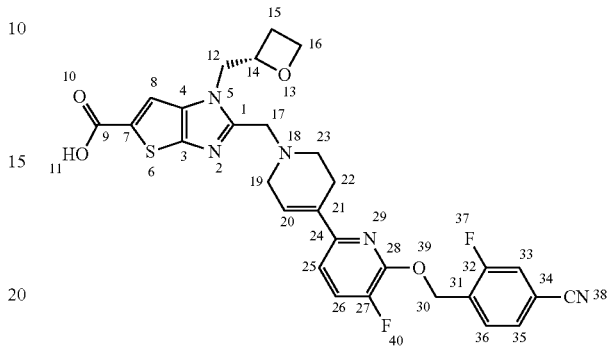

Experimental Embodiment 1. In Vitro Cell Activity Test

1. Materials:
1) Cell Line
The cell was constructed by Shanghai WuXi AppTec New Pharmaceutical Development Co., Ltd. The detailed information is as follows.

| Target | Host cell |
| --- | --- |
| GLP-1 | HEK293 |

2) Reagents:

| |
| --- |
| cAMP Detection Kit, Cisbio (Cat # 62AM4PEJ) |
| 1M HEPES, Invitrogen (Cat # 15630-106) |
| 1X HBSS, Invitrogen (Cat # 14025) |
| BSA, Sigma (Cat # B2064) |
| IBMX, Sigma (Cat # 15879) |
| Exenatide, Hao Yuan (HY-13443A) |

3) Instrument
OptiPlate-384, White, PerkinElmer (Cat #6007290); 384 well plate for Echo, Labcyte (Cat #P-05525); EnVision, PerkinElmer; Vi-cell counter, Beckman (Cat #Vi-CELL™ XR Cell Viability Analyzer)

4) Information of the Compound
The compound was formulated to a working concentration of 30 μM with DMSO. In this experiment, the amount of each sample used was 5 μL.

2. Methods
1) Experimental Materials:
Experimental Buffer

| Volume | Final concentration |
| --- | --- |
| 24.5 mL of Hanks Buffer Saline Solution (HBSS) | 1x |
| 125 μL of HEPES 1M | 5 mM |

-continued

| Volume | Final concentration |
|---|---|
| 333 µL of 7.5% BSA Solution | 0.1% |
| 25 µL of IBMX 500 mmol/L | 0.5 mmol/L |

The pH value was adjusted to 7.4 and diluted to 25 mL with HBSS 1×.

Preparation of Detection Reagent

Preparation of cAMP detection reagent, 250 µL of cAMP-D2 and 250 µL of anti-cAMP cryptate reagent were added to 4 mL of lysis buffer, and the mixture was mixed gently.

2) Experimental Methods:

a) Preparation of a Compound Plate:

The compound to be tested was 3-fold diluted at 10 points, the initial concentration was 30 µM, and the dilution was completed and treated by Bravo.

The reference compound exenatide was 3-fold diluted at 10 points, the initial concentration was 500 nM, and the dilution was completed and treated by Bravo.

b) Transferring Compounds:

1) 100 nL of the compound was transferred to OptiPlate-384 plate using Echo.

2) The OptiPlate-384 plate was centrifuged at 1000 rpm for 5 seconds.

c) Preparation of Cell Suspension

1) A cryopreservation tube of GLP-1 cells was quickly thawed in 37° C. warm water.

2) The cell suspension was transferred to a Transfer 15 mL centrifuge tube, and rinsed gently with 10 mL of HBSS.

3) The centrifuge tube was centrifuged at 1000 rpm for 1 minute at room temperature.

4) The supernatant was discarded.

5) The bottom cells were gently homogenized and then gently rinsed with 10 mL of HBSS, centrifuged and settled, the cells were finally re-suspend with experimental buffer.

6) Cell density and activity were measured by Vi-cell.

7) The concentration of GLP-1 cells was diluted to $2.0*10^5$/mL with experimental buffer.

8) 100 nL of diluted cell suspension was transferred into OptiPlate-384 plate.

9) The cells was incubated at room temperature for 30 minutes.

d) Detection Reagent was Added:

1) 10 µL of 800 nM gradient diluted cAMP standard was added to the empty well of OptiPlate-384 plate.

2) 10 µL of cAMP detection reagent was added.

3) The OptiPlate-384 plate was covered with TopSeal-A film and incubated at room temperature for 60 minutes.

TopSeal-A was removed and read by EnVision.

Experimental results are shown in Table 1:

TABLE 1

In vitro cell activity test result

| Compound | Human-GLP1, $EC_{50}$ (nM) |
|---|---|
| WXA001 | 0.67 |
| WXA002 | 2.7 |
| WXA003 | 1.07 |
| WXA004 | 1.9 |
| WXA005 | 0.37 |
| WXA006 | 1.44 |
| WXA007 | 0.20 |

TABLE 1-continued

In vitro cell activity test result

| Compound | Human-GLP1, $EC_{50}$ (nM) |
|---|---|
| WXA008 | 2.46 |
| WXA011 | 1.94 |
| WXA012 | 9.4 |
| WXA013 | 2.46 |
| WXA014 | 9.6 |
| WXA015 | 1.64 |
| WXA016 | 3.52 |

Conclusion: The compound of the present disclosure exhibits excellent agonistic ability to GLP-1 receptor.

Experimental Embodiment 2. DMPK Study in Mice

Experimental Objectives:

Male C57 mice were used as test animals, after a single dose, the plasma concentration of the compound was determined and the pharmacokinetic behavior was evaluated.

Experimental Operation:

Three healthy adult male C57 mice were selected as oral group. In the oral group, the solvent was 20% PEG400/10% solutol/70% water, the compounds to be tested were mixed with the solvent, the mixture was votexed and sonicated to prepare a 0.5 mg/mL clear solution. After oral administration of 5 mg/kg, the whole blood of mice was collected for a certain period of time, and the plasma was prepared, the drug concentration was analyzed by LC-MS/MS, and the pharmacokinetic parameters were calculated by Phoenix WinNonlin software (Pharsight Company, USA). Experimental results are shown in Table 2:

TABLE 2

PK test result of the compound of the present disclosure

| Number of the compound | $C_{max}$ (nM) | Oral DNAUC (nM · h/mpk) | $Vd_{ss}$ (L/kg) | Cl (mL/min/kg) | $T_{1/2}$ (h) | F % |
|---|---|---|---|---|---|---|
| WXA001 | 1763 | 647.4 | 1.87 | 104 | 2.07 | 220% |
| WXA005 | 835 | 301.8 | 2.84 | 63.6 | 2.47 | 63% |
| WXA006 | 865 | 307.4 | — | — | 1.43 | — |

Note:
— refers to untested; PEG refers to polyethylene glycol; solutol refers to polyethylene glycol-15 hydroxystearate; $C_{max}$ refers to maximum concentration; DNAUC = $AUC_{PO}$/Dose, $AUC_{PO}$ refers to oral exposure and Dose refers to drug dose; $Vd_{ss}$ refers to distribution volume; Cl refers to clearance rate; $T_{1/2}$ refers to half-life.

Conclusion: the compound of the present disclosure exhibits a higher oral exposure, a larger distribution volume and better oral bioavailability, demonstrating the advantages of good pharmacokinetic properties of oral drugs.

Experimental Embodiment 3. DMPK Study in Cynomolgus Monkey

Experimental Objectives:

Male cynomolgus monkey were used as test animals, after a single dose, the plasma concentration of the compound was determined and the pharmacokinetic behavior was evaluated.

Experimental Operation:

Two healthy male cynomolgus monkeys were selected as the oral group. The solvent of the oral group was 20% PEG 400+10% solutol+70% water. The compounds to be tested were mixed with the solvent, the mixture was votexed and sonicated to prepare a 0.5 mg/mL approximately clear solution. The oral dosage of cynomolgus monkeys was 3 mg/kg, after oral administration, the whole blood of cynomolgus monkeys was collected for a certain period of time, and the plasma was prepared, the drug concentration was analyzed by LC-MS/MS, and the pharmacokinetic parameters were calculated by Phoenix WinNonlin software (Pharsight Company, USA). Experimental results are shown in Table 3:

TABLE 3

PK test result of the compound of the present disclosure

| Number of the compound | $C_{max}$ (nM) | Oral DNAUC (nM · h/mpk) | $Vd_{ss}$ (L/kg) | Cl (mL/min/kg) | $T_{1/2}$ (h) | F % |
|---|---|---|---|---|---|---|
| WXA001 | 28.3 | 74 | 0.73 | 22.7 | ND | 5.6% |
| WXA005 | 245 | 889 | 0.59 | 10.7 | 4.94 | 31% |

Conclusion: the compound of the present disclosure exhibits a higher oral exposure, a larger distribution volume and better oral bioavailability, demonstrating the advantages of good pharmacokinetic properties of oral drugs.

Experimental Embodiment 4. hERG Test

1. Experimental Objective:

The effects of compounds on the current of hERG potassium channel (human Ether-a-go-go Related Gene potassium channel) were measured by the automatic patch clamp method.

2. Experimental Methods 2.1 Cell Preparation

CHO-hERG cells were cultured in a 175 cm² flask, when the cell density reached 60-80%, the culture medium was removed, the cells were washed once with 7 mL of PBS (Phosphate Buffered Saline), and then detached with 3 mL of Detachin. After digestion was completed, 7 mL of culture medium was added to neutralize, then the mixture was centrifuged, the supernatant was aspirated, and then 5 mL of culture medium was added to re-suspend, ensuring 2-5×10⁶/mL of cell density.

2.2 Solution Preparation

Extracellular fluid formulation (mM): 140 NaCl, 5 KCl, 1 CaCl$_2$, 1.25 MgCl$_2$, 10 HEPES and 10 Glucose, the pH value was adjusted to 7.4 with NaOH.

Intracellular fluid formulation (mM): 140 KCl, 1 MgCl$_2$, 1 CaCl$_2$, 10 EGTA and 10 HEPES, the pH value was adjusted to 7.2 with KOH.

2.3 Electrophysiological Recording Process

The process of single cell high impedance sealing and whole cell mode formation were all automatically completed by Qpatch instrument, after obtaining the whole cell recording mode, the cells were clamped at −80 mV, before giving a 5-second +40 mV depolarization stimulus, a 50 millisecond −50 mV prevoltage was given first, and then repolarized to −50 mV for 5 seconds, then returned to −80 mV. This voltage stimulation was applied every 15 seconds and after recording for 2 minutes, extracellular fluid was recordings for 5 minutes, and then the administration process was started, the compound concentration was given from the lowest test concentration, each test concentration was given for 2.5 minutes, and 3 µM of Cisapride as the positive control compound was given after all concentrations were continuously given. At least 3 cells (n≥3) were tested at each concentration.

2.4 Compound Preparation:

The mother liquor of the compound was diluted with DMSO, and 10 µL of mother liquor of the compound was added to 20 µL of DMSO solution, and was 3-fold diluted continuously to 6 DMSO concentrations. 4 µL of compounds with 6 DMSO concentrations were added to 396 µL of extracellular fluid, 100-fold diluted to 6 intermediate concentrations, and then 80 µL of the compounds with 6 intermediate concentrations were added to 320 µL of extracellular fluid, 5-fold diluted to the final concentration to be tested. The highest test concentration was 40 µM, in a total of 6 concentrations of 40, 13.3, 4.4, 1.48, 0.494 and 0.165 µM respectively. The content of DMSO in the final test concentration was not more than 0.2%, and this concentration of DMSO had no effect on hERG potassium channel. The whole dilution process of compound preparation was completed by Bravo instrument.

2.5 Data Analysis:

The experimental data were analyzed by GraphPad Prism 5.0 software.

2.6 Quality Control

Environment: humidity 20-50%, temperature 22-25° C.

Reagent: The experimental reagent used was purchased from Sigma Company, and the purity was >98%

The experimental data in the report must meet the following criteria:

Whole cell sealing impedance>100 M Ω

Tail current amplitude>300 pA

Pharmacological Parameters:

The inhibitory effect of multiple concentrations of Cisapride on hERG channel was set as positive control.

Experimental results are shown in Table 4:

TABLE 4 hERG test result of the compound of the present disclosure

| Compound | Maximum concentration inhibition rate (%) | IC$_{50}$ (µM) |
|---|---|---|
| WXA001 | 30.4% | >40 |
| WXA005 | 33.1% | >40 |

Conclusion: The compound of the present disclosure has weak inhibitory effect on hERG potassium channel current, lower risk of cardiotoxicity, and higher safety.

Experimental Embodiment 5. Permeability Test

The objective of this study was to determine the bidirectional permeability and efflux rate of the samples by using MDR1-MDCKII monolayer cell model.

MDR1-MDCKII cells (11th generation) were inoculated into 96-well cell culture plate and cultured continuously for 4-7 days for transport experiment. The sample was administered in both directions at a concentration of 2.00 µM. After incubation for 150 min, the sample was collected and the content of the test product in the sample was determined by liquid chromatography-tandem mass spectrometry (LC-MS/MS).

When the administration concentration was 2.00 the average apparent permeability coefficient (Papp) of the test product from the top to the basal end (A-B) direction, the average apparent permeability coefficient from the basal end to the top (B-A) direction, and the efflux ratio (ER) are shown in Table 5. Note: The boundaries of low and high permeability grades were equivalent to 50% and 80% of human "calculated Fa". The grading criteria were based on WuXi AppTec's routine MDR1-MDCK II permeability test (test concentration was 2 μM, incubation for 2.5 hours).

TABLE 5 permeability test result of the compound of the present disclosure

| Compound | Mean Papp ($10^{-6}$ cm/s) | | Efflux rate | Rank |
| --- | --- | --- | --- | --- |
| | A-B | B-A | | |
| WXA001 | 2.53 | 3.87 | 1.53 | Medium |
| WXA005 | 7.19 | 8.49 | 1.18 | High |

Conclusion: The compound of the present disclosure has good permeability.

What is claimed is:

1. A compound represented by formula (III) or a pharmaceutically acceptable salt thereof,

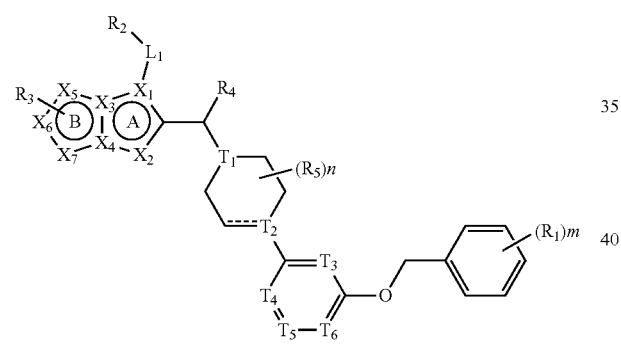

(III)

wherein,

≡≡≡ is selected from a single bond and a double bond;

$T_1$ is selected from N, C and $CR_6$;

$T_2$ is selected from N, C and CH;

$T_3$, $T_4$, $T_5$ and $T_6$ are each independently selected from N and $CR_7$;

$X_1$ and $X_2$ are N;

$X_3$ and $X_4$ are C;

$X_5$ is $CR_8$, N, NH, O and S;

$X_6$ is CH;

$X_7$ is CH, N, NH, O and S;

$X_1$, $X_2$, $X_3$ and $X_4$ constitute ring A;

$X_3$, $X_4$, $X_5$, $X_6$ and $X_7$ constitute ring B;

$L_1$ is selected from a single bond and —$C_{1-3}$ alkyl-;

$R_1$ is each independently selected from F, Cl, Br, I, OH, $NH_2$ and CN;

m is selected from 0, 1, 2, 3, 4 and 5;

$R_2$ is selected from

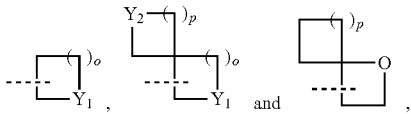

and the

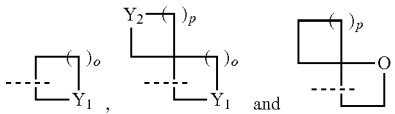

are optionally substituted by 1, 2 or 3 $R_a$;

$Y_1$ and $Y_2$ are each independently selected from CH, $CH_2$, N, NH and O;

o and p are each independently selected from 0, 1, 2 and 3;

$R_3$ is selected from —C(=O)—NH—$R_b$, —C(=O)—$R_b$, —C(=O)—NH—S(=O)$_2$—$R_b$, —S(=O)$_2$—NH—$R_b$, —S(=O)$_2$—$R_b$, —P(=O)($R_b$)$_2$, $C_{1-3}$ alkyl, tetrazolyl, isoxazolyl,

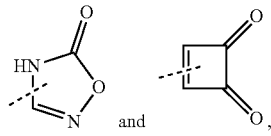

the $C_{1-3}$ alkyl, tetrazolyl, isoxazolyl,

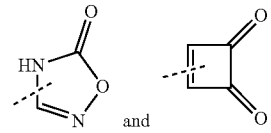

are optionally substituted by 1, 2 or 3 $R_b$;

$R_5$ is each independently selected from F, Cl, Br, I and $C_{1-3}$ alkyl;

n is selected from 0, 1 and 2;

or, two adjacent $R_5$ together form $C_{3-5}$ cycloalkyl;

$R_4$ is selected from H, F, Cl, Br, I and $CH_3$;

$R_6$ is selected from H, F, Cl, Br, I and $CH_3$;

or, $R_4$ and $R_6$ combining with the bonds to which they are attached form a double bond or $C_{3-5}$ cycloalkyl;

$R_7$ is each independently selected from H, F, Cl and CN;

$R_8$ is each independently selected from H, F, Cl and $CH_3$;

$R_a$ is selected from F, Cl, Br and I;

$R_b$ is selected from OH, CN, $C_{1-3}$ alkyl, $C_{1-3}$ alkoxy, $C_{1-3}$ alkylamino and oxazolyl, and the $C_{1-3}$ alkyl, $C_{1-3}$ alkoxy and oxazolyl are optionally substituted by 1, 2 or 3 R;

R is selected from F, Cl and Br.

2. The compound as defined in claim 1 or the pharmaceutically acceptable salt thereof, wherein, $R_2$ is selected from

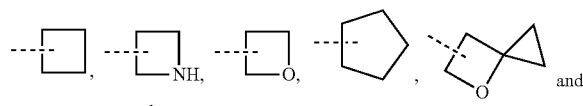

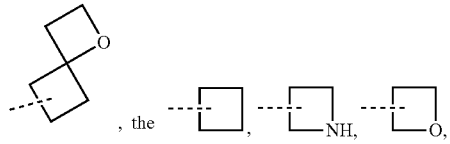

are optionally substituted by 1, 2 or 3 $R_a$.

3. The compound as defined in claim 2 or the pharmaceutically acceptable salt thereof, wherein, $R_2$ is selected from

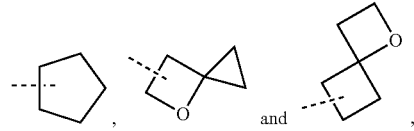

4. The compound as defined in claim 1 or the pharmaceutically acceptable salt thereof, wherein, $L_1$ is selected from a single bond and —$CH_2$—.

5. The compound as defined in claim 1 or the pharmaceutically acceptable salt thereof, wherein, m is selected from 0, 1 and 2.

6. The compound as defined in claim 1 or the pharmaceutically acceptable salt thereof, wherein, $R_b$, is selected from OH, CN, $CH_3$, $CF_3$ and $OCH_3$.

7. The compound as defined in claim 1 or the pharmaceutically acceptable salt thereof, wherein, $R_3$ is selected from —COON, —C(=O)—NH—CN, —C(=O)—NH—OH, —C(=O)—NH—$OCH_3$, —C(=O)—$CF_3$, —S(=O)$_2$—NH—$CH_3$ and —S(=O)$_2$—OH.

8. The compound as defined in claim 1 or the pharmaceutically acceptable salt thereof, wherein, the structural moiety

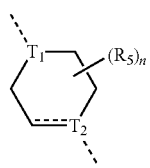

is selected from

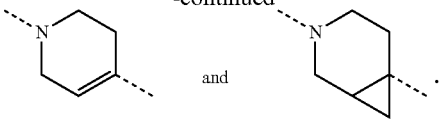

9. The compound as defined in claim 1 or the pharmaceutically acceptable salt thereof, wherein, the structural moiety

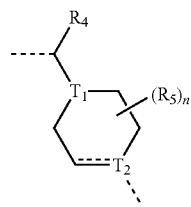

is selected from

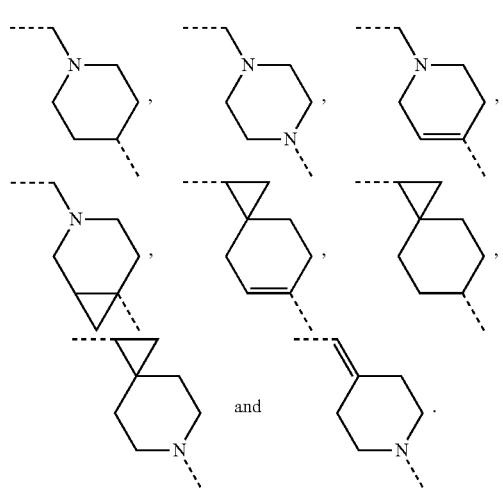

10. The compound as defined in claim 1 or the pharmaceutically acceptable salt thereof, wherein, the structural moiety

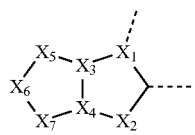

is selected from

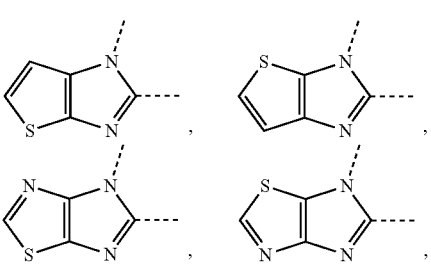

-continued

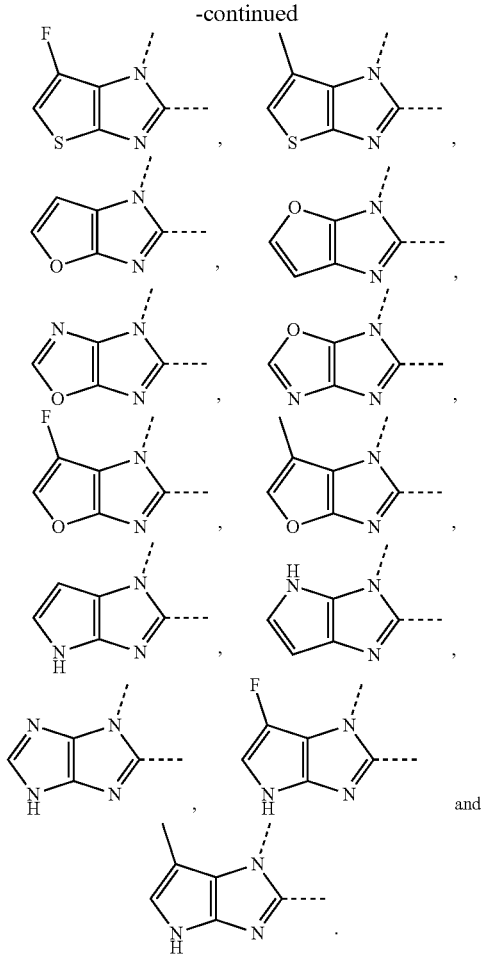

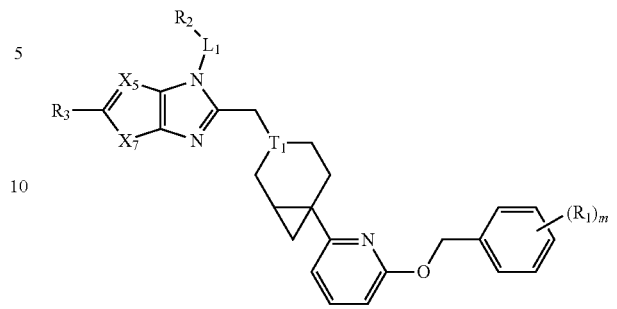

(I-2)

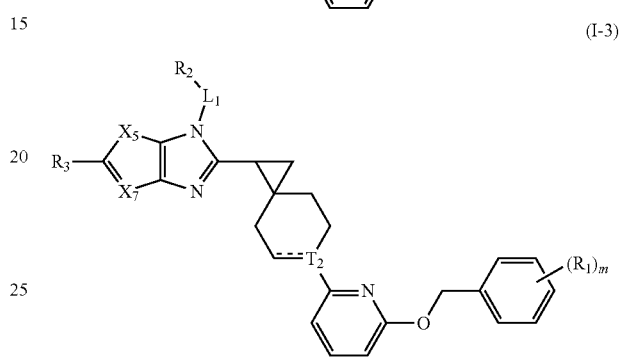

(I-3)

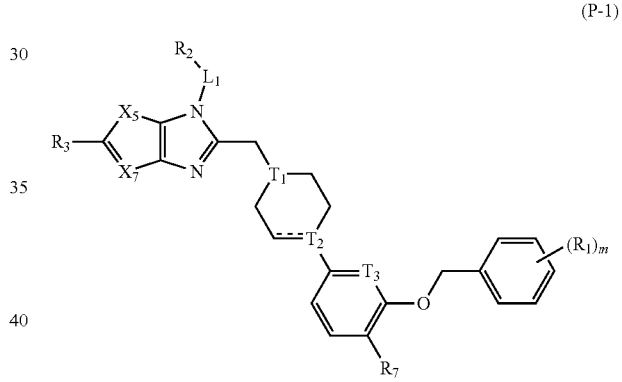

(P-1)

11. The compound as defined in claim 1 or the pharmaceutically acceptable salt thereof, wherein the structural moiety

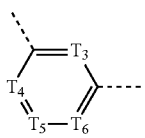

is selected from

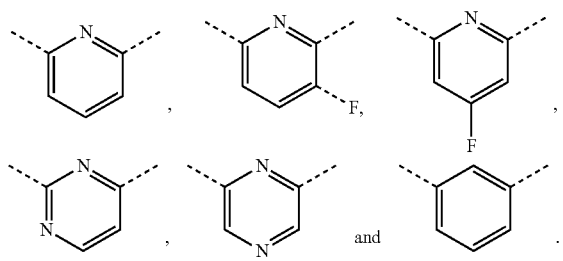

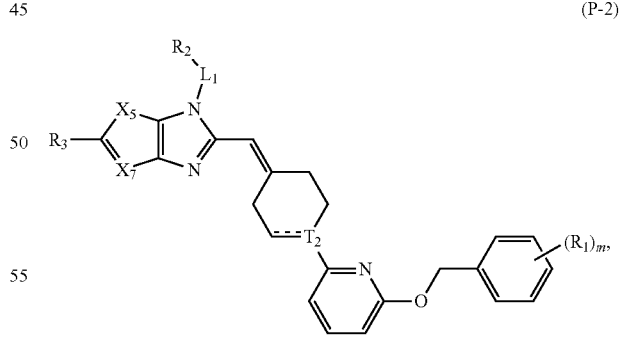

(P-2)

wherein,

--- is selected from a single bond and a double bond;

$R_1$, $R_2$, $R_3$, $L_1$, $T_1$, $T_2$, m, $X_5$ and $X_7$ are as defined in claim 1.

12. The compound as defined in claim 1 or the pharmaceutically acceptable salt thereof, wherein the compound is selected from, 13. The compound as defined in claim 12 or the pharmaceutically acceptable salt thereof, wherein the compound is selected from:

(III-1a)
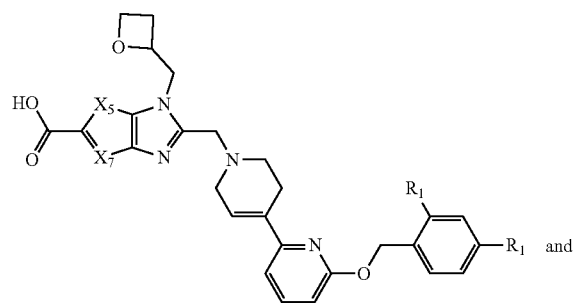
and
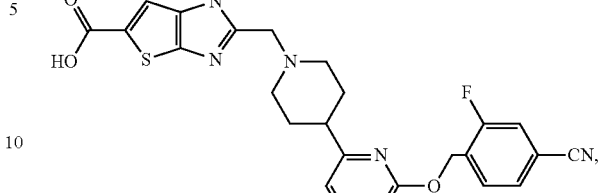
(III-1b)
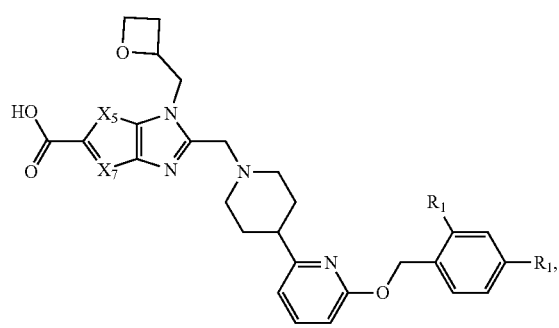
wherein, R₁, X₅ and X₇ are as defined in claim 12.
14. A compound represented by the following formula or a pharmaceutically acceptable salt thereof, wherein the compound is selected from:
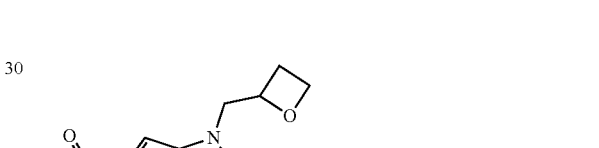
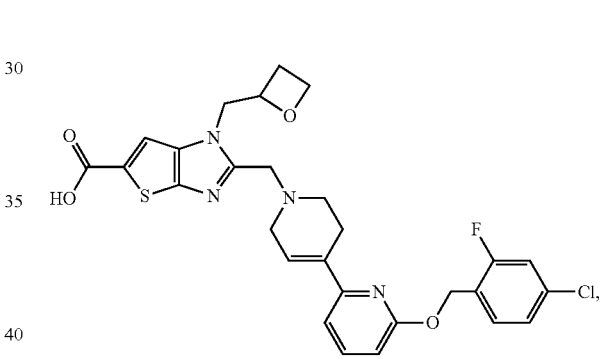
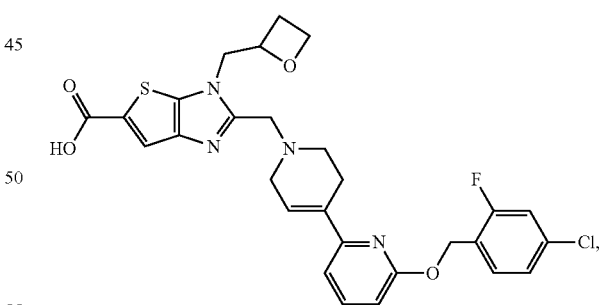
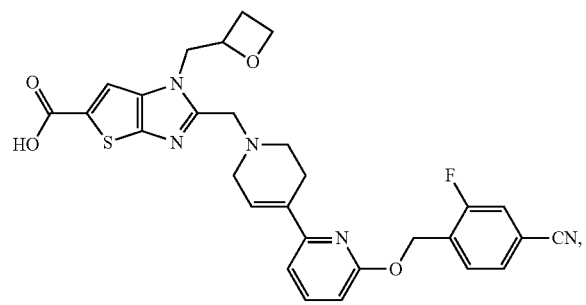
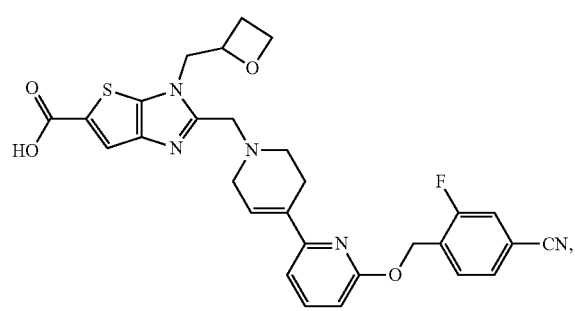

133
-continued
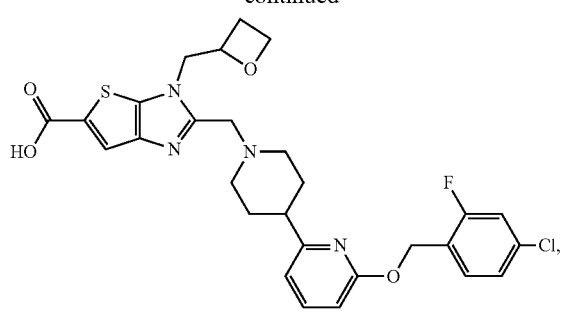
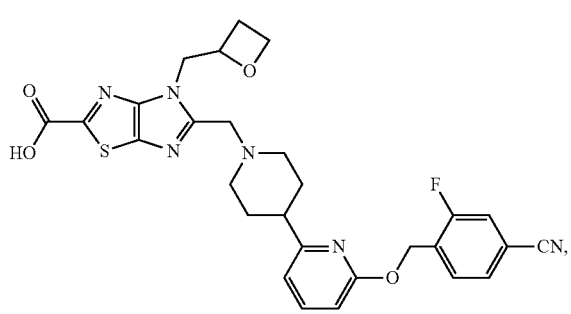
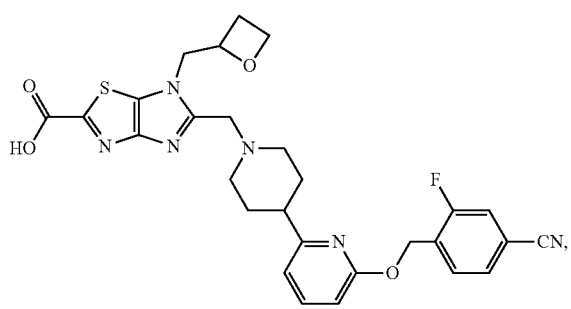
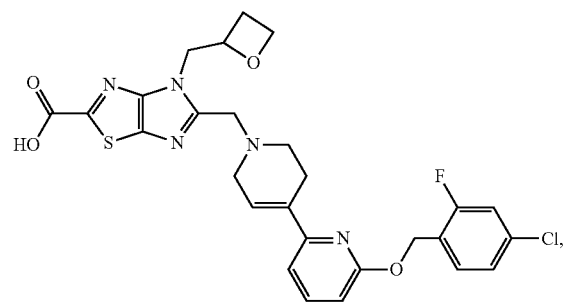
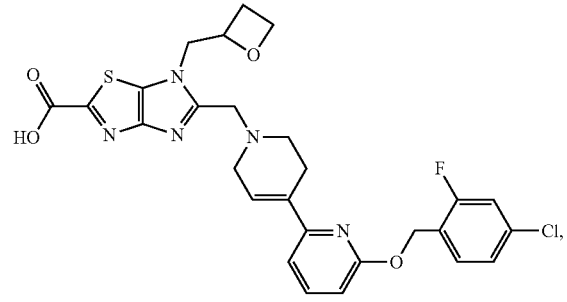
134
-continued
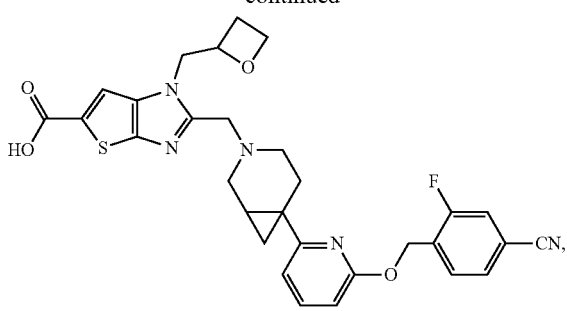
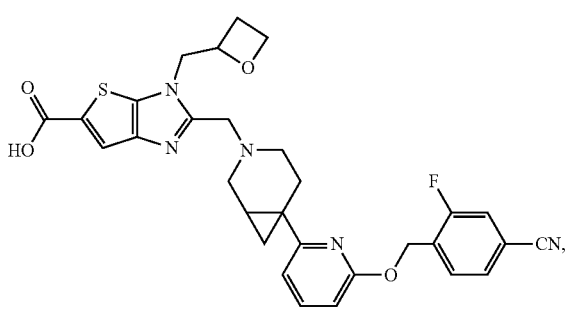
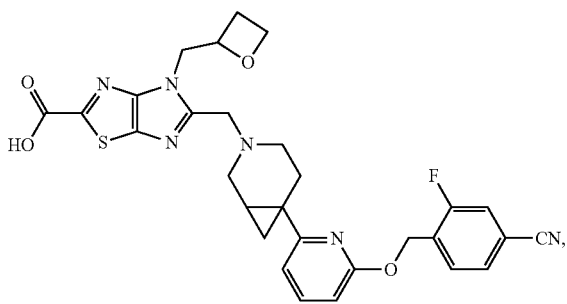
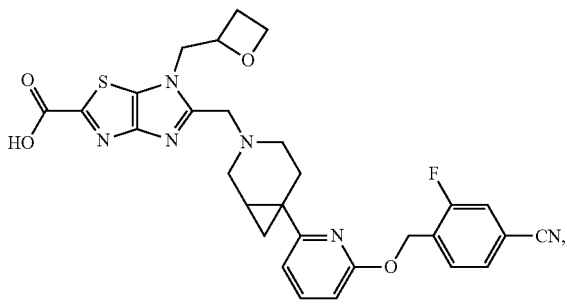
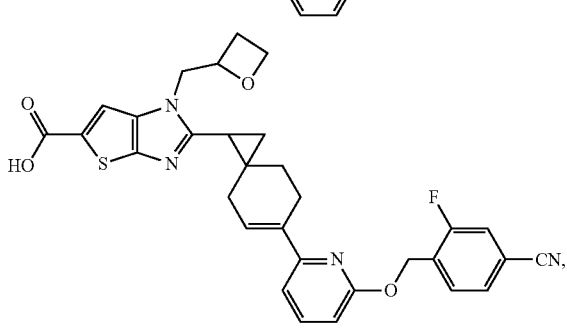

135
-continued
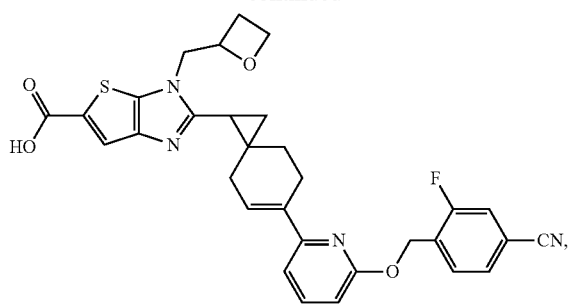
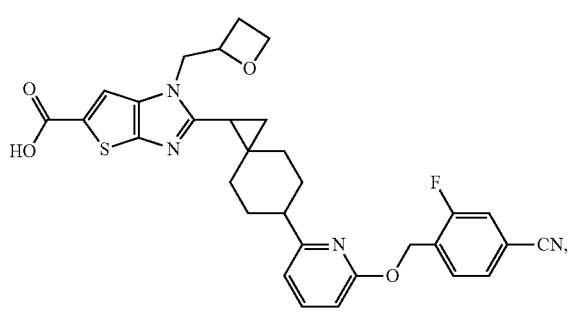
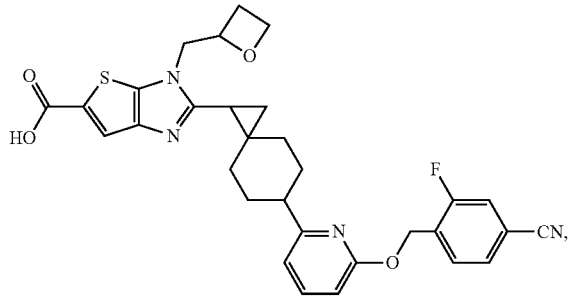
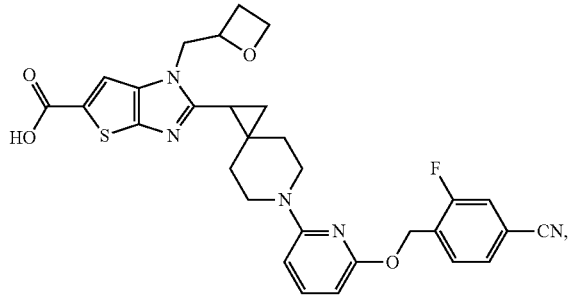
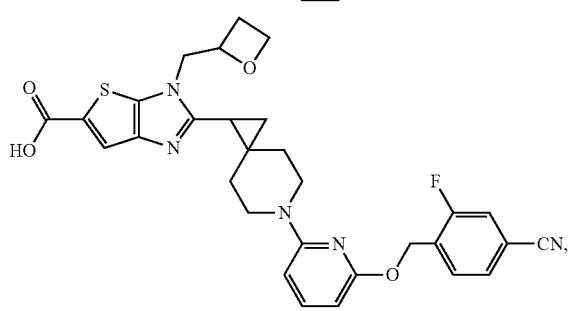
136
-continued
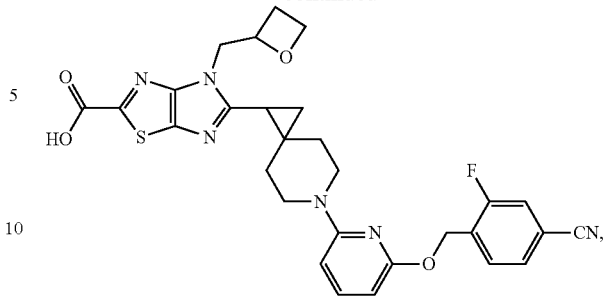
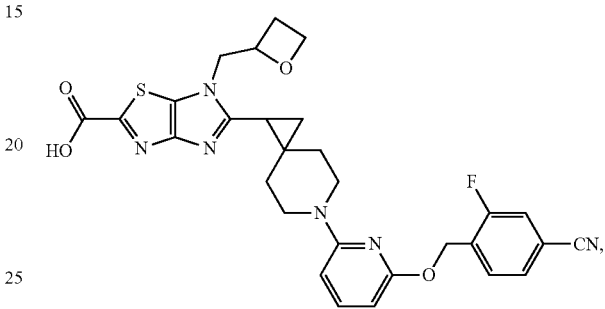
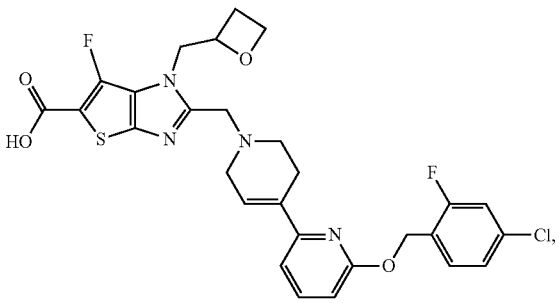
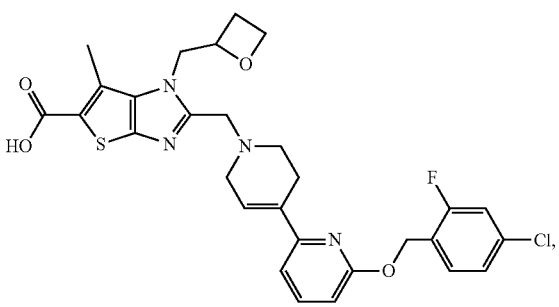

137
-continued
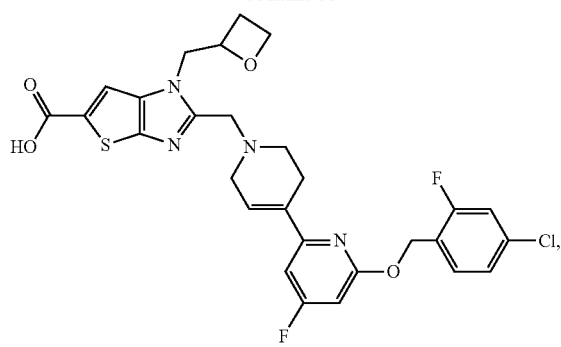
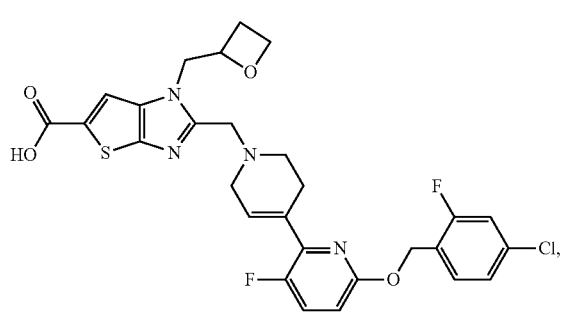
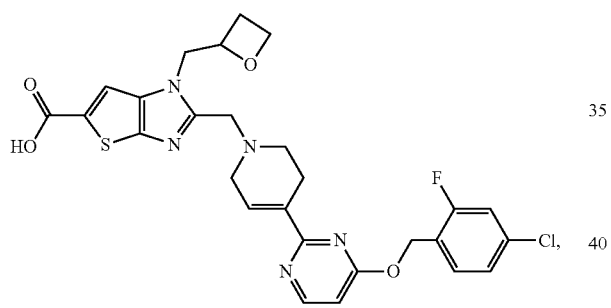
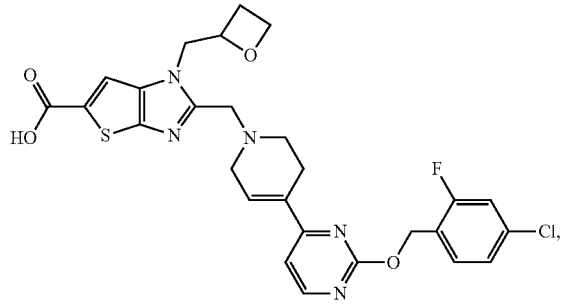
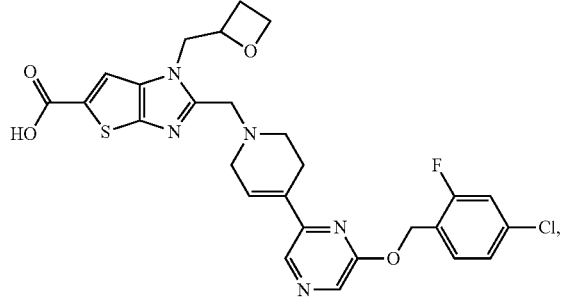
138
-continued
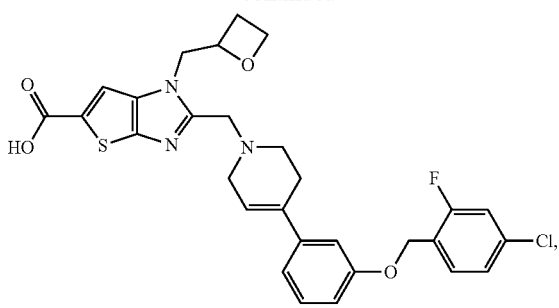
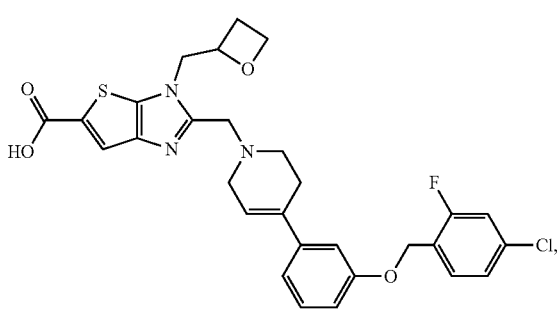
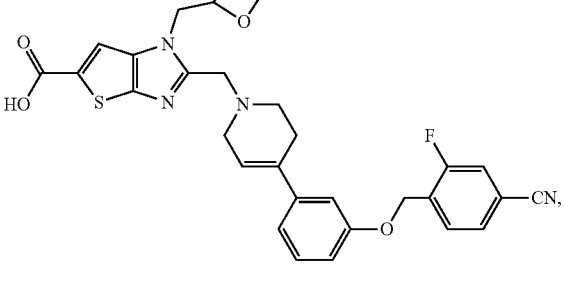
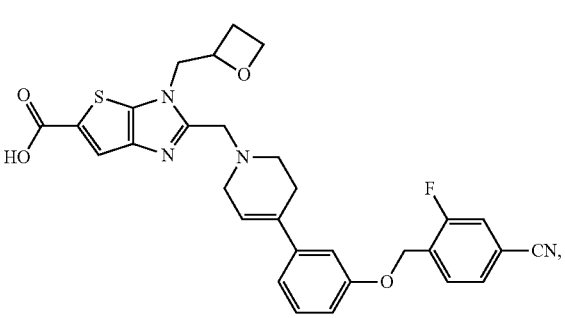
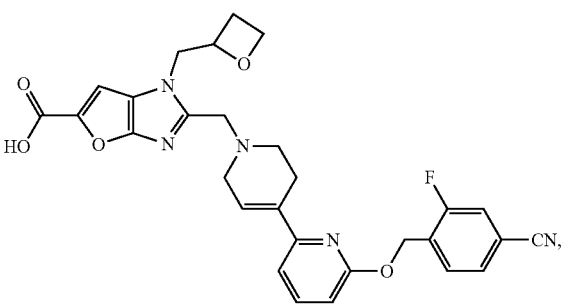

139 -continued
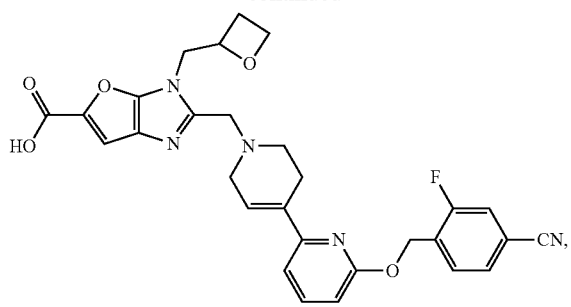
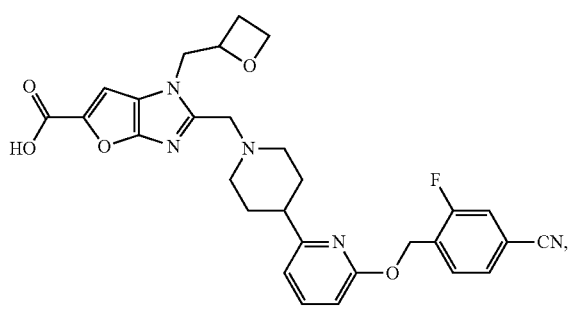
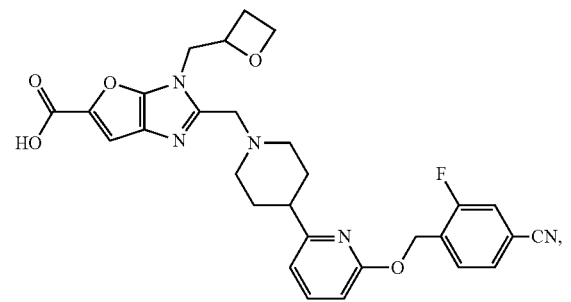
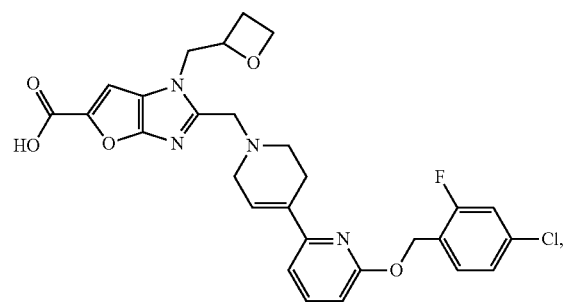
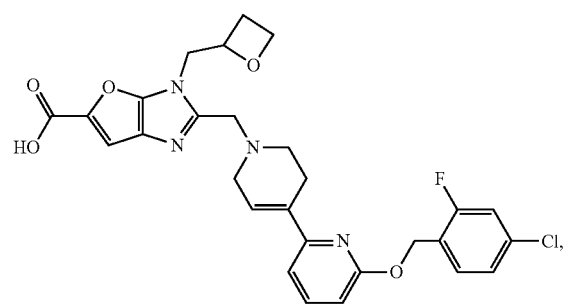
140 -continued
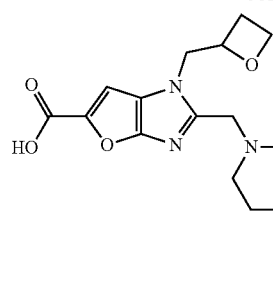
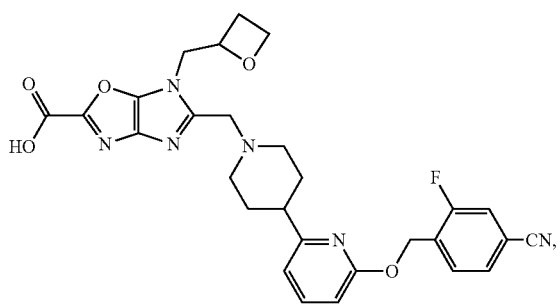
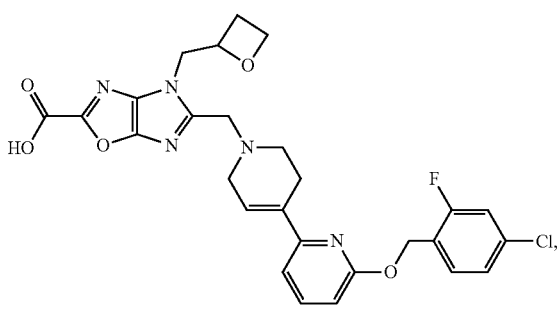

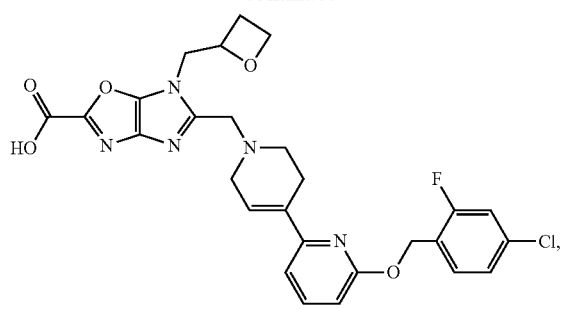
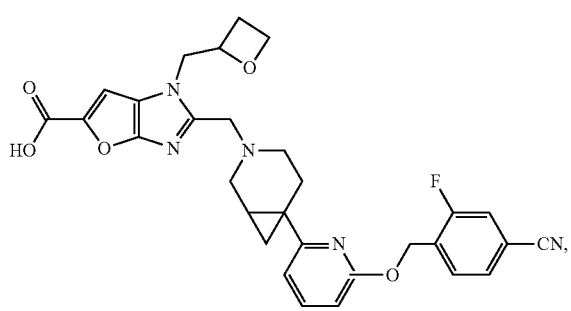
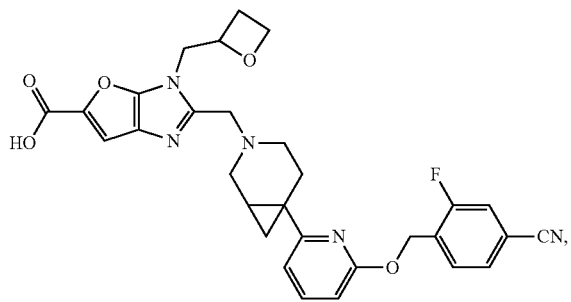
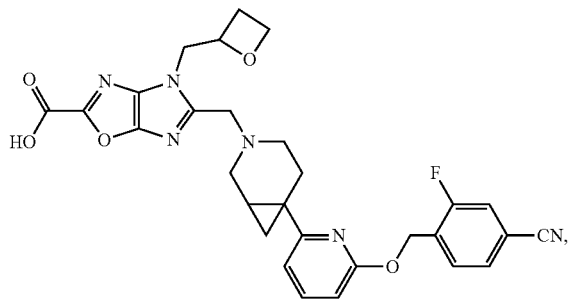
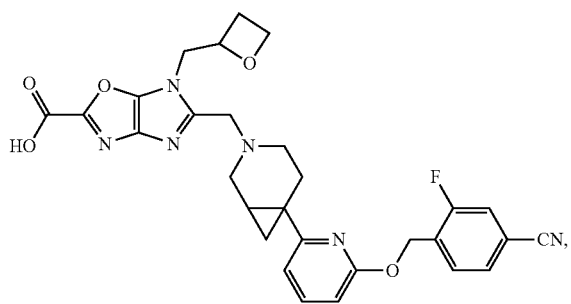
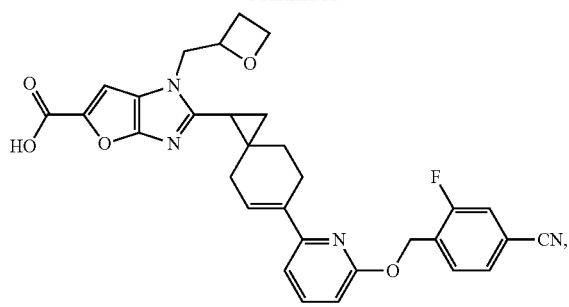
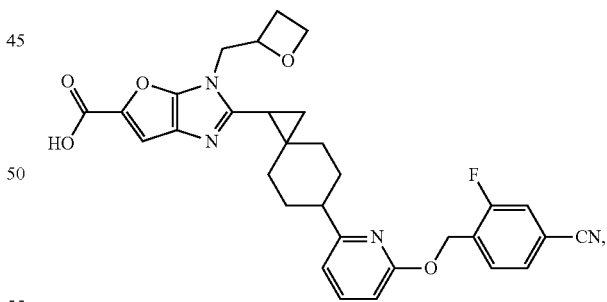
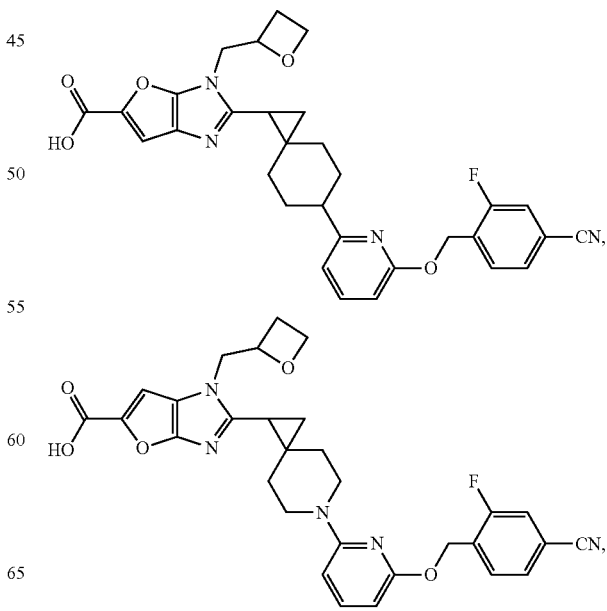

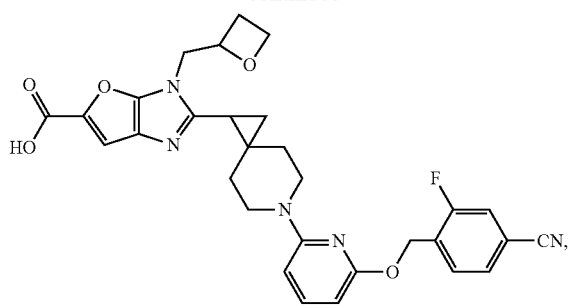
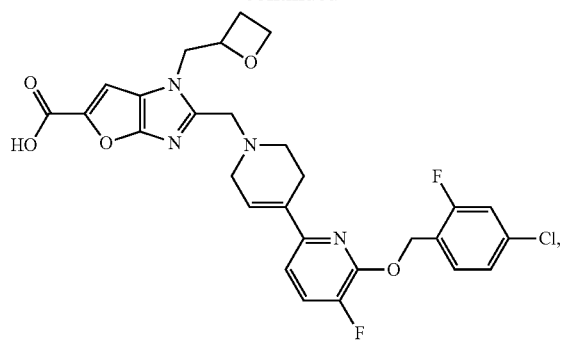
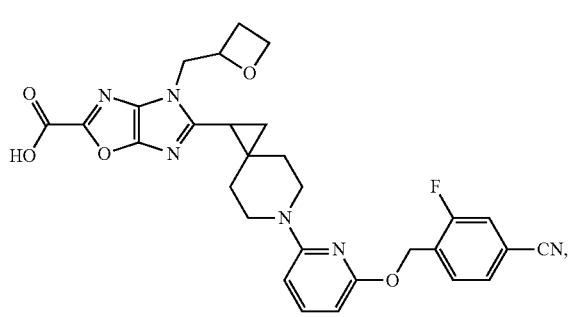
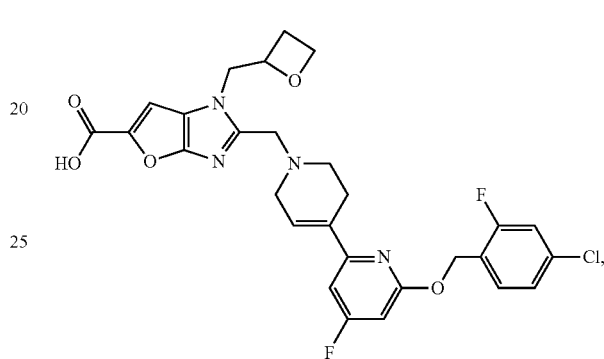
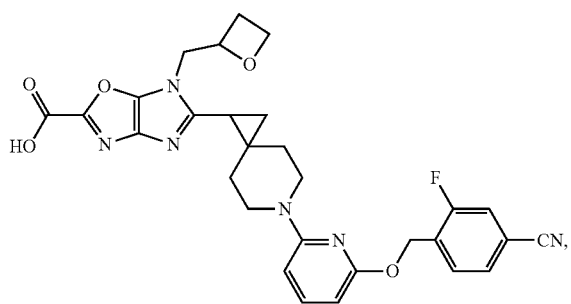
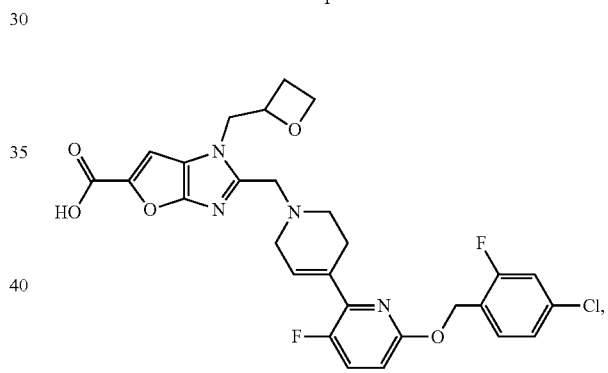
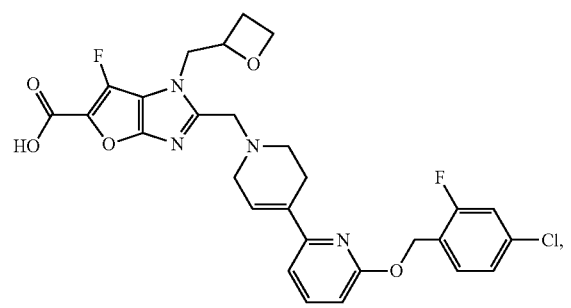
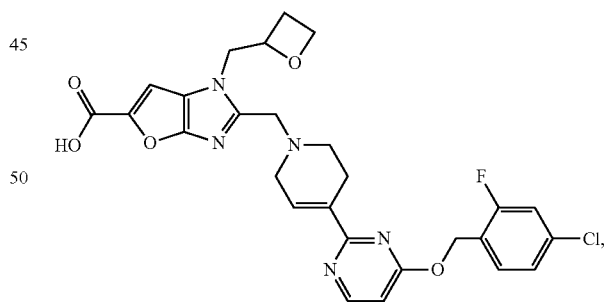
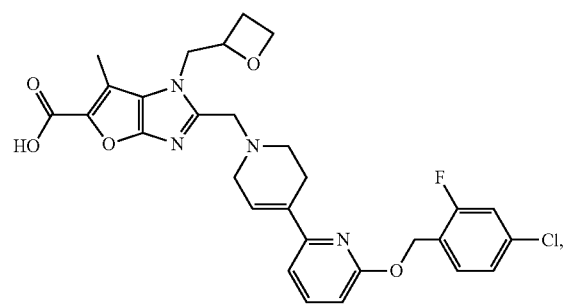
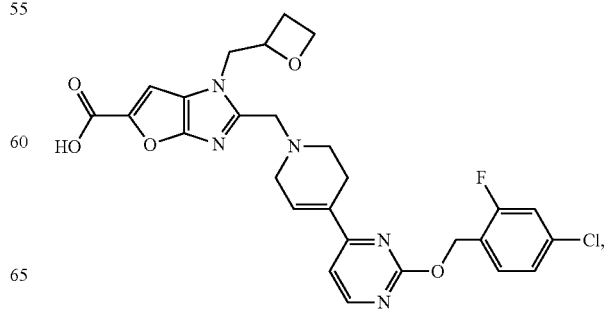

145
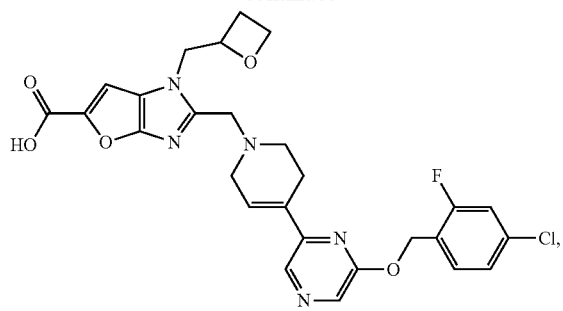
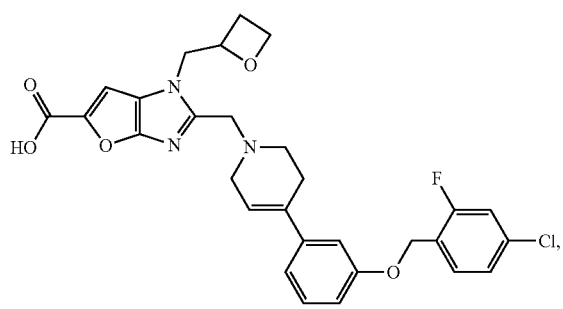
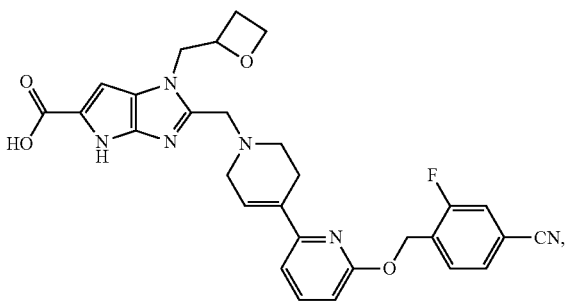
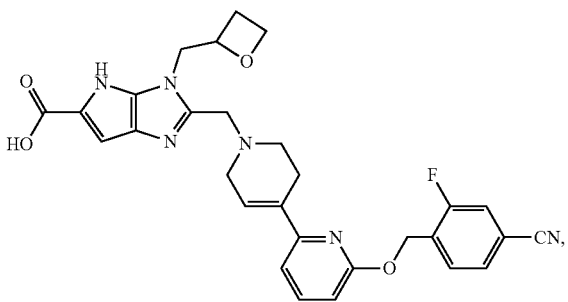
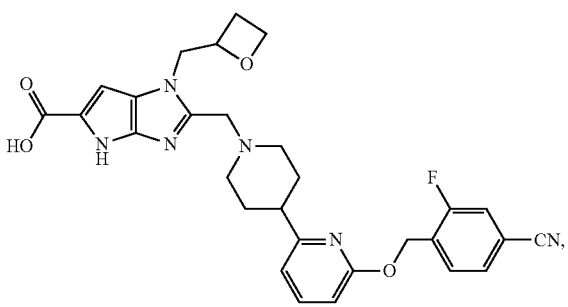
146
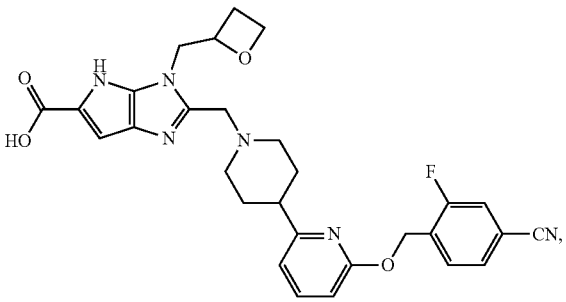

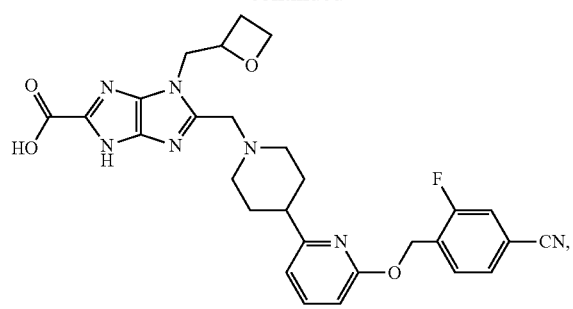
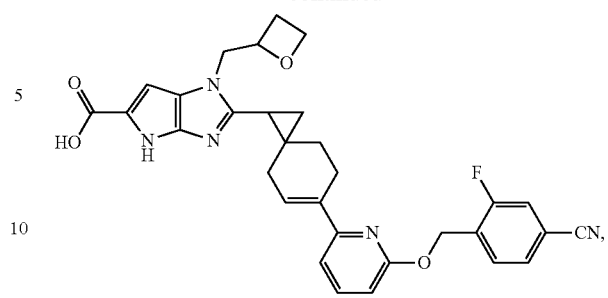

-continued
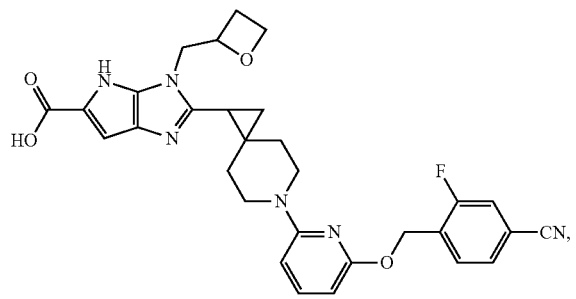
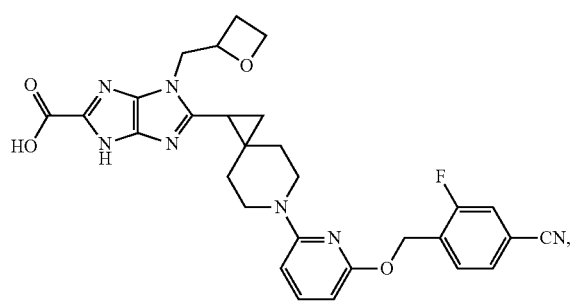
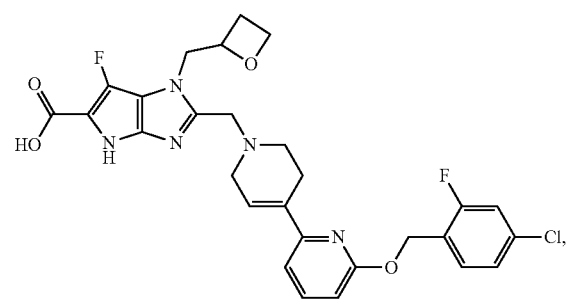
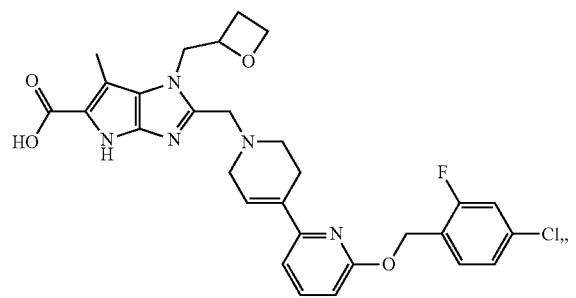
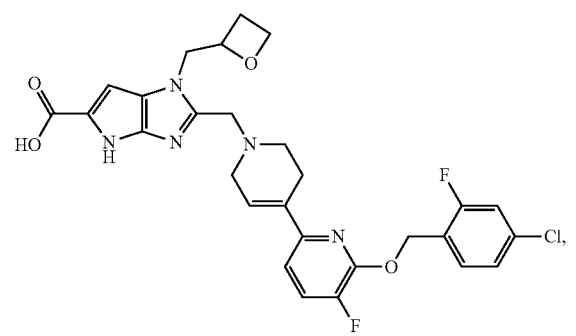
-continued
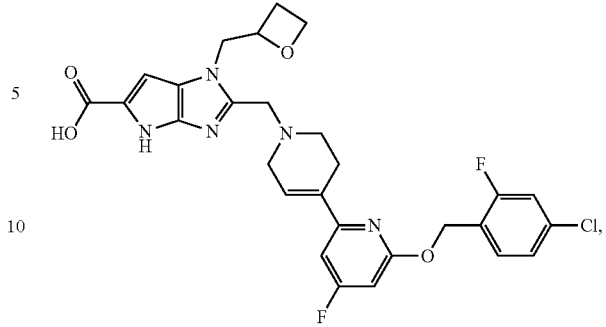
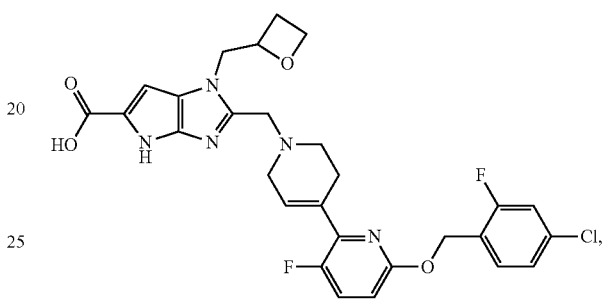
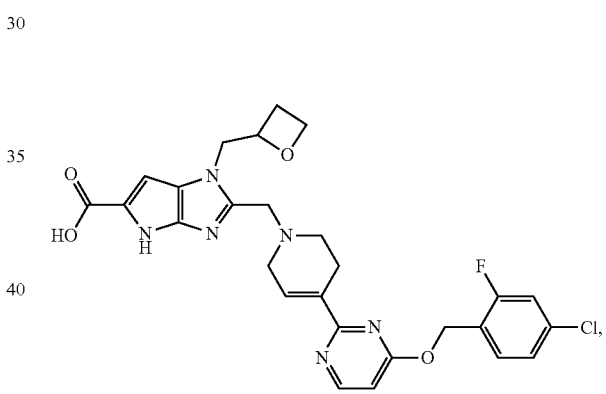
and
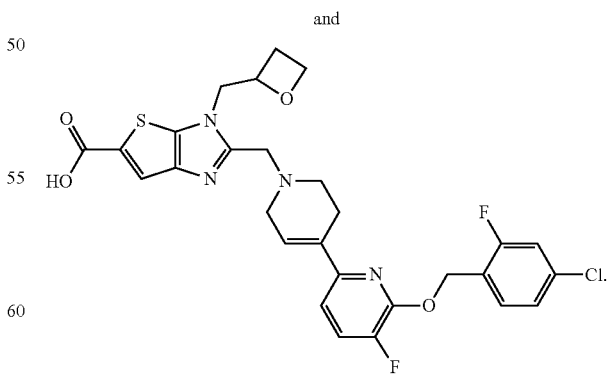
15. The compound as defined in claim 14 or the pharmaceutically acceptable salt thereof, wherein the compound is selected from:

151
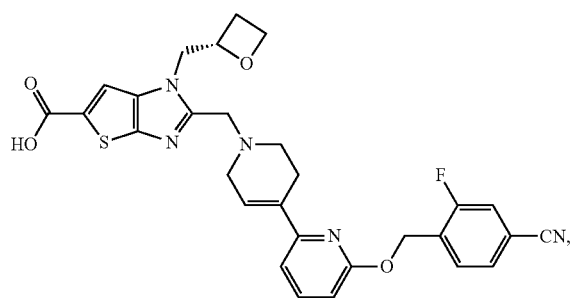
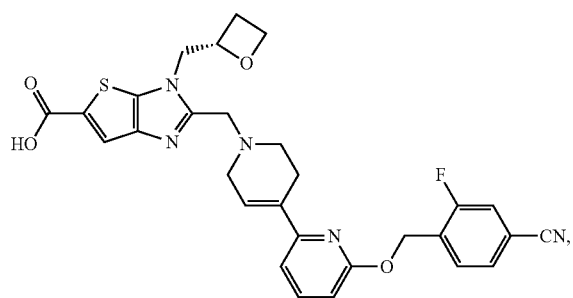
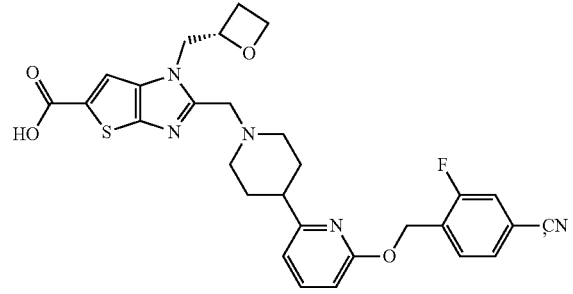
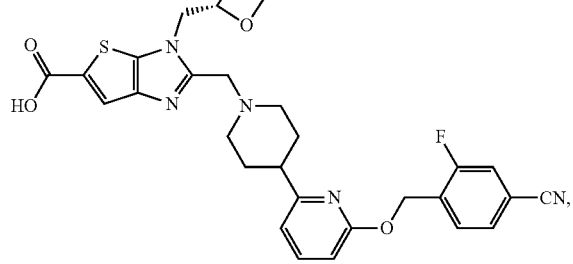
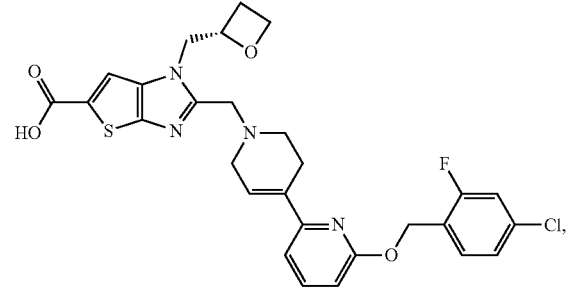
152
-continued
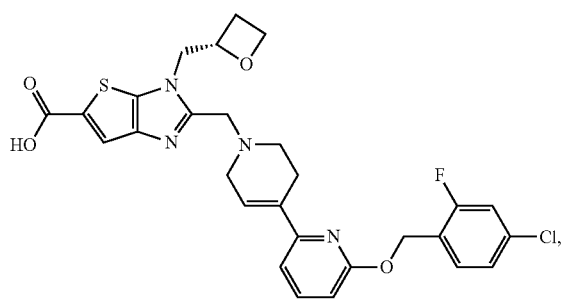
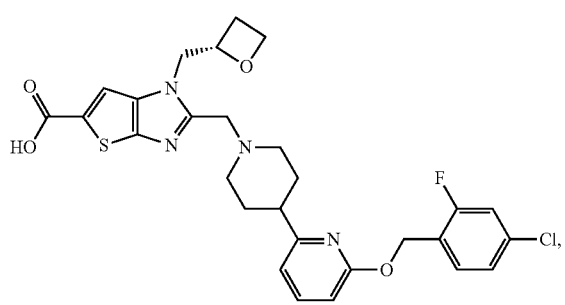
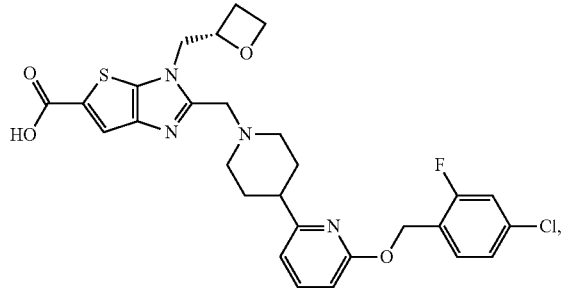
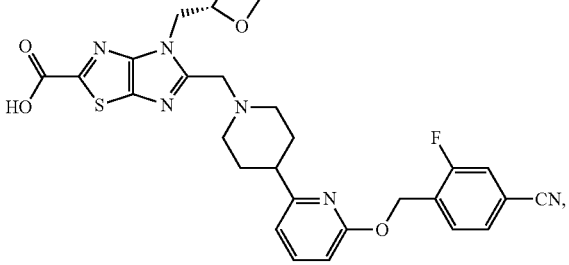
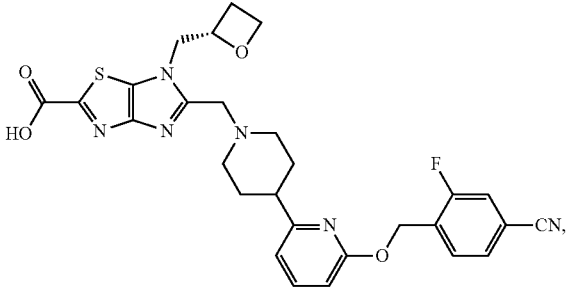

153
-continued
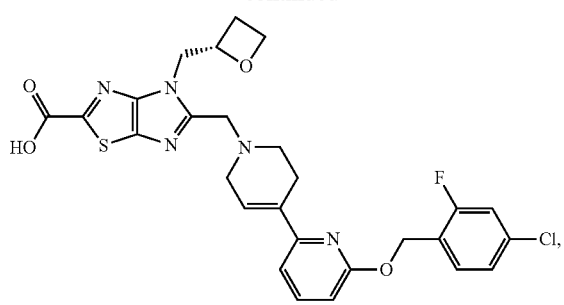
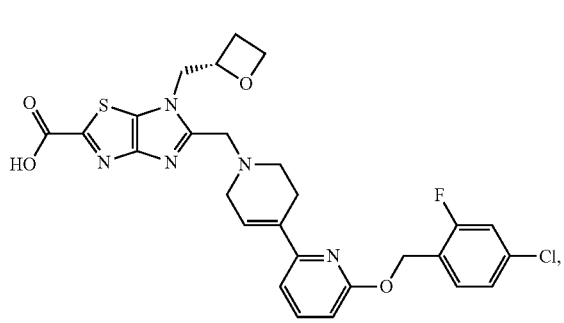
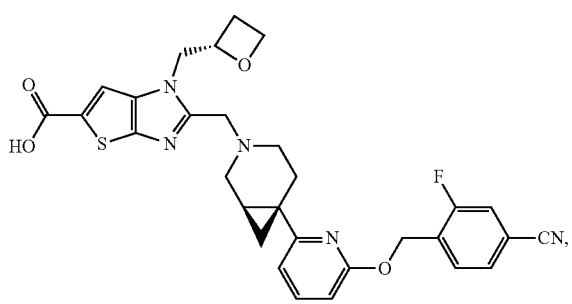
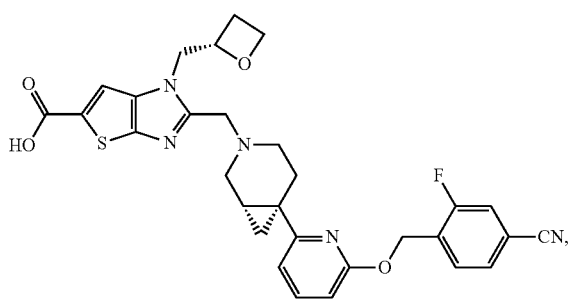
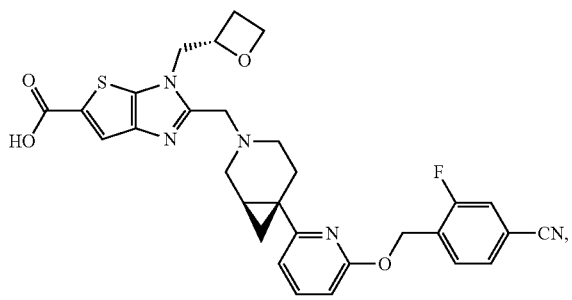
154
-continued
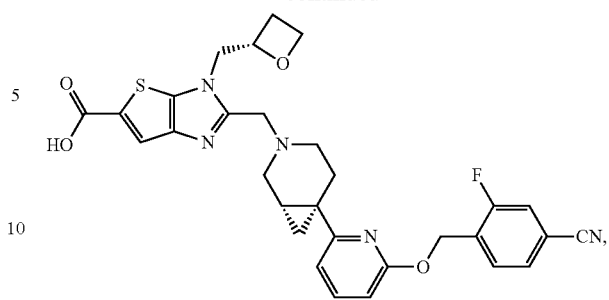
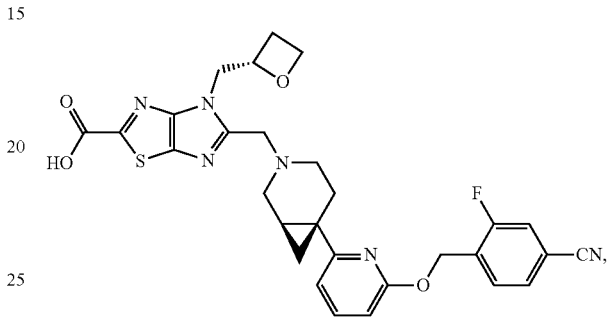
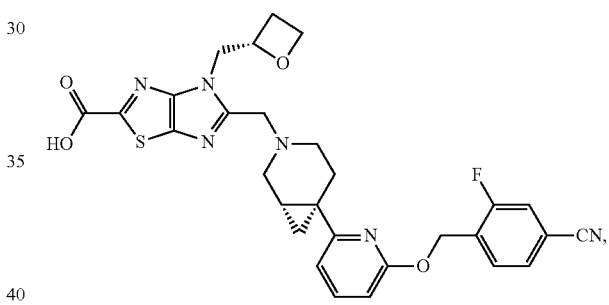
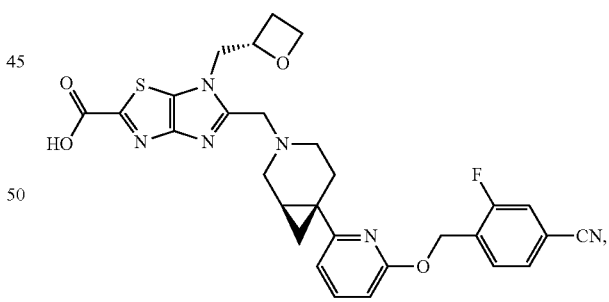
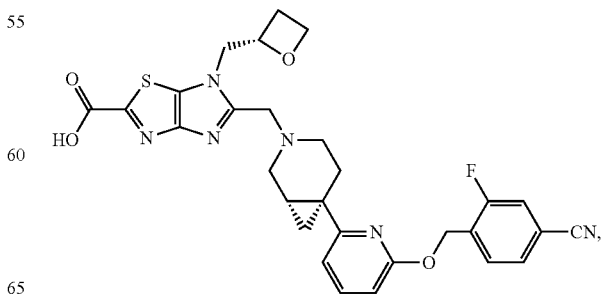

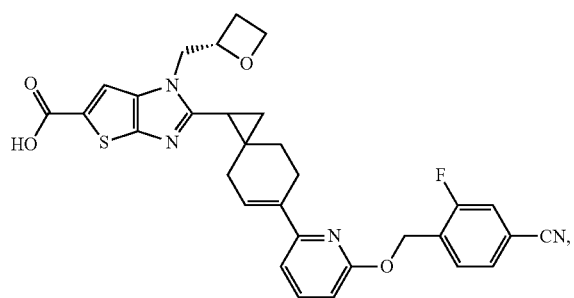
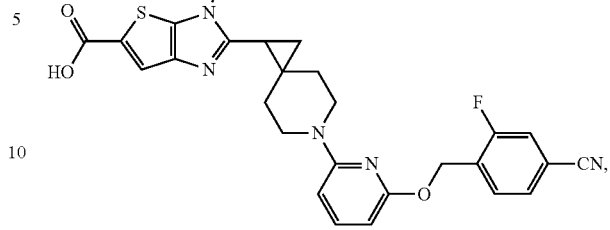
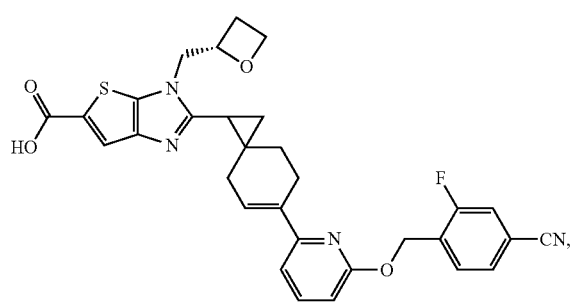
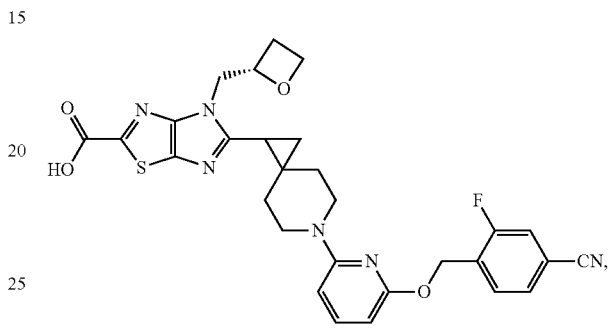
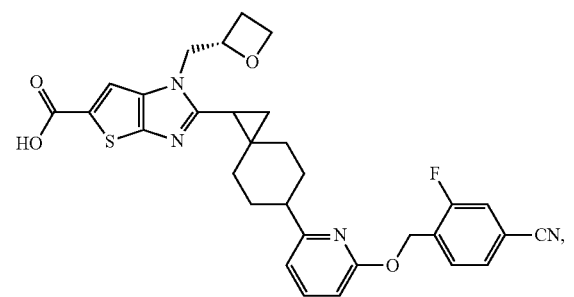
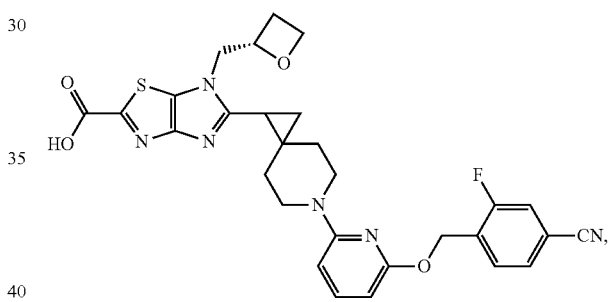
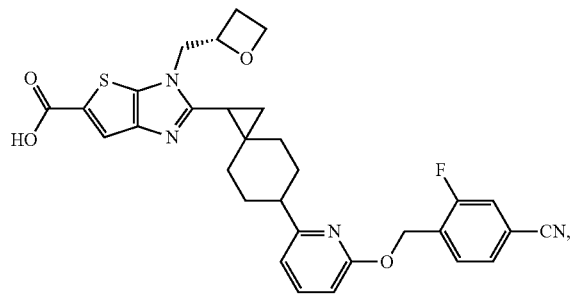
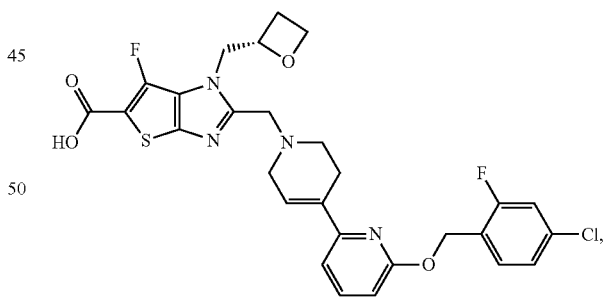
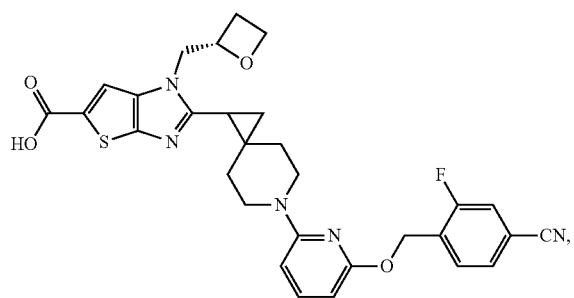
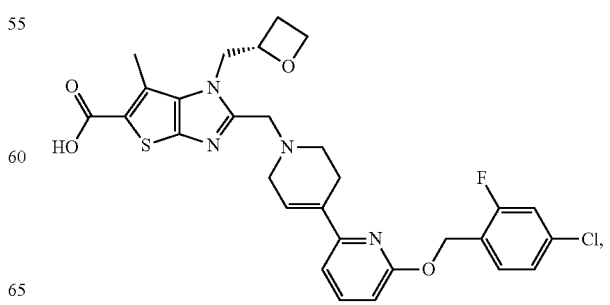

157
-continued
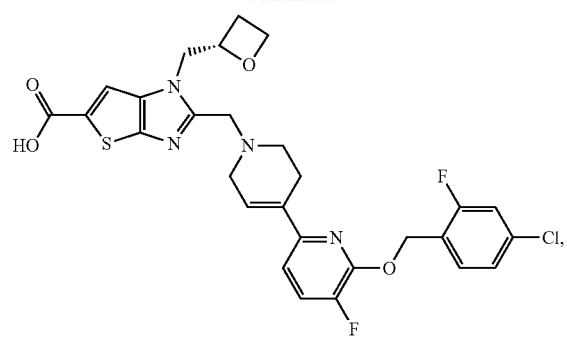
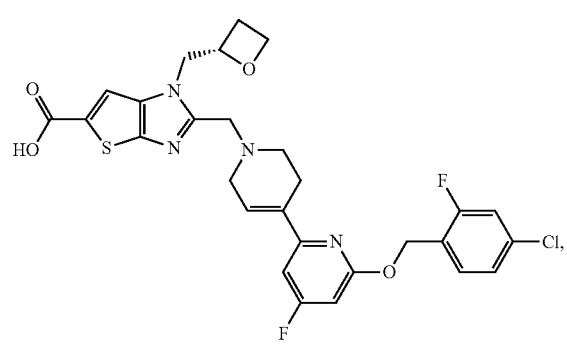
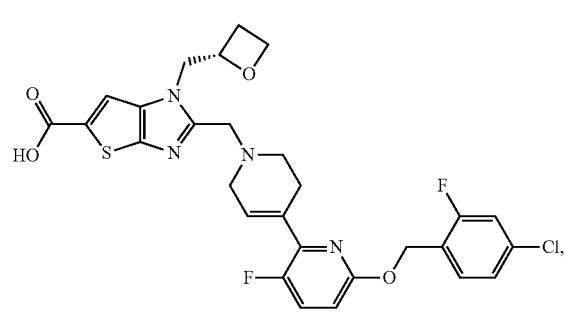
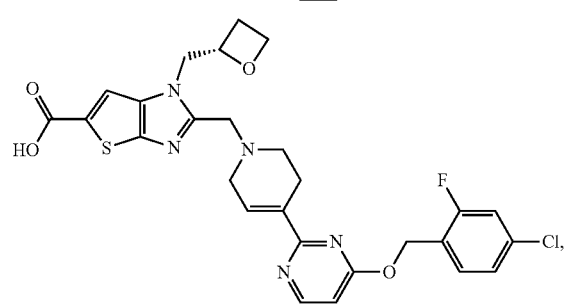
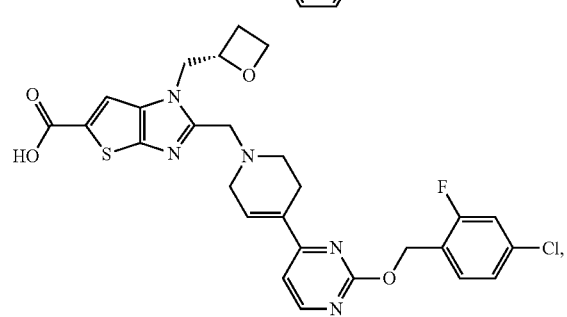
158
-continued
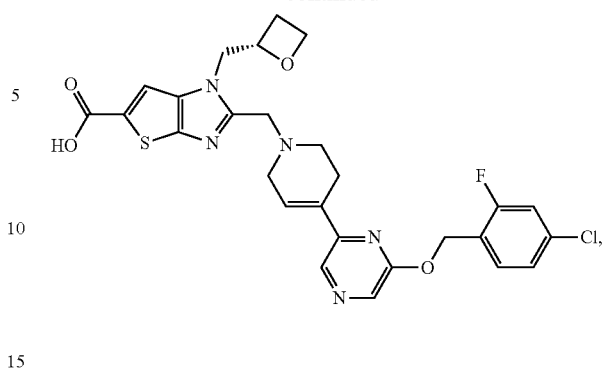
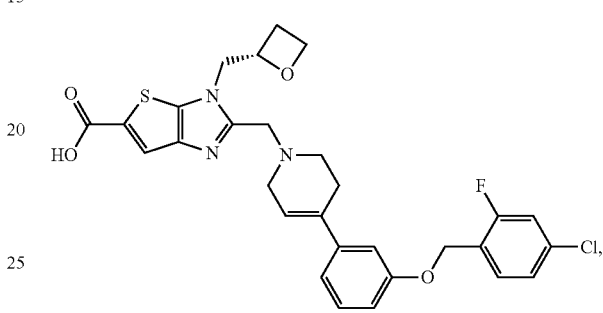
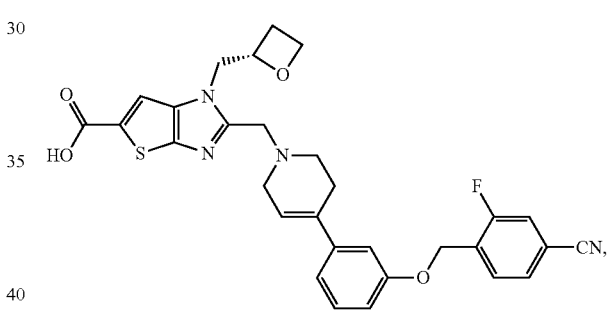
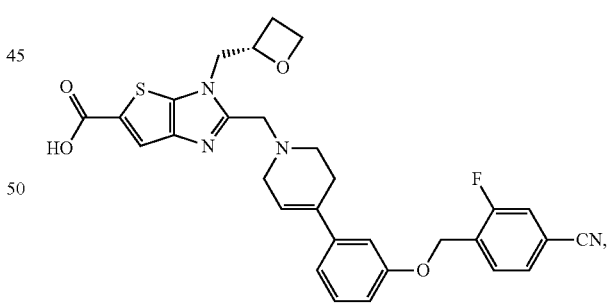
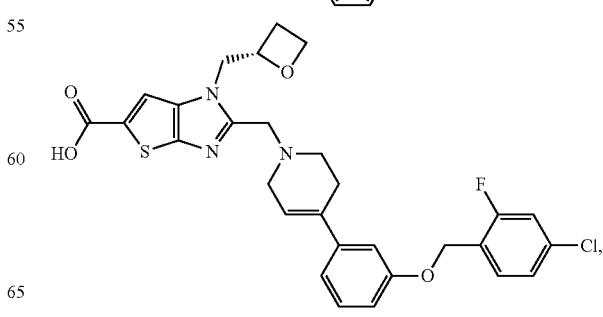

159
-continued
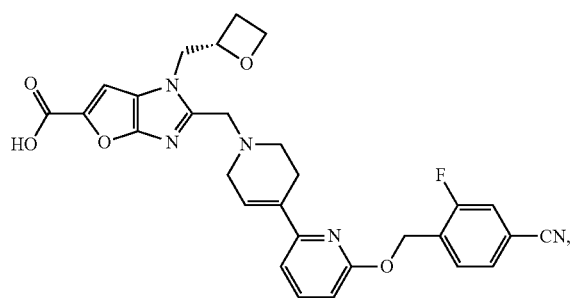
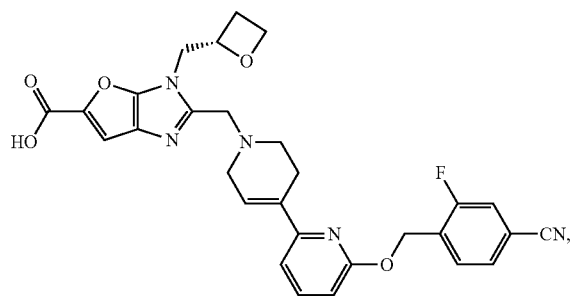
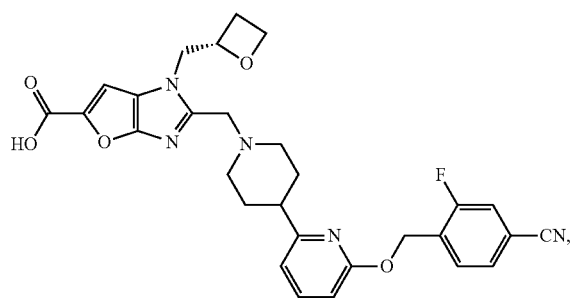
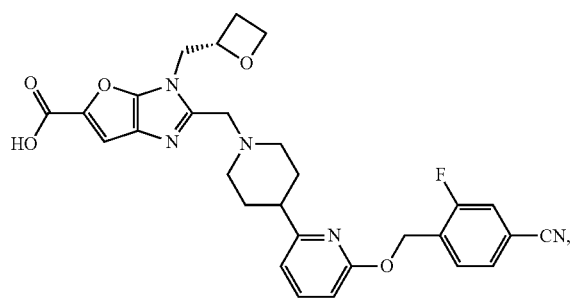
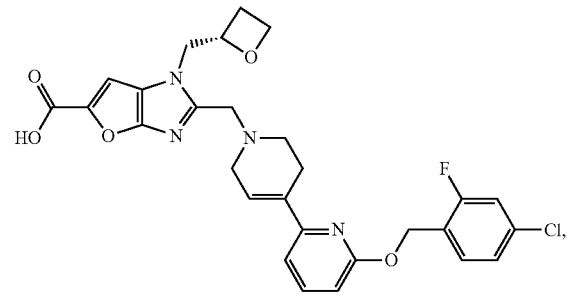
160
-continued
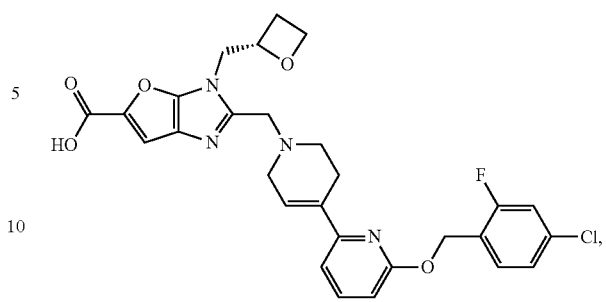
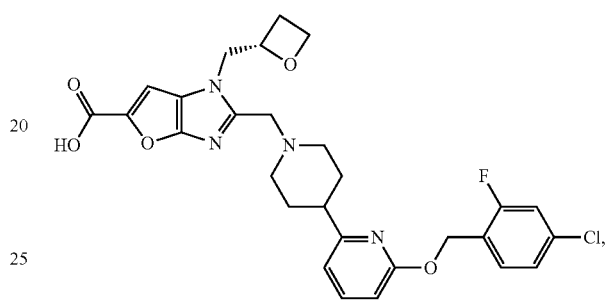
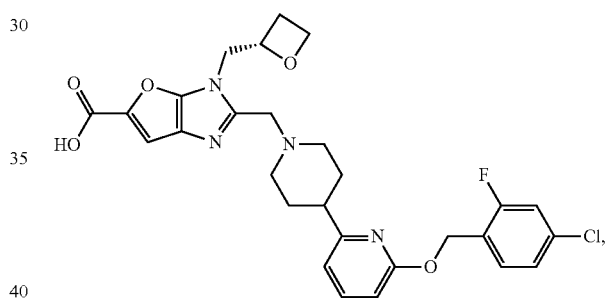
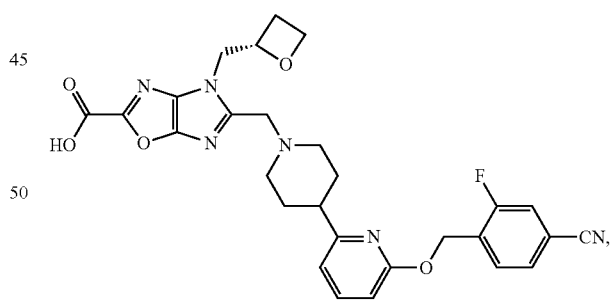
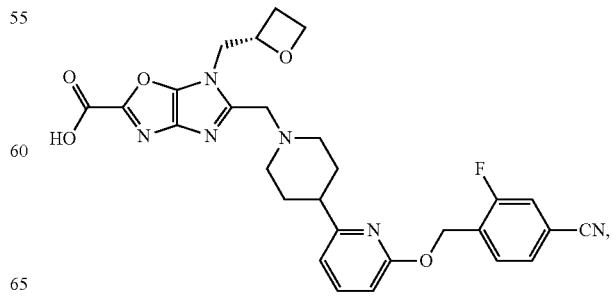

161
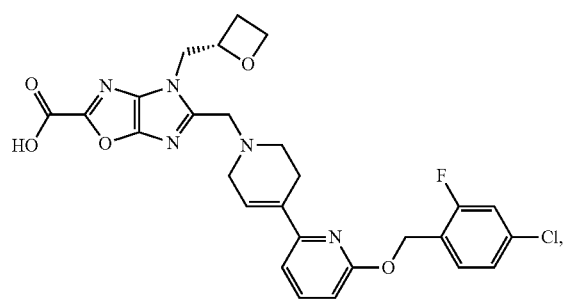
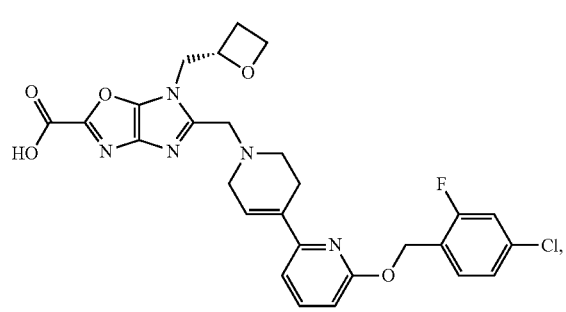
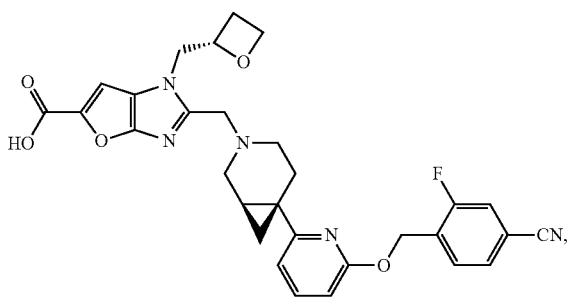
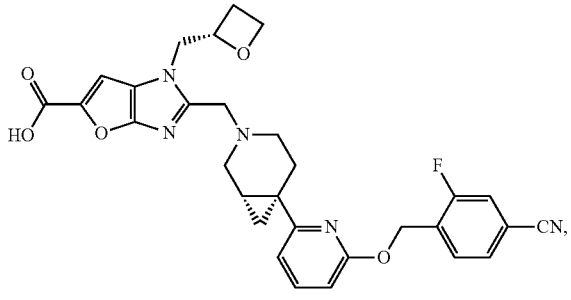
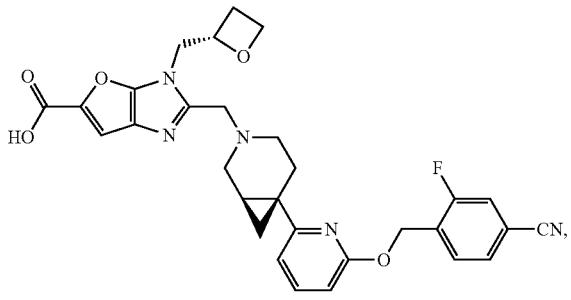
162
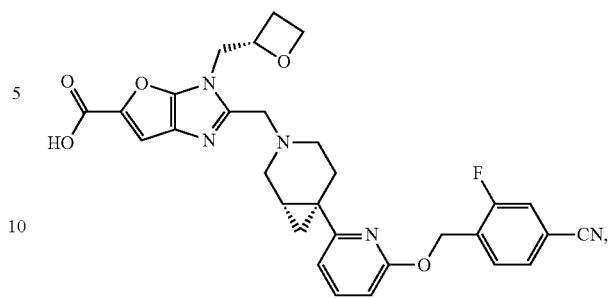
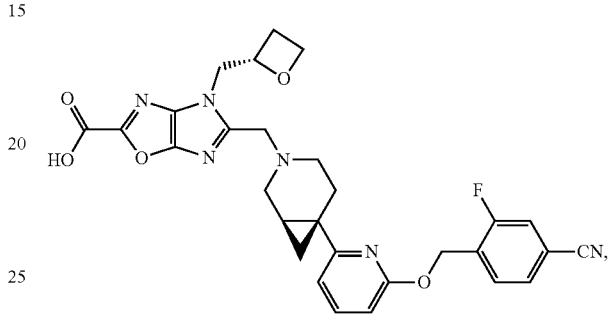
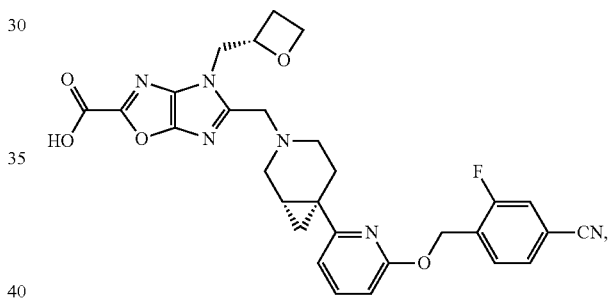
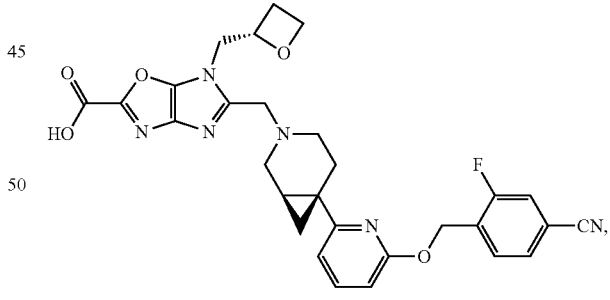
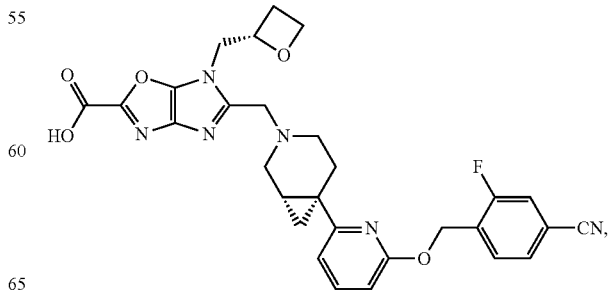

163
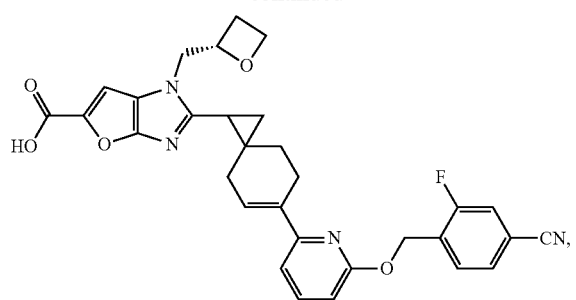
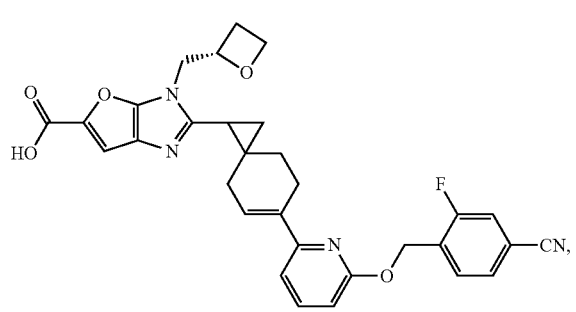
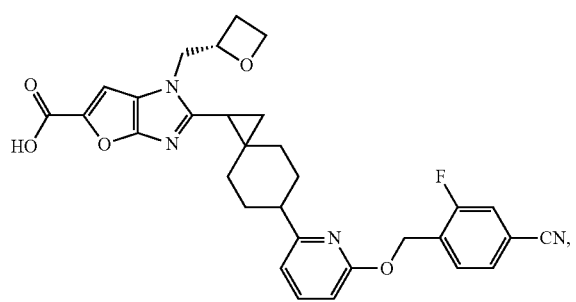
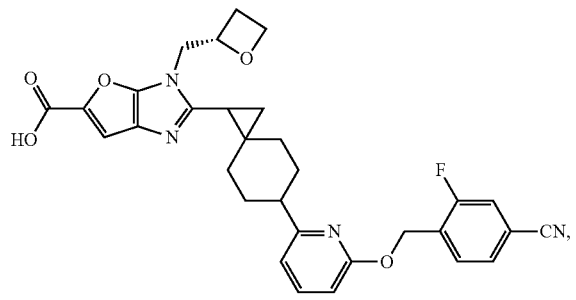
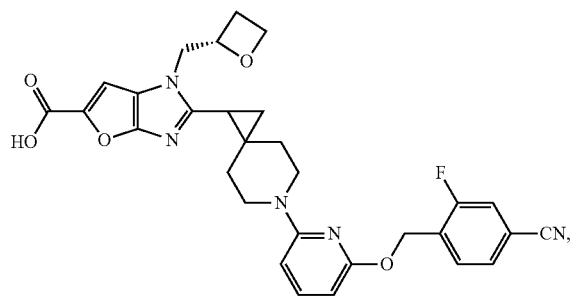
164
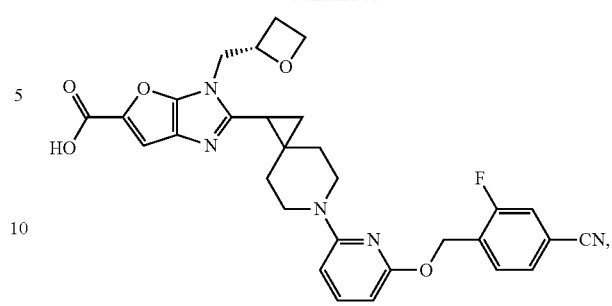
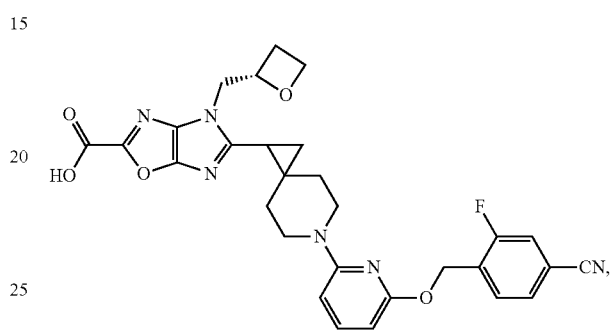
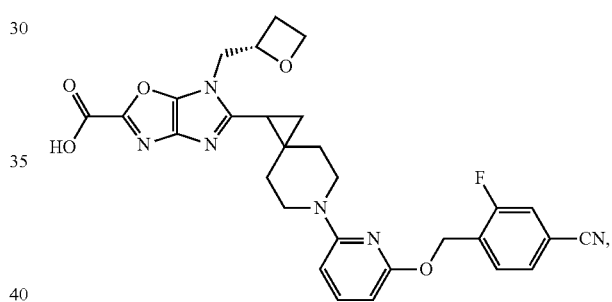
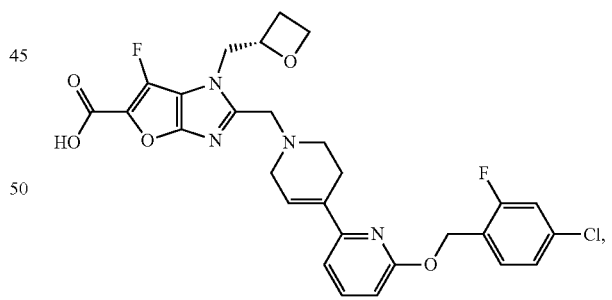
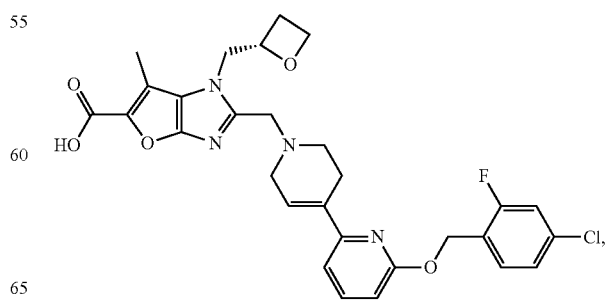

165
-continued
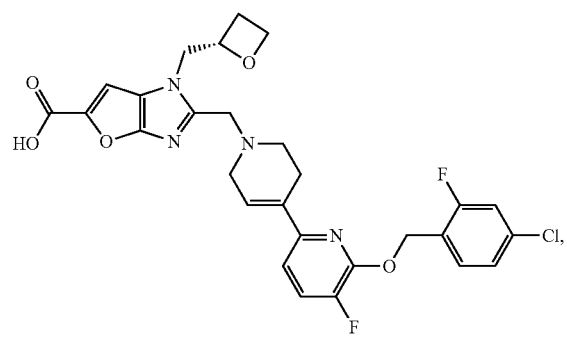
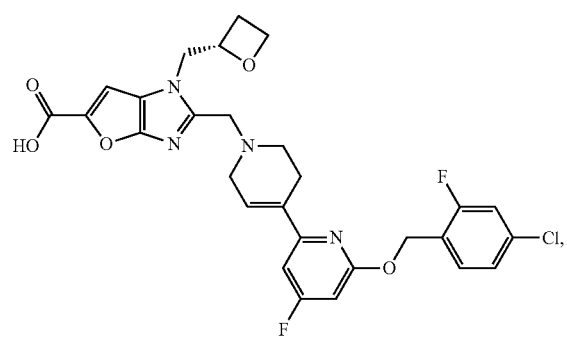
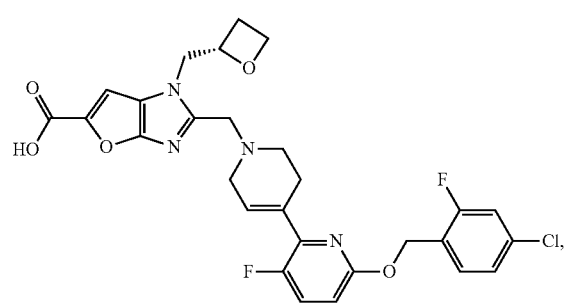
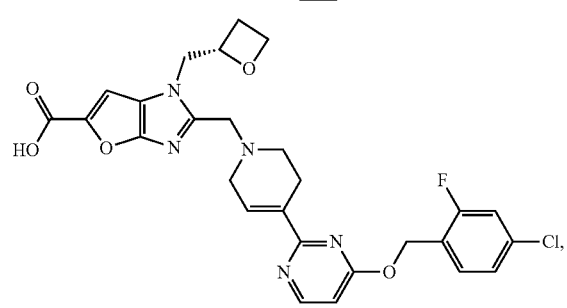
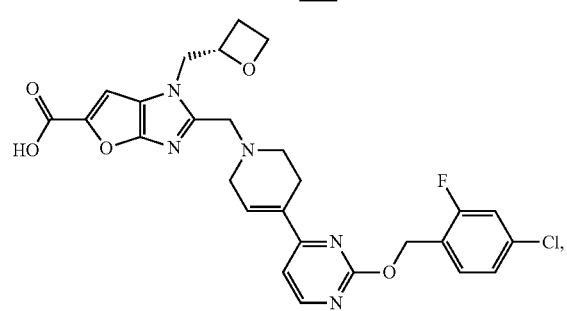
166
-continued
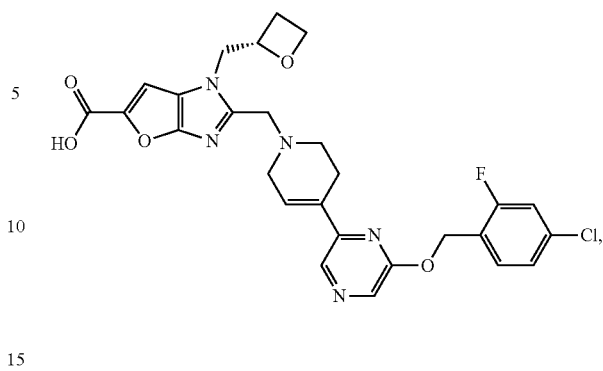
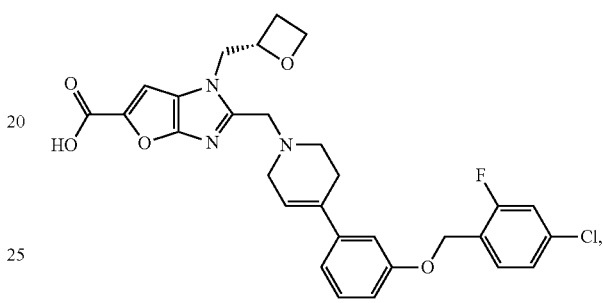
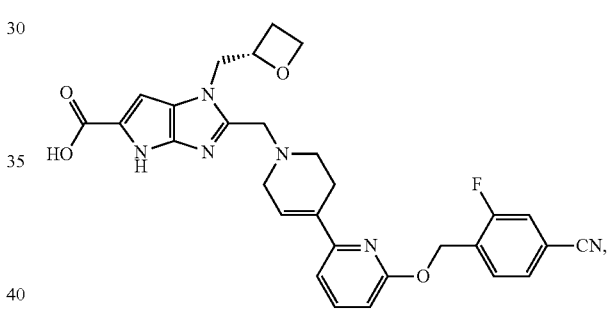
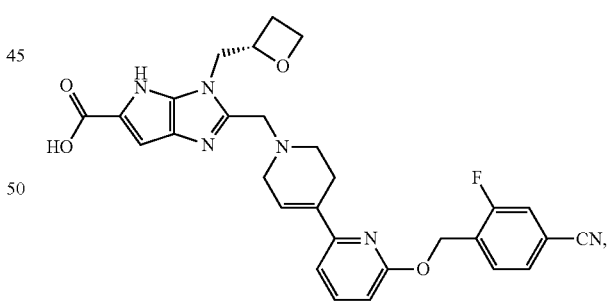
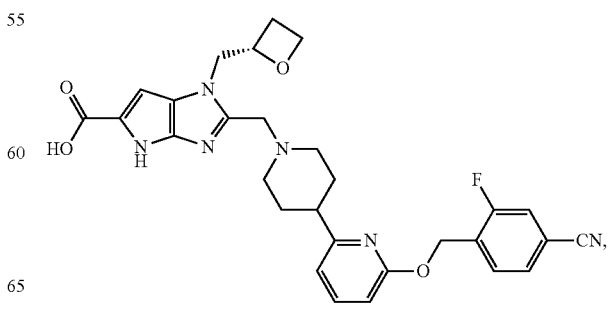

167
-continued
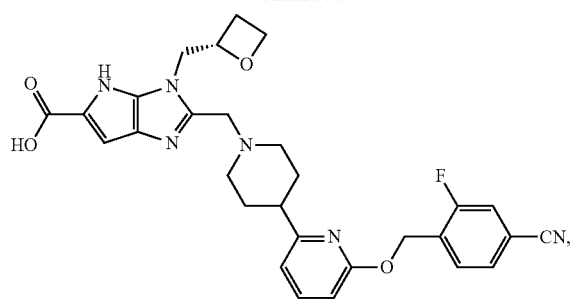
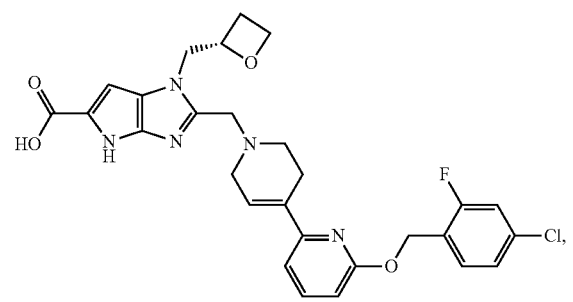
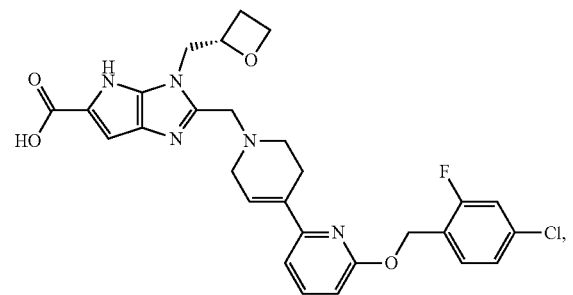
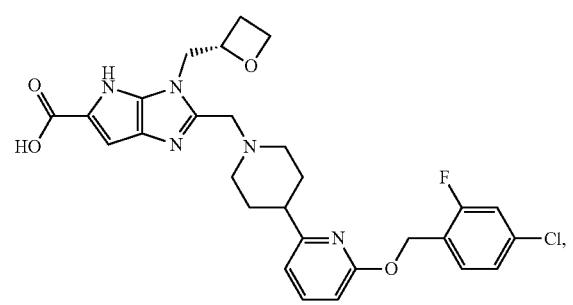
168
-continued
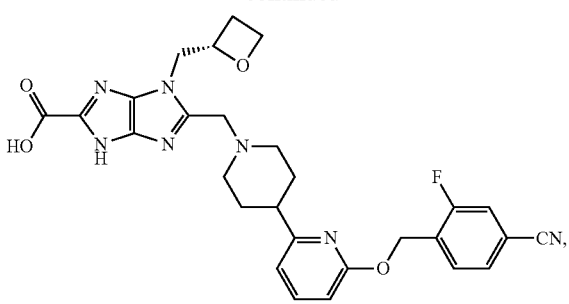
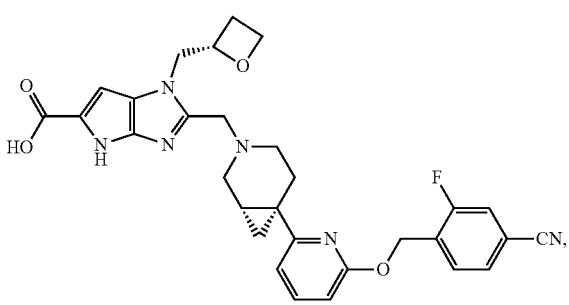
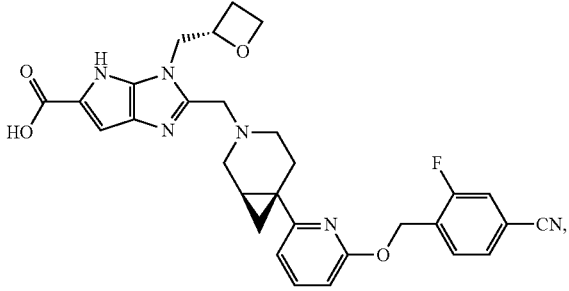

169
-continued
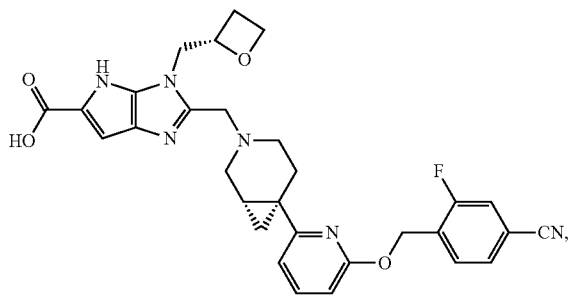
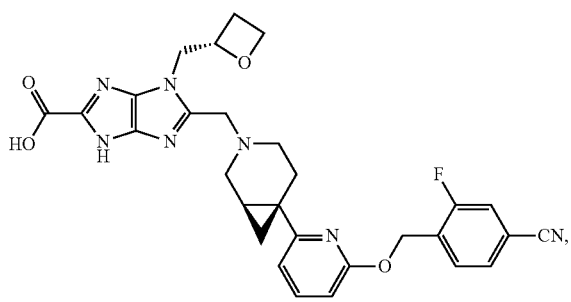
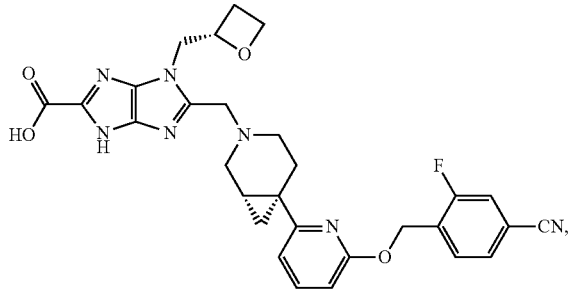
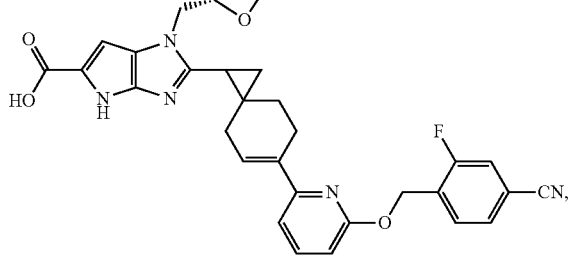
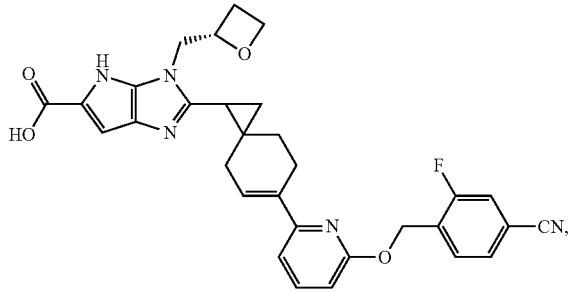
170
-continued
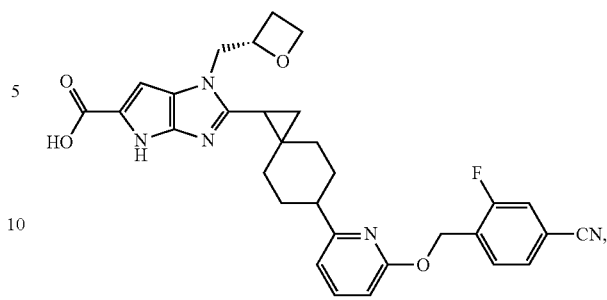
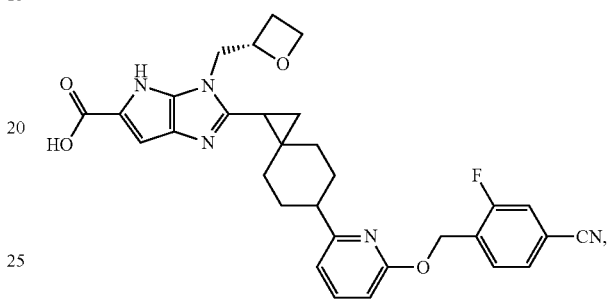
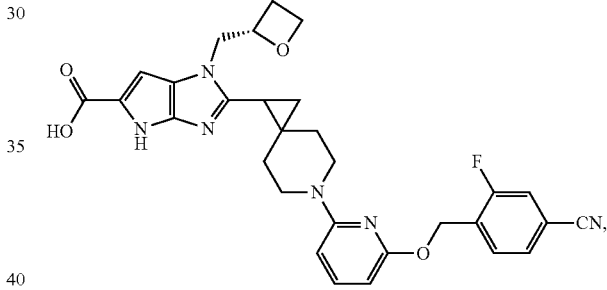
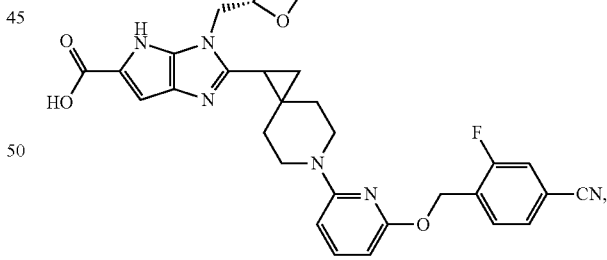
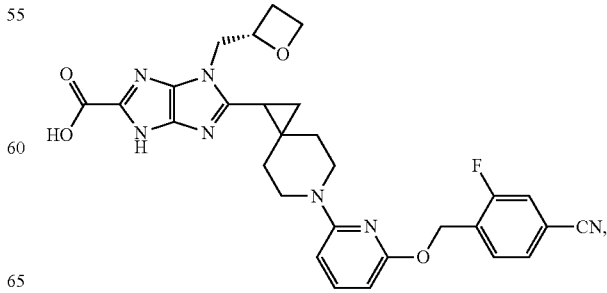

171
-continued

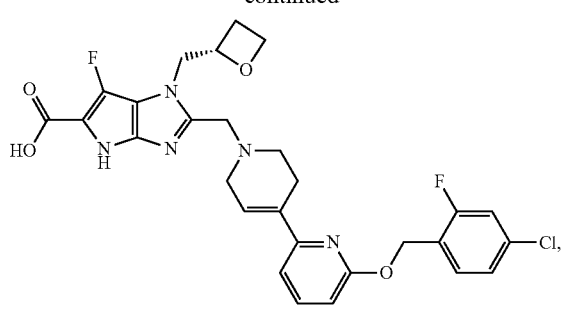

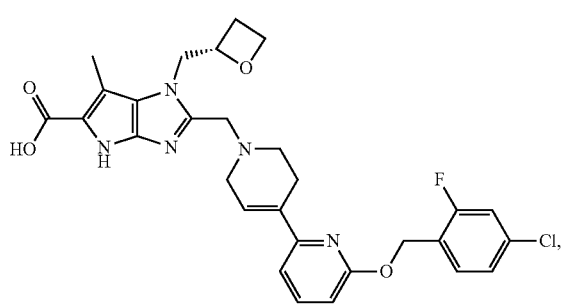

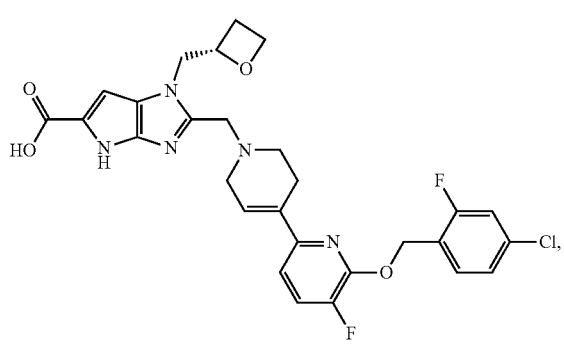

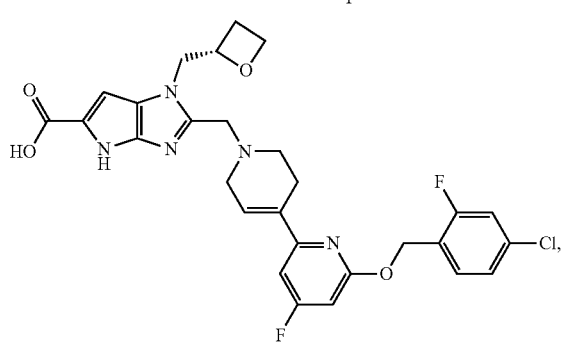

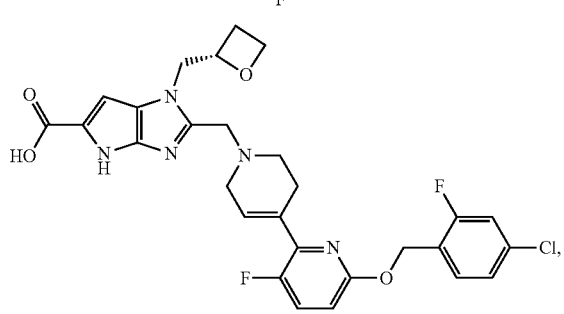

172
-continued

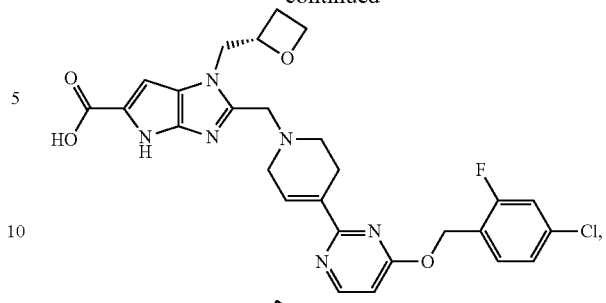

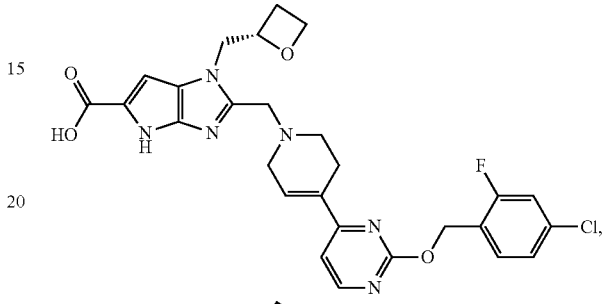

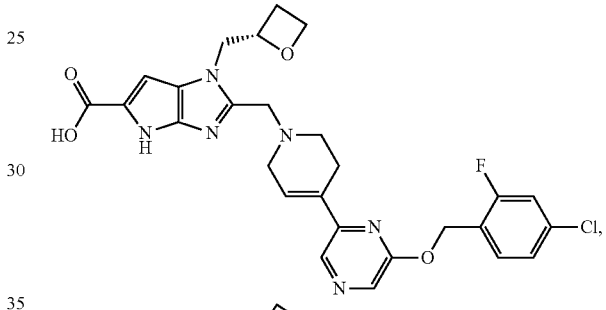

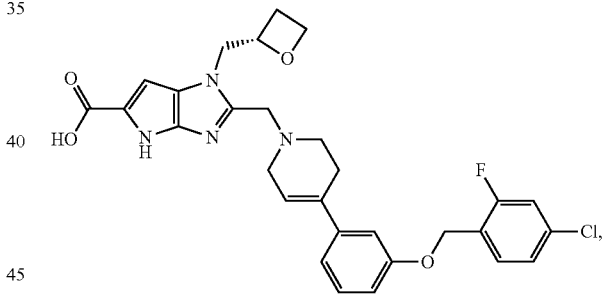

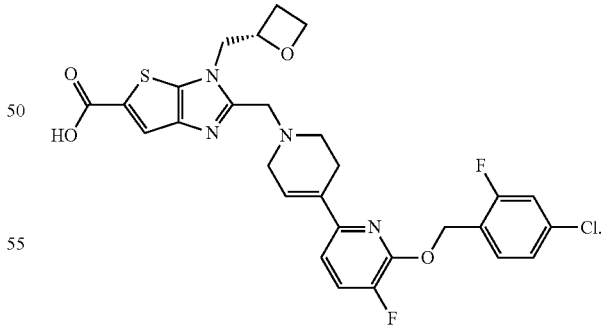

16. A method for activating GLP-1 receptor in a subject in need thereof, comprising administering to the subject an effective amount of the compound as defined in claim 1 or the pharmaceutically acceptable salt thereof.

17. A method for treating a disease related to GLP-1 receptor in a subject in need thereof, comprising administering to the subject an effective amount of the compound as defined in claim 1 or the pharmaceutically acceptable salt thereof, wherein the disease is type II diabetes.

18. A method for activating GLP-1 receptor in a subject in need thereof, comprising administering to the subject an effective amount of the compound as defined in claim 14 or the pharmaceutically acceptable salt thereof.

19. A method for treating a disease related to GLP-1 receptor in a subject in need thereof, comprising administering to the subject an effective amount of the compound as defined in claim 14 or the pharmaceutically acceptable salt thereof, wherein the disease is type II diabetes.

\* \* \* \* \*